United States Patent
Rafai Far et al.

(10) Patent No.: US 8,901,072 B2
(45) Date of Patent: Dec. 2, 2014

(54) GLYCOPEPTIDE AND LIPOGLYCOPEPTIDE ANTIBIOTICS WITH IMPROVED SOLUBILITY

(75) Inventors: Adel Rafai Far, Ville Mont-Royal (CA); Kelly Tanaka, Toronto (CA); Evelyne Dietrich, Laval (CA); Ranga Reddy, Hyderabad (IN); Ting Kang, Kirkland (CA)

(73) Assignee: The Medicines Company, Parsippany, NJ (US)

( * ) Notice: Subject to any disclaimer, the term of this patent is extended or adjusted under 35 U.S.C. 154(b) by 0 days.

(21) Appl. No.: 13/389,993

(22) PCT Filed: Aug. 11, 2010

(86) PCT No.: PCT/US2010/045201
§ 371 (c)(1),
(2), (4) Date: Feb. 24, 2012

(87) PCT Pub. No.: WO2011/019839
PCT Pub. Date: Feb. 17, 2011

(65) Prior Publication Data
US 2012/0149632 A1 Jun. 14, 2012

Related U.S. Application Data

(60) Provisional application No. 61/233,192, filed on Aug. 12, 2009.

(51) Int. Cl.
C07K 5/12 (2006.01)
A61K 38/12 (2006.01)
A61K 38/14 (2006.01)
A61P 31/04 (2006.01)
A61K 47/48 (2006.01)
C07K 9/00 (2006.01)
A61K 45/06 (2006.01)

(52) U.S. Cl.
CPC ........... *C07K 9/008* (2013.01); *A61K 47/48046* (2013.01); *A61K 38/12* (2013.01); *A61K 38/14* (2013.01); *A61K 45/06* (2013.01); *A61K 47/48038* (2013.01); *A61K 47/48215* (2013.01)
USPC ............................................. 514/3.1; 514/24

(58) Field of Classification Search
None
See application file for complete search history.

(56) References Cited

U.S. PATENT DOCUMENTS 6,951,840 B2   10/2005   Belvo et al.
2004/0087494 A1   5/2004   Linsell et al.

FOREIGN PATENT DOCUMENTS

WO   2008-077241   7/2008
WO   WO 2008077241 A1 *   7/2008
WO   2008-097364   8/2008
WO   2008-118784   10/2008

OTHER PUBLICATIONS

Stickley, R.G., "Formulation in Drug Discovery," Ann. Rep. Medicinal Chem. 43:419-451 (2008).*
Han, H.-K. "Targeted prodrug design to optimize drug delivery," AAPS Pharmsci. 2(1), Article 6:1-11 (2000).*
Beaumont, et, al "Design of Ester Prodrugs to Enhance Oral Absorption of Poorly Permeable Compounds: Challenges to the Discovery Scientist," Current Drug Metabolism 4:461-485 (2003).*
Muller, Christa E. "Prodrug Approaches for Enhancing the Bioavailability of Drugs with Low Solubility," Chemistry & Biodiversity, vol. 6:2071-2083 (2009).*
Singh, Yashveer et al, "Recent Trends in Targeted Anticancer Prodrug and Conjugate," DesignCurr Med Chem. 15(18):1802-1826 (2008).*
Ettmayer P. et al., "Lessons leared from marketed and investigational prodrugs," J. Med. Chem. 47(10):2393-2404 (2004).*
Testa, B. "Prodrug research: futile or fertile?" Biochemical Pharmacology 68:2097-2106 (2004).*
Clardy, J. et al., New antibiotics from bacterial natural products, Nature Biotechnology, 2006, vol. 24, No. 12, pp. 1541-1550.
Kahne, D. et al., Glycopeptide and lipoglycopeptide antibiotics, Chem. Rev., 2005, vol. 105, pp. 425-448.
International Search Report for PCT/US2010/045201, dated Apr. 29, 2011.

* cited by examiner

*Primary Examiner* — Christina Bradley
*Assistant Examiner* — Kristina M Hellman
(74) *Attorney, Agent, or Firm* — Roylance, Abrams, Berdo & Goodman, L.L.P.

(57) ABSTRACT

The invention relates to derivatives of glycopeptide and lipoglycopeptide antibiotics possessing an altered ionization state with respect to the parent glycopeptide or lipoglycopeptide antibiotic, and having the ability to be regenerated as the parent glycopeptide or lipoglycopeptide antibiotic under physiological conditions. These compounds are useful as antibiotics for the prevention and/or the treatment of bacterial infections.

21 Claims, No Drawings

GLYCOPEPTIDE AND LIPOGLYCOPEPTIDE ANTIBIOTICS WITH IMPROVED SOLUBILITY

BACKGROUND OF THE INVENTION

Glycopeptide and lipoglycopeptide antibiotics are a class of biologically produced or semi-synthetic antimicrobial agents with activity on bacterial cell walls and/or on membrane integrity (Williams, D. H et al, Angewandte Chemie International Edition in English (1999) 38: 1172-1193; Nicolaou, K. C. et al, Angewandte Chemie International Edition in English (1999) 38:2097-2152; Kahne, D. et al Chemical Reviews (2005) 105:425-448; Pace, J. L. et al, Biochemical Pharmacology (2006) 71:968-980). Well-known glycopeptide and lipoglycopeptide antibiotics include vancomycin, teicoplanin, oritavancin (U.S. Pat. No. 5,840,684), dalbavancin (U.S. Pat. No. 5,750,509) and telavancin (U.S. Pat. No. 6,635,618). The two first drugs have been proven clinically and microbiologically to have potent activity against gram-positive organisms and the latter three drugs are in clinical trials. Oritavancin, dalbavancin and telavancin possess extremely attractive pharmacological profiles with potent activity against gram-positive organisms, including methicillin-resistant *Staphylococcus aureus*, intermediate and fully vancomycin-resistant *Staphylococcus aureus*, vancomycin-resistant *Enterococcus* spp., and *Streptococcus* spp.

Glycopeptides are known to produce localized side effects upon administration and typically require large volumes for administration by infusion. The side effects present themselves as inflammatory responses such as phlebitis, pruritus and the "Red-Man" syndrome (Sivagnanam, S. et al, Critical Care (2003) 7:119-120; Bertolissi, M. et al, Critical Care (2002) 6:234-239; Wilson, A. P. R., International Journal of Antimicrobial Agents (1998) 10:143-152; Korman, T. M. et al, Journal of Antimicrobial Chemotherapy (1997) 39:371-381). The problem may be that the lack of solubility of the glycopeptide and/or its presence at high concentrations induces an inflammatory response. A prodrug which could simultaneously improve the solubility of the drug and mask its presence at the time and the site of administration may be able to decrease such inflammatory responses.

In addition, the lack of solubility of glycopeptide antibacterial agents results in the need for administration of low concentrations of the drug in large volumes over a prolonged period of time, which is an impediment in emergency situations where rapid administration is needed.

Improvements to the solubility of therapeutic materials in isotonic aqueous media can be brought about through a number of means (Stella V. J. et al Advanced Drug Delivery Reviews (2007) 59: 677-694). With respect to glycopeptides, improvements in solubility can be brought about by the use of poly(ethylene glycol) chains (WO2008118784), but at the cost of a marked increase in the size of the molecule administered.

In view of the above, there is a need for highly active glycopeptide antibiotics for the prevention and treatment of infections without the potential adverse events associated with their administration. More particularly, there is a need for glycopeptide and lipoglycopeptide antibiotics with the ability to overcome bacterial resistance, that can be administered in reduced volumes, and that have greater solubility in circulating biological fluids.

The present invention fulfills these needs and also other needs as will be apparent to those skilled in the art upon reading the following specification.

SUMMARY OF THE INVENTION

The present invention is directed to antimicrobial compounds with improved solubility. More particularly, the invention is directed to derivatives of glycopeptide and lipoglycopeptide antibiotics possessing an altered ionization state with respect to the parent glycopeptide or lipoglycopeptide antibiotic from which they are derived. The glycopeptide and lipoglycopeptide antibiotics with altered ionization states of the present invention have the ability to be regenerated as the parent glycopeptide or lipoglycopeptide antibiotic under physiological conditions. These antimicrobial compounds present an improved profile as a consequence of the ability to use a reduced volume of the compounds in an injection and in the diminution of side effects stemming from the poor solubility of the parent antibiotics, in particular injection-site and infusion related events. These compounds are useful as antibiotics for the prevention or treatment of Gram positive bacterial infections.

In a first embodiment, the compounds of the invention are represented by Formula (I):

$$[[[L^a{}_\beta\text{-M}]_\alpha\text{-}L^b{}_\delta]_\gamma\text{-}L^c{}_\epsilon]_y\text{-}A \qquad (I)$$

and pharmaceutically acceptable salts, esters, stereoisomers and prodrugs thereof, wherein:

each M is independently a chemical group that is ionizable under physiological conditions, having between 0 and 3 $L^a$ bonded thereto;

each $L^a$ is independently a chemical group structurally or electronically assisting M in maintaining a charge;

each $L^b$ is independently a bond or a multivalent linking group, wherein each $L^b$ links between 1 and 6 $[L^a{}_\beta\text{-M}]$ groups to each other, to $L^c$, or to each other and to $L^c$, wherein when $L^b$ is present, at least one $L^b$ links at least one $[L^a{}_\beta\text{-M}]$ group to at least one $L^c$;

each $L^c$ is independently a bond or a multivalent linking group which is cleavable under physiological conditions, wherein each $L^c$ links between 1 and 10 $[[L^a{}_\beta\text{-M}]_\alpha\text{-}L^b{}_\delta]$ groups to A, or links each $[L^a{}_\beta\text{-M}]$ group to A when $\delta$ is 0;

A is a glycopeptide or lipoglycopeptide antimicrobial molecule;

$\alpha$ is an integer between 1 and 6;

$\gamma$ is an integer between 1 and 10;

$\beta$ is an integer $\leq 3$;

$\delta$ is an integer $\leq 2\alpha$;

$\epsilon$ is an integer $\leq \alpha\gamma$;

y is an integer between 1 and 7.

In preferred aspects, $\alpha$ is 1, 2 or 3 and y is 1 or 2.

In the first embodiment, each M is individually selected from the group of:

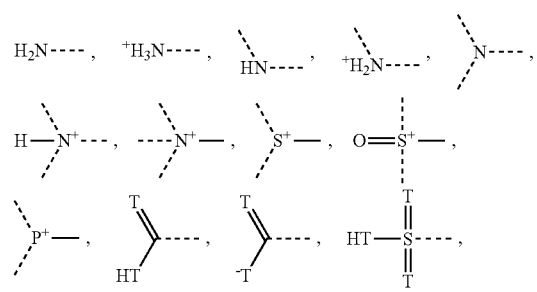

-continued

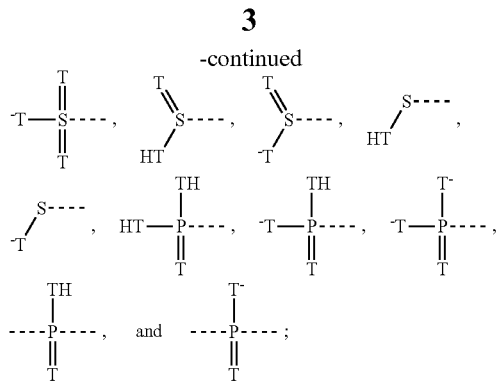

wherein:

each T is O or S; and the dashed bonds - - - indicate the points of attachment to another M, $L^a$, $L^b$, $L^c$ or A.

In the first embodiment, each $L^a$ is individually selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and

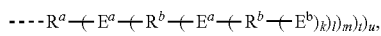

$----R^a-(\!-E^a-(\!-R^b-(\!-E^a-(\!-R^b-(\!-E^b)_k)_l)_m)_t)_u,$ wherein:

each $R^a$ is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, —(CO)-(substituted alkenylene)-, —(CO)-alkynylene-, —(CO)-(substituted alkynylene)-, —(CO)-arylene- and —(CO)-(substituted arylene)-;

each $R^b$ is independently selected from the group consisting of a covalent bond, alkylene, substituted alkylene, alkenylene, substituted alkenylene, alkynylene, substituted alkynylene, arylene and substituted arylene;

each $E^a$ is independently selected from the group consisting of a covalent bond, methylene, oxygen, sulfur,

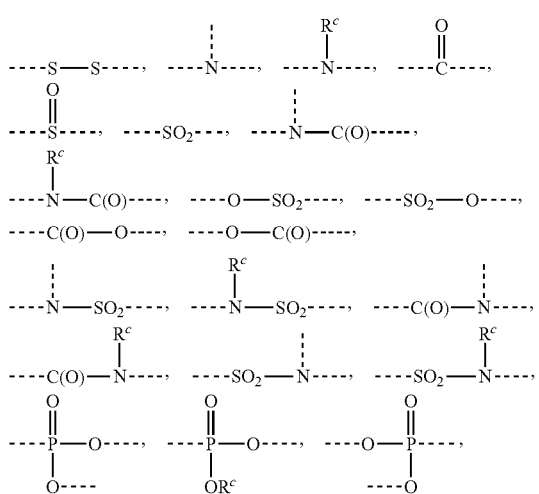

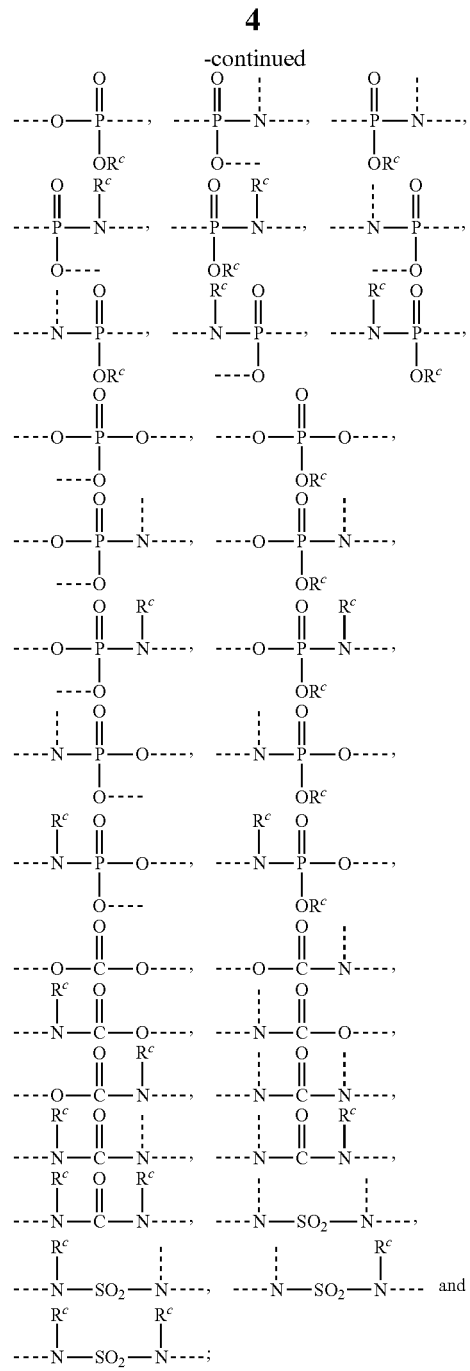

each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

each $E^b$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, and substituted aryloxy; and each k, l, m, t, u is independently a nonnull integer ≤5.

In the first embodiment, each $L^b$ is individually selected from the group consisting of a covalent bond, alkylene, substituted alkylene, alkenylene, substituted alkenylene, alkynylene, substituted alkynylene, cycloalkylene, substituted cycloalkylene, cycloalkenylene, substituted cycloalkenylene, arylene, heteroarylene and

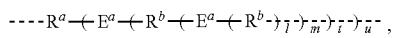

wherein:

each $R^a$ is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, —(CO)-(substituted alkenylene)-, —(CO)-alkynylene-, —(CO)-(substituted alkynylene)-, —(CO)-arylene- and —(CO)-(substituted arylene)-;

each $R^b$ is independently selected from the group consisting of a covalent bond, alkylene, substituted alkylene, alkenylene, substituted alkenylene, alkynylene, substituted alkynylene, arylene and substituted arylene;

each $E^a$ is independently selected from the group consisting of a covalent bond, methylene, oxygen, sulfur,

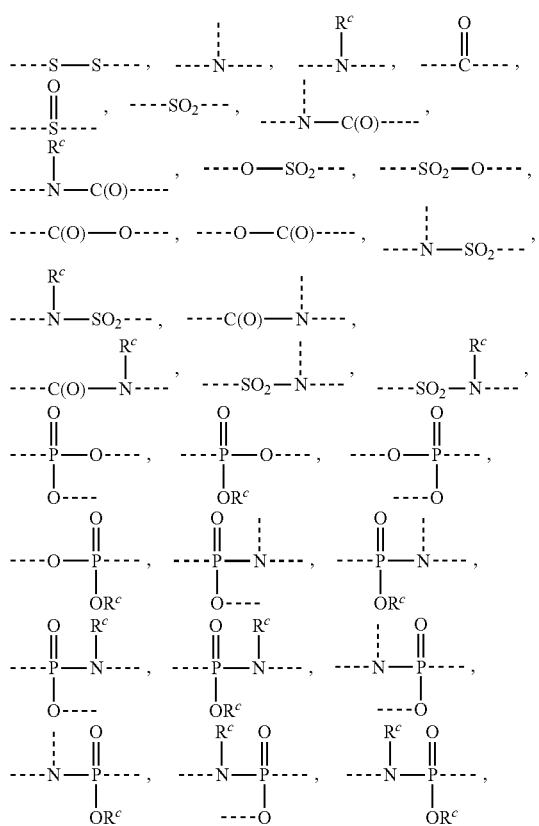

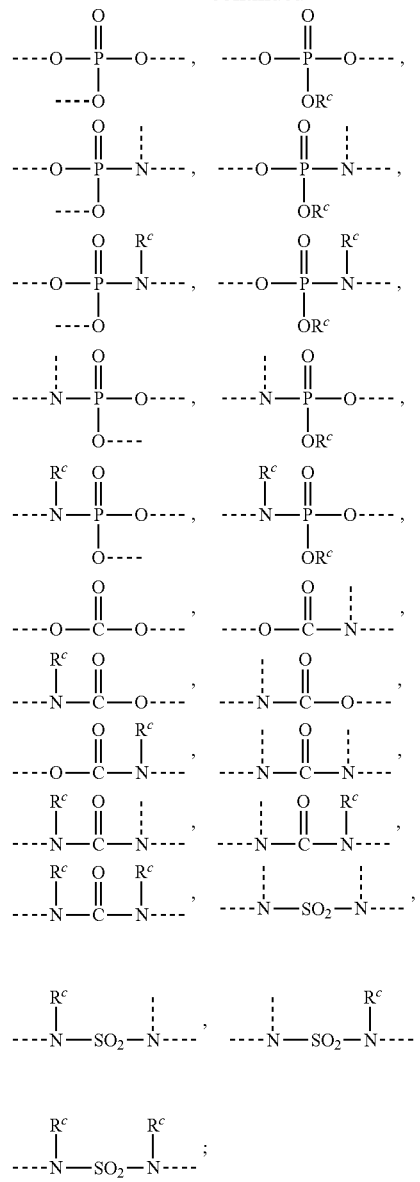

each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; and each l, m, t, u is independently a nonnull integer ≤5.

In the first embodiment, each $L^c$ is independently selected from the group consisting of a covalent bond, alkylene, substituted alkylene, alkenylene, substituted alkenylene, alkynylene, substituted alkynylene, cycloalkylene, substituted cycloalkylene, cycloalkenylene, substituted cycloalkenylene, arylene, and heteroarylene, or $L^c$ is individually represented by the following formula ($L_1$):

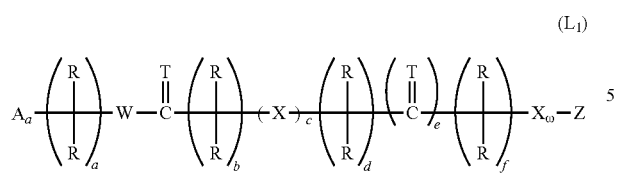

(L₁)

wherein:

$A_a$ indicates the point of attachment to the glycopeptide or lipoglycopeptide antimicrobial molecule A;

W is a covalent bond or is selected from the group of consisting of

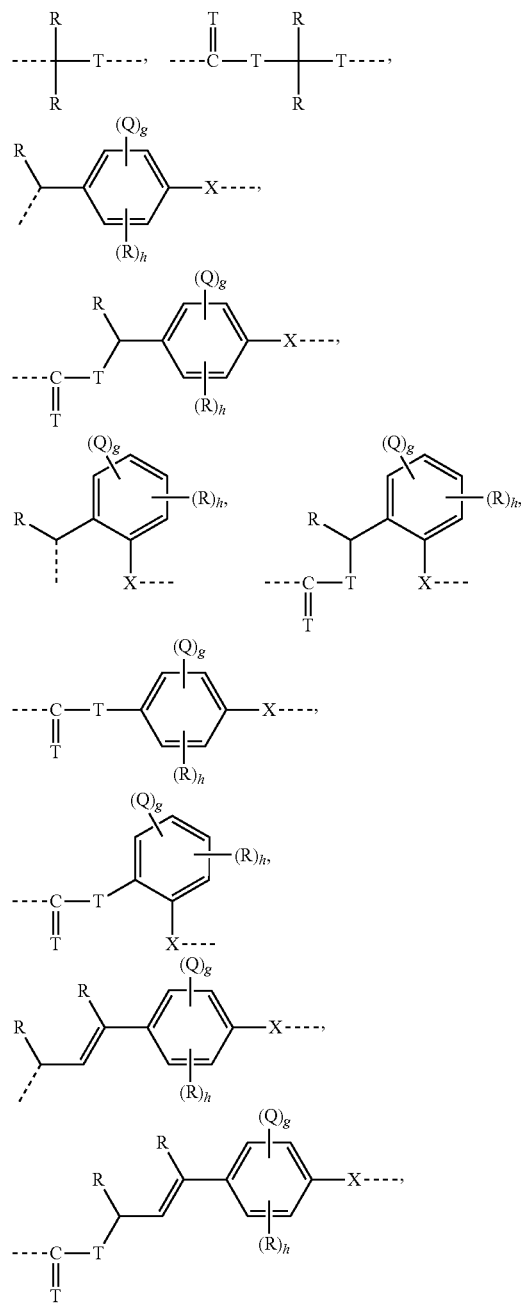

each T is independently oxygen or sulfur;

each R is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, substituted aryloxy, $M_a$ and —$R^a$—Y—$R^b$—Y—$R^b$-$M_a$;

each $R^a$ is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, —(CO)-(substituted alkenylene)-, —(CO)-alkynylene-, —(CO)-(substituted alkynylene)-, —(CO)-arylene- and —(CO)-(substituted arylene)-;

each $R^b$ is independently selected from the group consisting of a covalent bond, alkylene, substituted alkylene, alkenylene, substituted alkenylene, alkynylene, substituted alkynylene, arylene and substituted arylene;

$M_a$ indicates the point of attachment to [[$L^a_\beta$-M]$_\alpha$-$L^b_\delta$];

each Q is independently nitro, chloro, bromo, iodo or fluoro;

each X is independently —O—, —S— or —N(R)—;

each Y is independently selected from the group consisting of a covalent bond, methylene, oxygen, sulfur,

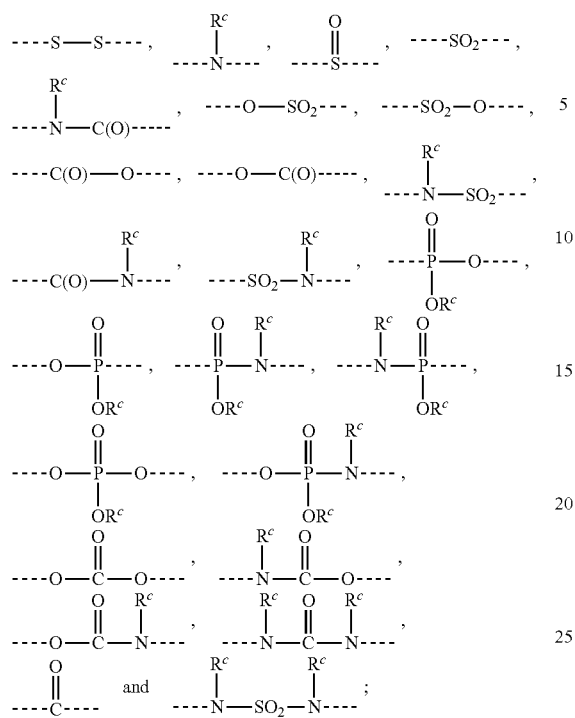

each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

Z is selected from the group consisting of hydrogen, acyl, substituted acyl, aroyl, substituted aroyl, alkoxycarbonyl, substituted alkoxycarbonyl, aryloxycarbonyl, substituted aryloxycarbonyl,

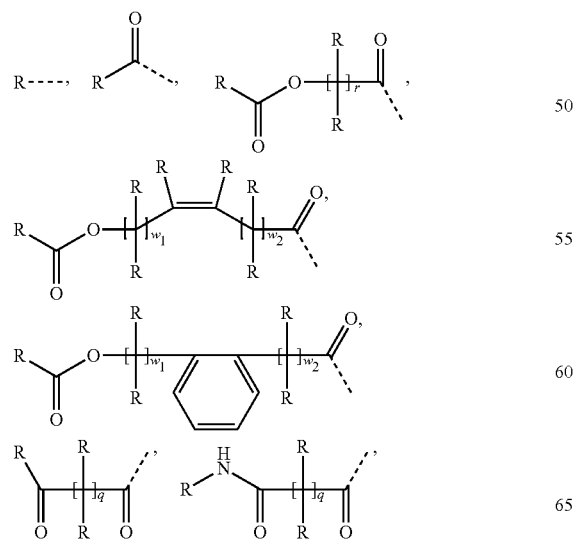

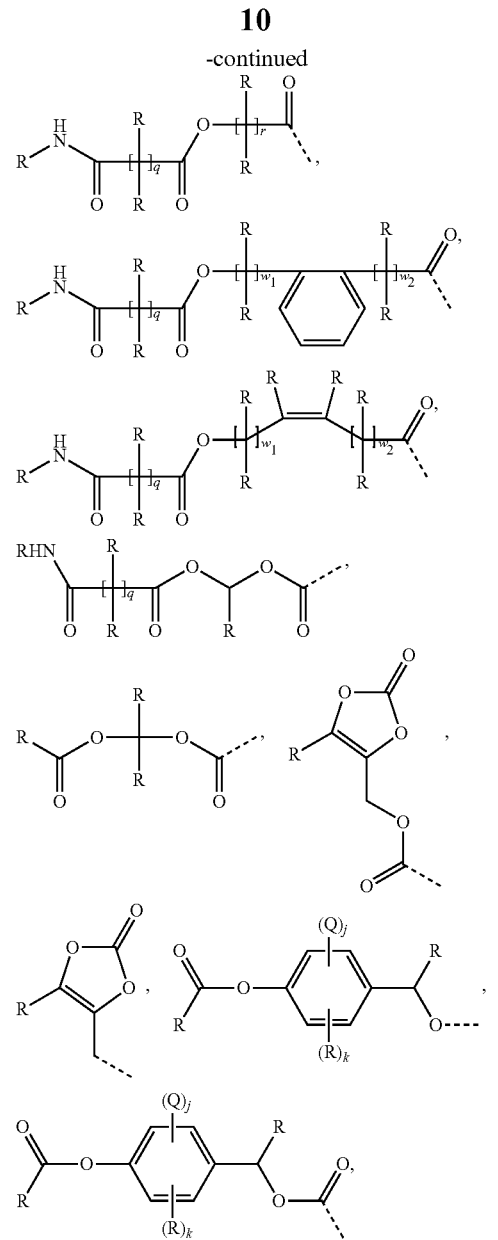

-continued

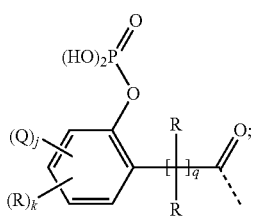

q is 2 or 3;

r is 1, 2, 3, 4 or 5;

j and k are each independently 0, 1, 2, 3 or 4;

$w_1$ and $w_2$ are each integers $\geq 0$ such that their sum ($w_1+w_2$) is 1, 2 or 3;

a is an integer $\leq 10$;

b, c, d, e and f are integers such that $b+c+d+e+f \leq 7$ or null;

g and h are integers $\geq 0$ such that $g+h=4$;

ω is 0 or 1;

with the proviso that at least one R is $-M_a$ or $-R^a-Y-R^b-Y-R^b-M_a$; and with the further proviso that either W is a group of atoms or $a+b+d+f \geq 1$.

In one aspect of the first embodiment, at least one of the linker $L^c$ couples at least one of the $[[L^a{}_\beta-M]_\alpha-L^b{}_\delta]$ to a hydroxyl functionality on the glycopeptide or lipoglycopeptide antibiotic A, wherein each of the linker $L^c$ coupling $[[L^a{}_\beta-M]_\alpha-L^b{}_\delta]$ to the hydroxyl functionality is independently selected from the group consisting of:

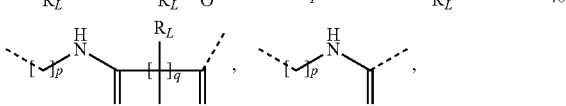

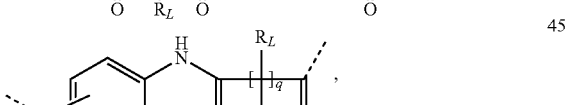

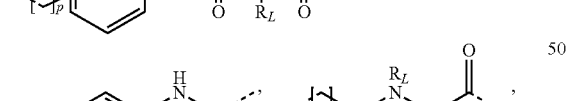

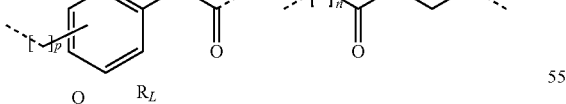

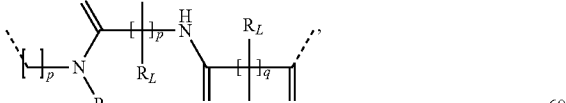

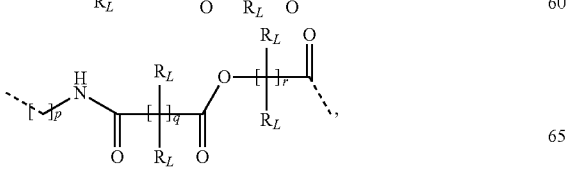

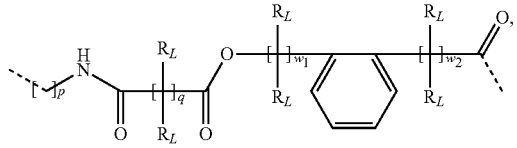

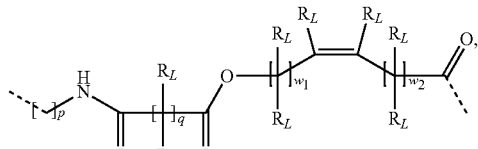

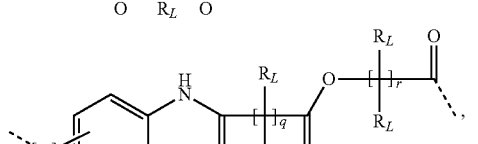

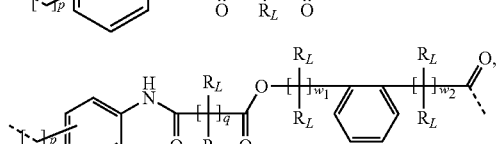

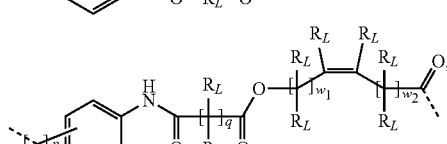

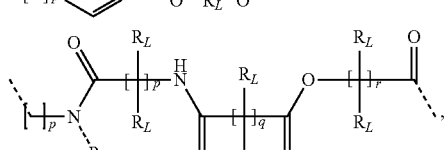

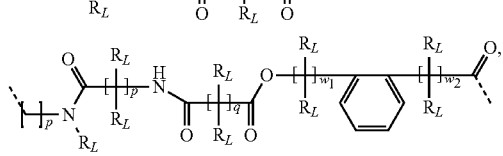

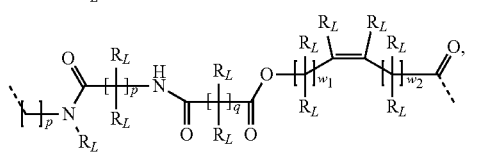

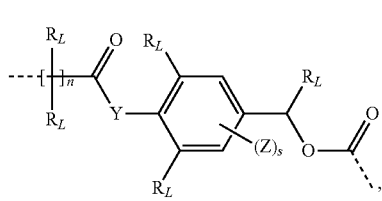

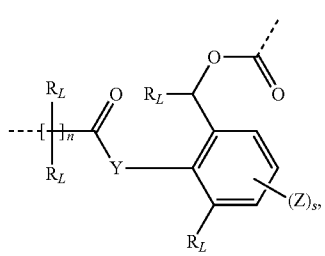

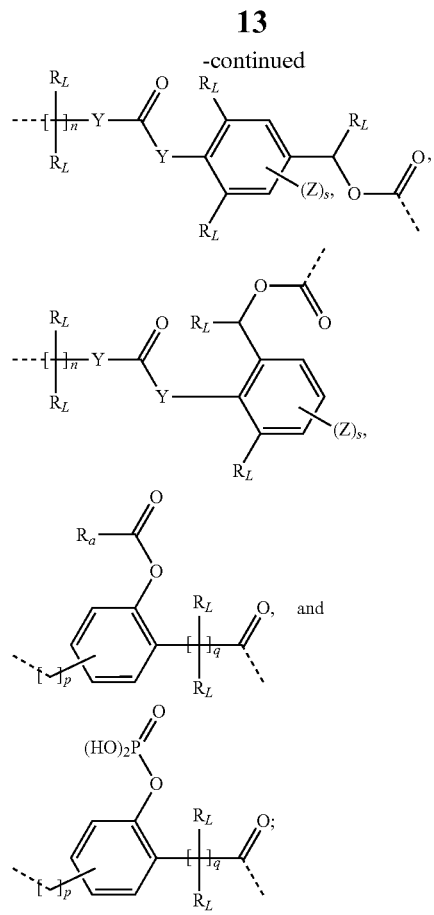

wherein:
  each p is independently 0 or an integer ≤10;
  each $R_L$ is independently selected from the group consisting of H, ethyl and methyl;
  q is 2 or 3;
  n is an integer ≤10;
  r is 1, 2, 3, 4 or 5;
  $w_1$ and $w_2$ are each integers ≥0 such that their sum ($w_1+w_2$) is 1, 2 or 3;
  each Y is independently selected from the group consisting of —O—, —S—, and —$NR_L$—;
  each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro;
  s is 1, 2, 3 or 4; and
  $R_a$ is $C_xH_y$ where x is an integer of 0 to 20 and y is an integer of 1 to 2x+1.

In a second aspect of the first embodiment, at least one of the linker $L^c$ couples at least one of the $[[L^a{}_\beta\text{-}M]_\alpha\text{-}L^b{}_\delta]$ to a nitrogen atom on the glycopeptide or lipoglycopeptide antibiotic A, wherein each of the linker $L^c$ coupling $[[L^a{}_\beta\text{-}M]_\alpha\text{-}L^b{}_\delta]$ to a nitrogen atom is independently selected from the group consisting of:

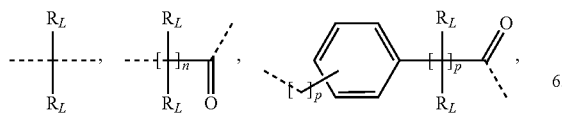

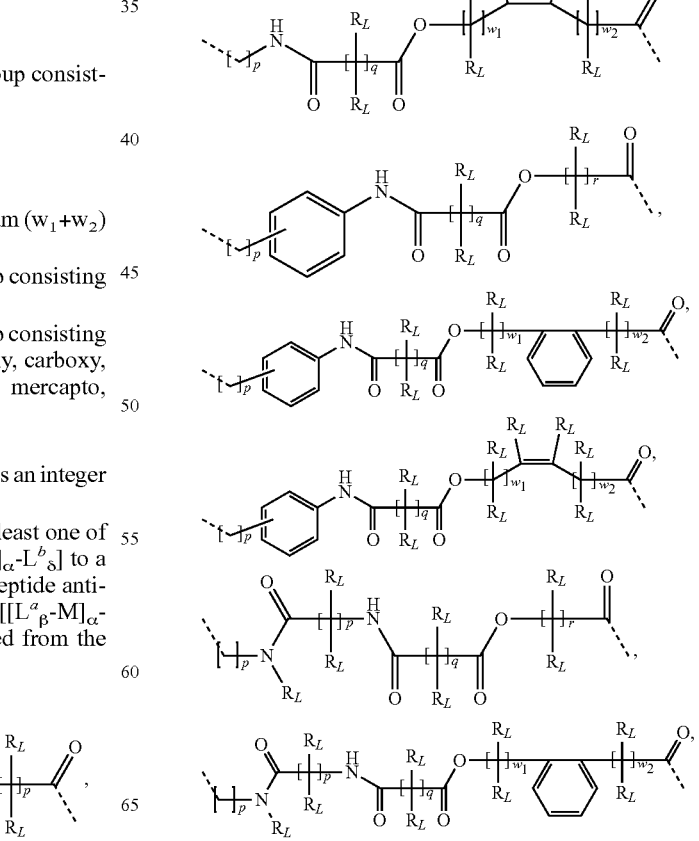

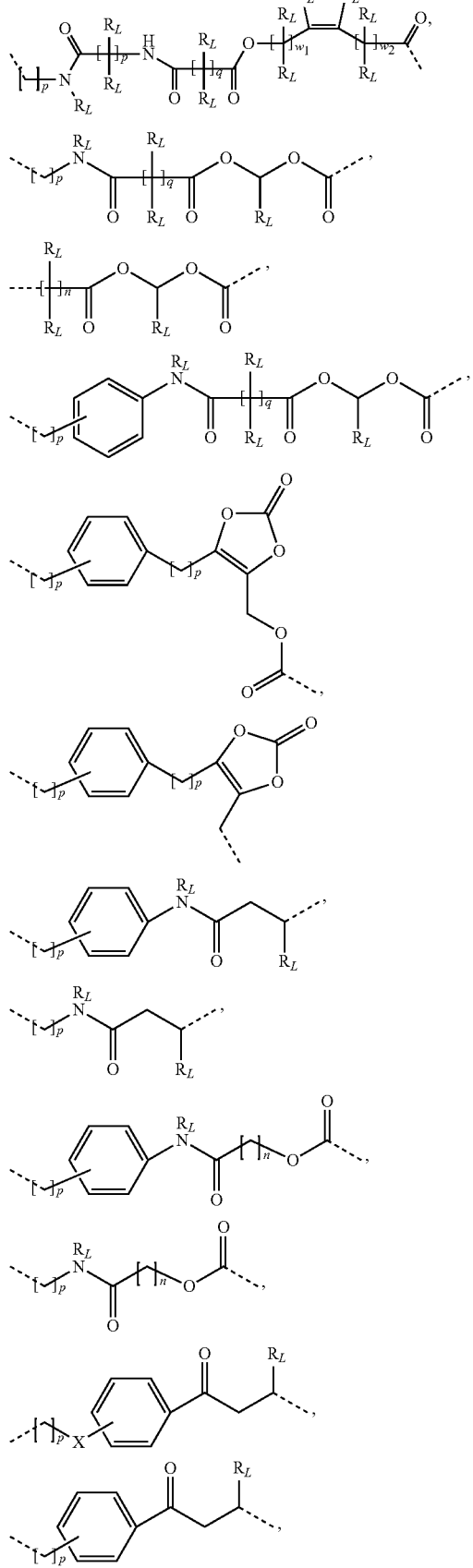
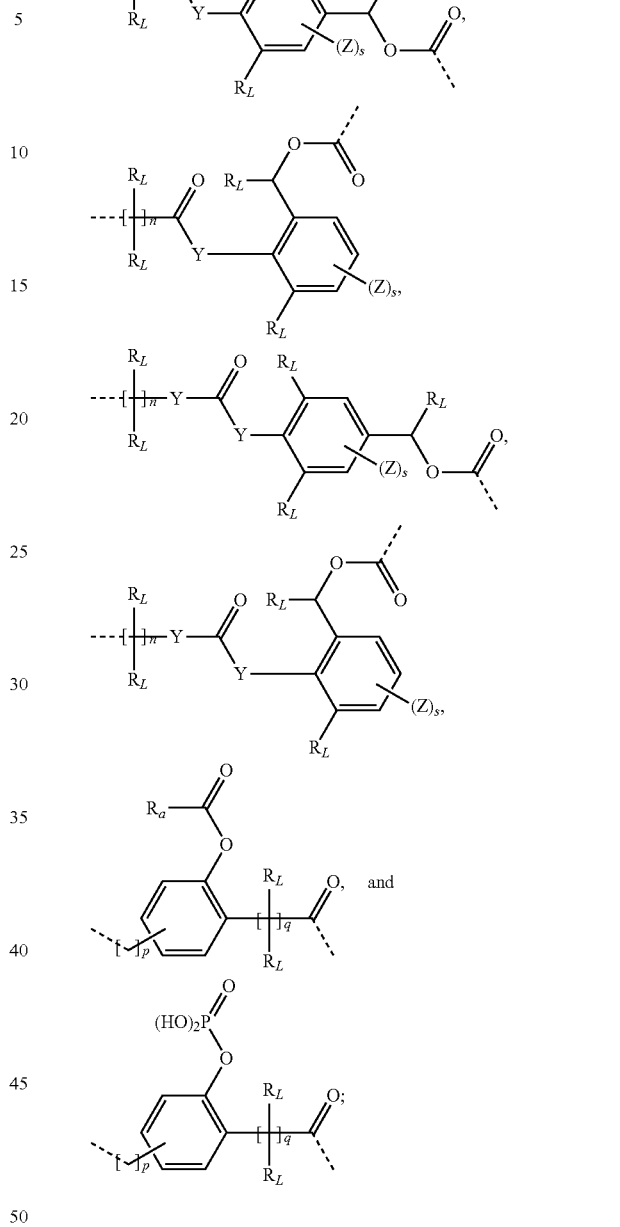

wherein:
n is an integer ≤10;
each p is independently 0 or an integer ≤10;
each $R_L$ is independently selected from the group consisting of H, ethyl and methyl;
q is 2 or 3;
r is 1, 2, 3, 4 or 5;
$w_1$ and $w_2$ are each integers ≥0 such that their sum $(w_1+w_2)$ is 1, 2 or 3;
X is $CH_2$, —$CONR_L$—, —CO—O—$CH_2$—, or —CO—O—;
each Y is independently selected from —O—, —S—, and —$NR_L$—;
each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro;

s is 1, 2, 3 or 4; and $R_a$ is $C_xH_y$, where x is an integer of 0 to 20 and y is an integer of 1 to 2x+1.

In a third aspect of the first embodiment, at least one of the linker $L^c$ couples at least one of the $[[L^a{}_\beta\text{-M}]_\alpha\text{-}L^b{}_\delta]$ to the carbonyl of a carboxylate group on the glycopeptide or lipoglycopeptide A, wherein each of the linker $L^c$ coupling $[[L^a{}_\beta\text{-M}]_\alpha\text{-}L^b{}_\delta]$ to the carbonyl of a carboxylate group is independently selected from the group consisting of: a covalent bond,

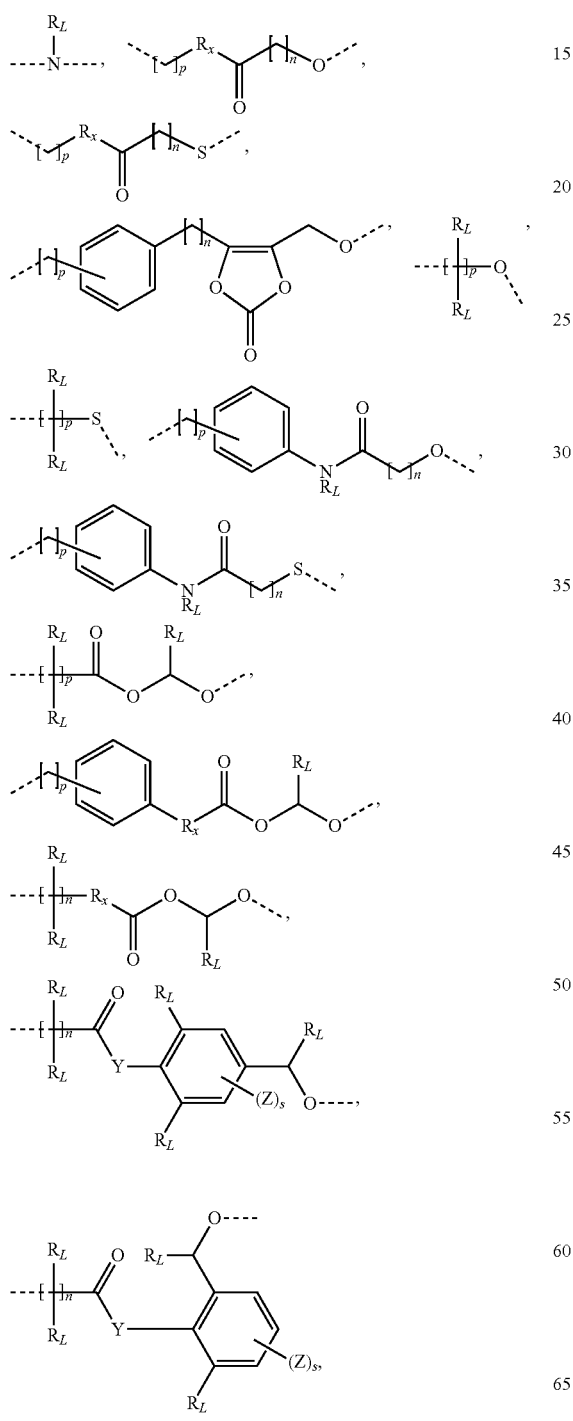
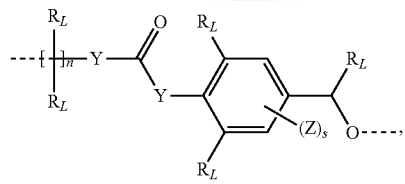
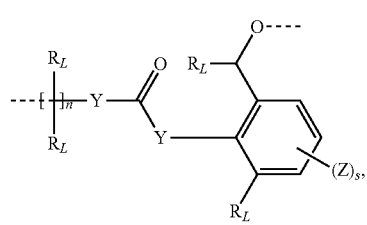
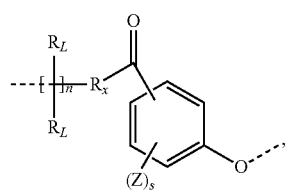
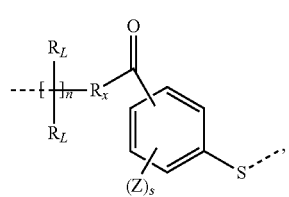
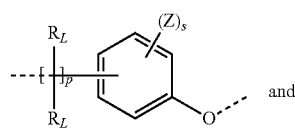
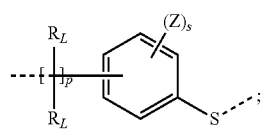

wherein:

n is an integer ≤10;

p is 0 or an integer ≤10;

each $R_L$ is independently selected from the group consisting of H, ethyl and methyl;

$R_x$ is S, $C(R_L)_2$, $NR_L$ or O;

each Y is independently selected from —O—, —S—, and —$NR_L$—;

each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro; and s is 1, 2, 3 or 4.

In the first embodiment, A has a structure represented by the following Formula (A₁):

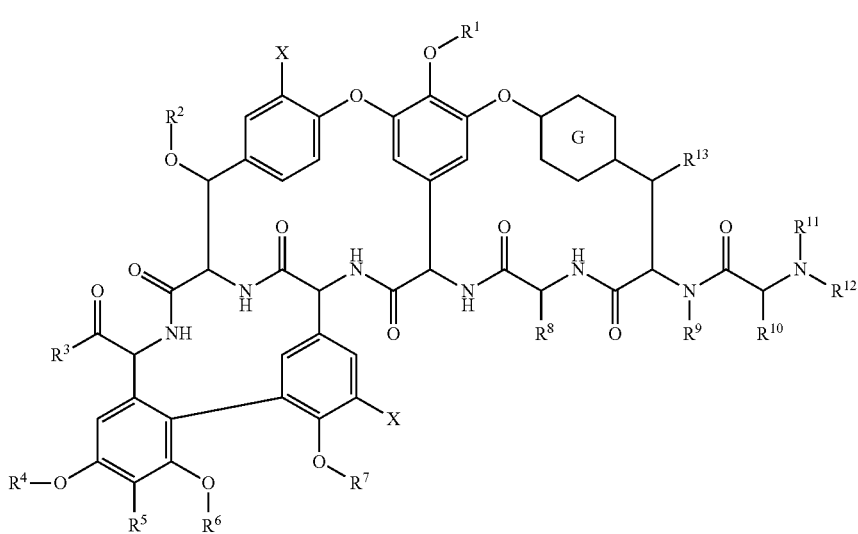

(A₁)

wherein:

$R^1$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$—$(Z)_x$; or $R^1$ is a saccharide group optionally substituted with —$R^a$—Y—$R^b$—$(Z)_x$, $R^f$, —C(O)$R^f$, or —$R^a$—$(R^b)_z$—$(Z)_x$, —C(O)—$R^a$—Y—$R^b$—$(Z)_x$;

$R^2$ is hydrogen or a saccharide group optionally substituted with —$R^a$—Y—$R^b$—$(Z)_x$, $R^f$, —C(O)$R^f$, —$R^a$—$(R^b)_z$—$(Z)_x$ or —C(O)—$R^a$—Y—$R^b$—$(Z)_x$;

$R^3$ is selected from the group consisting of —OR$^c$, —NR$^c$R$^c$, —O—$R^a$—Y—$R^b$—$(Z)_x$, —NR$^c$—$R^a$—Y—$R^b$—$(Z)_x$, —NR$^c$R$^e$, and —O—R$^e$;

$R^4$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)R$^d$ and a saccharide group optionally substituted with —$R^a$—Y—$R^b$—$(Z)_x$, $R^f$, or —C(O)—$R^a$—Y—$R^b$—$(Z)_x$, or $R^4$ and $R^5$ can be joined, together with the atoms to which they are attached, to form a heterocyclic ring optionally substituted with —NR$^c$—$R^a$—Y—$R^b$—$(Z)_x$;

$R^5$ is selected from the group consisting of hydrogen, halo, —CH(R$^c$)—NR$^c$R$^c$, —CH(R$^c$)—NR$^c$R$^e$, —CH(R$^c$)—NR$^c$—$R^a$—Y—$R^b$—$(Z)_x$, —CH(R$^c$)—R$^x$, and —CH(R$^c$)—NR$^c$—$R^a$—C(O)—R$^x$;

$R^6$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)R$^d$ and a saccharide group optionally substituted with —$R^a$—Y—$R^b$—$(Z)_x$, —$R^a$—$(R^b)_z$—$(Z)_x$, $R^f$, —C(O)$R^f$, or —C(O)—$R^a$—Y—$R^b$—$(Z)_x$, or $R^5$ and $R^6$ can be joined, together with the atoms to which they are attached, to form a heterocyclic ring optionally substituted with —NR$^c$—$R^a$—Y—$R^b$—$(Z)_x$;

$R^7$ is selected from the group consisting of hydrogen, alkyl, substituted alkyl, alkenyl, substituted alkenyl, alkynyl, substituted alkynyl, —$R^a$—Y—$R^b$—$(Z)_x$, and —C(O)R$^d$;

$R^8$ is selected from the group consisting of hydrogen, alkyl, substituted alkyl, alkenyl, substituted alkenyl, alkynyl, substituted alkynyl, cycloalkyl, substituted cycloalkyl; cycloalkenyl, substituted cycloalkenyl, aryl, heteroaryl, heterocyclic and —$R^a$—Y—$R^b$—$(Z)_x$;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^{10}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or $R^8$ and $R^{10}$ are joined to form —Ar$^1$—O—Ar$^2$—, where Ar$^1$ and Ar$^2$ are independently arylene or heteroarylene;

$R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or $R^{10}$ and $R^{11}$ are joined, together with the carbon and nitrogen atoms to which they are attached, to form a heterocyclic ring;

$R^{12}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)R$^d$, —C(NH)R$^d$, —C(O)NR$^c$R$^c$, —C(O)OR$^d$, —C(NH)NR$^c$R$^c$, —$R^a$—Y—$R^b$—$(Z)_x$, and —C(O)—$R^b$—Y—$R^b$—$(Z)_x$, or $R^{11}$ and $R^{12}$ are joined, together with the nitrogen atom to which they are attached, to form a heterocyclic ring;

$R^{13}$ is selected from the group consisting of hydrogen and —OR$^{14}$;

$R^{14}$ is selected from the group consisting of hydrogen, —C(O)R$^d$ and a saccharide group;

each $R^a$ is independently selected from the group consisting of alkylene, substituted alkylene, alkenylene, substituted alkenylene, alkynylene and substituted alkynylene;

each $R^b$ is independently selected from the group consisting of a covalent bond, arylene, alkylene, substituted alkylene, alkenylene, substituted alkenylene, alkynylene and substituted alkynylene;

each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

each $R^e$ is a saccharide group;

each $R^f$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, and heterocyclic;

$R^x$ is an N-linked amino saccharide or an N-linked heterocycle;

each X is independently selected from the group consisting of hydrogen, fluoro, chloro, bromo and iodo;

each Y is independently selected from the group consisting of, —CH$_2$—, oxygen, sulfur, —S—S—, —N$R^c$—, —S(O)—, —SO$_2$—, —N$R^c$C(O)—, —OSO$_2$—, —OC(O)—, —N($R^c$)SO$_2$—, —C(O)N$R^c$—, —C(O)O—, —SO$_2$N$R^c$—, —SO$_2$O—, —P(O)(O$R^c$)O—, —P(O)(O$R^c$)N$R^c$—, —OP(O)(O$R^c$)O—, —OP(O)(O$R^c$)N$R^c$—, —OC(O)O—, —N$R^c$C(O)O—, —N$R^c$C(O)N$R^c$—, —OC(O)N$R^c$—, —C(O)—, and —N($R^c$)SO$_2$N$R^c$—;

each Z is independently selected from the group consisting of hydrogen, aryl, cycloalkyl, cycloalkenyl, heteroaryl, heterocyclic, and a saccharide;

x is 1 or 2;

z is 1, 2, 3 or 4; and

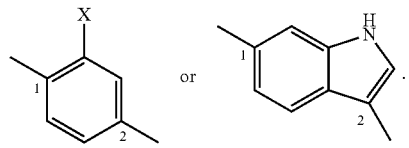

or is selected from

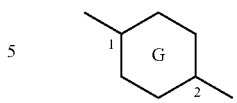

In particular aspects of the first embodiment, A is vancomycin or a derivative thereof, teicoplanin or a derivative thereof, oritavancin or a derivative thereof, dalbavancin or a derivative thereof, or telavancin or a derivative thereof.

In other aspects of the first embodiment, A is selected from the group consisting of compound A35512 A, compound A35512 C, compound A35512 E, compound A35512 F, compound A35512 G, compound A35512 H, compound A40926 A, compound A40926 B, compound A40926 PB, parvodicin B2, parvodicin C1, parvodicin C3, compound A41030, compound A42867, compound A477, compound A47934, compound A51568A, N-demethylvancomycin, compound A80407, compound A83850, compound A84575, compound AB65, compound AM374, actaplanin, compound A4696, actinoidin, ardacin, aricidin, compound AAD216, avoparcin, compound LL-AV290, azureomycin, balhimycin, balhimycin V, chloroorienticin, compound A82846B, compound LY264826, chloroeremomycin, chloropeptin, chloropolysporin, complestatin, decaplanin, dechlorobalhimycin, dechlorobalhimycin V, chlorobalhimycin, chlorobromobalhimycin, fluorobalhimycin, deglucobalhimycin, N-demethylbalhimycin, N-demethylvancomycin, devancosamine-vancomycin, eremomycin, galacardin, helvecardin, izupeptin, kibdelin, kistamicin, mannopeptin, methylbalhimycin, compound MM47761, compound MM47766, compound MM47767, compound MM49721, compound MM49727, compound MM55256, compound MM55260, compound MM55266, compound MM55268, compound MM55270, compound MM55272, compound MM56597, compound MM56598, nogabecin F, compound OA7653, orienticin, dechloroeremomycin, compound PA42867, compound PA45052, chloroorienticin, parvodicin, rhamnosyl-balhimycin, ristocetin, ristomycin, spontin, symnonicin, teichomycin, Targocid, ureido-balhimycin and [Ψ[CH$_2$NH]Tpg$^4$]Vancomycin.

Examples of antimicrobial compounds of the first embodiment include the following:

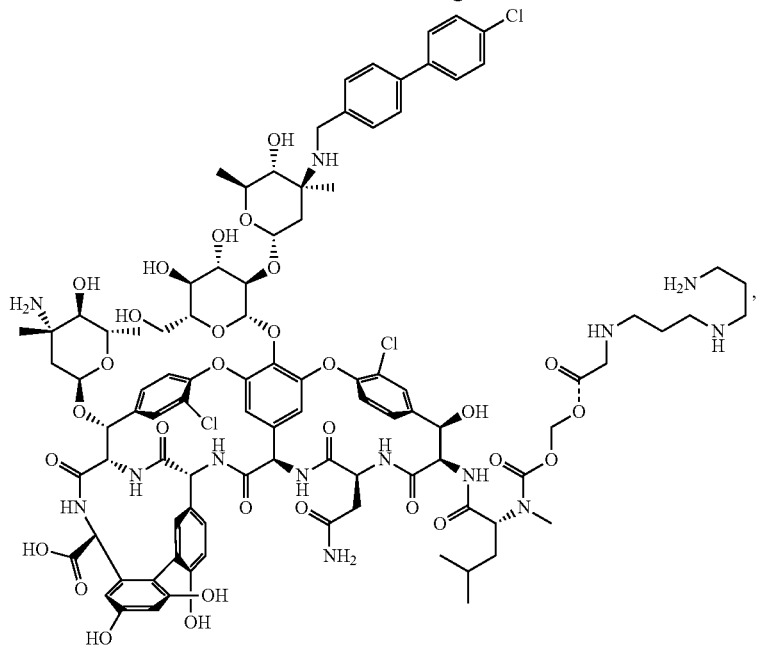

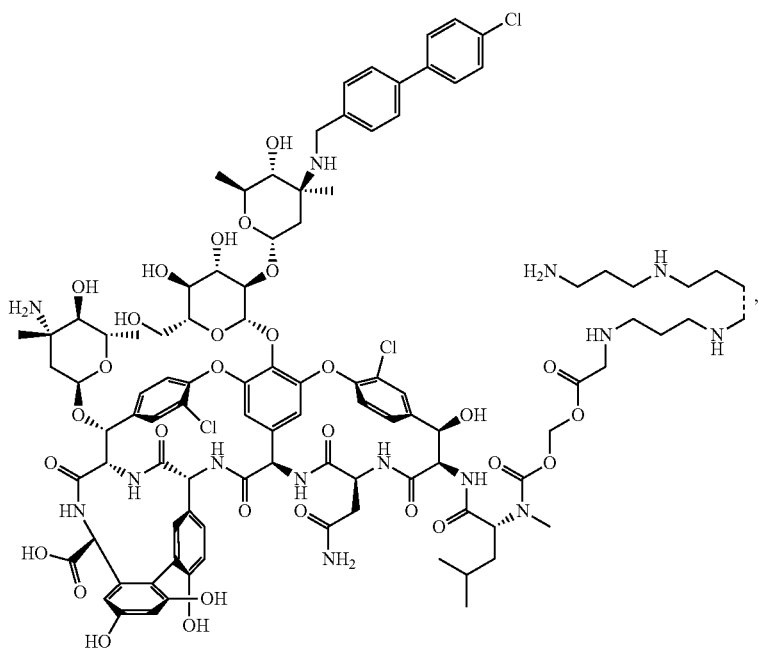
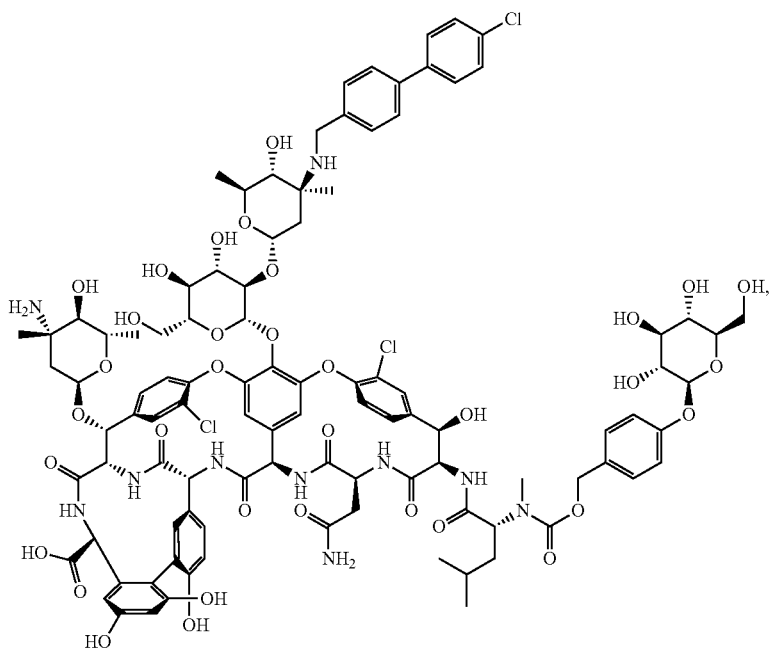

-continued
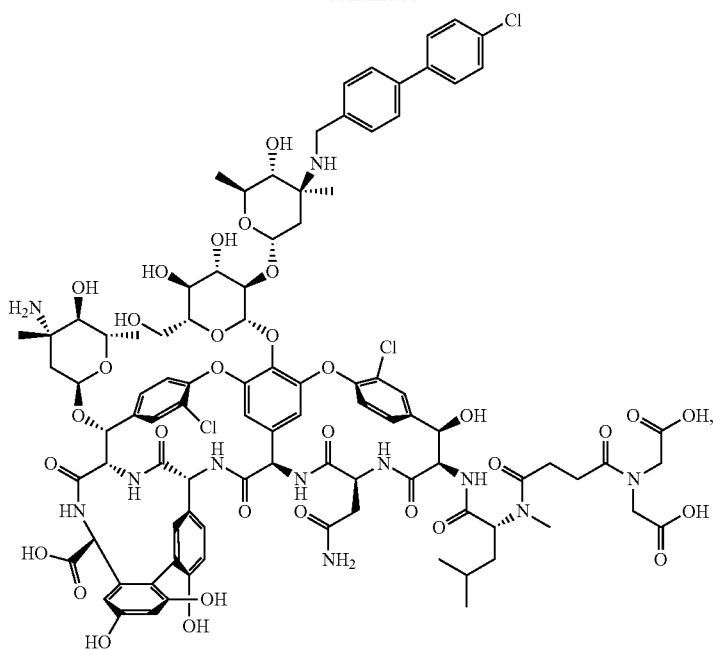
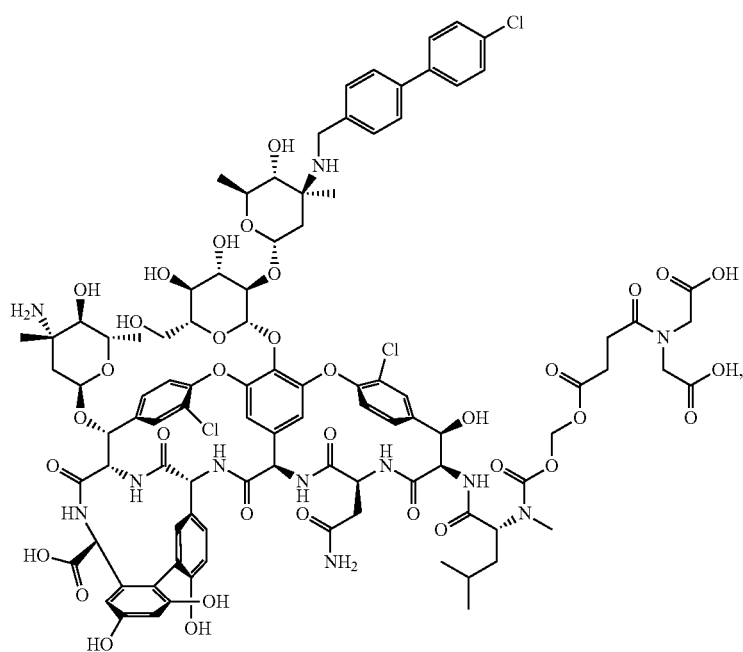

-continued
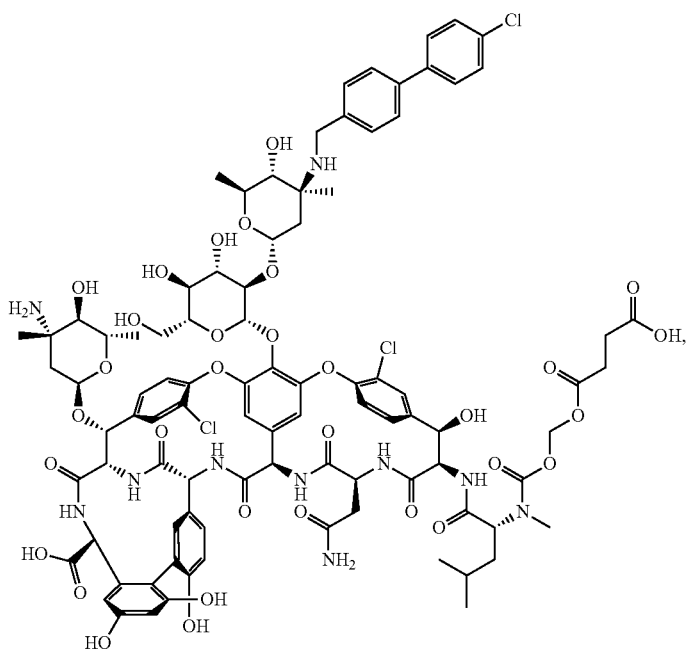
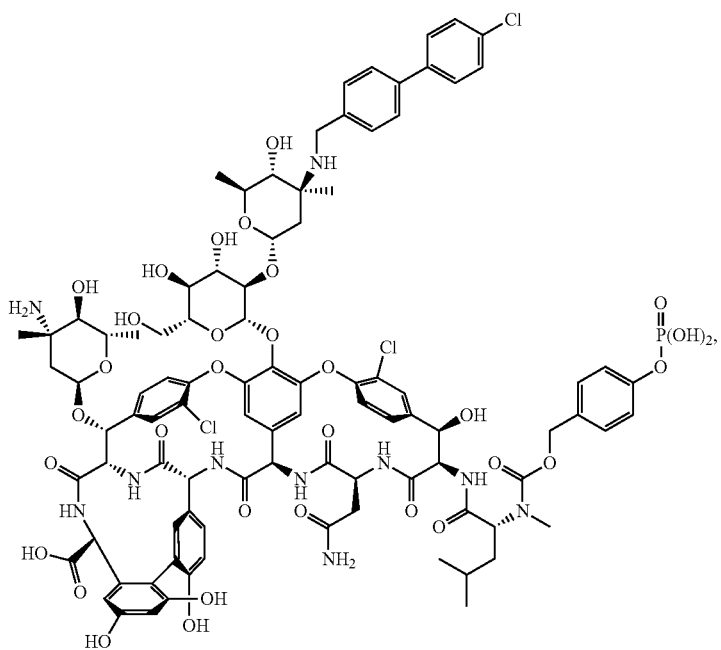

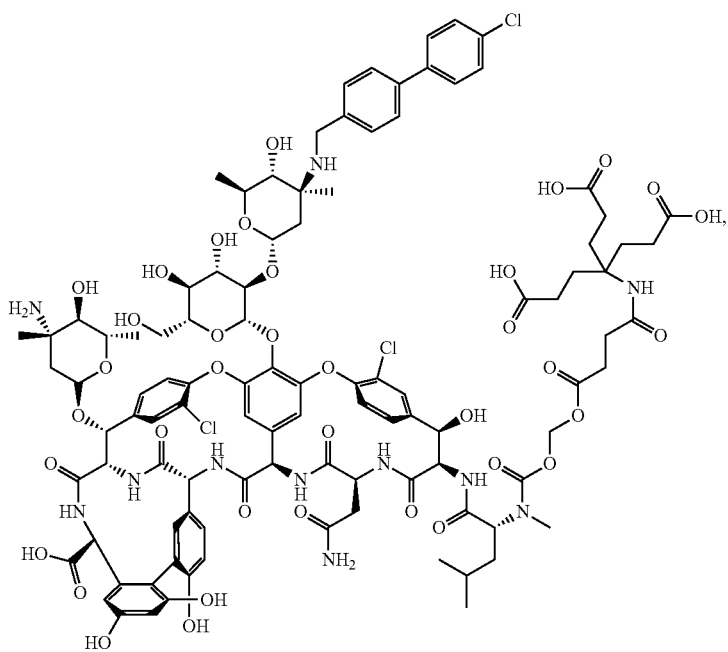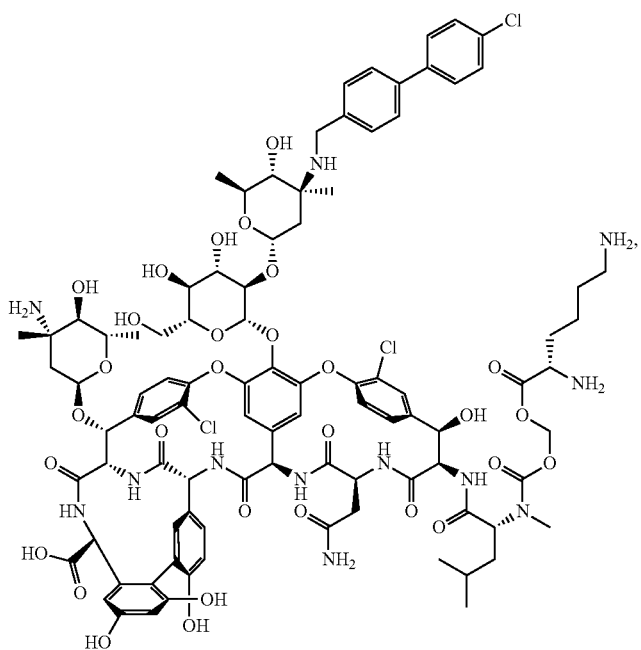

-continued
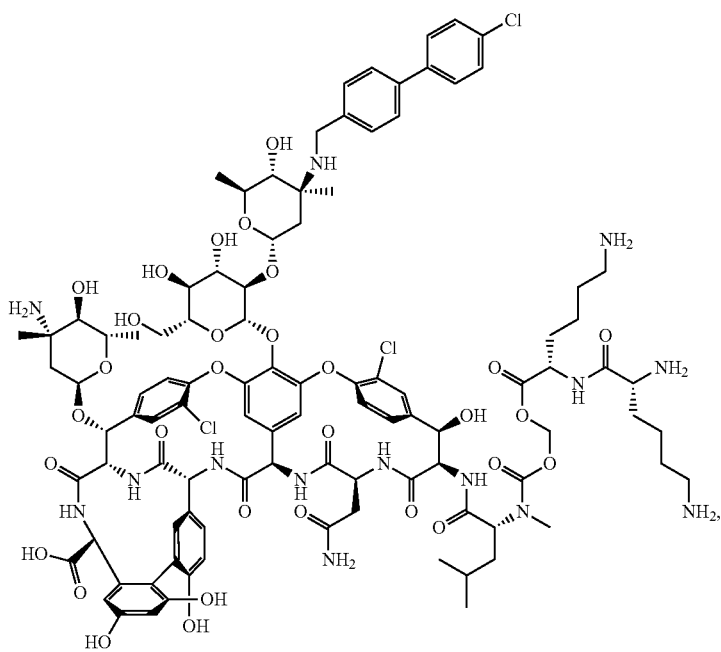
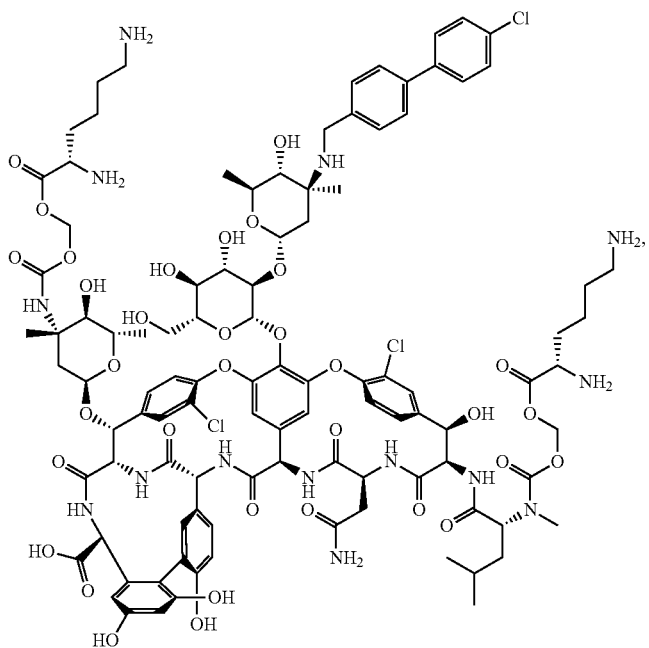

-continued
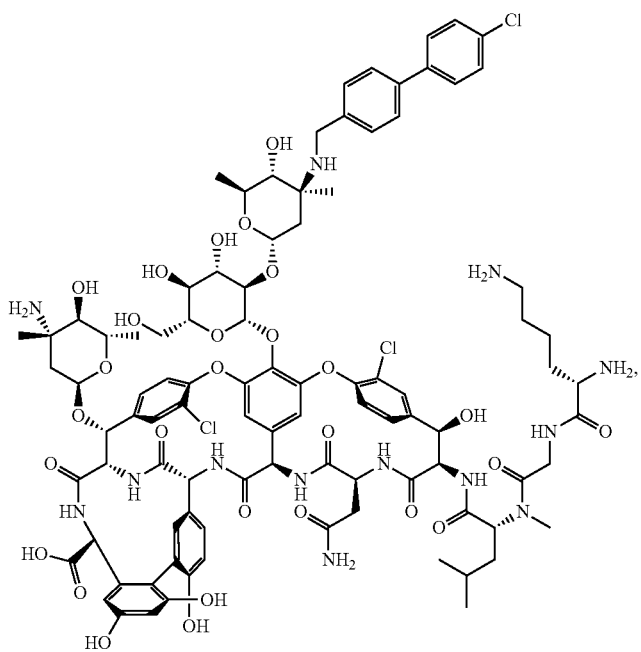
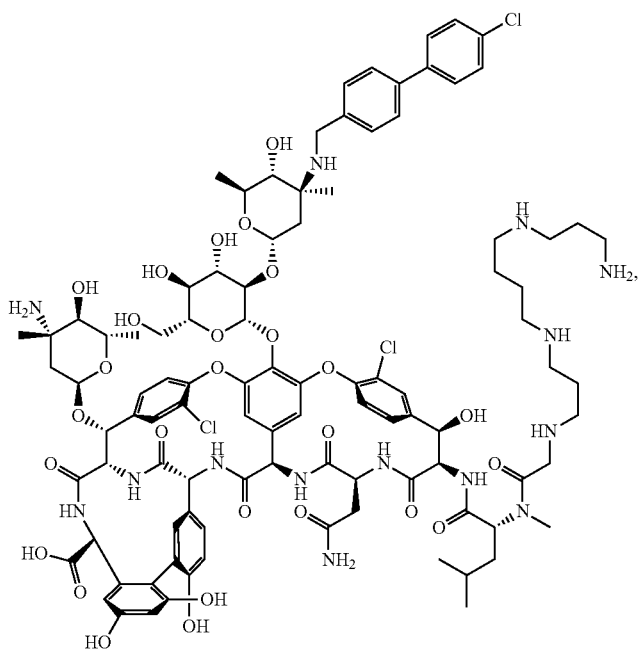

-continued
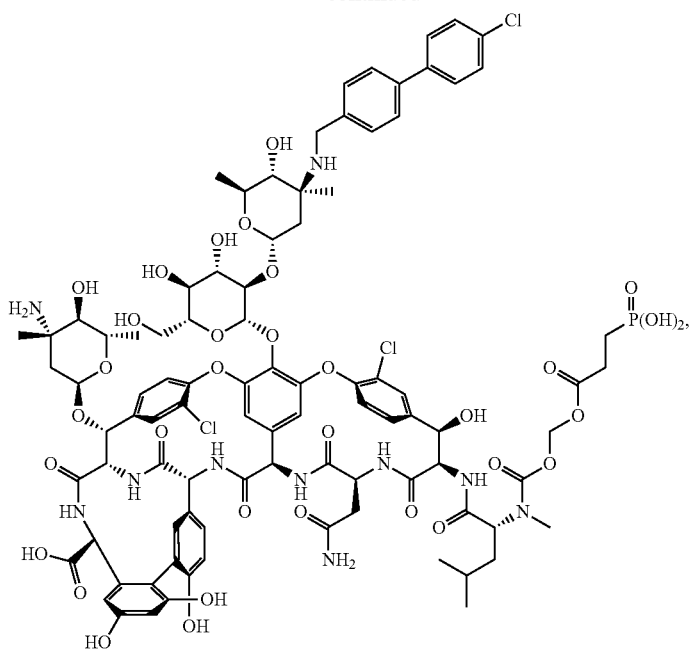
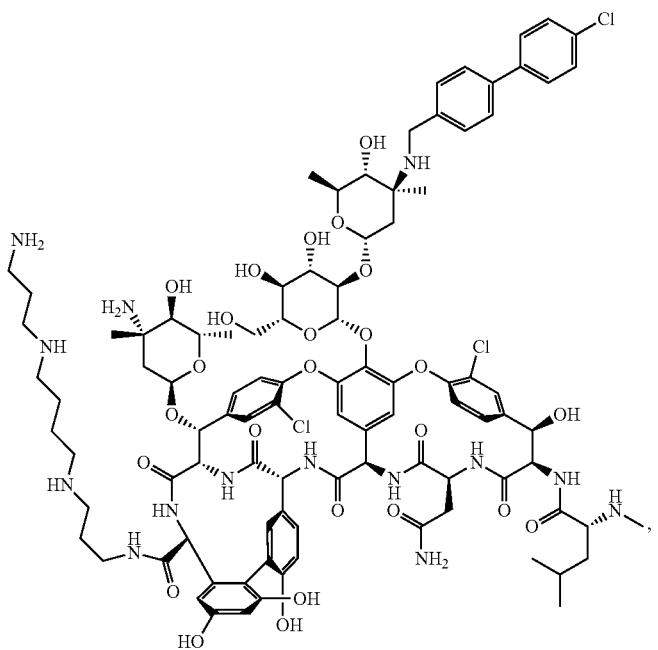

-continued
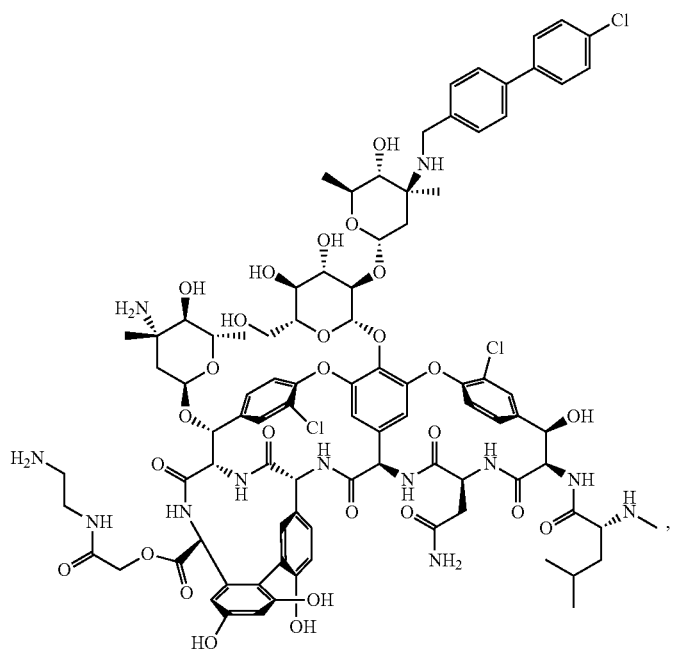
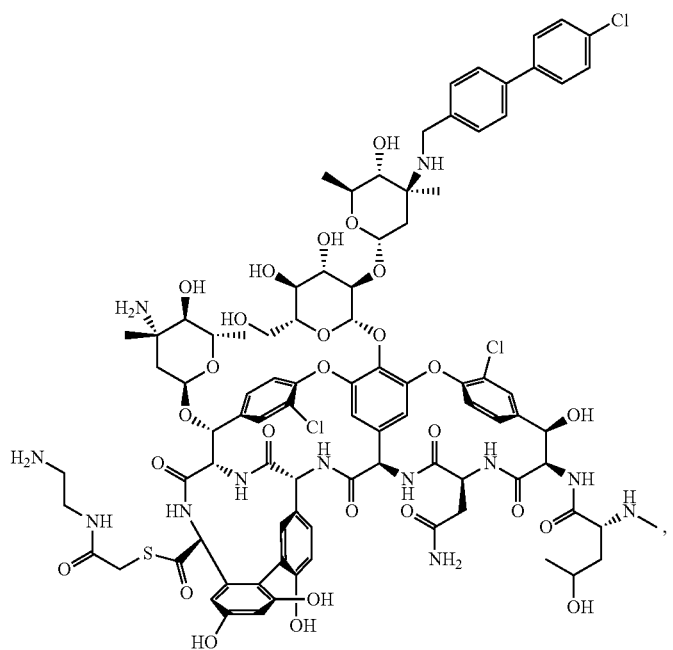

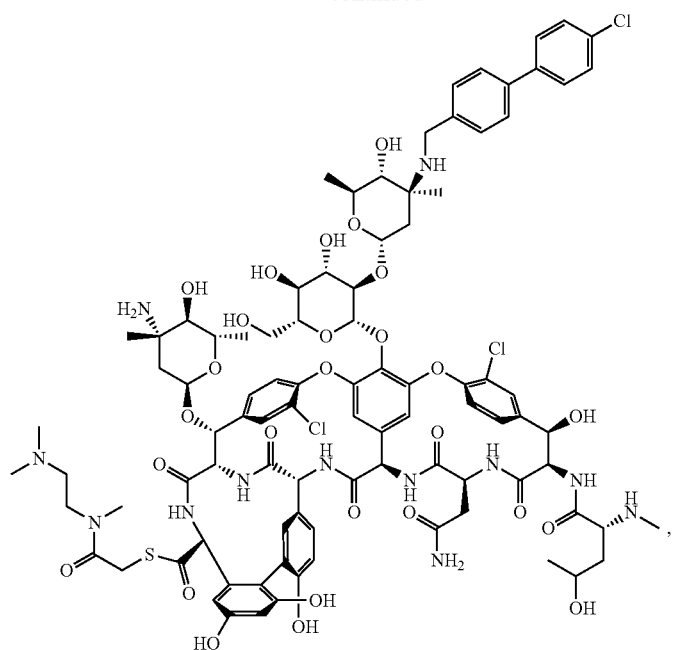
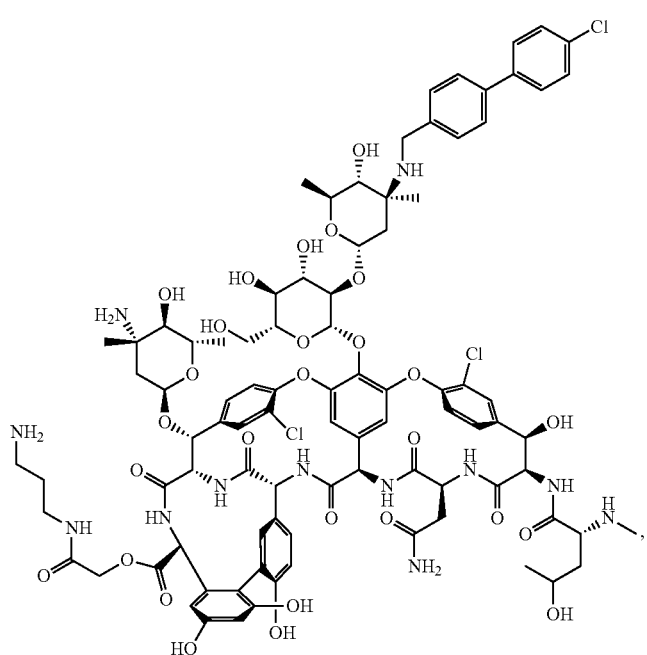

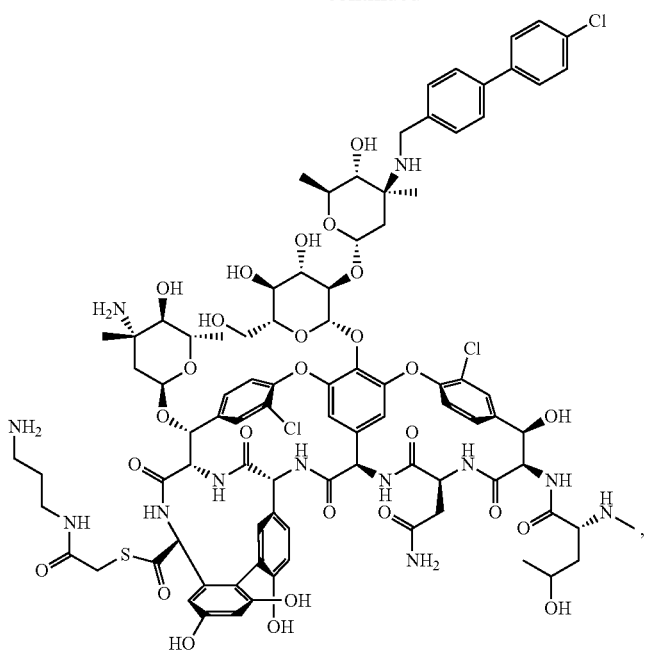
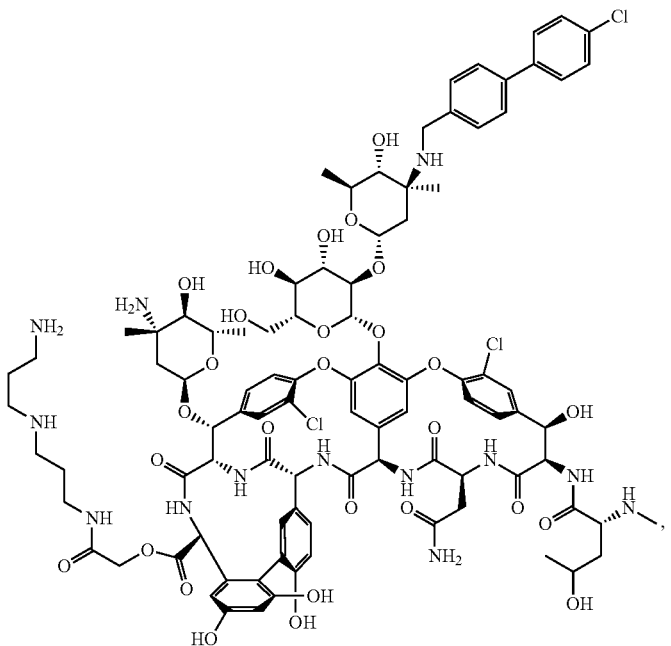

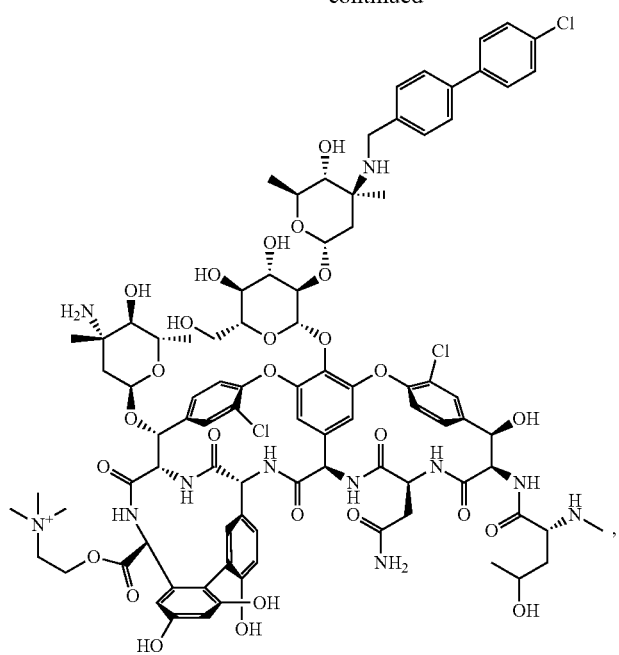
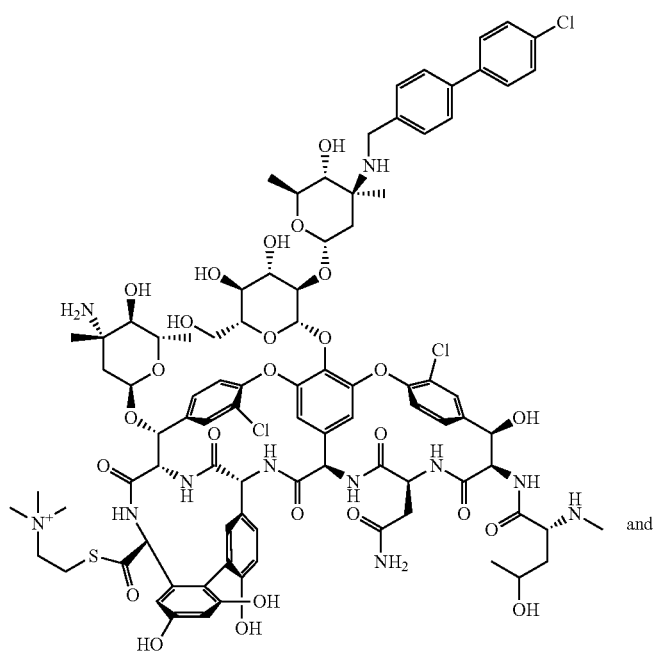

-continued

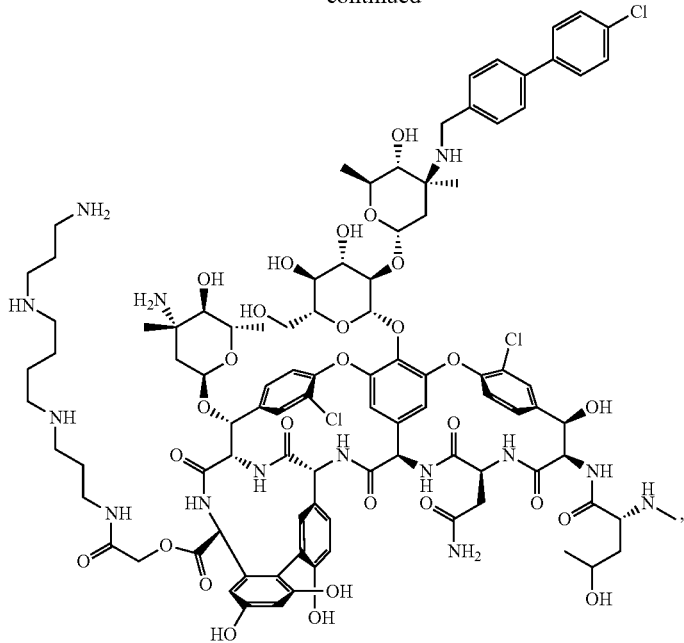

and pharmaceutically acceptable salts, esters, stereoisomers and prodrugs thereof.

In a further aspect of the first embodiment of the invention, the compounds of the invention include compounds represented by Formula (II):

(II)

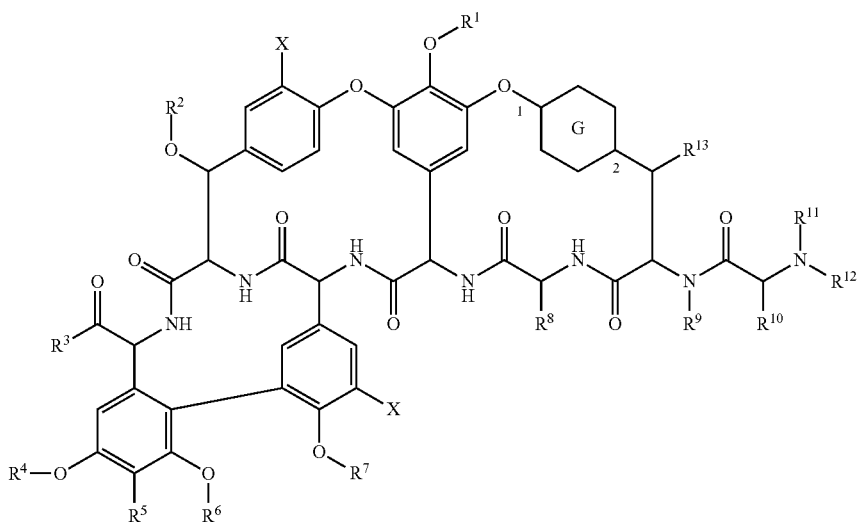

and pharmaceutically acceptable salts, esters, stereoisomers and prodrugs thereof, wherein:

$R^1$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, $-R^a-Y-R^b-(Z)_x$ and $-L^{c1}$; or $R^1$ is a saccharide group optionally substituted with $-R^a-Y-R^b-(Z)_x$, $R^f$, $-C(O)R^f$, $-C(O)-R^a-Y-R^b-(Z)_x$, $-C(NL^{c2})R^f$, $-R^a-(R^b)_z-(Z)_x$ or $-C(NL^{c3})-R^a-Y-R^b-(Z)_x$;

$R^2$ is hydrogen, $-L^{c4}$ or a saccharide group optionally substituted with $-R^a-Y-R^b-(Z)_x$, $R^f$, $-C(O)R^f$, $-C(O)-R^a-Y-R^b-(Z)_x$, $-C(NL^{c5})R^f$, $-R^a-(R^b)_z-(Z)_x$ or $-C(NL^{c6})-R^a-Y-R^b-(Z)_x$;

$R^3$ is selected from the group consisting of $-OR^c$, $-NR^cR^c$, $-SR^c$, $-O-R^a-Y-R^b-(Z)_x$, $-NR^c-R^a-Y-R^b-(Z)_x$, $-NR^cR^e$, $-O-R^e$, $-L^{c7}$, $-NL^{c8}R^c$, and $-NL^{c9}R^e$;

$R^4$ is selected from the group consisting of hydrogen, alkyl, substituted alkyl, alkenyl, substituted alkenyl, alkynyl, substituted alkynyl, $-L^{c10}$, $-R^a-Y-R^b-(Z)_x$, $-C(O)R^d$, $-C(NL^{c11})R^d$ and a saccharide group optionally substituted with $-R^a-Y-R^b-(Z)_x$, $R^f$, $-C(O)-R^a-Y-R^b-(Z)_x$, or $-C(NL^{c12})-R^a-Y-R^b-(Z)_x$, or $R^4$ and $R^5$ can be joined, together with the atoms to which they are attached, to form a heterocyclic ring optionally substituted with $-NR^c-R^a-Y-R^b-(Z)_x$ or $-NL^{c13}-R^a-Y-R^b-(Z)_x$;

$R^5$ is selected from the group consisting of hydrogen, halo, $-CH(R^c)-NR^cR^c$, $-CH(R^c)-NR^cR^e$, $-CH(R^c)-NR^c-R^a-Y-R^b-(Z)_x$, $-CH(R^c)-R^x$, $-CH(R^c)-NR^c-R^a-C(O)-R^x$; $-CH(R^c)-NL^{c14}R^c$, $-CH(R^c)-$ $NL^{c15}R^e$, —CH($R^c$)—$NL^{c16}$-$R^a$—Y—$R^b$—$(Z)_x$, —CH($R^c$)—$NL^{c17}$-$R^a$—C(O)—$R^x$ and —CH($R^c$)—$NR^c$—$R^a$—C($NL^{c18}$)-$R^x$;

$R^6$ is selected from the group consisting of hydrogen, alkyl, substituted alkyl, alkenyl, substituted alkenyl, alkynyl, substituted alkynyl, -$L^{c19}$, —$R^a$—Y—$R^b$—$(Z)_x$, —C(O)$R^d$, —C($NL^{c20}$)$R^d$ and a saccharide group optionally substituted with —$R^a$—Y—$R^b$—$(Z)_x$, —$R^a$—$(R^b)_z$—$(Z)_x$, $R^f$, —C(O)$R^f$, —C(O)—$R^a$—Y—$R^b$—$(Z)_x$, —C($NL^{c21}$)$R^f$, or —C($NL^{c22}$)-$R^a$—Y—$R^b$—$(Z)_x$, or $R^5$ and $R^6$ can be joined, together with the atoms to which they are attached, to form a heterocyclic ring optionally substituted with —$NR^c$—$R^a$—Y—$R^b$—$(Z)_x$ or —$NL^{c23}$-$R^a$—Y—$R^b$—$(Z)_x$;

$R^7$ is selected from the group consisting of hydrogen, alkyl, substituted alkyl, alkenyl, substituted alkenyl, alkynyl, substituted alkynyl, -$L^{c24}$, —$R^a$—Y—$R^b$—$(Z)_x$, —C(O)$R^d$, and —C($NL^{c25}$)$R^d$;

$R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$—$(Z)_x$;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, and -$L^{c26}$;

$R^{10}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or $R^8$ and $R^{10}$ are joined to form —$Ar^1$—O—$Ar^2$—, where $Ar^1$ and $Ar^2$ are independently arylene or heteroarylene which may optionally be substituted with —$OL^{c27}$;

$R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and -$L^{c28}$, or $R^{10}$ and $R^{11}$ are joined, together with the carbon and nitrogen atoms to which they are attached, to form a heterocyclic ring which may optionally be substituted with —$OL^{c29}$, —C(O)-$L^{c30}$ or —$NL^{c31}R^c$;

$R^{12}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, -$L^{c32}$, —C(O)$R^d$, —C(NH)$R^d$, —C(O)$NR^cR^c$, —C(O)O$R^d$, —C(NH)$NR^cR^c$, —$R^a$—Y—$R^b$—$(Z)_x$, —C(O)—$R^b$—Y—$R^b$—$(Z)_x$, —C($NL^{c33}$)$R^d$, —C(O)$NL^{c34}R^c$, —C(O)-$L^{c35}$, —C(NH)$NL^{c36}R^c$, —C($NL^{c37}$)$NR^cR^c$ and —C($NL^{c38}$)-$R^b$—Y—$R^b$—$(Z)_x$, or $R^{11}$ and $R^{12}$ are joined, together with the nitrogen atom to which they are attached, to form a heterocyclic ring which may optionally be substituted with —$OL^{c39}$, —C(O)-$L^{c40}$ or —$NL^{c41}R^c$;

$R^{13}$ is selected from the group consisting of hydrogen and —$OR^{14}$;

$R^{14}$ is selected from the group consisting of hydrogen, -$L^{c42}$, —C(O)$R^d$, —C($NL^{c43}$)$R^d$ and a saccharide group optionally substituted with —$R^a$—Y—$R^b$—$(Z)_x$, $R^f$, —C(O)$R^f$, —C(O)—$R^a$—Y—$R^b$—$(Z)_x$, —C($NL^{c44}$)$R^f$, or —C($NL^{c45}$)-$R^a$—Y—$R^b$—$(Z)_x$;

each $R^a$ is independently selected from the group consisting of alkylene, substituted alkylene, alkenylene, substituted alkenylene, alkynylene and substituted alkynylene;

each $R^b$ is independently selected from the group consisting of a covalent bond, alkylene, substituted alkylene, alkenylene, substituted alkenylene, alkynylene and substituted alkynylene;

each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

each $R^e$ is a saccharide group optionally substituted with —$R^a$—Y—$R^b$—$(Z)_x$, $R^f$, —C(O)$R^f$, —C(O)—$R^a$—Y—$R^b$—$(Z)_x$, —C($NL^{c46}$)$R^f$, or —C($NL^{c47}$)-$R^a$—Y—$R^b$—$(Z)_x$;

each $R^f$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, and heterocyclic;

$R^x$ is an N-linked amino saccharide or an N-linked heterocycle both of which may be optionally substituted with —$R^a$—Y—$R^b$—$(Z)_x$, $R^f$, —C(O)$R^f$, —C(O)—$R^a$—Y—$R^b$—$(Z)_x$, —C($NL^{c48}$)$R^f$, or —C($NL^{c49}$)-$R^a$—Y—$R^b$—$(Z)_x$;

each X is independently selected from the group consisting of hydrogen, fluoro, chloro, bromo and iodo;

each Y is independently selected from the group consisting of —$CH_2$—, oxygen, sulfur, —S—S—, —$NR^c$—, —S(O)—, —$SO_2$—, —$NR^cC(O)$—, —$OSO_2$—, —CO(O)—, —N($R^c$)$SO_2$—, —C(O)$NR^c$—, —C(O)O—, —$SO_2NR^c$—, —$SO_2O$—, —P(O)(O$R^c$)O—, —P(O)(O$R^c$)$NR^c$—, —OP(O)(O$R^c$)O—, —OP(O)(O$R^c$)$NR^c$—, —OC(O)O—, —$NR^cC(O)O$—, —$NR^cC(O)NR^c$—, —OC(O)$NR^c$, —C(O)—, —N($R^c$)$SO_2NR^c$—, —$NL^{c50}$-, —$NL^{c51}$C(O)-, —$OSO_2$—, —OC(O)—, —N($L^{c52}$)$SO_2$—, —C(O)$NL^{c53}$-, —$SO_2NL^{c54}$-, —P(O)($L^{c55}$)O—, —P(O)($L^{c56}$)$NR^c$—, —P(O)(O$R^c$)$NL^{c57}$-, —OP(O)($L^{c58}$)O—, —OP(O)($L^{c55}$)$NR^c$—, —OP(O)(O$R^c$)$NL^{c60}$-, —$NL^{c61}$C(O)O—, —$NL^{c62}$C(O)$NR^c$—, —$NR^cC(O)NL^{c63}$-, —OC(O)$NL^{c64}$-, —N($L^{c65}$)$SO_2NR^c$— and —N($R^c$)$SO_2NL^{c66}$-;

each Z is independently selected from the group consisting of hydrogen, aryl, cycloalkyl, cycloalkenyl, heteroaryl, heterocyclic, a saccharide, -$L^{c67}$, -$L^{c68}$ and -$L^{c69}$;

x is 1 or 2;

z is 1, 2, 3 or 4; and

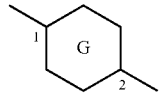

is selected from

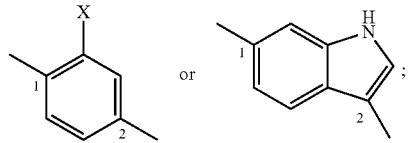

each $L^{c1}$, $L^{c4}$, $L^{c10}$, $L^{c19}$, $L^{c24}$, $L^{c27}$, $L^{c29}$, $L^{c39}$, $L^{c42}$, and $L^{c67}$ is a linker independently selected from the group of consisting of the following linkers:

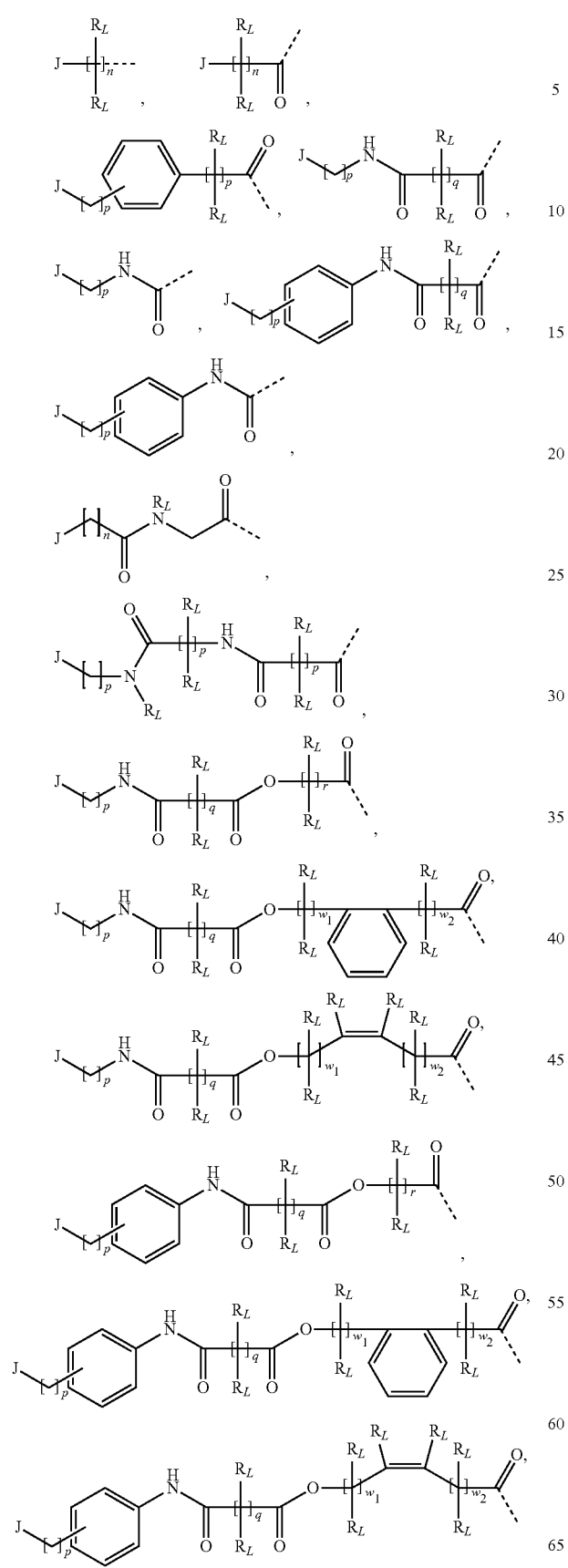
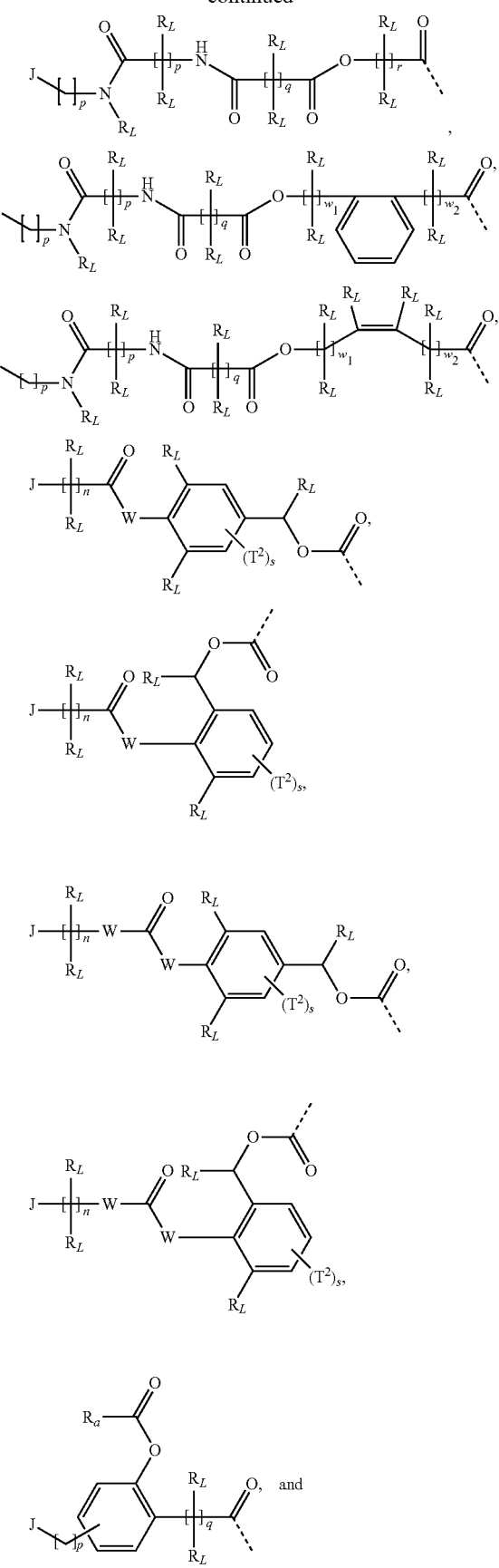

51
-continued
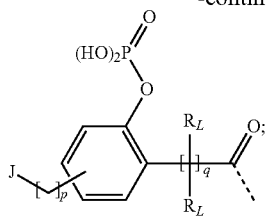
each $L^{c8}$, $L^{c9}$, $L^{c13}$, $L^{c14}$, $L^{c15}$, $L^{c16}$, $L^{c17}$, $L^{c23}$, $L^{c26}$, $L^{c28}$, $L^{c31}$, $L^{c32}$, $L^{c34}$, $L^{c36}$, $L^{c37}$, $L^{c41}$, $L^{c50}$, $L^{c51}$, $L^{c52}$, $L^{c53}$, $L^{c54}$, $L^{c57}$, $L^{c60}$, $L^{c61}$, $L^{c62}$, $L^{c63}$, $L^{c64}$, $L^{c65}$, $L^{c66}$ and $L^{c68}$ is a linker independently selected from the group of consisting of the following linkers:
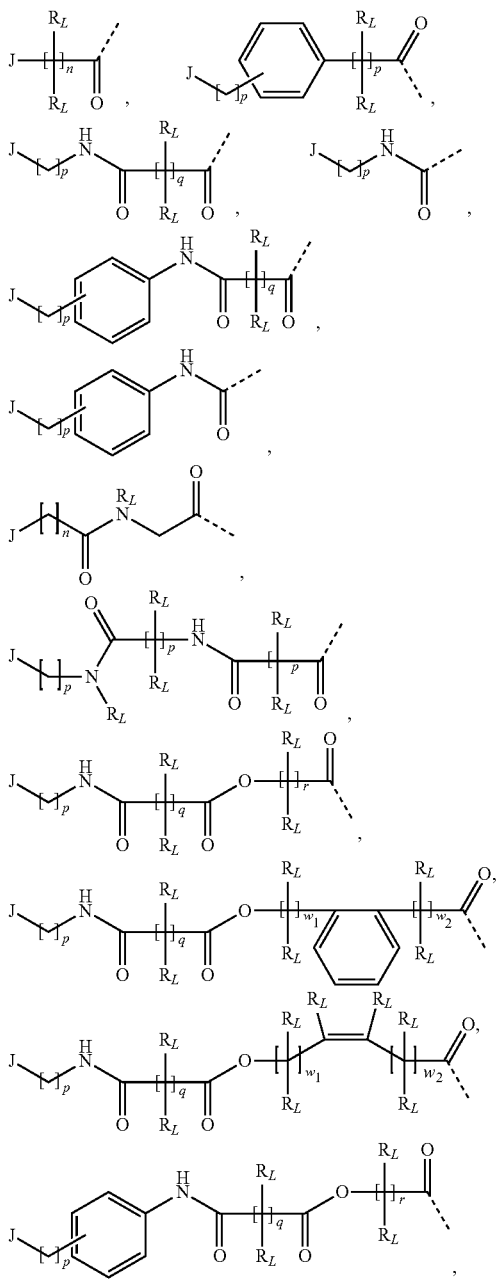
52
-continued
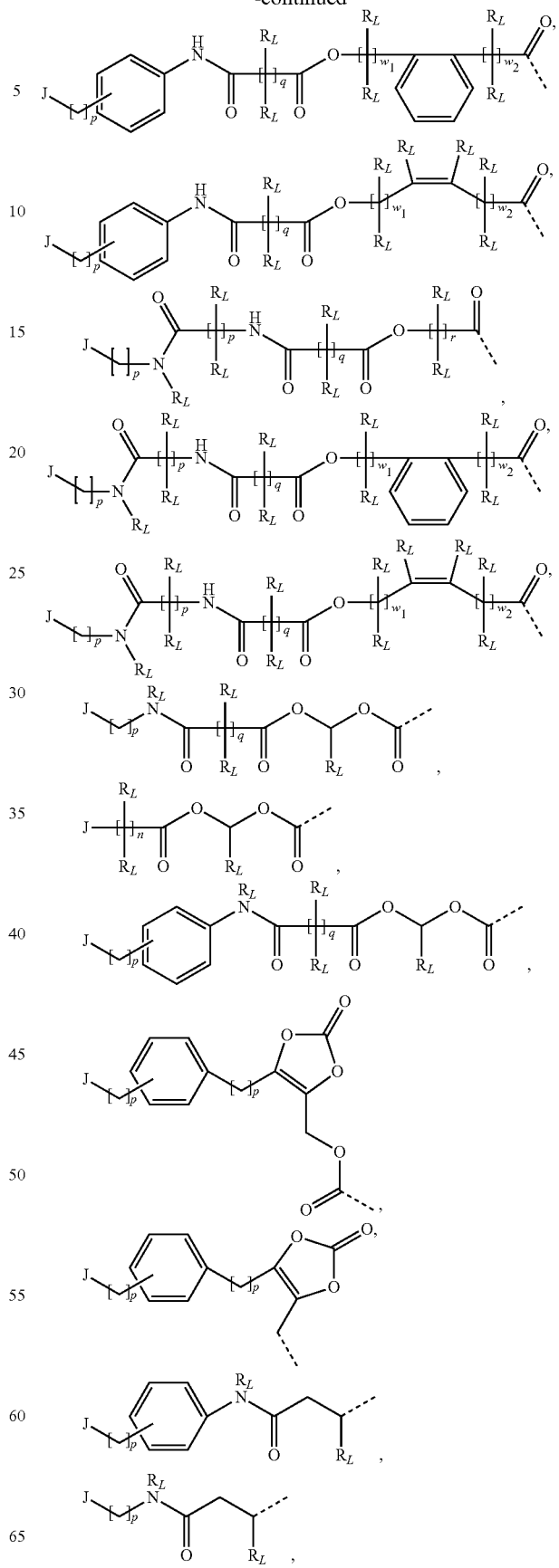

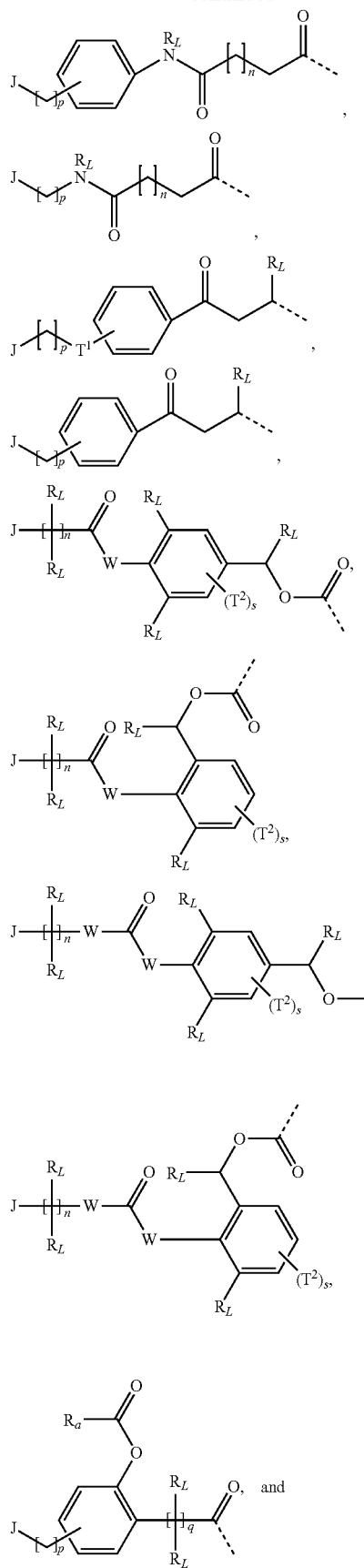
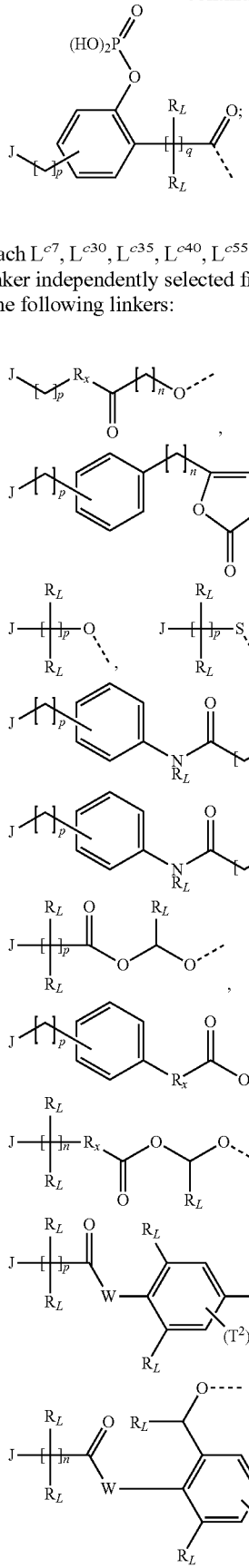
each $L^{c7}$, $L^{c30}$, $L^{c35}$, $L^{c40}$, $L^{c55}$, $L^{c56}$, $L^{c58}$, $L^{c59}$ and $L^{c69}$ is a linker independently selected from the group of consisting of the following linkers:

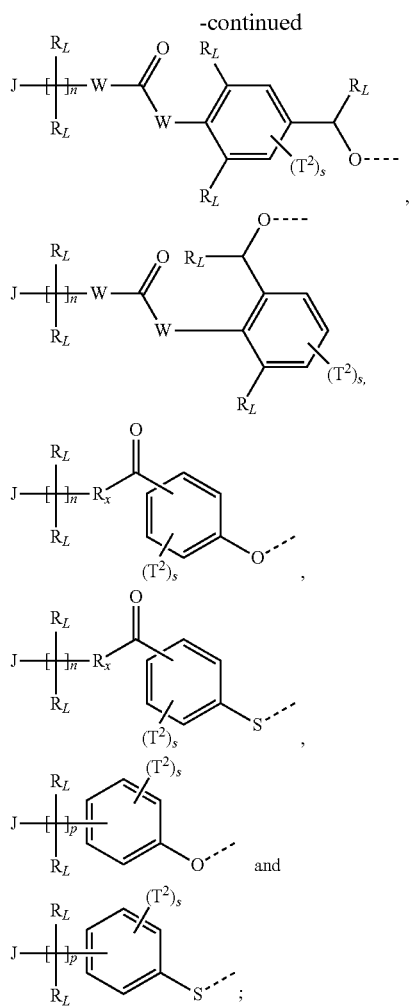

each $L^{c2}$, $L^{c3}$, $L^{c5}$, $L^{c6}$, $L^{c11}$, $L^{c12}$, $L^{c18}$, $L^{c20}$, $L^{c21}$, $L^{c22}$, $L^{c25}$, $L^{c33}$, $L^{c38}$, $L^{c43}$, $L^{c44}$, $L^{c45}$, $L^{c46}$, $L^{c47}$, $L^{c48}$, and $L^{c49}$ is a linker independently selected from the group of consisting of

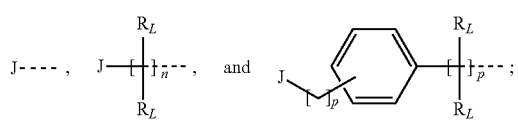

wherein:
n is an integer ≤10;
each p is independently 0 or an integer ≤10;
each $R_L$ is independently selected from the group consisting of H, ethyl and methyl;
q is 2 or 3;
r is 1, 2, 3, 4 or 5;
$w_1$ and $w_2$ are each integers ≥0 such that their sum ($w_1+w_2$) is 1, 2 or 3;
each W is independently selected from —O—, —S—, and —$NR_L$—;
$T^1$ is $CH_2$, —$CONR_L$—, —CO—O—$CH_2$—, or —CO—O—;
each $T^2$ is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro;

s is 1, 2, 3 or 4;
$R_a$ is $C_xH_y$ where x is an integer of 0 to 20 and y is an integer of 1 to 2x+1;
$R_x$ is selected from the group consisting of a covalent bond, S, $NR_L$ and O; and
J is $[[L^a_\beta\text{-}M]_\alpha\text{-}L^b_\delta]$;
wherein:
each M is individually selected from the group of:

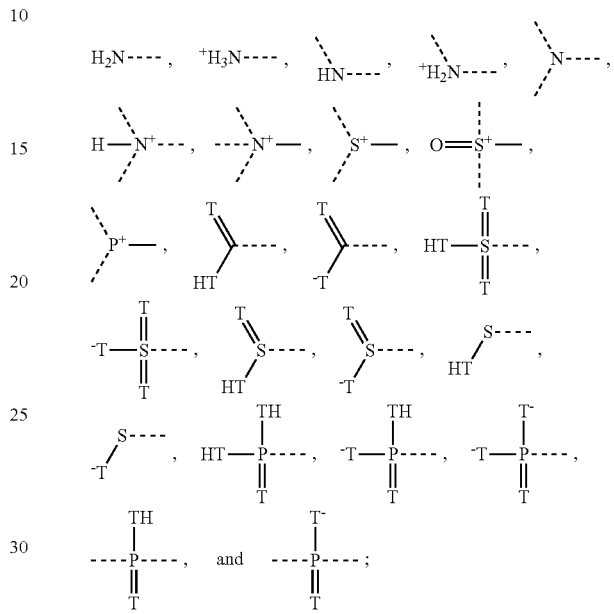

wherein:
each T is O or S; and
the dashed bonds - - - indicate the points of attachment to $L^a$, $L^b$, or the linker;
each $L^a$ is individually selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and

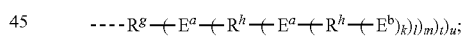

each $L^b$ is individually selected from the group consisting of a covalent bond, alkylene, substituted alkylene, alkenylene, substituted alkenylene, alkynylene, substituted alkynylene, cycloalkylene, substituted cycloalkylene, cycloalkenylene, substituted cycloalkenylene, arylene, heteroarylene and

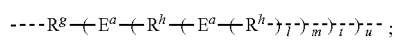

wherein:
each $R^g$ is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, —(CO)-(substituted alkenylene)-, —(CO)-alkynylene-, —(CO)-(substituted alkynylene)-, —(CO)-arylene- and —(CO)-(substituted arylene)- each $R^h$ is independently selected from the group consisting of a covalent bond, alkylene, substituted alkylene, alkenylene, substituted alkenylene, alkynylene, substituted alkynylene, arylene and substituted arylene;

each $E^a$ is independently selected from the group consisting of a covalent bond, methylene, oxygen, sulfur,

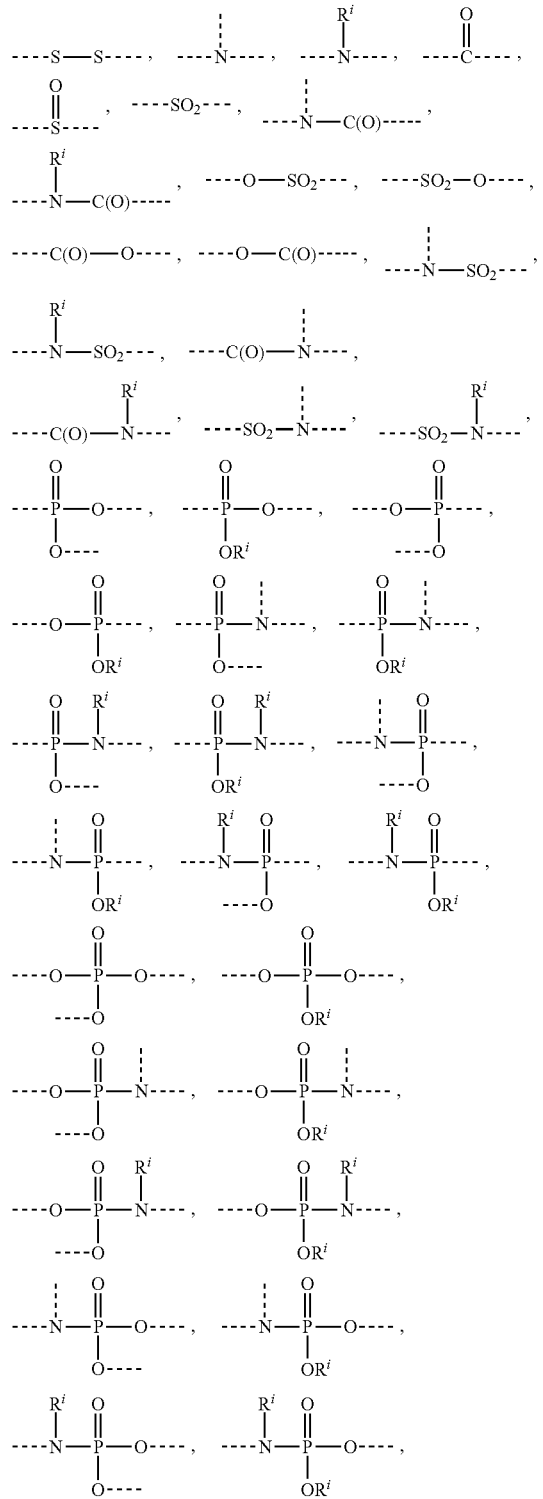

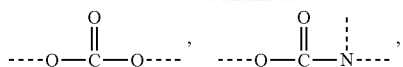

each $R^i$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^j$;

each $R^j$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

each $E^b$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, and substituted aryloxy;

each k, l, m, t, u is independently a nonnull integer ≤5;

α is an integer between 1 and 6;

β is an integer ≤3; and

δ is an integer ≤2α;

and with the further proviso that at least one of $L^{c1}$, $L^{c2}$, $L^{c3}$, $L^{c4}$, $L^{c5}$, $L^{c6}$, $L^{c7}$, $L^{c8}$, $L^{c9}$, $L^{c10}$, $L^{c11}$, $L^{c12}$, $L^{c13}$, $L^{c14}$, $L^{c15}$, $L^{c16}$, $L^{c17}$, $L^{c18}$, $L^{c19}$, $L^{c20}$, $L^{c21}$, $L^{c22}$, $L^{c23}$, $L^{c24}$, $L^{c25}$, $L^{c26}$, $L^{c27}$, $L^{c28}$, $L^{c29}$, $L^{c30}$, $L^{c31}$, $L^{c32}$, $L^{c33}$, $L^{c34}$, $L^{c35}$, $L^{c36}$, $L^{c37}$, $L^{c38}$, $L^{c39}$, $L^{c40}$, $L^{c41}$, $L^{c42}$, $L^{c43}$, $L^{c44}$, $L^{c45}$, $L^{c46}$, $L^{c47}$, $L^{c48}$, $L^{c49}$, $L^{c50}$, $L^{c51}$, $L^{c52}$, $L^{c53}$, $L^{c54}$, $L^{c55}$, $L^{c56}$, $L^{c57}$, $L^{c58}$, $L^{c59}$, $L^{c60}$, $L^{c61}$, $L^{c62}$, $L^{c63}$, $L^{c64}$, $L^{c65}$, $L^{c66}$, $L^{c67}$, $L^{c68}$ and $L^{c69}$ is present.

In an additional aspect of the first embodiment of the invention, the compounds of the invention include compounds represented by Formula (III):

(III)

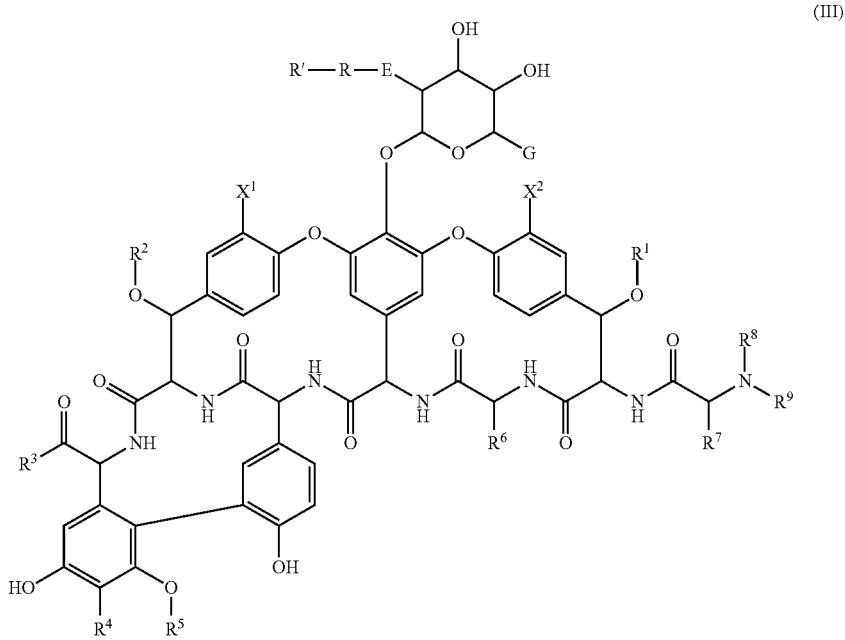

and pharmaceutically acceptable salts, esters, stereoisomers and prodrugs thereof, wherein:

R is selected from the group consisting of —C(O)$R^f$, vancosaminyl, 4-epi-vancosaminyl, L-acosaminyl, L-ristosaminyl, and L-actinosaminyl;

R' is attached to the amino group of R and is selected from the group of —$R^a$—Y—$R^b$—$(Z)_x$, —$R^f$, —C(O)$R^f$, —C(O)—$R^a$—Y—$R^b$—$(Z)_x$, and —$R^a$—$(R^b)_z$—$(Z)_x$ or R' is absent if R is —C(O)$R^f$;

$R^1$ is hydrogen or mannopyranosyl;

$R^2$ is hydrogen or a saccharide group optionally N-substituted with —$R^a$—Y—$R^b$—$(Z)_x$, —$R^f$, —C(O)$R^f$, —C(O)—$R^a$—Y—$R^b$—$(Z)_x$, or —$R^a$—$(R^b)_z$—$(Z)_x$;

$R^3$ is hydroxyl or -$L^c$;

$R^4$ is selected from the group consisting of hydrogen, halo, —CH($R^c$)—$NR^cR^c$ and —CH($R^c$)—$NR^c$—$R^a$—Y—$R^b$—$(Z)_x$;

$R^5$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)$R^d$, and a saccharide group optionally substituted with —$R^a$—Y—$R^b$—$(Z)_x$, —$R^a$—$(R^b)_z$—$(Z)_x$, $R^f$, —C(O)$R^f$, and —C(O)—$R^a$—Y—$R^b$—$(Z)_x$;

$R^6$ is selected from the group consisting of —$CH_2$(CO)$NH_2$, benzyl, 4-hydroxyphenyl, and 3-chloro-4-hydroxyphenyl;

$R^7$ is selected from the group consisting of —$CH_2$CH($CH_3$)$_2$, 3-chloro-4-hydroxyphenyl, 4-rhamnosylphenyl, 4-(rhamnosyl-galactosyl)phenyl, 4-(galactosyl-galactosyl)phenyl, and 4(methoxyrhamnosyl)phenyl; or $R^6$ and $R^7$ are joined to form

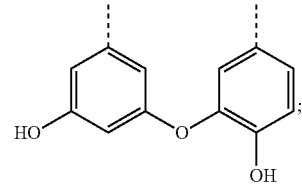

$R^8$ is hydrogen or methyl;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, acyl and substituted acyl;

G is —$CH_2$OH, —$CO_2$H or —C(O)-$L^c$;

E is —O— or —NH—;

$R^a$ is each independently selected from the group consisting of alkylene, substituted alkylene, alkenylene, substituted alkenylene, alkynylene and substituted alkynylene;

$R^b$ is each independently selected from the group consisting of a covalent bond, alkylene, substituted alkylene, alkenylene, substituted alkenylene, alkynylene and substituted alkynylene;

$R^c$ is each independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

$R^d$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^f$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, and heterocyclic;

each $X^1$ and $X^2$ is independently selected from the group consisting of hydrogen, and chloro;

each Y is independently selected from the group consisting of —$CH_2$—, oxygen, sulfur, —S—S—, —N($R^c$)—, —S(O)—, —$SO_2$—, —N($R^c$)—C(O)—, —$OSO_2$—, —CO(O)—, —N($R^c$)$SO_2$—, —C(O)—N($R^c$)—, —C(O)O—, —$SO_2$—N($R^c$)—, —$SO_2$O—, —P(O)(O$R^c$)O—, —P(O)(O$R^c$)N($R^c$)—, —OP(O)(O$R^c$)O—, —OP(O)(O$R^c$)N($R^c$)—, —OC(O)O—, —N($R^c$)—C(O)—O—, —N($R^c$)—C(O)—N($R^c$)—, —O—C(O)—N($R^c$)—, —C(O)—, and —N($R^c$)—$SO_2$—N($R^c$)—;

each Z is independently selected from the group consisting of hydrogen, aryl, cycloalkyl, cycloalkenyl, heteroaryl, heterocyclic, and a saccharide;

x is 1 or 2;

z is 1, 2, 3 or 4;

each $L^c$ is a linker independently selected from the group of consisting of the following linkers:

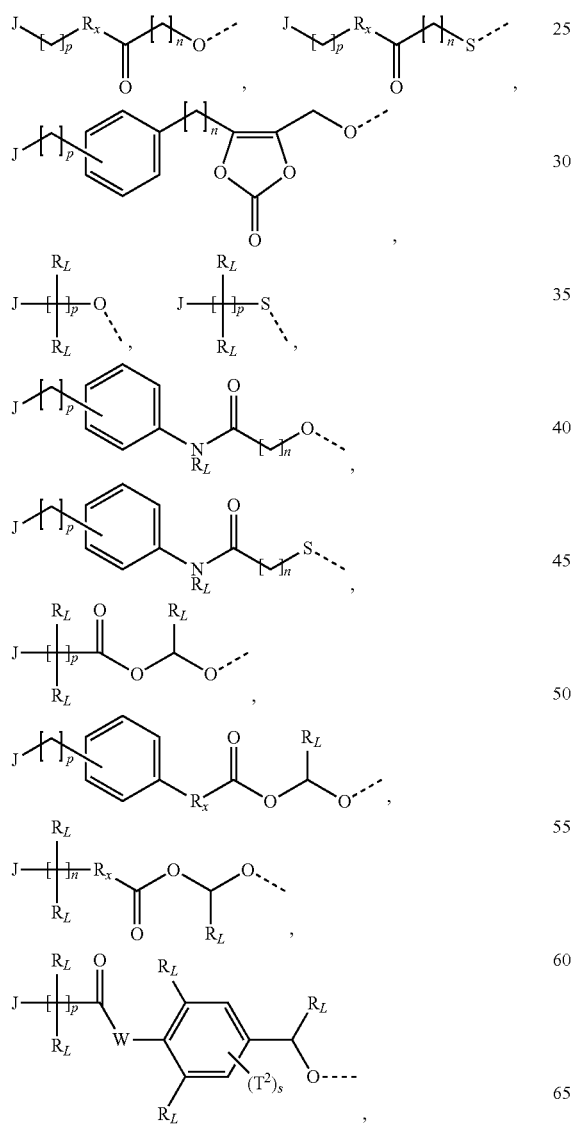

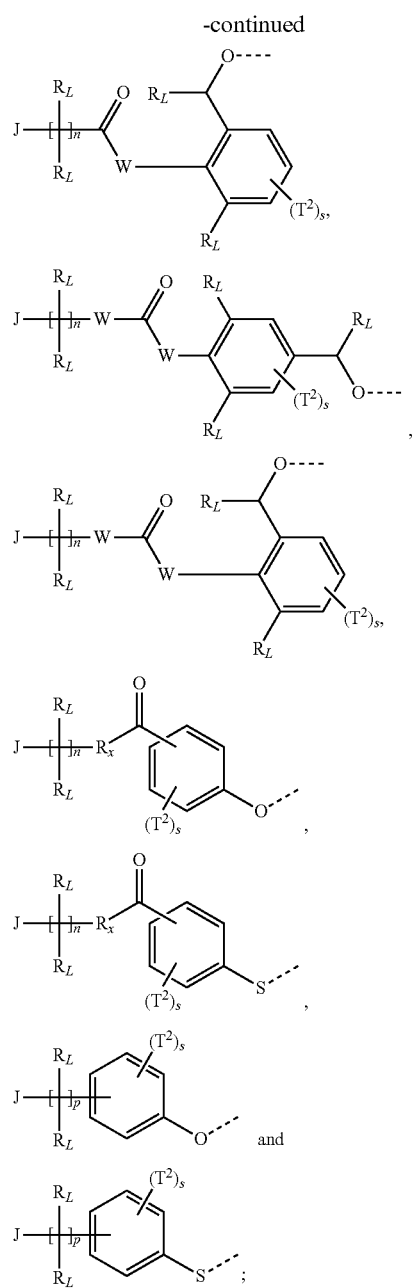

n is an integer ≤10;

each p is independently 0 or an integer ≤10;

each $R_L$ is independently selected from the group consisting of H, ethyl and methyl;

each W is independently selected from —O—, —S—, and —$NR_L$—;

each $T^2$ is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro;

s is 1, 2, 3 or 4;

$R_x$ is selected from the group consisting of a covalent bond, S, $NR_L$ and O; and J is $[[L^a{}_\beta\text{-M}]_\alpha\text{-}L^b{}_\delta]$;

wherein:
each M is individually selected from the group of:

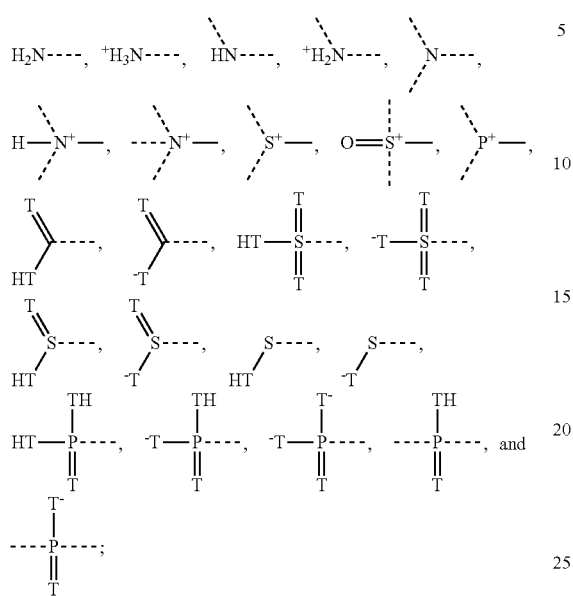

wherein:
each T is O or S; and
the dashed bonds - - - indicate the points of attachment to $L^a$, $L^b$, or the linker;
each $L^a$ is individually selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and

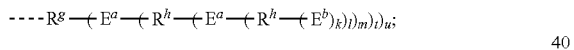

each $L^b$ is individually selected from the group consisting of a covalent bond, alkylene, substituted alkylene, alkenylene, substituted alkenylene, alkynylene, substituted alkynylene, cycloalkylene, substituted cycloalkylene, cycloalkenylene, substituted cycloalkenylene, arylene, heteroarylene and

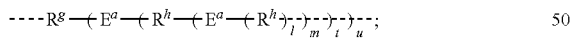

wherein:
each $R^g$ is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, —(CO)-(substituted alkenylene)-, —(CO)-alkynylene-, —(CO)-(substituted alkynylene)-, —(CO)-arylene- and —(CO)-(substituted arylene)-;
each $R^h$ is independently selected from the group consisting of a covalent bond, alkylene, substituted alkylene, alkenylene, substituted alkenylene, alkynylene, substituted alkynylene, arylene and substituted arylene;
each $E^a$ is independently selected from the group consisting of a covalent bond, methylene, oxygen, sulfur,

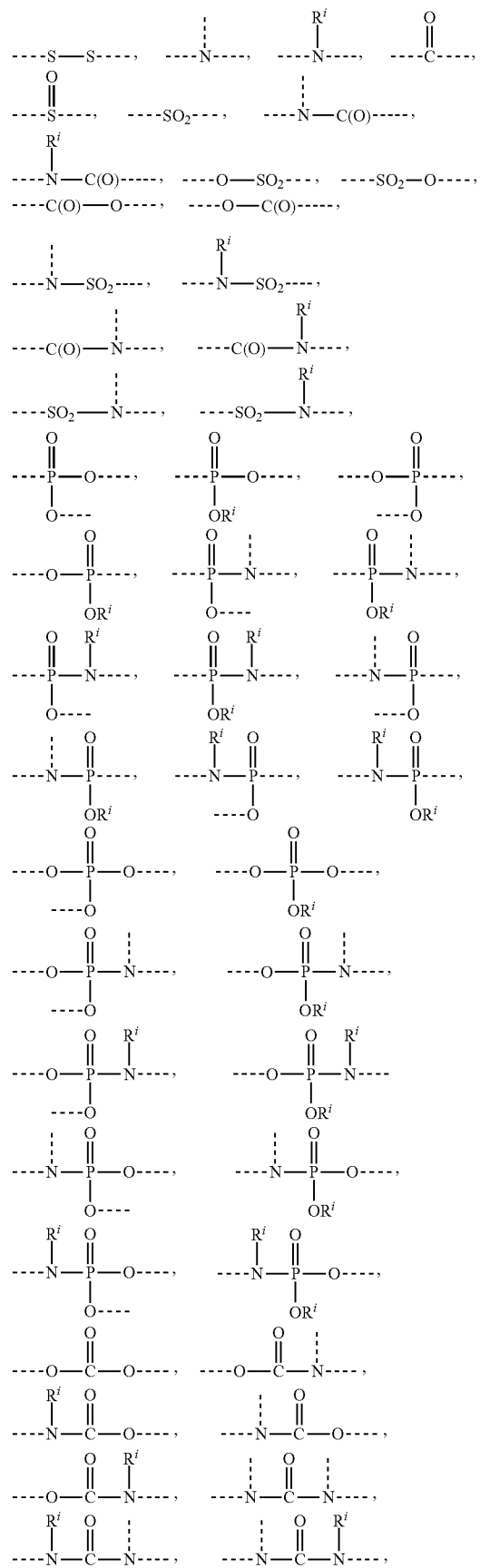

-continued

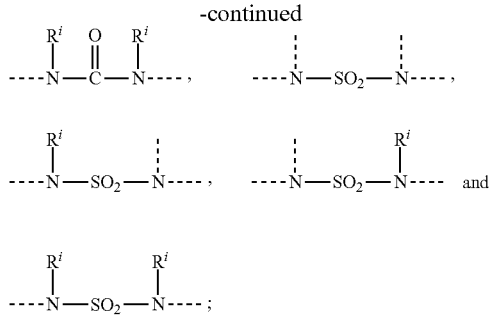

each $R^i$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^j$;

each $R^j$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

each $E^b$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, and substituted aryloxy;

each k, l, m, t, u is independently a nonnull integer ≤5;

α is an integer between 1 and 6;

β is an integer ≤3; and

δ is an integer ≤2α; and with the proviso that either $R^3$ is $L^c$, or G is —C(O)-$L^c$, or both $R^3$ is $L^c$ and G is —C(O)-$L^c$.

In yet a further aspect of the first embodiment of the invention, the compounds of the invention include compounds represented by Formula (IV):

and pharmaceutically acceptable salts, esters, stereoisomers and prodrugs thereof, wherein:

R is selected from the group consisting of —C(O)$R^f$, vancosaminyl, 4-epi-vancosaminyl, L-acosaminyl, L-ristosaminyl, and L-actinosaminyl;

R' is attached to the amino group of R and is selected from the group of —$R^a$—Y—$R^b$—(Z)$_x$, —$R^f$, —C(O)$R^f$, —C(O)—$R^a$—Y—$R^b$—(Z)$_x$, —$R^a$—($R^b$)$_z$—(Z)$_x$ and $L^c$, or R' is absent if R is —C(O)$R^f$;

$R^1$ is hydrogen or mannopyranosyl;

$R^2$ is hydrogen or a saccharide group optionally N-substituted with —$R^a$—Y—$R^b$—(Z)$_x$, —$R^f$, —C(O)$R^f$, —C(O)—$R^a$—Y—$R^b$—(Z)$_x$, —$R^a$—($R^b$)$_z$—(Z)$_x$ or $L^c$;

$R^3$ is selected from the group consisting of hydroxyl, —N($R^c$)—$R^a$—Y—$R^b$—(Z)$_x$, —O—$R^a$—Y—$R^b$—(Z)$_x$ and —S—$R^a$—Y—$R^b$—(Z)$_x$;

$R^4$ is selected from the group consisting of hydrogen, halo, —CH($R^c$)—NR$^c$R$^c$, and —CH($R^c$)—NR$^c$—$R^a$—Y—$R^b$—(Z)$_x$;

$R^5$ is selected from the group consisting of hydrogen, alkyl, substituted alkyl, alkenyl, substituted alkenyl, alkynyl, substituted alkynyl, —$R^a$—Y—$R^b$—(Z)$_x$, —C(O)$R^d$, and a saccharide group optionally substituted with —$R^a$—Y—$R^b$—(Z)$_x$, —$R^a$—($R^b$)$_z$—(Z)$_x$, $R^f$, —C(O)$R^f$, or —C(O)—$R^a$—Y—$R^b$—(Z)$_x$;

$R^6$ is selected from the group consisting of —CH$_2$(CO)NH$_2$, benzyl, 4-hydroxyphenyl, and 3-chloro-4-hydroxyphenyl;

$R^7$ is selected from the group consisting of —CH$_2$CH(CH$_3$)$_2$, 3-chloro-4-hydroxyphenyl, 4-rhamnosylphenyl, 4-(rhamnosyl-galactosyl)phenyl, 4-(galactosyl-galactosyl)phenyl, and 4(methoxyrhamnosyl)phenyl; or $R^6$ and $R^7$ are joined to form (IV)

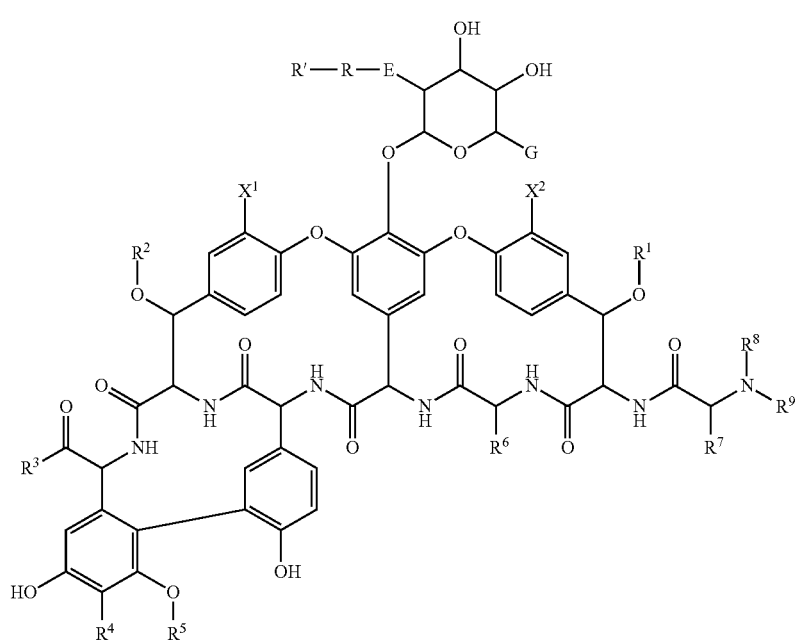

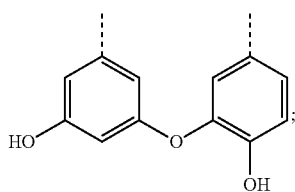

R[8] is hydrogen, methyl or -L[c];

R[9] is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, acyl, substituted acyl and -L[c];

G is —CH$_2$OH or —CO$_2$H;

E is —O— or —NH—;

each R[a] is independently selected from the group consisting of alkylene, substituted alkylene, alkenylene, substituted alkenylene, alkynylene and substituted alkynylene;

each R[b] is independently selected from the group consisting of a covalent bond, alkylene, substituted alkylene, alkenylene, substituted alkenylene, alkynylene and substituted alkynylene;

each R[c] is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R[d];

each R[d] is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

each R[f] is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, and heterocyclic;

each X[1] and X[2] is independently selected from the group consisting of hydrogen, and chloro;

each Y is independently selected from the group consisting of —CH$_2$—, oxygen, sulfur, —S—S—, —N(R[c])—, —N(L[c])-, —S(O)—, —SO$_2$—, —N(R[c])—C(O)—, —OSO$_2$—, —OC(O)—, —N(R[c])SO$_2$—, —C(O)—N(R[c])—, —C(O)O—, —SO$_2$—N(R[c])—, —SO$_2$O—, —P(O)(OR[c])O—, —P(O)(OR[c])N(R[c])—, —OP(O)(OR[c])O—, —OP(O)(OR[c])N(R[c])—, —OC(O)O—, —N(R[c])—C(O)—O—, —N(R[c])—C(O)—N(R[c])—, —O—C(O)—N(R[c])—, —C(O)—, and —N(R[c])—SO$_2$—N(R[c])—;

each Z is independently selected from the group consisting of hydrogen, aryl, cycloalkyl, cycloalkenyl, heteroaryl, heterocyclic, and a saccharide;

x is 1 or 2;

z is 1, 2, 3 or 4;

each L[c] is a linker independently selected from the group of consisting of the following linkers:

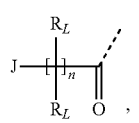, 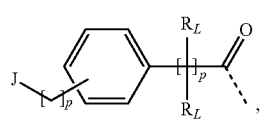,

-continued

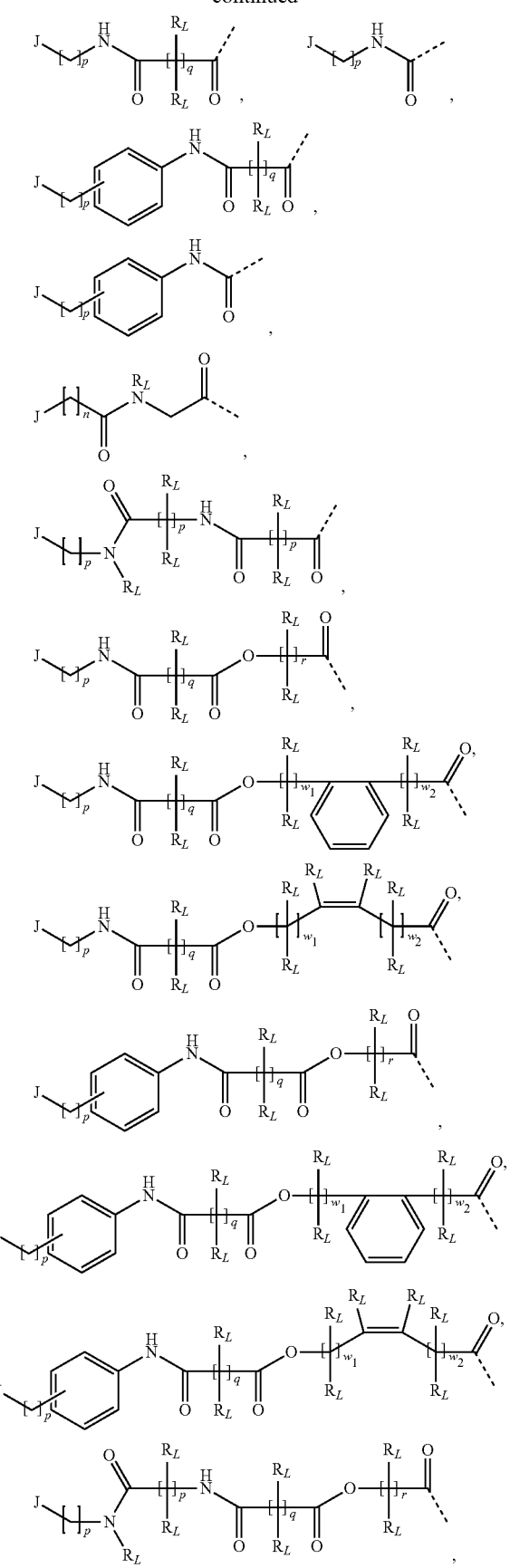

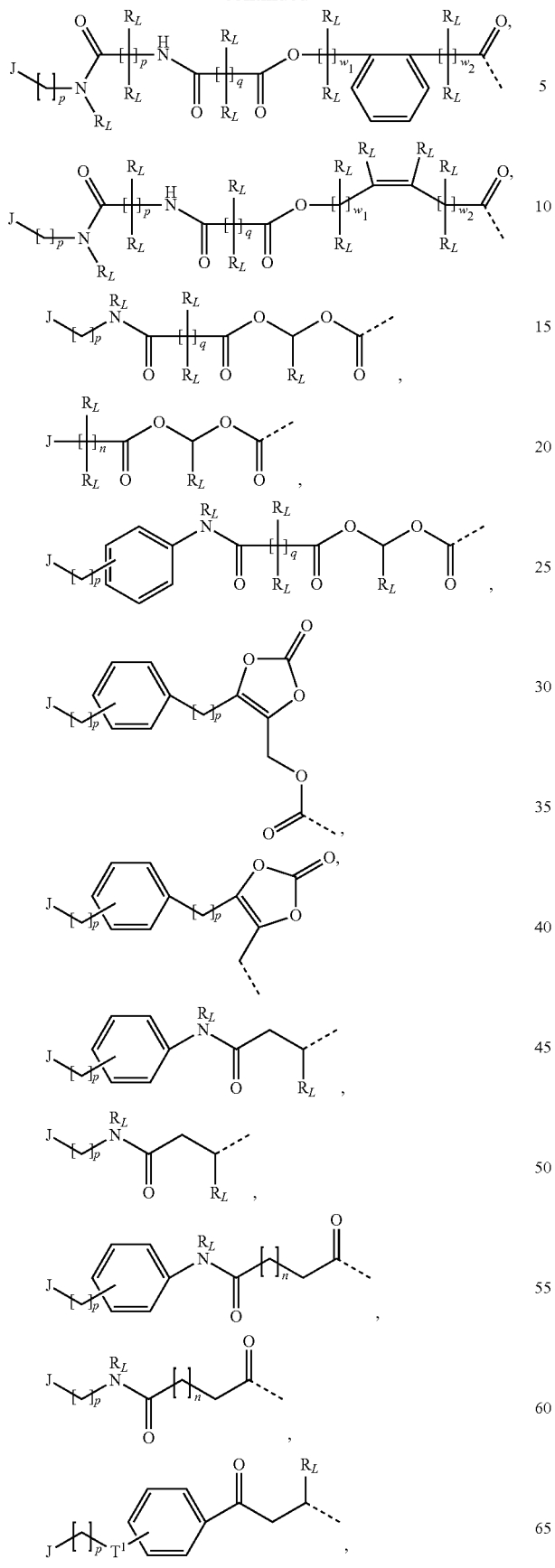
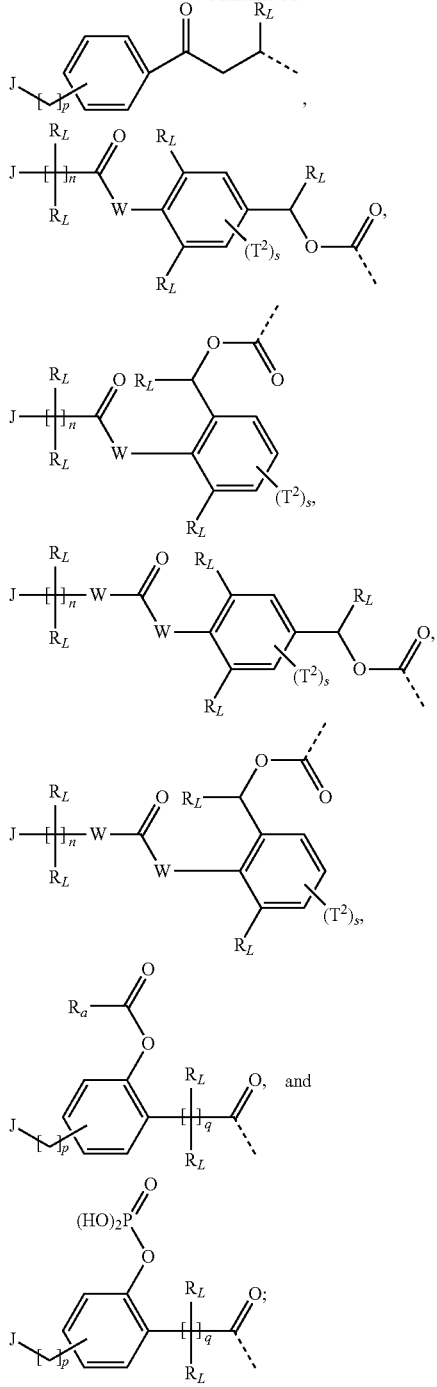
n is an integer ≤10;
each p is independently 0 or an integer ≤10;
each $R_L$ is independently selected from the group consisting of H, ethyl and methyl;
q is 2 or 3;
r is 1, 2, 3, 4 or 5;
$w_1$ and $w_2$ are each integers ≥0 such that their sum ($w_1+w_2$) is 1, 2 or 3;
each W is independently selected from —O—, —S—, and —$NR_L$—;
$T^1$ is $CH_2$, —$CONR_L$—, —CO—O—$CH_2$—, and —CO—O—;

each $T^2$ is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro;

s is 1, 2, 3 or 4;

$R_a$ is $C_xH_y$, where x is an integer of 0 to 20 and y is an integer of 1 to 2x+1;

$R_x$ is selected from the group consisting of a covalent bond, S, $NR_L$ and O; and J is $[[L^a{}_\beta\text{-}M]_\alpha\text{-}L^b{}_\delta]$;

wherein:

each M is individually selected from the group of:

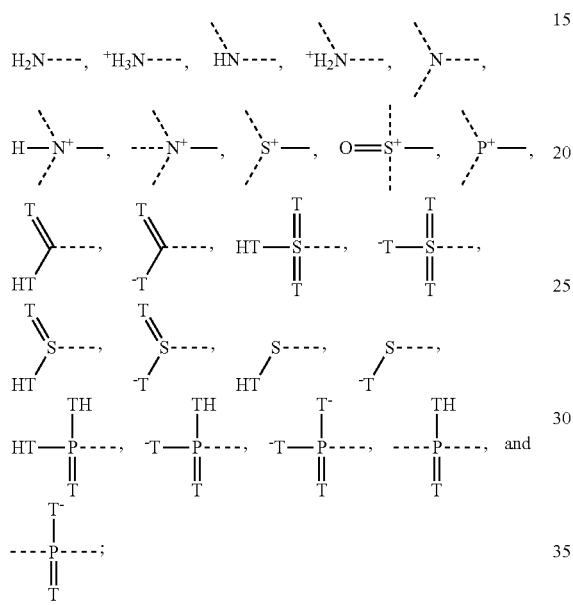

wherein:
each T is O or S; and
the dashed bonds - - - indicate the points of attachment to $L^a$, $L^b$, or the linker;

each $L^a$ is individually selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and

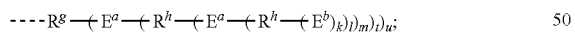

each $L^b$ is individually selected from the group consisting of a covalent bond, alkylene, substituted alkylene, alkenylene, substituted alkenylene, alkynylene, substituted alkynylene, cycloalkylene, substituted cycloalkylene, cycloalkenylene, substituted cycloalkenylene, arylene, heteroarylene and

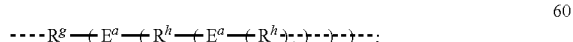

wherein:
each $R^g$ is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, —(CO)-(substituted alkenylene)-, —(CO)-alkynylene-, —(CO)-(substituted alkynylene)-, —(CO)-arylene- and —(CO)-(substituted arylene)-;

each $R^h$ is independently selected from the group consisting of a covalent bond, alkylene, substituted alkylene, alkenylene, substituted alkenylene, alkynylene, substituted alkynylene, arylene and substituted arylene;

each $E^a$ is independently selected from the group consisting of a covalent bond, methylene, oxygen, sulfur,

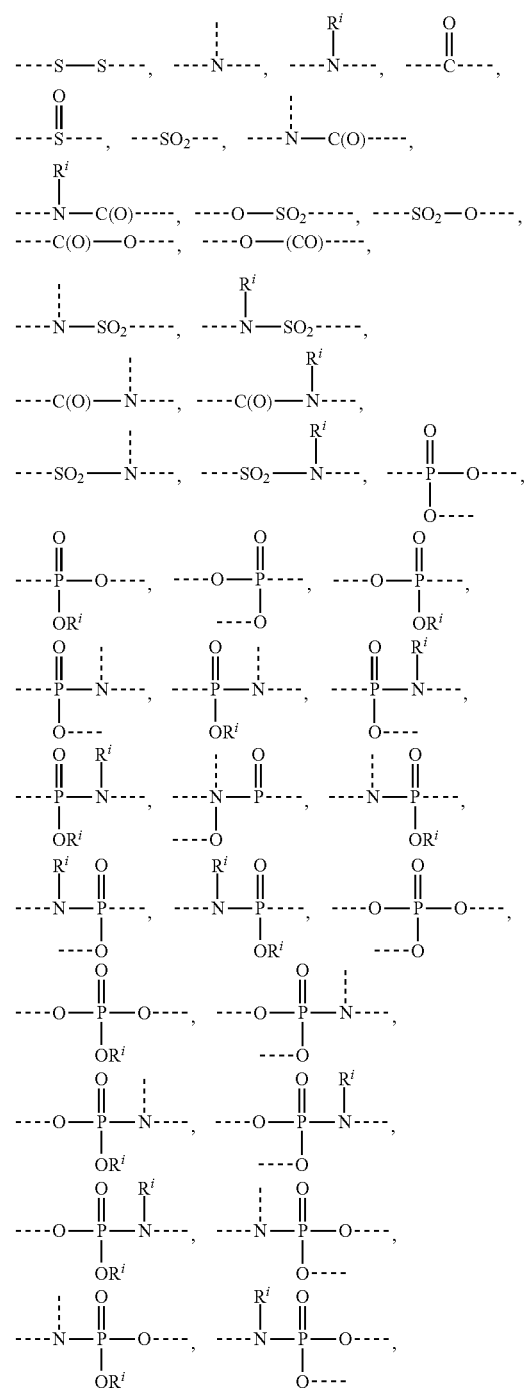

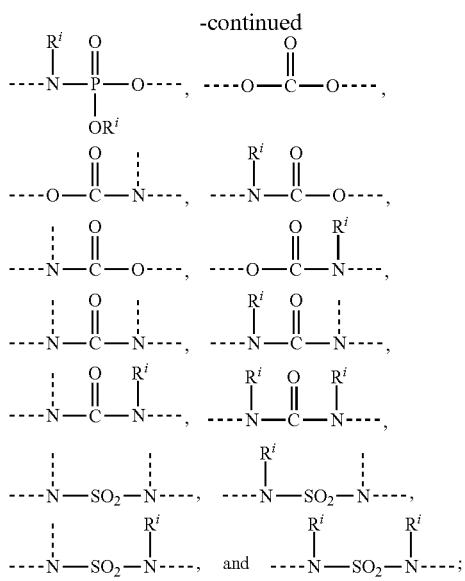

each $R^i$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^j$;

each $R^j$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

each $E^b$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, and substituted aryloxy;

each k, l, m, t, u is independently a nonnull integer ≤5;

α is an integer between 1 and 6;

β is an integer ≤3;

δ is an integer ≤2α; and with the proviso that one or more of the following is present: R' is $L^c$, $R^8$ is $L^c$, $R^9$ is $L^c$ or Y is —N($L^c$)-.

In a second embodiment of the invention, the invention includes pharmaceutical compositions comprising at least one of the antimicrobial compounds of the invention, or a pharmaceutically acceptable salt, ester, stereoisomer or prodrug thereof, and a pharmaceutically acceptable carrier or excipient. For example, the invention includes a pharmaceutical composition comprising at least one compound of Formula (I), (II), (III) or (IV), or a pharmaceutically acceptable salt, ester, stereoisomer or prodrug thereof, and a pharmaceutically acceptable carrier or excipient.

In a third embodiment of the invention, the invention includes methods for treating a bacterial infection in a subject using the antimicrobial compounds of the invention. In one aspect, the methods for treating a bacterial infection in a subject comprise administering to a subject in need of treatment a pharmaceutical composition comprising a pharmaceutically effective amount of at least one compound of the invention, or a pharmaceutically acceptable salt, ester, stereoisomer or prodrug thereof, and a pharmaceutically acceptable carrier or excipient, thereby treating a bacterial infection in a subject. For example, the invention includes methods for treating a bacterial infection in a subject comprising administering to a subject in need of treatment a pharmaceutical composition comprising a pharmaceutically effective amount of at least one compound of Formula (I), (II), (III) or (IV), or a pharmaceutically acceptable salt, ester, stereoisomer or prodrug thereof, and a pharmaceutically acceptable carrier or excipient, thereby treating a bacterial infection in a subject.

In a fourth embodiment of the invention, the invention includes methods for preventing bacterial infections in a subject using the antimicrobial compounds of the invention. In one aspect, the methods for preventing a bacterial infection in a subject comprise administering to a subject in need of prevention a pharmaceutical composition comprising a pharmaceutically effective amount of at least one compound of the invention, or a pharmaceutically acceptable salt, ester, stereoisomer or prodrug thereof, and a pharmaceutically acceptable carrier or excipient, thereby preventing a bacterial infection in a subject. For example, the invention includes methods for preventing a bacterial infection in a subject comprising administering to a subject in need of prevention a pharmaceutical composition comprising a pharmaceutically effective amount of at least one compound of Formula (I), (II), (III) or (IV), or a pharmaceutically acceptable salt, ester, stereoisomer or prodrug thereof, and a pharmaceutically acceptable carrier or excipient, thereby preventing a bacterial infection in a subject.

In a fifth embodiment of the invention, the invention includes methods for providing prophylaxis for a bacterial infection in a subject using the antimicrobial compounds of the invention. In one aspect, the methods for providing prophylaxis for a bacterial infection in a subject comprise administering to a subject in need of prophylaxis a pharmaceutical composition comprising a prophylactically effective amount of at least one compound of the invention, or a pharmaceutically acceptable salt, ester, stereoisomer or prodrug thereof, and a pharmaceutically acceptable carrier or excipient, thereby providing prophylaxis for a bacterial infection in a subject. For example, the invention includes methods for providing prophylaxis for a bacterial infection in a subject comprising administering to a subject in need of prophylaxis a pharmaceutical composition comprising a prophylactically effective amount of at least one compound of Formula (I), (II), (III) or (IV), or a pharmaceutically acceptable salt, ester, stereoisomer or prodrug thereof, and a pharmaceutically acceptable carrier or excipient, thereby providing prophylaxis for a bacterial infection in a subject.

In each of the methods of the invention, the subject may be a human.

In each of the methods of the invention, the methods may further comprise administering a second therapeutic agent concurrent with administration of said pharmaceutical composition. Preferably the second therapeutic agent is an antibiotic. Suitable second therapeutic agents include fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, a minocycline derived antibacterial agent, sancycline, a sancycline derived antibacterial agent, methacycline, a methacycline derived antibacterial agent, an oxazolidinone antibacterial agent, an aminoglycoside antibacterial agent, a quinolone antibacterial agent, daptomycin, a daptomycin derived antibacterial agent, rifamycin, a rifamycin derived antibacterial agent, rifampin, a rifampin derived antibacterial agent, rifalazil, a rifalazil derived antibacterial agent, rifabutin, a rifabutin derived antibacterial agent, rifapentin, a rifapentin derived antibacterial agent, rifaximin and a rifaximin derived antibacterial agent.

In a sixth embodiment, the invention included methods for preparing the glycopeptide and lipoglycopeptide antibiotics having altered ionization states as disclosed herein.

An advantage of the invention is that it provides antimicrobial compounds having an increased solubility in pharmaceutically acceptable excipients and in circulating biological fluids, and capable of being administered in a reduced volume.

Additional objects, advantages and features of the present invention will become more apparent from the following non-restrictive description of preferred embodiments which are exemplary and should not be interpreted as limiting the scope of the present invention.

DETAILED DESCRIPTION OF THE INVENTION

The present invention discloses derivatives of glycopeptide and lipoglycopeptide antibiotics possessing an altered ionization state with respect to the parent glycopeptide or lipoglycopeptide antibiotic and the ability to be regenerated as the parent glycopeptide or lipoglycopeptide antibiotic under physiological conditions. The compounds of the invention include the compounds of Formula (I), (II), (III) and (IV), and pharmaceutically acceptable salts, esters, stereoisomers and prodrugs thereof, as defined above and below. These compounds are useful antimicrobial agents effective against a number of human and veterinary pathogens.

The essence of the invention lies in the attachment of one or more additional ionically charged groups to a glycopeptide or lipoglycopeptide antibiotic. Since glycopeptides are globally uncharged or singly charged at physiological pH, their solubility is reduced significantly. The present inventors have found that the solubility of glycopeptide and lipoglycopeptide antibiotics can be increased in aqueous media by tethering an ionically charged solubilizing group to such an antibiotic. Such action blocks a negatively charged functional group and replaces it covalently and reversibly with a positively charged functional group, or blocks a positively charged functional group and replaces it covalently and reversibly with a negatively charged functional group. Achieving high concentrations of glycopeptide and lipoglycopeptide antibiotics in aqueous media will improve the formulation and reduce the volume of injection or infusion. In addition, the presence of the ionically charged group will allow masking the antibiotic during injection or infusion. The combination of these two factors may therefore allow a reduction of the side effects observed during the administration of glycopeptide or lipoglycopeptide antibiotics not bearing such pendant ionically charged groups.

The present inventors have synthesized such derivatives of glycopeptide and lipoglycopeptide antibiotics possessing an altered ionization state with respect to the parent glycopeptide or lipoglycopeptide antibiotic and demonstrated that these derivatives have an increased solubility with respect to the parent drug in media isotonic to physiological fluids. The present inventors have also shown that these more soluble derivatives maintain antibacterial properties including against glycopeptide-resistant variants of generally glycopeptide susceptible microorganisms. Finally, the present inventors have shown that these more soluble derivatives maintain the ability to treat infections in accepted animal models. Accordingly, the compounds of the invention are particularly useful alternatives for the treatment of infections.

The compounds of the present invention, encompassed by Formula (I), (II), (III) and (IV), each have at least one moiety bearing at least one ionically charged group coupled via a linker to a glycopeptide or lipoglycopeptide antimicrobial molecule. This linker can be cleaved under physiological conditions and a dissociation of the glycopeptide or lipoglycopeptide antibacterial agent from its additional ionically charged moiety may occur in vivo.

A) DEFINITIONS

In order to provide an even clearer and more consistent understanding of the invention, including the scope given herein to particular terms, the following general definitions are provided:

The term "alkyl" refers to saturated aliphatic groups including straight-chain, branched-chain, cyclic groups, and combinations thereof, having the number of carbon atoms specified, or if no number is specified, having 1 to 12 carbon atoms (preferably 1 to 6). Examples of alkyl groups include, but are not limited to groups such as methyl, ethyl, n-propyl, isopropyl, n-butyl, isobutyl, sec-butyl, t-butyl, n-pentyl, neopentyl, cyclopropyl, cyclobutyl, cyclopentyl, cyclohexyl, cyclobutylmethyl, cyclobutylethyl, cyclopentylmethyl, cyclopentylethyl, and adamantyl. Cyclic alkyl groups (e.g. cycloalkyl or heterocycloalkyl) can consist of one ring, including, but not limited to, groups such as cycloheptyl, or multiple fused rings, including, but not limited to, groups such as adamantyl or norbornyl.

The term "alkylaryl" refers to an alkyl group having the number of carbon atoms designated, appended to one, two, or three aryl groups.

The term "N-alkylaminocarbonyl" refers to the radical —C(O)NHR where R is an alkyl group.

The term "N,N-dialkylaminocarbonyl" refers to the radical —C(O)NR$_a$R$_b$ where R$_a$ and R$_b$ are each independently an alkyl group.

The term "alkylthio" refers to the radical —SR where R is an alkyl group.

The term "alkoxy" as used herein refers to an alkyl, alkenyl, or alkynyl linked to an oxygen atom and having the number of carbon atoms specified, or if no number is specified, having 1 to 12 carbon atoms (preferably 1 to 6). Examples of alkoxy groups include, but are not limited to, groups such as methoxy, ethoxy, tert-butoxy, and allyloxy. The term "alkoxycarbonyl" refers to the radical —C(O)OR where R is an alkyl. The term "alkylsulfonyl" refers to the radical —SO$_2$R where R is an alkyl group.

The term "alkylene" means a saturated divalent aliphatic group including straight-chain, branched-chain, cyclic groups, and combinations thereof, having the number of carbon atoms specified, or if no number is specified, having 1 to 12 carbon atoms (preferably 1 to 6), e.g., methylene, ethylene, 2,2-dimethylethylene, propylene, 2-methyl-propylene, butylene, pentylene, cyclopentylmethylene, and the like.

The term "substituted alkyl" means an alkyl group as defined above that is substituted with one or more substituents, preferably one to three substituents selected from the group consisting of halogen, alkyl, aryl, alkoxy, acyloxy, amino, mono or dialkylamino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. The phenyl group may optionally be substituted with one to three substituents selected from the group consisting of halogen, alkyl, aryl, alkoxy, acyloxy, amino, mono or dialkylamino, hydroxyl, mercapto, carboxy, benzyloxy, benzyl, cyano, nitro, thioalkoxy, carboxaldehyde, carboalkoxy and carboxamide.

Examples of substituted alkyl groups include, but are not limited to —CF$_3$, —CF$_2$—CF$_3$, hydroxymethyl, 1- or 2-hydroxyethyl, methoxymethyl, 1- or 2-ethoxyethyl, carboxymethyl, 1- or 2-carboxyethyl, methoxycarbonylmethyl, 1- or 2-methoxycarbonyl ethyl, benzyl, pyrdinylmethyl, thiophenylmethyl, imidazolinylmethyl, dimethylaminoethyl and the like.

The term "substituted alkylene" means an alkylene group as defined above that is substituted with one or more substituents, preferably one to three substituents, selected from the group consisting of halogen, alkyl, aryl, alkoxy, acyloxy, amino, mono or dialkylamino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. The phenyl group may optionally be substituted with one to three substituents selected from the group consisting of halogen, alkyl, aryl, alkoxy, acyloxy, amino, mono or dialkylamino, hydroxyl, mercapto, carboxy, benzyloxy, benzyl, cyano, nitro, thioalkoxy, carboxaldehyde, carboalkoxy and carboxamide. Examples of substituted alkyl groups include, but are not limited to —CF$_2$—, —CF$_2$—CF$_2$—, hydroxymethylene, 1- or 2-hydroxyethylene, methoxymethylene, 1- or 2-ethoxyethylene, carboxymethylene, 1- or 2-carboxyethylene, and the like.

The term "alkenyl" refers to unsaturated aliphatic groups including straight-chain, branched-chain, cyclic groups, and combinations thereof, having the number of carbon atoms specified, or if no number is specified, having 1 to 12 carbon atoms (preferably 1 to 6), which contain at least one double bond (—C=C—). Examples of alkenyl groups include, but are not limited to allyl vinyl, —CH$_2$—CH=CH—CH$_3$, —CH$_2$—CH$_2$-cyclopentenyl and —CH$_2$—CH$_2$-cyclohexenyl where the ethyl group can be attached to the cyclopentenyl, cyclohexenyl moiety at any available carbon valence.

The term "alkenylene" refers to unsaturated divalent aliphatic groups including straight-chain, branched-chain, cyclic groups, and combinations thereof, having the number of carbon atoms specified, or if no number is specified, having 1 to 12 carbon atoms (preferably 1 to 6), which contain at least one double bond (—C=C—). Examples of alkenylene groups include, but are not limited to —CH=CH—, —CH$_2$—CH=CH—CH$_2$—, —CH$_2$—CH(cyclopentenyl)- and the like.

The term "alkynyl" refers to unsaturated aliphatic groups including straight-chain, branched-chain, cyclic groups, and combinations thereof, having the number of carbon atoms specified, or if no number is specified, having 1 to 12 carbon atoms (preferably 1 to 6), which contain at least one triple bond (—C≡C—). Examples of alkynyl groups include, but are not limited to acetylene, 2-butynyl, and the like.

The term "alkynylene" refers to unsaturated divalent aliphatic groups including straight-chain, branched-chain, cyclic groups, and combinations thereof, having the number of carbon atoms specified, or if no number is specified, having 1 to 12 carbon atoms (preferably 1 to 6), which contain at least one triple bond (—C≡C—). Examples of alkynylene groups include, but are not limited to —C≡C—, —C≡C—CH$_2$—, and the like.

The term "substituted alkenyl" or "substituted alkynyl" refers to the alkenyl and alkynyl groups as defined above that are substituted with one or more substituents selected from the group consisting of halogen, alkyl, aryl, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of substituted alkenyl and alkynyl groups include, but are not limited to —CH=CF$_2$, methoxyethenyl, methoxypropenyl, bromopropynyl, and the like.

The term "substituted alkenylene" or "substituted alkynylene" refers to the alkenylene and alkynylene groups as defined above that are substituted with one or more substituents selected from the group consisting of halogen, alkyl, aryl, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

The term "aryl" or "Ar" refers to an aromatic carbocyclic group of 6 to 14 carbon atoms having a single ring (including but not limited to groups such as phenyl) or multiple condensed rings (including but not limited to groups such as naphthyl or anthryl), and includes both unsubstituted and substituted aryl groups. Substituted aryl is an aryl group that is substituted with one or more substituents, preferably one to three substituents, selected from the group consisting of alkyl, aryl, alkenyl, alkynyl, halogen, alkoxy, acyloxy, amino, mono or dialkylamino, hydroxyl, mercapto, carboxy, benzyloxy, phenyl, aryloxy, benzyl, cyano, nitro, thioalkoxy, carboxaldehyde, carboalkoxy and carboxamide, or a functionality that can be suitably blocked, if necessary for purposes of the invention, with a protecting group. Representative examples include, but are not limited to naphthyl, phenyl, chlorophenyl, iodophenyl, methoxyphenyl, carboxyphenyl, and the like. The term "aryloxy" refers to an aryl group linked to an oxygen atom at one of the ring carbons. Examples of alkoxy groups include, but are not limited to, groups such as phenoxy, 2-, 3-, or 4-methylphenoxy, and the like. The term "arylthio group" refers to the radical —SR$_c$, where R$_c$ is an aryl group. The term "heteroarylthio group" refers to the radical —SR$_d$ where R$_d$ is a heteroaryl.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "N-alkylamino" and "N,N-dialkylamino" means a radical —NHR and —NRR' respectively where R and R' independently represent an alkyl group as defined herein. Representative examples include, but are not limited to N,N-dimethylamino, N-ethyl-N-methylamino, N,N-di(1-methylethyl)amino, N-cyclohexyl-N-methylamino, N-cyclohexyl-N-ethylamino, N-cyclohexyl-N-propylamino, N-cyclohexylmethyl-N-methylamino, N-cyclohexylmethyl-N-ethylamino, and the like.

The term "thioalkoxy" means a radical —SR where R is an alkyl as defined above e.g., methylthio, ethylthio, propylthio, butylthio, and the like.

The term "acyl group" means a radical —C(O)R$^f$, where R is hydrogen, halogen, alkyl, aryl, heteroaryl, alkoxy, aryloxy, N-alkylamino, N,N-dialkylamino, N-arylamino, thioalkoxy, thioaryloxy or substituted alkyl wherein alkyl, aryl, heteroaryl, and substituted alkyl are as defined herein.

The term "thioacyl group" means a radical —C(S)R, where R is hydrogen, halogen, alkyl, aryl, heteroaryl, alkoxy, aryloxy, N-alkylamino, N,N-dialkylamino, N-arylamino, thioalkoxy, thioaryloxy or substituted alkyl wherein alkyl, aryl, heteroaryl, and substituted alkyl are as defined herein.

The term "sulfonyl group" means a radical —SO$_2$R, where R is hydrogen, halogen, alkyl, aryl, heteroaryl, alkoxy, aryloxy, N-alkylamino, N,N-dialkylamino, N-arylamino, thioalkoxy, thioaryloxy or substituted alkyl wherein alkyl, aryl, heteroaryl, and substituted alkyl are as defined herein.

The term "acyloxy" means a radical —OC(=O)R, where R is hydrogen, alkyl, aryl, heteroaryl or substituted alkyl wherein alkyl, aryl, heteroaryl, and substituted alkyl are as defined herein. Representative examples include, but are not limited to formyloxy, acetyloxy, cylcohexylcarbonyloxy, cyclohexylmethylcarbonyloxy, benzoyloxy, benzylcarbonyloxy, and the like.

The term "heteroalkyl," "heteroalkenyl," and "heteroalkynyl" refers to alkyl, alkenyl, and alkynyl groups respectively as defined above, that contain the number of carbon atoms specified (or if no number is specified, having 1 to 12 carbon atoms, preferably 1 to 6) which contain one or more heteroatoms, preferably one to three heteroatoms, as part of the main, branched, or cyclic chains in the group. Heteroatoms are independently selected from the group consisting of —NR—, —NRR, —S—, —S(O)—, —S(O)$_2$—, —O—, —SR, —S(O)R, —S(O)$_2$R, —OR—PR—, —PRR, —P(O)R— and —P(O)RR; (where each R is hydrogen, alkyl or aryl) preferably —NR where R is hydrogen or alkyl and/or O. Heteroalkyl, heteroalkenyl, and heteroalkynyl groups may be attached to the remainder of the molecule either at a heteroatom (if a valence is available) or at a carbon atom. Examples of heteroalkyl groups include, but are not limited to, groups such as —O—CH$_3$, —CH$_2$—O—CH$_3$, —CH$_2$—CH$_2$—O—CH$_3$, —S—CH$_2$—CH$_2$—CH$_3$, —CH$_2$—CH(CH$_3$)—S—CH$_3$, —CH$_2$—CH$_2$—NH—CH$_2$—CH$_3$, 1-ethyl-6-propylpiperidino, 2-ethylthiophenyl, piperazino, pyrrolidino, piperidino, morpholino, and the like. Examples of heteroalkenyl groups include, but are not limited to groups such as —CH=CH—CH$_2$—N(CH$_3$)$_2$, and the like.

The term "heteroaryl" or "HetAr" refers to an aromatic monovalent monocyclic, bicyclic, or tricyclic radical containing 4, 5, 6, 7, 8, 9, 10, 11, 12, 13, 14, 15, 16, 17, or 18-member ring atoms, including 1, 2, 3, 4, or 5 heteroatoms, preferably one to three heteroatoms including, but not limited to heteroatoms such as N, O, P, or S, within the ring. Representative examples include, but are not limited to single ring such as imidazolyl, pyrazolyl, pyrazinyl, pyridazinyl, pyrimidinyl, pyrrolyl, pyridyl, thiophene, and the like, or multiple condensed rings such as indolyl, quinoline, quinazoline, benzimidazolyl, indolizinyl, benzothienyl, and the like.

The heteroalkyl, heteroalkenyl, heteroalkynyl and heteroaryl groups can be unsubstituted or substituted with one or more substituents, preferably one to three substituents, selected from the group consisting of alkyl, alkenyl, alkynyl, benzyl, halogen, alkoxy, acyloxy, amino, mono or dialkylamino, hydroxyl, mercapto, carboxy, benzyloxy, phenyl, aryloxy, cyano, nitro, thioalkoxy, carboxaldehyde, carboalkoxy and carboxamide, or a functionality that can be suitably blocked, if necessary for purposes of the invention, with a protecting group. Examples of such substituted heteroalkyl groups include, but are not limited to, piperazine, pyrrolidine, morpholine, or piperidine, substituted at a nitrogen or carbon by a phenyl or benzyl group, and attached to the remainder of the molecule by any available valence on a carbon or nitrogen, —NH—S(=O)$_2$-phenyl, —NH—(C=O)O-alkyl, —NH—C(=O)O-alkyl-aryl, and the like. The heteroatom(s) as well as the carbon atoms of the group can be substituted. The heteroatom(s) can also be in oxidized form.

The term "heteroarylene" refers to the diradical group derived from heteroaryl (including substituted heteroaryl), as defined above, and is exemplified by the groups 2,6-pyridinylene, 2,4-pyridinylene, 1,2-quinolinylene, 1,8-quinolinylene, 1,4-benzofuranylene, 2,5-pyridinylene, 2,5-indolenylene, and the like.

The term "heteroalkylene", "heteroalkenylene", and "heteroalkynylene" refers to the diradical group derived from heteroalkyl, heteroalkenyl, and heteroalkynyl (including substituted heteroalkyl, heteroalkenyl, and heteroalkynyl) as defined above.

The term "carboxaldehyde" means —CHO.

The term "carboalkoxy" means —C(=O)OR where R is alkyl as defined above and include groups such as methoxycarbonyl, ethoxycarbonyl, and the like.

The term "carboxamide" means —C(=O)NHR or —C(=O)NRR' where R and R' are independently hydrogen, aryl or alkyl as defined above. Representative examples include groups such as aminocarbonyl, N-methylaminocarbonyl, N,N-dimethylaminocarbonyl, and the like.

The term "carboxy" refers to the radical —C(O)OH.

The term "carbamoyl" refers to the radical —C(O)NH$_2$.

The term "halogen" or "halo" as used herein refer to Cl, Br, F or I substituents, preferably fluoro or chloro.

The term "hydroxy" refers to a —OH radical.

The term "isomers" refers to compounds that have the same molecular formula (or elemental composition) but differ in the nature or sequence of bonding of their atoms or the arrangement of their atoms in space. Isomers in which the connectivity between atoms is the same but which differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example which is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either an individual enantiomer or as a mixture thereof. A mixture containing equal proportions of the enantiomers is called a "racemic mixture".

The compounds of this invention possess more than one asymmetric center. Such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The description is also intended to include all possible diastereomers and mixtures thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The term "optically pure" refers to a compound that is enantiomerically pure. As used herein, the term "optically pure" is intended to mean a compound which comprises at least a sufficient amount of a single enantiomer to yield a compound having the desired pharmacological activity. Preferably, "optically pure" is intended to mean a compound that comprises at least 90% of a single isomer (80% enantiomeric excess), preferably at least 95% (90% e.e.), more preferably at least 97.5% (95% e.e.), and most preferably at least 99% (98% e.e.). Preferably, the compounds of the invention are optically pure.

The term "protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) Protective Groups in Organic Synthesis, 2nd Ed. (John Wiley & Sons, Inc., New York). Preferred amino protecting groups include, but are not limited to, benzyloxycarbonyl (CBz), t-butyloxycarbonyl (Boc), t-butyldimethylsilyl (TBDMS), 9-fluorenylmethyl-oxycarbonyl (Fmoc), or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5-bromo-7-nitroindolinyl, and the like. Preferred hydroxyl protecting groups include acetyl (Ac), benzoyl (Bz), benzyl (Bn), Tetrahydropyranyl (THP), TBDMS, photolabile protecting groups (such as nitroveratryl oxymethyl ether (Nvom)), Mom (methoxy methyl ether), and Mem (methoxy ethoxy methyl ether). Particularly preferred protecting groups include NPEOC (4-nitrophenethyloxycarbonyl) and NPEOM (4-nitrophenethyloxy-methyloxycarbonyl).

The term "saccharide" refers to saturated polyhydroxylated compounds. The term is sometimes limited to polyhydroxylated carbon chains possessing an aldehyde or a ketone moiety either free or masked as an acetal or a ketal functionality. In this case, it is intended to include monosaccharides, oligosaccharides and polysaccharides as well as substances derived from monosaccharides by reduction of the carbonyl group (alditols), by oxidation of one or more terminal groups to carboxylic acids, by oxidation of one or more secondary hydroxyl groups to ketones, by replacement of one or more hydroxy group(s) by a hydrogen atom, an amino group, an O-linked ester group, a C-linked ester group, an N-linked amide group, a C-linked amide group, an alkyl group, an aryl group, a thiol group or similar heteroatomic groups and/or by replacement of one or more of the hydrogens bonded to carbons by a C-linked ester group, a C-linked amide group, an alkyl group, an aryl group or other heteroatomic groups. It also includes oligomers of modified and unmodified monosaccharides as well as derivatives of these compounds.

Unmodified, oxidized, reduced or substituted saccharide monoradicals are covalently attached to the glycopeptide via any atom of the saccharide moiety, preferably a carbon. Representative saccharide include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(α-L-vancosaminyl)-β-D-glucopyranose, 2-O-(α-L-3-epivancosaminyl)-β-D-glucopyranose, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units. These saccharides are can be either in their open or preferably in their pyranose or furanose forms.

The saccharide may be linked to the aglycone of the glycopeptide or lipoglycopeptide antimicrobial agent indirectly via an additional spacer such as an ethylene, propylene, butylenes or phenylene group.

The term "amino-containing saccharide group" refers to a saccharide group having an amino substituent. Representative amino-containing saccharide include L-vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine and the like.

A "pharmaceutically acceptable active metabolite" is intended to mean a pharmacologically active product produced through metabolism in the body of a compound of Formula (I), (II), (III) or (IV) as defined herein.

A "pharmaceutically acceptable solvate" is intended to mean a solvate that retains the biological effectiveness and properties of the biologically active components of the compounds of Formula (I), (II), (III) and (IV). Examples of pharmaceutically acceptable solvates include, but are not limited to water, isopropanol, ethanol, methanol, DMSO, ethyl acetate, acetic acid, and ethanolamine.

The term "antibacterial" refers to those compounds that inhibit, halt or reverse growth of bacteria, those compounds that inhibit, halt, or reverse the activity of bacterial enzymes or biochemical pathways, those compounds that kill or injure bacteria, and those compounds that block or slow the development of a bacterial infection.

The term "subject" is intended to mean an animal, such as a mammal, including humans, other higher primates, lower primates, and animals of veterinary importance, such as dogs, cats, horses, sheep, goats, and cattle.

B) COMPOUNDS

As will be described above and hereinafter, the inventors have prepared glycopeptide and lipoglycopeptide antibiotics possessing an altered ionization state with respect to the parent glycopeptide or lipoglycopeptide antibiotic. These compounds have the ability to be regenerated as the parent glycopeptide or lipoglycopeptide antibiotic under physiological conditions, and they have an improved solubility profile in aqueous media.

Each of the compounds of the present invention is encompassed within Formula (I), defined above in the summary of the invention as the first embodiment of the invention:

$$[[[L^a_\beta\text{-}M]_\alpha\text{-}L^b_\delta]_\gamma\text{-}L^c_\epsilon]_\gamma\text{-}A \qquad (I)$$

wherein:

each M is independently a chemical group that is ionizable under physiological conditions, having between 0 and 3 $L^a$ bonded thereto;

each $L^a$ is independently a chemical group structurally or electronically assisting M in maintaining a charge;

each $L^b$ is independently a bond or a multivalent linking group, wherein each $L^b$ links between 1 and 6 $[L^a_\beta\text{-}M]$ groups to each other, to $L^c$, or to each other and to $L^c$, wherein when $L^b$ is present, at least one $L^b$ links at least one $[L^a_\beta\text{-}M]$ group to at least one $L^c$;

each $L^c$ is independently a bond or a multivalent linking group which is cleavable under physiological conditions, wherein each $L^c$ links between 1 and 10 $[[L^a_\beta\text{-}M]_\alpha\text{-}L^b_\delta]$ groups to A, or links each $[L^a_\beta\text{-}M]$ group to A when δ is 0;

A is a glycopeptide or lipoglycopeptide antimicrobial molecule;

α is an integer between 1 and 6;

γ is an integer between 1 and 10;

β is an integer ≤3;
δ is an integer ≤2α;
ε is an integer ≤αγ;
γ is an integer between 1 and 7.

The present invention includes pharmaceutically acceptable salts, esters, stereoisomers and prodrugs of the compounds of Formula (I).

Ionically Charged Groups

As mentioned previously, the essence of the invention lies in the presence of one or more additional ionically charged groups attached to a glycopeptide or lipoglycopeptide antibiotic. Ionically charged groups are arrangements of covalently linked atoms wherein the total number of electrons and protons in the group is not the same. These groups include ionizable chemical groups, which are arrangements of atoms capable of stabilizing an imbalance in protons and electrons, in particular at physiological pH. Examples of ionizable chemical groups suitable for the present invention include but are not limited to those groups defined as M in the summary of the invention above.

Ionizable chemical groups can additionally be substituted with ligands $L^a$ which are not critical to the ability to sustain a charge but are present for structural purposes, in particular to respect valence and to provide stability to the molecular architecture. Examples of such ligands suitable for the present invention include but are not limited to those ligands defined as $L^a$ in the summary of the invention above. Each ionizable chemical group M may independently have 0, 1, 2, 3, 4, 5, 6 or more ligands $L^a$ bonded to it.

Ionizable chemical groups can additionally be substituted with ligands $L^b$ which are similarly not critical to the ability to sustain a charge but are there for structural purposes, in particular to link ionizable functional groups together, to provide ionically charged moieties possessing several ionizable groups, or to serve as a linker while respecting the rules of valence and to provide stability to the molecular architecture. Examples of such ligands suitable for the present invention include but are not limited to those defined as $L^b$ in the summary of the invention above. The ligand $L^b$ may serve to link 0, 1, 2, 3, 4, 5, 6 or more M, whether substituted with ligands $L^a$ or unsubstituted, with other M, with a cleavable linker $L^c$ as defined herein, or with both M and with a cleavable linker $L^c$. In preferred embodiments, at least one ligand $L^b$ links at least one M to at least one cleavable linker $L^c$.

As shown in Example 2 hereinafter, glycopeptide and lipoglycopeptide derivatives possessing such additional ionically charged groups are more soluble than the parent in aqueous media, in particular aqueous media isotonic to physiological fluids, or formulations while maintaining antibacterial and therapeutic properties associated with it.

Linkers

A cleavable linker $L^c$ covalently and reversibly couples the additional ionically charged groups to a site on the glycopeptide or lipoglycopeptide antimicrobial molecule A. As used herein, the term "cleavable" refers to a group that is chemically or biochemically unstable under physiological conditions. The chemical instability preferably results from decomposition due to a reversible chemical process, an intramolecular chemical reaction or hydrolysis (i.e. splitting of the molecule or group into two or more new molecules or groups due to the net insertion of one or more water molecules) when it depends on an intermolecular chemical reaction. This chemical instability may occur as a spontaneous chemical event or as a result of the interaction with biomolecular catalysts or reagents.

Cleavage of the linker may be very rapid or very slow. For instance, the half-life of the cleavable linker may be of about 1 minute, about 15 minutes, about 30 minutes, about 1 hour, about 5 hours, about 10 hours, about 15 hours, about 1 day or about 48 hours. The cleavable linker may be an enzyme-sensitive linker that is cleavable only by selected specific enzymes (e.g. amidase, esterase, metalloproteinase, etc) or may be susceptible to cleavage by other chemical means, such as but not limited to acid/base catalysis or self-cleavage. For instance, the linker may be selected such that only 1%, 5%, 10%, 15%, 20%, 25%, 30%, 35%, 40%, 50%, 60%, or 70% of the glycopeptide or lipoglycopeptide antibiotic possessing an altered ionization state is converted into its parent antibiotic through a time period extending to 1 minute, 15 minutes, 30 minutes, 1 hour, 5 hours, 10 hours, 15 hours, 1 day, 2 days, 3 days, 4 days, 5 days, 6 days 7 days, one week, two weeks, three weeks or more following administration of the compound of the invention. Preferably, the linker is selected such that a majority of the ionically charged compound is converted to its parent glycopeptide or lipoglycopeptide antimicrobial molecule per hour. The choice of the linker may vary according to factors such as (i) the site of attachment of the additional ionically charged group to the glycopeptide or lipoglycopeptide antimicrobial molecule, (ii) the type of ionically charged group used; (iii) the identity of glycopeptide or lipoglycopeptide antimicrobial molecule used, and (iv) the desired ease of cleavage of the linker and associated release of the glycopeptide or lipoglycopeptide antimicrobial molecule. Examples of such cleavable linkers suitable for the present invention include but are not limited to those defined as $L^c$ in the summary of the invention above.

The cleavable linker $L^c$ may couple the ionically charged group to a glycopeptide or lipoglycopeptide antimicrobial molecule A through one or more hydroxyl functionalities on A, through one or more nitrogen atoms on A, through one or more carbonyls of a carboxylate group on A, or a combination of one or more hydroxyl functionalities, one or more nitrogen atoms, and/or one or more carbonyls of a carboxylate group, on A. Specific examples of cleavable linkers suitable for coupling ionically charged groups to a glycopeptide or lipoglycopeptide antimicrobial molecule A through a hydroxyl functionality on A include but are not limited to those cleavable linkers defined as $L^c$ in the summary of the invention above for use in such couplings. Specific examples of cleavable linkers suitable for coupling ionically charged groups to a glycopeptide or lipoglycopeptide antimicrobial molecule A through a carbonyl of a carboxylate group on A include but are not limited to those cleavable linkers defined as $L^c$ in the summary of the invention above for use in such couplings. Specific examples of cleavable linkers suitable for coupling ionically charged groups to a glycopeptide or lipoglycopeptide antimicrobial molecule A through a nitrogen atom on A include but are not limited to those cleavable linkers defined as $L^c$ in the summary of the invention above for use in such couplings.

Each cleavable linker $L^c$ may link 1, 2, 3, 4, 5, 6, 7, 8, 9, 10 or more additional ionically charged groups to A. Similarly, if the additional ionically charged group bears more than one point of attachment for the linker $L^c$, then several glycopeptide or lipoglycopeptide antimicrobial molecules A may be coupled to each additional ionically charged group, one for each point of attachment, through any combination of linkers $L^c$. Preferably there are ≤5 glycopeptide or lipoglycopeptide antimicrobial molecules A coupled to each additional ionically charged group, more preferably there are 1, 2 or 3 glycopeptide or lipoglycopeptide antimicrobial molecules A coupled to each additional ionically charged group. The additional ionically charged group linked by the linker $L^c$ to A is M that is unsubstituted or substituted with ligands $L^a$ and/or $L^b$, as defined herein.

The linker is facultative because its presence is dependent upon (i) the site of attachment of the ionically charged group to the glycopeptide or lipoglycopeptide molecule, (ii) the type of functionality present on the ionically charged group used; (iii) the type of glycopeptide or lipoglycopeptide used, and (iv) the desired ease of cleavage of the linker and associated release of the glycopeptide or lipoglycopeptide antibiotic. For instance, it is possible to avoid the linker and tether an additional ionically charged group directly to the carboxyl group of oritavancin.

A pH-sensitive linker that is cleaved only at a predetermined range of pH may also be used in the compounds of the invention. In one embodiment, the pH-sensitive linker is a base-sensitive linker that is cleaved at a basic pH ranging from about 7 to about 9. According to another embodiment, the linker is an acid-sensitive linker that is cleaved at an acidic pH ranging from about 7.5 to about 4, preferably from about 6.5 and lower. It is hypothesized that such an acid-sensitive linker would allow a specific release of the glycopeptide or lipoglycopeptide antibiotic mostly at a site of bacterial infection because it is known that acidification of tissues commonly occurs during infection (O'Reilley et al., *Antimicrobial Agents and Chemotherapy* (1992) 36(12):2693-97).

Glycopeptide and Lipoglycopeptide Antibiotics

Glycopeptide and lipoglycopeptide antibiotics are a well known class of biologically produced or semi-synthetic Gram-positive antimicrobial agents (Williams, D. H et al, Angewandte Chemie International Edition in English (1999) 38:1172-1193; Nicolaou, K. C. et al, Angewandte Chemie International Edition in English (1999) 38:2097-2152; Kahne, D. et al *Chemical Reviews* (2005) 105:425-448; Pace, J. L. et al, *Biochemical Pharmacology* (2006) 71:968-980). Vancomycin and teicoplanin are the best known compounds in this class. Both drugs were proven clinically and microbiologically to have potent activity against Gram-positive organisms. Oritavancin (U.S. Pat. No. 5,840,684), dalbavancin (U.S. Pat. No. 5,750,509) and telavancin (U.S. Pat. No. 6,635, 618) are recent examples of this class of compounds possessing extremely attractive pharmacological profiles with potent activity against gram-positive organisms, including methicillin-resistant *Staphylococcus aureus*, intermediate and fully vancomycin-resistant *Staphylococcus aureus*, vancomycin-resistant *Enterococcus* spp., and *Streptococcus* spp. The present invention is not restricted to a specific glycopeptide or lipoglycopeptide antibiotic, but encompasses all kinds of glycopeptide and lipoglycopeptide molecules having a suitable antimicrobial activity including, but not limited to, those disclosed in the above-listed US patents (incorporated herein by reference) and other glycopeptide and lipoglycopeptide antibiotic derivatives and hybrids such as glycopeptide-cephalosporin (as described in US patent application No 20050239691 for example). Examples of suitable glycopeptide and lipoglycopeptide antimicrobial molecules for use in the present invention include but are not limited to those defined as A in the summary of the invention above.

In particular aspects, A is vancomycin or a derivative thereof, teicoplanin or a derivative thereof, chloroeremomycin or a derivative thereof, oritavancin or a derivative thereof, dalbavancin or a derivative thereof, or telavancin or a derivative thereof. The chemical structures of some relevant examples of these molecules are illustrated hereinafter. Arrows indicate preferred sites for attachment of additional ionically charged groups (direct attachment or via an optional linker), but those skilled in the art will recognize that all hydroxyl, amino, amido and carboxyl groups may be possible sites for attachment:

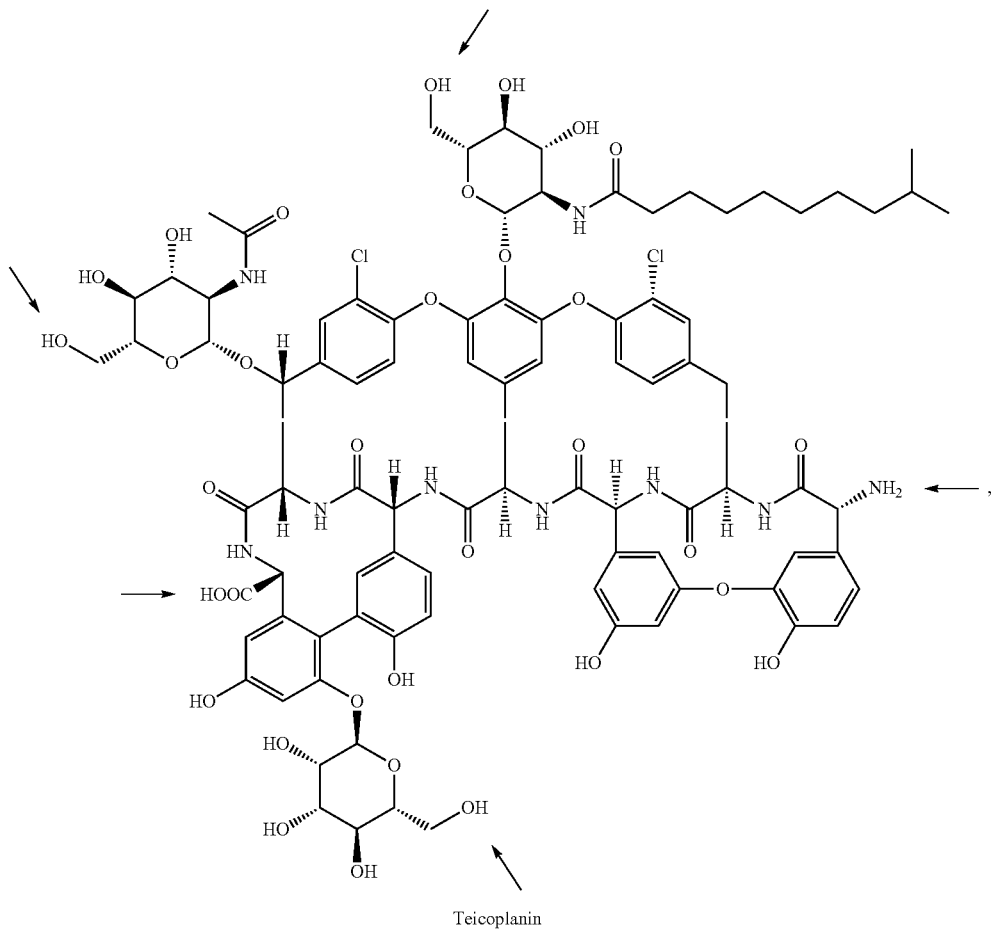

Teicoplanin

-continued
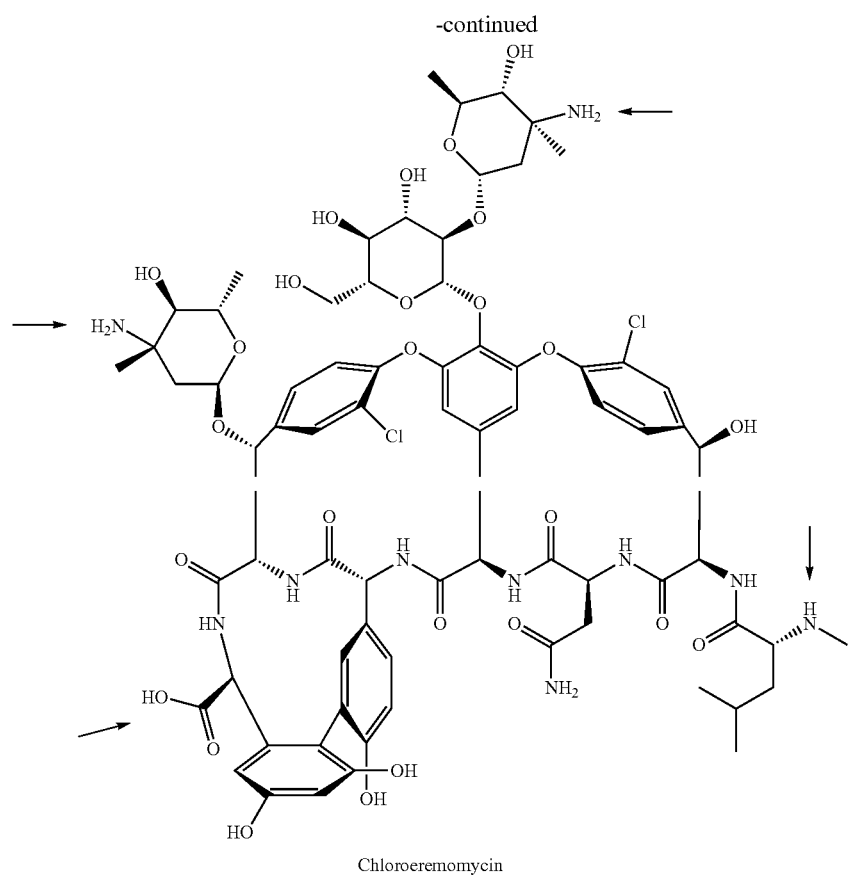
Chloroeremomycin
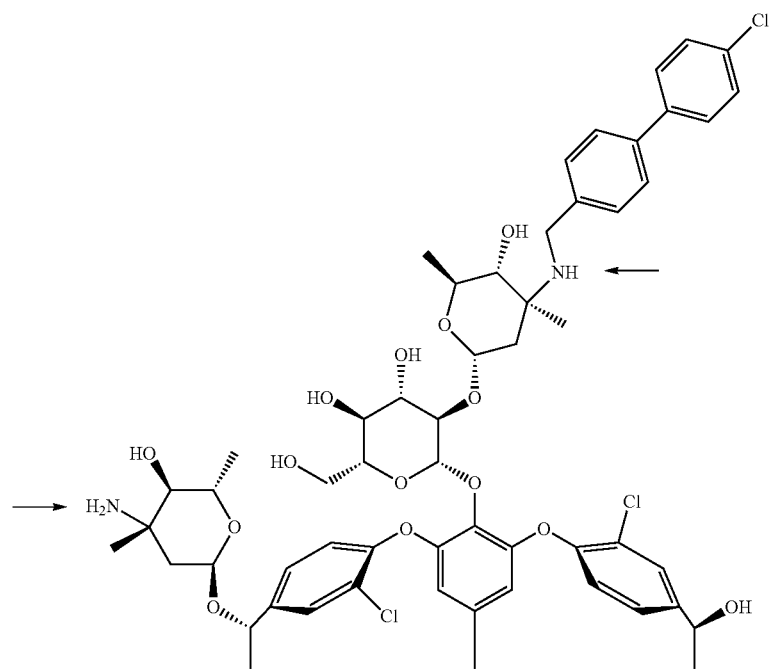

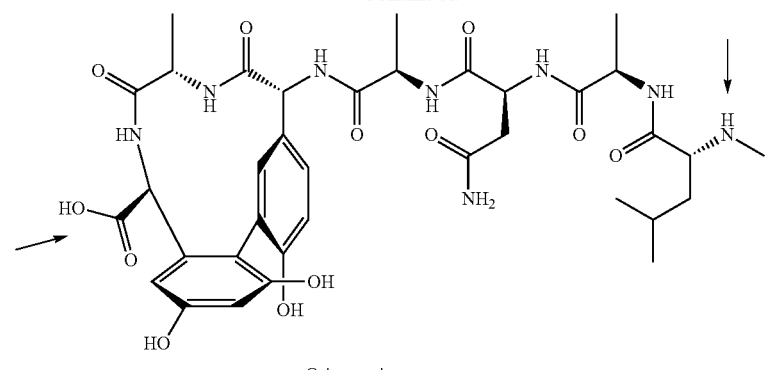
Oritavancin
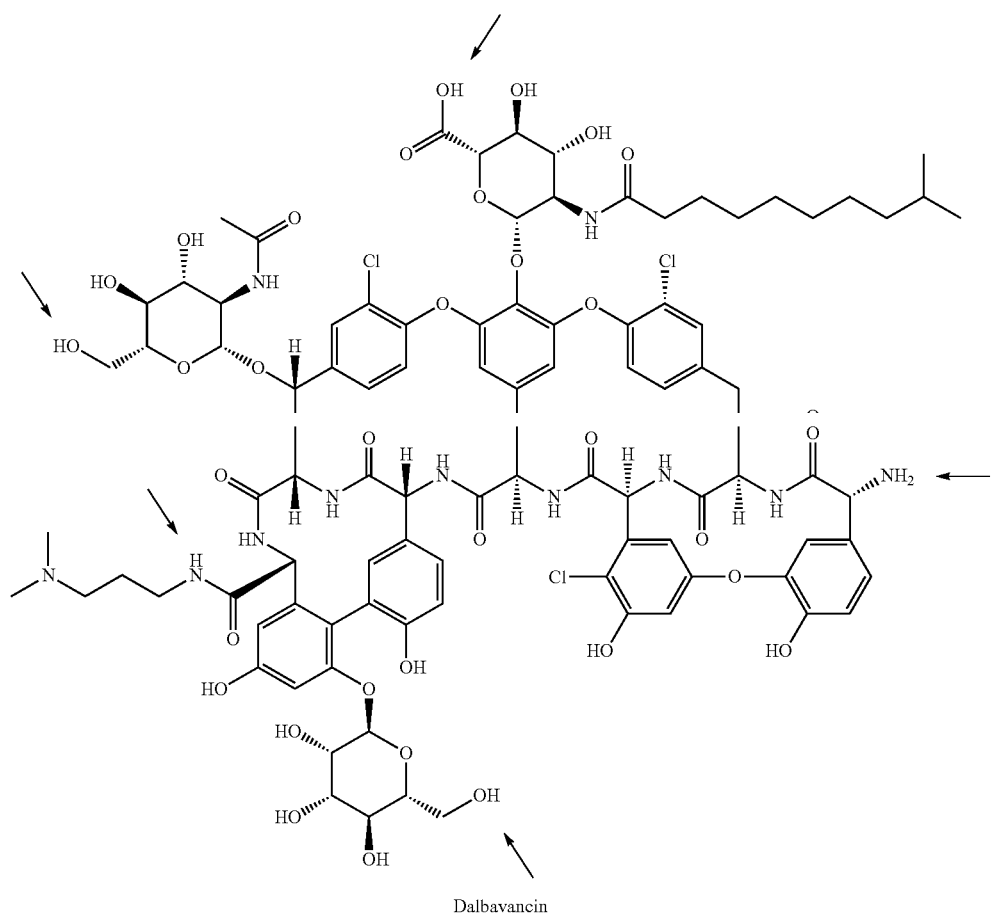
Dalbavancin

-continued

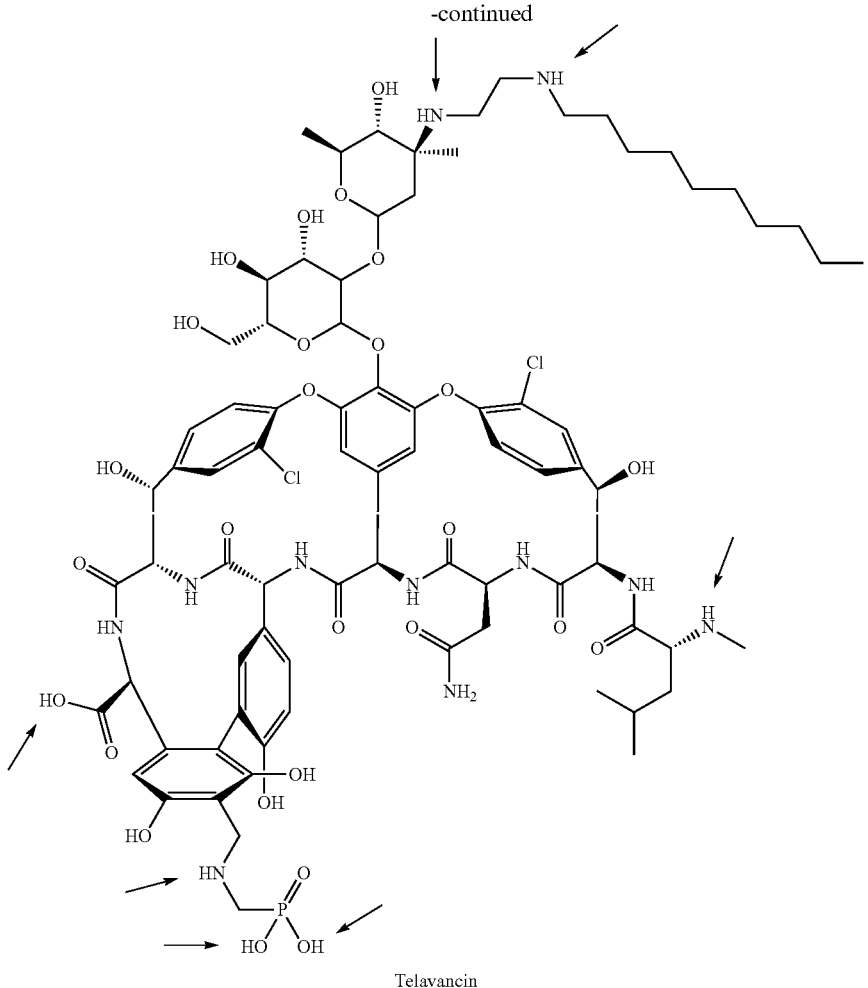

Telavancin

Specific examples of oritavancin derivatives according to the invention are shown in the Exemplification section. Even though in the examples the additional ionically charged groups have not been attached to all the preferred attachment sites shown by the arrows, the results presented in the Exemplification section confirm that it is possible to synthesize biologically active glycopeptide and lipoglycopeptide derivatives having improved solubility in aqueous media isotonic to physiological fluids. Similarly, the invention encompasses glycopeptide and lipoglycopeptide derivatives having more than just one additional ionically charged group (one at the carboxy and one at one of the amino groups on the oritavancin molecule, for instance). As mentioned previously, the above identified sites of attachment are only preferred sites for tethering additional ionically charged groups and all other potential sites (on any of the hydroxyl groups, for instance) are encompassed by the present invention.

Furthermore, while the compounds described in the Exemplification section are based on oritavancin, additional compounds based on dalbavancin, telavancin, teicoplanin and chloroeremomycin, although not described in the Exemplification section, are included as part of the invention.

In other aspects, A is selected from the group consisting of compound A35512 A, compound A35512 C, compound A35512 E, compound A35512 F, compound A35512 G, compound A35512 H, compound A40926 A, compound A40926 B, compound A40926 PB, parvodicin B2, parvodicin C1, parvodicin C3, compound A41030, compound A42867, compound A477, compound A47934, compound A51568A, N-demethylvancomycin, compound A80407, compound A83850, compound A84575, compound AB65, compound AM374, actaplanin, compound A4696, actinoidin, ardacin, aricidin, compound AAD216, avoparcin, compound LL-AV290, azureomycin, balhimycin, balhimycin V, chloroorienticin, compound A82846B, compound LY264826, chloropeptin, chloropolysporin, complestatin, decaplanin, dechlorobalhimycin, dechlorobalhimycin V, chlorobalhimycin, chlorobromobalhimycin, fluorobalhimycin, deglucobalhimycin, N-demethylbalhimycin, N-demethylvancomycin, devancosamine-vancomycin, eremomycin, galacardin, helvecardin, izupeptin, kibdelin, kistamicin, mannopeptin, methylbalhimycin, compound MM47761, compound MM47766, compound MM47767, compound MM49721, compound MM49727, compound MM55256, compound MM55260, compound MM55266, compound MM55268, compound MM55270, compound MM55272, compound MM56597, compound MM56598, nogabecin F, compound OA7653, orienticin, dechloroeremomycin, compound PA42867, compound PA45052, chloroorienticin, parvodicin, rhamnosyl-balhimycin, ristocetin, ristomycin, spontin, symnonicin, teichomycin, Targocid, ureido-balhimycin and [Ψ[CH$_2$NH]Tpg$^4$]Vancomycin.

Those skilled in the art will readily identify, isolate and/or prepare the suitable glycopeptide or lipoglycopeptide antimicrobial molecules according to the invention. If necessary, reference may be made to the numerous literatures found in the art, including the US patents and PCT patent applications listed hereinbefore, and more particularly to U.S. Pat. Nos. 5,840,684, 5,750,509 and 6,635,618.

The compounds encompassed within the scope of the invention include those compounds encompassed by Formula (II), Formula (III) and Formula (IV). Each of the compounds encompassed by Formula (II), Formula (III) and Formula (IV) is also encompassed within Formula (I). Formula (II) is similar in scope to Formula (I), but provides a more detailed chemical structure. Formula (III) is directed to a subset of compounds that fall within the scope of Formula (II). Formula (IV) is also directed to a subset of compounds that fall within the scope of Formula (II). Formula (II), Formula (III) and Formula (IV) are as defined in the summary of the invention above.

In addition to the compounds of Formula (I), (II), (III) and (IV), the invention encompasses pharmaceutically acceptable salts, esters, stereoisomers and prodrugs of these compounds. While salts, esters, stereoisomers and prodrugs are discussed below, the skilled artisan will understand that "pharmaceutically acceptable" means suitable for administration to a subject, such as a mammal, preferably a human.

Salts of glycopeptide and lipoglycopeptide antibiotics possessing an altered ionization state with respect to the parent glycopeptide or lipoglycopeptide antibiotic of the present invention means a salt that retains or improves the biological effectiveness and properties of the free acids and bases of the parent compound as defined herein or that takes advantage of an intrinsically charged functionality on the molecule and that is not biologically or otherwise undesirable. Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycolates, tartrates, methanesulfonates, propanesulfonates, naphthalene-1-sulfonates, naphthalene-2-sulfonates, and mandelates.

If the inventive compound is a base, the desired salt may be prepared by any suitable method known to the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such as p-toluenesulfonic acid or ethanesulfonic acid, or the like.

If the inventive compound is an acid, the desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum, and lithium.

In the case of compounds, salts, or solvates that are solids, it is understood by those skilled in the art that the inventive compounds, salts, and solvates may exist in different crystal forms, all of which are intended to be within the scope of the present invention.

An in vivo hydrolysable ester of a compound of Formula (I), (II), (III) or (IV) containing carboxy or hydroxy group is, for example, a pharmaceutically acceptable ester which is hydrolyzed in the human or animal body to produce the parent acid or alcohol. Suitable pharmaceutically acceptable esters containing a carboxy group include (1-6C)alkoxymethyl esters, for example methoxymethyl; (1-6C)alkanoyloxymethyl esters, for example pivaloyloxymethyl; phthalidyl esters; (3-8C)cycloalkoxycarbonyloxy(1-6C)alkyl esters, for example 1-cyclohexylcarbonyloxyethyl; 1,3-dioxolen-2-onylmethyl esters, for example 5-methyl-1,3-dioxolen-2-onylmethyl; and (1-6C)alkoxycarbonyloxyethyl esters, for example 1-methoxycarbonyloxyethyl, and may be formed at any carboxy group in the compounds of this invention.

An in vivo hydrolysable ester of a compound of Formula (I), (II), (III) or (IV) containing a hydroxy group includes inorganic esters such as phosphate esters and alpha-acyloxyalkyl ethers and related compounds which, as a result of in vivo hydrolysis of the ester, break down to give the parent hydroxy group. Examples of alpha-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

The compounds of Formula (I), (II), (III) and (IV) may exist as single stereoisomers, racemates and/or mixtures of enantiomers and/or diastereomers. All such single stereoisomers, racemates and mixtures thereof are intended to be within the scope of the present invention. Preferably, the inventive compounds are used in an optically pure form.

The compounds of Formula (I), (II), (III) and (IV) may be formulated as prodrugs. According to the present invention, a prodrug is an inactive (or significantly less active) form of any of the glycopeptide and lipoglycopeptide antimicrobial compounds of the present invention. Upon in vivo processing, prodrugs of the present invention release an active glycopeptide or lipoglycopeptide antimicrobial molecule. Prodrugs of glycopeptide and lipoglycopeptide antimicrobial molecules of the present invention may be prepared by modifying functional groups present on the glycopeptide and lipoglycopeptide antimicrobial molecules in such a way that the modifications may be cleaved in vivo to release the glycopeptide and lipoglycopeptide antimicrobial molecules.

Prodrugs include compounds of Formula (I), (II), (III) and (IV) wherein a hydroxyl, carboxyl or amino group in the glycopeptide and lipoglycopeptide antimicrobial molecule portion of the compound is bonded to any group that may be cleaved in vivo to regenerate the free hydroxyl, carboxyl or amino group, respectively. Such prodrug groups are in addition to the linker that may be coupled to a hydroxy, carboxy and/or amino group of a glycopeptide or lipoglycopeptide antimicrobial molecule. Examples of prodrug groups include, but are not limited to, esters (e.g., acetate, formate, and benzoate derivatives) and carbamates (e.g., N,N-dimethylaminocarbonyl) on hydroxy functional groups of the glycopeptide and lipoglycopeptide antimicrobial molecule portion of the compounds of the present invention. The present invention also includes those prodrugs requiring two or more events in prodrug cleavage. According to that embodiment, more complex compounds would release, upon cleavage, a prodrug of a glycopeptide or lipoglycopeptide antimicrobial molecule, the latter prodrug being activatable to release a desired glycopeptide or lipoglycopeptide antimicrobial molecule. The skilled artisan will understand that prodrugs of glycopeptide and lipoglycopeptide antimicrobial molecules of the present invention may undergo two cleavage events, or that a single cleavage event may be the result of a succession of distinct or concomitant chemical steps. Thus cleavage of the cleavable linker may release a functional group from the prodrug leaving a second moiety that is cleaved subsequently to release the free drug.

C) PHARMACEUTICAL COMPOSTIONS

The compounds of the present invention may be formulated for administration to a subject, such as a human, as pharmaceutical compositions. The pharmaceutical compositions of the invention comprise at least one compound of Formula (I), (II), (III) or (IV), or a pharmaceutically acceptable salt, ester, stereoisomer or prodrug thereof, and a pharmaceutically acceptable carrier or excipient.

Pharmaceutically acceptable carriers and excipient are those compounds, solutions, substances or materials that can be used to produce formulations of the antimicrobial compounds of the present invention that are suitable for administered to a subject. In particular, carriers and excipients of the present invention are those useful in preparing a pharmaceutical composition that is generally safe, non-toxic and neither biologically nor otherwise undesirable, and that may present pharmacologically favorable profiles, and includes carriers and excipient that are acceptable for veterinary use as well as human pharmaceutical use. Suitable pharmaceutically acceptable carriers and excipients are well known in art and can be determined by those of skill in the art as the clinical situation warrants. The skilled artisan will understand that diluents are included within the scope of the terms carriers and excipients. Examples of suitable carriers and excipients include saline, buffered saline, dextrose, water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin; see, e.g., U.S. patent application publication 20060194717), hydrophilic and hydrophobic carriers, and combinations thereof. Hydrophobic carriers include, for example, fat emulsions, lipids, PEGylated phospholids, polymer matrices, biocompatible polymers, lipospheres, vesicles, particles, and liposomes. The terms specifically exclude cell culture medium. More particularly: (1) Dulbecco's phosphate buffered saline, pH about 7.4, containing about 1 mg/ml to 25 mg/ml human serum albumin, (2) 0.9% saline (0.9% w/v NaCl), (3) 5% (w/v) dextrose, or (4) water, may be used.

Excipients included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavouring agents, coloring agents, administration aids, and combinations thereof.

The compositions may contain common carriers and excipients, such as cornstarch or gelatin, lactose, sucrose, microcrystalline cellulose, kaolin, mannitol, dicalcium phosphate, sodium chloride, alginic acid, croscarmellose sodium, and sodium starch glycolate.

The particular carrier, diluent or excipient used will depend upon the means and purpose for which the active ingredient is being applied.

Pharmaceutically acceptable excipients also include tonicity agents that make the composition compatible with blood. Tonicity agents are particularly desirable in injectable formulations.

Acceptable methods for preparing the pharmaceutical compositions according to the invention are known to those skilled in the art. For example, pharmaceutical compositions may be prepared following conventional techniques of the pharmaceutical chemist involving steps such as mixing, granulating, and compressing when necessary for tablet forms, or mixing, filling, and dissolving the ingredients as appropriate, to give the desired products for various routes of administration.

D) METHODS OF TREATMENT

The invention is also concerned with the use of compounds of the invention in the treatment or prevention of bacterial infections. The invention therefore includes methods of inhibiting bacterial growth, and more particularly growth of Gram-positive bacteria. The methods of the invention comprise contacting bacteria for the purpose of such inhibition with an effective amount of at least one compound of Formula (I), (II), (III) or (IV), or a pharmaceutically acceptable salt, ester, stereoisomer or prodrug thereof. For example, one can inhibit cell wall biosynthesis in a Gram-positive bacterium by contacting such a bacterium with a compound of the invention. Non-limiting examples of the methods of the invention are provided above in the summary of the invention.

The contacting may be carried out in vitro (in biochemical and/or cellular assays), in vivo in a non-human animal, in vivo in mammals, including humans and/or ex vivo (e.g. for sterilization purposes). As used herein, the term "contacting" is meant to broadly refer to bringing a bacterial cell and a molecule of a compound of the present invention into sufficient proximity such that the compound can exert an effect on the bacterial cell. The compound may be transported to the location of the bacterial cell, or the compound may be situated in a location to which the bacterial cell travels or is brought into contact. The skilled artisan will understand that the term "contacting" includes physical interaction between a compound and a bacterial cell, as well as interactions that do not require physical interaction.

The activity of the inventive compounds as inhibitors of cell-wall biosynthesis may be measured by any of the methods available to those skilled in the art, including in vivo and in vitro assays. Some examples of suitable assays have been described for measurement of binding to cell-wall fragments (Chu et al. Journal of Organic Chemistry (1992), 57:3524-3525; Cooper et al, Chemical Communications (1997), 1625-1626), binding to whole cell walls (Cegelski et al. Journal of Molecular Biology (2006), 357; 1253-1262), inhibition of enzymatic processes leading to cell wall components (Branstrom et al. FEMS Microbiology Letters (2000), 191:187-

190; Leimkuhler et al. Journal of the American Chemical Society (2005), 127: 3250-3251) and inhibition of cell wall biosynthesis at the cellular level (Higgins et al., Antimicrobial Agents and Chemotherapy (2005), 49: 1127-1134).

A related aspect of the invention concerns the use of a compound of the invention as an active ingredient in a pharmaceutical, therapeutic or anti-bacterial composition for treatment purposes. Thus the invention includes methods of treating bacterial infections through the administration of a pharmaceutically effective amount of at least one compound of the invention (i.e., the compounds of Formula (I), (II), (III), and (IV)) to a subject in need of treatment. Preferably, the compounds of the invention are administered to the subject in the form of a pharmaceutical composition, as defined herein. The terms "treating" and "treatment" mean at least the mitigation of a disease condition or symptom associated with a bacterial infection in a subject, including mammals such as a human, that is achieved by a reduction of growth, replication, and/or propagation of any bacterium, such as Gram-positive organisms, and includes curing, healing, inhibiting, relieving from, improving and/or alleviating, in whole or in part, the disease condition. The mitigation may be about 100%, 99%, 98%, 97%, 96%, 95%, 90%, 80%, 70%, 60%, 50%, 40%, 30%, 20%, 10%, 5% or 1% in the subject, versus a subject to which a pharmaceutical composition has not been administered. Non-limiting examples of the methods of the invention are provided above in the summary of the invention.

The invention also includes methods of preventing bacterial infections in a subject through the administration of a pharmaceutically effective amount of at least one compound of the invention (i.e., the compounds of Formula (I), (II), (III), and (IV)) to a subject in need of prevention. Preferably, the compounds of the invention are administered to the subject in the form of a pharmaceutical composition, as defined herein. The terms "prevent" and "prevention" mean blocking or stopping a disease condition associated with a bacterial infection from developing in a mammal, preferably a human. Such methods may be practiced, for example, on subjects having a higher risk for bacterial infection than the general population, including patients undergoing treatment for bacterial infections whereby normal gut flora is inhibited by antimicrobial therapy, patients with impaired immune function (e.g., immunoglobulin deficiency, splenic dysfunction, splenectomy, HIV infection, impaired leukocyte function, hemoglobinopathies), the elderly (Loo et al., 2005. NEJM 353:2442), people with certain malignancies (e.g., multiple myeloma, chronic lympocytic leukemia, lymphoma), people at increased occupational risk (e.g., public services workers, such a fire, water, sanitary, police, medical, and laboratory workers, hospital workers), people in closed populations (e.g., prisons, military, nursing homes) and others that have immunological deficiencies that might enhance their susceptibility to bacterial infection. The prevention may be protection of about 100%, 99%, 98%, 97%, 96%, 95%, 90%, 80%, 70%, 60%, 50%, 40%, 30%, 20%, 10%, 5% or 1% in the subject, versus a subject to which a pharmaceutical composition has not been administered. The prevention lasts at least about 0.5, 1, 2, 3, 4, 5, 6, 7, 8, 9, 10, 12, 14, 16, 18, 20, 25, 30, 35, 40, 45, 50 or more days after administration of a pharmaceutical composition.

In order to prevent infection, the compound(s) of the invention could be administered once, twice, thrice or more, from 1, 2, 3, 4, 5, 6, 7 days or more, up to 10, 9, 8, 7, 6, 5, 4, 3, 2, or 1 hour or less before the subject has the potential to be exposed to the bacteria. Non-limiting examples of the methods of the invention are provided above in the summary of the invention.

An additional use that is particularly contemplated for the compounds of the invention is for prophylaxis purposes. Indeed, many surgeons consider that humans should be considered for antibiotic prophylaxis before a procedure to mitigate the potential for an infection resulting from ineffective sterility during the procedure. Deep infection is a serious complication sometimes requiring subsequent medical interventions and is accompanied by significant morbidity and mortality. The compounds and compositions of the invention may therefore be used as a replacement for, or in addition to, prophylactic antibiotics in this situation. For instance, the compounds and/or compositions of the invention may be administered by injection to achieve a systemic and/or local effect against relevant bacteria shortly before an invasive medical treatment, such as surgery or insertion of an in-dwelling device (e.g. joint replacement (hip, knee, shoulder, etc.)). Treatment may be continued after invasive medical treatment, such as post-operatively or during the in-body time of the device.

Thus, the invention also includes methods of providing propylaxis for bacterial infections in a subject through the administration of a prophylactically effective amount of at least one compound of the invention (i.e., the compounds of Formula (I), (II), (III), and (IV)) to a subject in need of propylaxis. Preferably, the compounds of the invention are administered to the subject in the form of a pharmaceutical composition, as defined herein. Non-limiting examples of the methods of the invention are provided above in the summary of the invention.

The term "prophylaxis" is intended to mean at least a reduction in the likelihood that a disease condition associated with a bacterial infection will develop in a mammal, preferably a human. In particular, the term is related to the treatment of a mammal to reduce the likelihood of the occurrence of a bacterial infection, such as bacterial infection that may occur during or following a surgery involving bone reparation or replacement. The term also includes reducing the likelihood of a bacterial infection when the mammal is found to be predisposed to having a disease condition but not yet diagnosed as having it. For example, one can reduce the likelihood of a bacterial infection in a mammal by administering a compound of Formula (I), (II), (II) or (IV), or a pharmaceutically acceptable salts, esters, stereoisomers and prodrug thereof, before occurrence of such infection. The prophylaxis may be about a reduction of about 100%, 99%, 98%, 97%, 96%, 95%, 90%, 80%, 70%, 60%, 50%, 40%, 30%, 20%, 10%, 5% or 1% in the subject, versus a subject to which a pharmaceutical composition has not been administered. The prophylaxis lasts at least about 0.5, 1, 2, 3, 4, 5, 6, 7, 8, 9, 10, 12, 14, 16, 18, 20, 25, 30, 35, 40, 45, 50 or more days after administration of a pharmaceutical composition.

In each instance, the compound(s) of the invention could be administered once, twice, thrice or more, from 1, 2, 3, 4, 5, 6, 7 days or more, up to 10, 9, 8, 7, 6, 5, 4, 3, 2, or 1 hour or less before surgery for permitting an advisable systemic or local presence of the compounds, preferably in the areas potentially exposed to bacterial contamination during the surgical procedure. The compound(s) may be administered after the invasive medical treatment for a period of time, such as 1, 2, 3, 4, 5 or 6 days, 1, 2, 3 or more weeks, or, for example, for the entire time in which an in-dwelling medical device is present in the body of the subject.

Although the invention is preferably directed to the prevention and/or treatment of bacterial infections, the invention encompasses therapeutic and prophylactic methods against other diseases caused by or related to bacterial infection, including but not limited to otitis, conjunctivitis, pneumonia, bacteremia, sinusitis, pleural emphysema and endocarditis, low grade infections in the vicinity of calcifications of atherosclerotic vessels, osteomyelitis and meningitis. In such methods, an effective therapeutic or prophylactic amount of an antibacterial compound and/or composition as defined hereinbefore, is administered to a mammal (preferably a human) in an amount sufficient to provide a therapeutic effect and thereby prevent or treat the infection of the mammal. Exact amounts can be routinely determined by one skilled in the art and will vary depending on several factors, such as the particular bacterial strain involved and the particular antibacterial compound used.

The pharmaceutical compositions and compounds of the present invention may be formulated, for example, for oral, sublingual, intranasal, intraocular, rectal, transdermal, mucosal, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used to effect such administration.

Formulations for parenteral administration can be in the form of aqueous or non-aqueous isotonic sterile injection solutions, suspensions or fat emulsions. The parenteral form used for injection must be fluid to the extent that easy syringability exists. These solutions or suspensions can be prepared from sterile concentrated liquids, powders or granules.

Excipients used in parenteral preparations may also include, without limitation, stabilizing agents (e.g. carbohydrates, amino acids and polysorbates, such as 5% dextrose), solubilizing agents (e.g. cetrimide, sodium docusate, glyceryl monooleate, polyvinylpyrolidone (PVP) and polyethylene glycol (PEG)), surfactants (e.g. polysorbates, tocopherol PEG succinate, poloxamer and Cremophor™), buffers (e.g. acetates, citrates, phosphates, tartrates, lactates, succinates, amino acids and the like), antioxidants and preservatives (e.g. BHA, BHT, gentisic acids, vitamin E, ascorbic acid, sodium ascorbate and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vaso-constrictors for prolongation and agents that increase tissue permeability), and combinations thereof.

Parenteral formulations using hydrophobic carriers include, for example, fat emulsions and formulations containing lipids, lipospheres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In another embodiment, the parenteral unit dosage form of pharmaceutical compositions and compounds of the present invention can be a ready-to-use solution of the pharmaceutical compositions and compounds in a suitable carrier in sterile, hermetically sealed ampoules or in sterile pre-loaded syringes. The suitable carrier optionally comprises any of the above-mentioned excipients.

Alternatively, the unit dosage of the pharmaceutical compositions and compounds of the present invention can be in a concentrated liquid, powder or granular form for ex tempore reconstitution in the appropriate pharmaceutically acceptable carrier, such as sterile water, at the time of delivery. In addition to the above-mentioned excipients, powder forms optionally include bulking agents (e.g. mannitol, glycine, lactose, sucrose, trehalose, dextran, hydroxyethyl starch, ficoll and gelatin), and cryo or lyoprotectants.

In intravenous (IV) use, a sterile formulation of the pharmaceutical compositions of the present invention and optionally one or more additives, including solubilizers or surfactants, can be dissolved or suspended in any of the commonly used intravenous fluids and administered by infusion. Intravenous fluids include, without limitation, physiological saline, phosphate buffered saline, 5% dextrose in water or Ringer's™ solution.

In intramuscular preparations, a sterile formulation of the pharmaceutical compositions of the present invention can be dissolved and administered in a pharmaceutical diluent such as Water-for-Injection (WFI), physiological saline or 5% dextrose in water. A suitable insoluble form of the pharmaceutical compositions may be prepared and administered as a suspension in an aqueous base or a pharmaceutically acceptable oil base, e.g. an ester of a long chain fatty acid such as ethyl oleate.

For oral use, the oral pharmaceutical composition may be made in the form of a unit dosage containing a therapeutically-effective amount of the pharmaceutical compositions. Solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, tablets, capsules, suspensions or liquid syrups or elixirs, wafers and the like. For general oral administration, excipient or additives include, but are not limited to inert diluents, fillers, disintegrating agents, binding agents, wetting agents, lubricating agents, sweetening agents, flavoring agents, coloring agents and preservatives.

Oral liquid preparations, generally in the form of aqueous or oily solutions, suspensions, emulsions or elixirs, may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, microcrystalline cellulose, methyl or propyl para-hydroxybenzoate, propylene glycol, sorbitol, or sorbic acid.

For topical use, the pharmaceutical compositions of present invention can also be prepared in suitable forms to be applied to the skin, or mucus membranes of the nose and throat, and can take the form of creams, ointments, nasal drops, liquid sprays or inhalants, lozenges, or throat paints. Such topical formulations further can include chemical compounds such as dimethylsulfoxide (DMSO) to facilitate surface penetration of the active ingredient. For application to the eyes or ears, the pharmaceutical compositions can be presented in liquid or semi-liquid form formulated in hydrophobic or hydrophilic bases as ointments, creams, lotions, paints or powders. For rectal administration the pharmaceutical compositions can be administered in the form of suppositories admixed with conventional carriers such as cocoa butter, wax or other glyceride.

In a preferred intravenous (IV) formulation for use in the methods of the present invention, the compounds are administered in a dosage of between about 100 mg and 2000 mg, preferably about 100, 125, 150, 175, 200, 225, 250, 275, 300, 325, 350, 375, 400, 450, 500, 600, 700, 800, 900, 1000, 1100, 1200, 1300, 1400, 1500 or more mg, by IV infusion over approximately 60, 90, 120 or more minutes, every 6, 12, 18 or 24 hours for 1, 2, 3, 4, 5, 6, 7, 8, 9, 10 or more days. In this embodiment, the compounds may be reconstituted in sterile water for injection (WFI). Further in this embodiment, the compounds may be diluted in 5% dextrose in water (D5W) to a total volume of at least 250 mL. Preferably the resultant concentration is no more than 0.8 mg/mL for a 200-mg dose, 1.0 mg/mL for a 250-mg dose, and 1.2 mg/mL for a 300-mg dose.

In a preferred oral formulation for use in the methods of the present invention, the compounds are administered in an oral dosage of between about 0.5 to about 100 mg per kg body weight of the subject to which the oral formulation is being administered, more preferably about 5 to about 30 mg per kg body weight, including about 5, 10, 15, 20, 25 and 30 mg per kg body weight. The course of treatment via oral administration may be a single dose or multiple doses. When multiple doses are administered orally, administration may be once, twice, thrice or more times per day. A course of oral treatment may be for one or more days, such as two, three, four, five, six, seven, eight, nine, ten or more days. In one embodiment, the compounds may be formulated in 10% hydroxypropyl beta-cyclodextrin. In a further embodiment the compounds may be formulated in 85% polyethylene glycol 400 (PEG400) in sterile water. The oral formulation may be in the form of a liquid to be drunk by the subject, in the form of a capsule containing the formulation, or other means known to the skilled artisan for administering an oral formulation.

The terms "dose", "unit dose", "unit dosage", or "effective dose" refer to physically discrete units that contain a predetermined quantity of active ingredient calculated to produce a desired therapeutic effect. These terms are synonymous with pharmaceutically effective amounts, therapeutically effective amounts, prophylactically effective amounts and amounts sufficient to achieve the stated goals of the methods disclosed herein.

The pharmaceutically effective amount of the compounds of the present invention and the amounts sufficient to achieve the stated goals of the methods disclosed herein vary depending upon the physical characteristics of the subject, the severity of the subject's symptoms, the identity of the bacteria, the formulation and the means used to administer the drug, and the method being practiced. The specific dose for a given subject is usually set by the judgment of the attending physician. However, a pharmaceutically effective and/or sufficient amount of a compound of the present invention is typically between about 0.5 mg/kg body weight to 100 mg/kg body weight, preferably from 1 to 50 mg/kg, more preferably from 5 to 30 mg/kg, regardless of the formulation. In equally preferred embodiments, a pharmaceutically effective amount used for a single dose is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 mg/kg body weight, regardless of the formulation. In some situations, a dose less than 0.5 mg/kg body weight or greater than 100 mg/kg body weight may be effective.

Suitable frequencies of administration may vary based on whether administration is for the purposes of treatment, prophylaxis or prevention. Administration frequencies of doses for the treatment of a subject having a bacterial infection, or for prophylaxis or prevention of a bacterial infection, include 4, 3, 2 or once daily, every other day, every third day, every fourth day, every fifth day, every sixth day, once weekly, every eight days, every nine days, every ten days, bi-weekly, monthly and bi-monthly. In certain methods and embodiments of the present invention a single dose or infrequent dose (e.g., 2, 3, 4, 5 or six doses) can be sufficient to achieve the stated goals of the methods claimed herein. In other embodiments, the course of treatment may required the administration of many doses over many days, such as administration of a dose 4, 3, 2 or once daily over 1, 2, 3, 4, 5, 6, 7, 8, 9, 10, 11, 12, 13, 14, 15 or more days.

Depending on the means of administration, the dosage may be administered all at once, such as with an oral formulation in a capsule, or slowly over a period of time, such as with an intravenous administration. For slower means of administration, the administering period can be a matter of minutes, such as about 5, 10, 15, 20, 25, 30, 35, 40, 45, 50, 55, 60, 65, 70, 75, 80, 85, 90, 95, 100, 105, 110, 115, 120 or more minutes, or a period of hours, such as about 0.5, 1, 1.5, 2, 2.5, 3, 3.5, 4, 4.5, 5 or more hours.

While the treatment can be administered in a systemic manner through the means described above, it may also be administered in a localized manner. For example, the treatment may be administered directly, such as through a topical composition or directly into a subcutaneous or other form of wound.

Each of the methods of the present invention may also be practiced by administering an additional therapeutic agent to the subject. Such additional therapeutic agents are in addition to the compounds of the invention that are used in the pharmaceutical formulations. A wide range of second therapeutic agents, such as antibiotics, can be used in combination with the compounds, compositions and methods of the present invention. Antibiotics used as second therapeutic agents may act by interfering with cell wall synthesis, plasma membrane integrity, nucleic acid synthesis, ribosomal function, folate synthesis, etc. A non-limiting list of useful antibiotics includes: fusidic acid, trimethoprim, sulfadiazine, sulfamethoxazole, a penicillin, a monobactam, a penam, a penem, a clavam, a clavem, a carbopenam, a carbopenem, a cepham, a cephem, an oxacepham, an oxacephem, a carbocepham, a carbocephem, a cephalosporin, tetracycline, a tetracycline derived antibacterial agent, glycylcycline, a glycylcycline derived antibacterial agent, minocycline, a minocycline derived antibacterial agent, sancycline, a sancycline derived antibacterial agent, methacycline, a methacycline derived antibacterial agent, an oxazolidinone antibacterial agent, an aminoglycoside antibacterial agent, a quinolone antibacterial agent, daptomycin, a daptomycin derived antibacterial agent, rifamycin, a rifamycin derived antibacterial agent, rifampin, a rifampin derived antibacterial agent, rifalazil, a rifalazil derived antibacterial agent, rifabutin, a rifabutin derived antibacterial agent, rifapentin, a rifapentin derived antibacterial agent, rifaximin and a rifaximin derived antibacterial agent.

The second therapeutic agent may be administered before, concurrently with, or after a pharmaceutical formulation of the present invention is administered to a subject.

The compounds and compositions of the invention are conceived to have a broad spectrum of activity, including antibiotic resistant strains, mostly against Gram-positive (e.g. *Staphylococcus aureus, Staphylococcus epidermis, Streptococcus pyogenes, Streptococcus pneumoniae, Enterococcus faecalis, Enterococcus faecium* and *Clostridium difficile* (both vegetative form and spores)). Thus, the methods of the present invention may be used in the treatment, prevention and/or prophylaxis of one or more of *Staphylococcus aureus, Staphylococcus epidermis, Streptococcus pyogenes, Streptococcus pneumoniae, Enterococcus faecalis, Enterococcus faecium* and *Clostridium difficile* (both vegetative form and spores), in addition to other Gram-positive bacteria.

E) METHODS OF PREPARATION

The inventive compounds, and their salts, esters, solvates, crystal forms, active metabolites, and prodrugs, may be prepared by employing the techniques available in the art using starting materials that are readily available. Certain novel and exemplary methods of preparing the inventive compounds are described in the Exemplification section below. Such methods are within the scope of this invention.

EXAMPLES

The Examples set forth herein below provide exemplary syntheses of certain representative compounds of the invention. Also provided are exemplary methods for assaying the minimum inhibitory concentration (MIC) of the compounds of the invention against microorganisms, and methods for testing in vivo activity.

Example 1

Synthesis of Oritavancin Poly(Ethylene Glycol) Conjugates

A) General Experimental Procedures
A 1) Preparation of Building Blocks

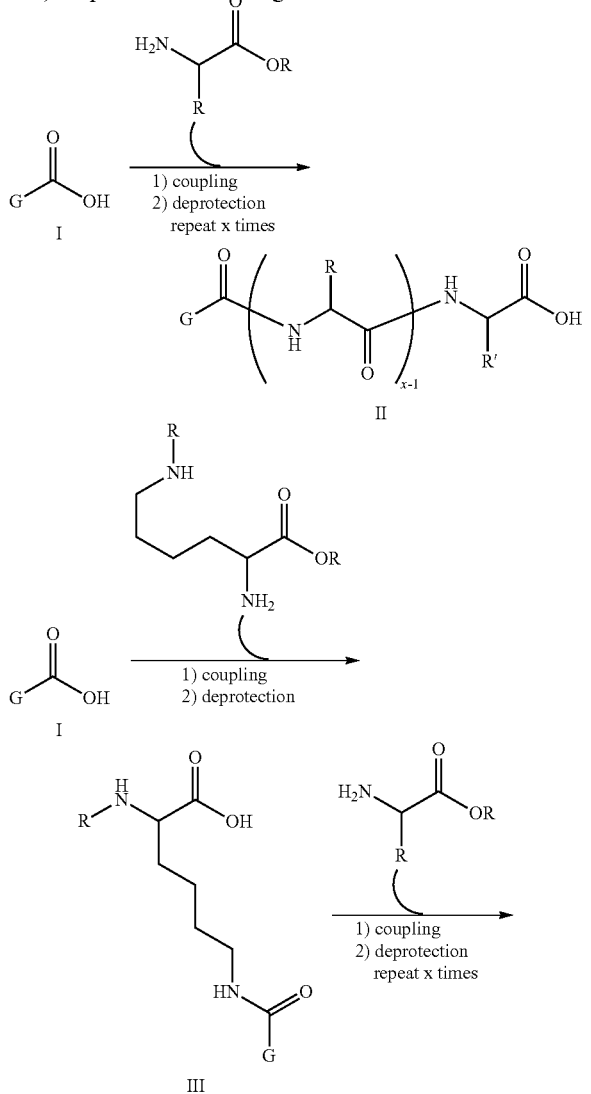

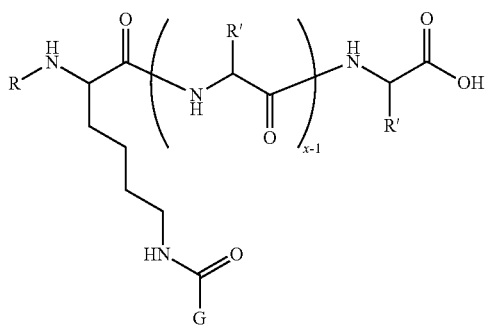

IV

Ionizable groups G, adequately protected (for instance as reviewed in "*Protective Groups in Organic Synthesis*", Greene, T. W. and Wuts, P. M. G., Wiley-Interscience, New York, 1999) may be prepared as part of a molecule possessing a free carboxylic group (I). These may be used directly or can be extended by the insertion of an amino acid (x=1) or a short peptide (x>1) in acids II, III and IV. This transformation can be made by coupling I with an amino acid protected at the carboxylate function in the presence of a standard peptide coupling reagent such as a carbodiimide or an activated uronium salt. The carboxylate of the coupled amino acid can then be deprotected under standard conditions and this process may be repeated to extend the chain further. A similar process can be used but starting with a coupling to the ε amino group of a lysine protected at both the carboxylate and the α-amino acid groups. This can give, after deprotection, a carboxylic acid of general formula III, which can be further extended to acids of general formula IV.

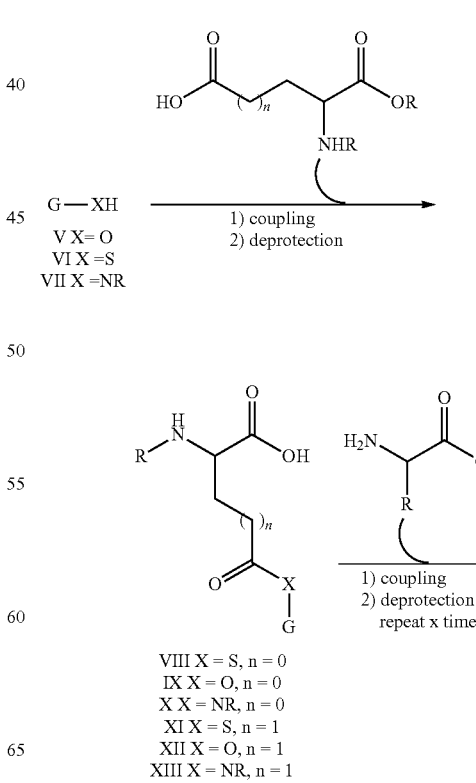

VIII X = S, n = 0
IX X = O, n = 0
X X = NR, n = 0
XI X = S, n = 1
XII X = O, n = 1
XIII X = NR, n = 1

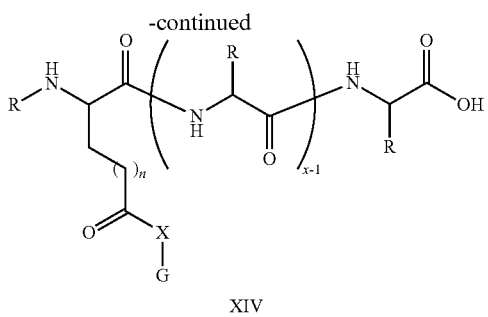

XIV

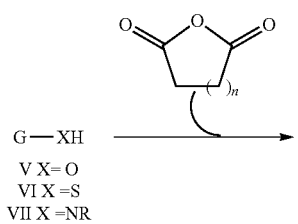

G—XH
V X= O
VI X =S
VII X =NR

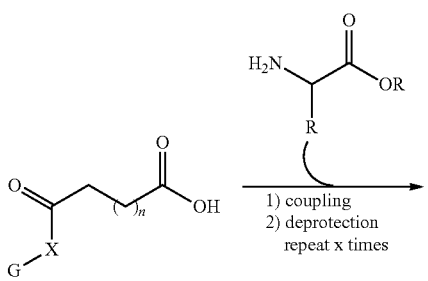

XV X = S, n = 1
XVI X = O, n = 1
XVII X = NR, n = 1
XVIII X = S, n = 2
XIX X = O, n = 2
XX X = NR, n = 2

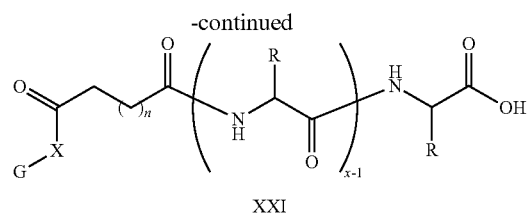

XXI

Ionizable groups G, adequately protected, may be prepared as part of a molecule possessing free hydroxyl (V), thiol (VI) or primary or secondary amino (VII) groups. These compounds can be further extended by the addition of an amino acid or a short peptide sequence by coupling, under standard peptide coupling conditions, to the ε carboxylate of an aspartic acid or a glutamic acid protected at both the α-carboxylate and the α-amino acid groups. Deprotection of the carboxylate can result directly in acids of the general formula VIII-XIII. Alternatively compounds V-VII can be treated with a cyclic anhydride such as succinic or glutaric anhydrides, under basic conditions to furnish acids XV-XX. Acids V-VII and XV-XX may be further extended by cycles of coupling to the amino group of an amino acid and deprotection, to give acids of general formula XIV and XXII.

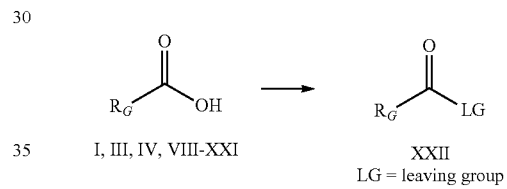

I, III, IV, VIII-XXI    XXII
                        LG = leaving group

Acids I, III, IV and VIII-XXI can be converted to their parent activated esters, of general formula XXII, by treatment with a coupling reagent such as a carbodiimide and a compound with an activated hydroxyl group such as N-hydroxysuccinimide, N-hydroxybenzotriazole, p-nitrophenol and o,p-dinitrophenol.

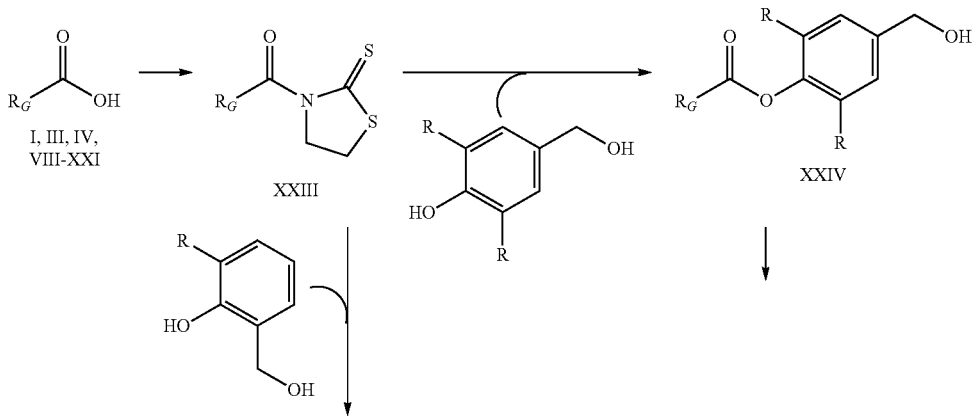

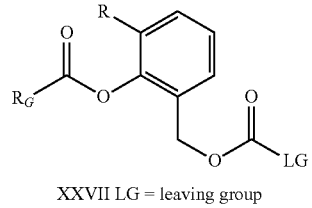

XXVII LG = leaving group

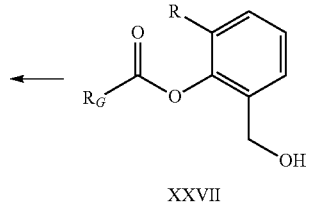

XXVII

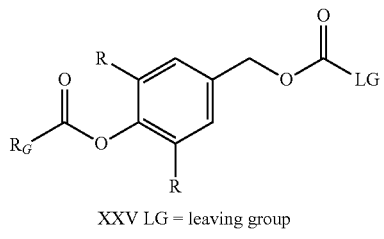

XXV LG = leaving group

Acids I, III, IV and VIII-XXI can also be converted to their parent para- or ortho-hydroxymethylphenyl esters, respectively of the general formula XXIVI and XXVII, by activation through a form such as XXIII which reacts specifically with phenoxides generated in situ in the presence of non-phenolic alcohol groups. The remaining hydroxymethyl group can then be further derivatized as activated carbonates such as XXV and XXVII, by treatment with an deactivated carbonate, such as N,N'-disuccinimidyl carbonate, or a chloroformate, such p-nitrophenyl chloroformate or o,p-dinitrophenyl chloroformate, in the presence of a suitable tertiary amine base.

Alcohols V and thiols VI can be converted to activated carbonates of the general formula XXVIII by treatment with an deactivated carbonate, such as N,N'-disuccinimidyl carbonate, or a chloroformate, such p-nitrophenyl chloroformate or o,p-dinitrophenyl chloroformate, in the presence of a suitable tertiary amine base. Such activated carbonates XXVIII can then be reacted with an o- or a p-aminobenzyl alcohols to give N-(hydroxymethylphenyl)carbamates of general formulae XXIX and XXXI. The remaining hydroxymethyl group can then be further derivatized as activated carbonates such as XXX and XXXII, by the same treatment with a deactivated carbonate or a chloroformate in the presence of a suitable tertiary amine base.

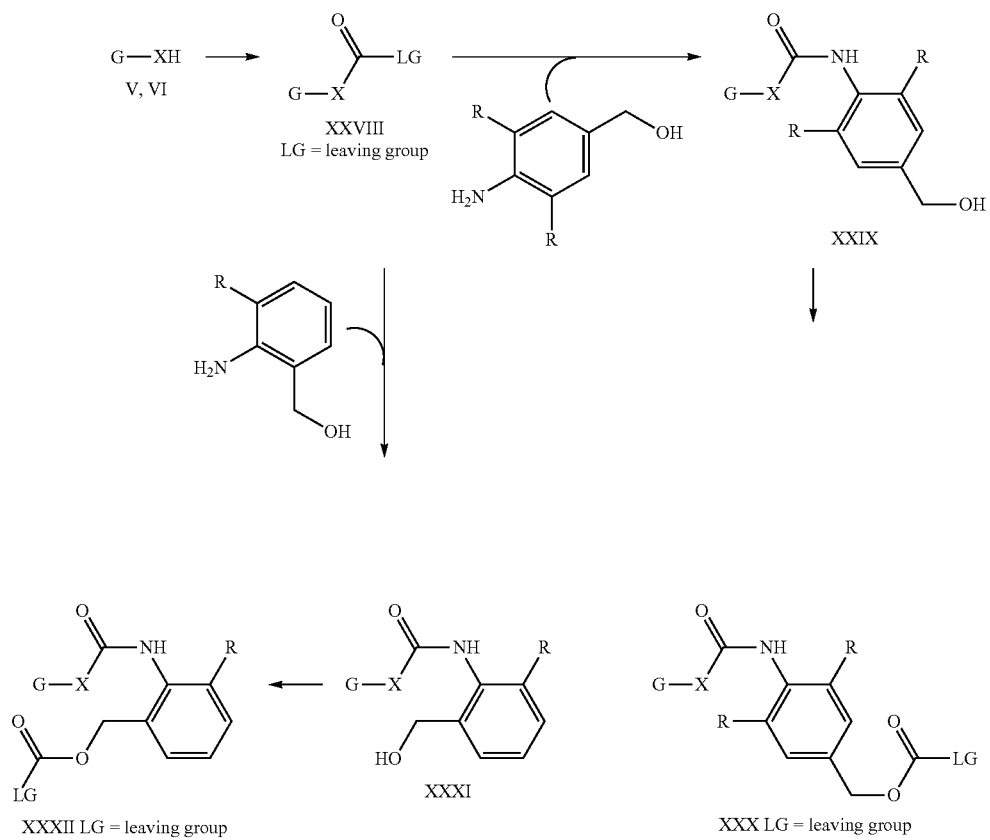

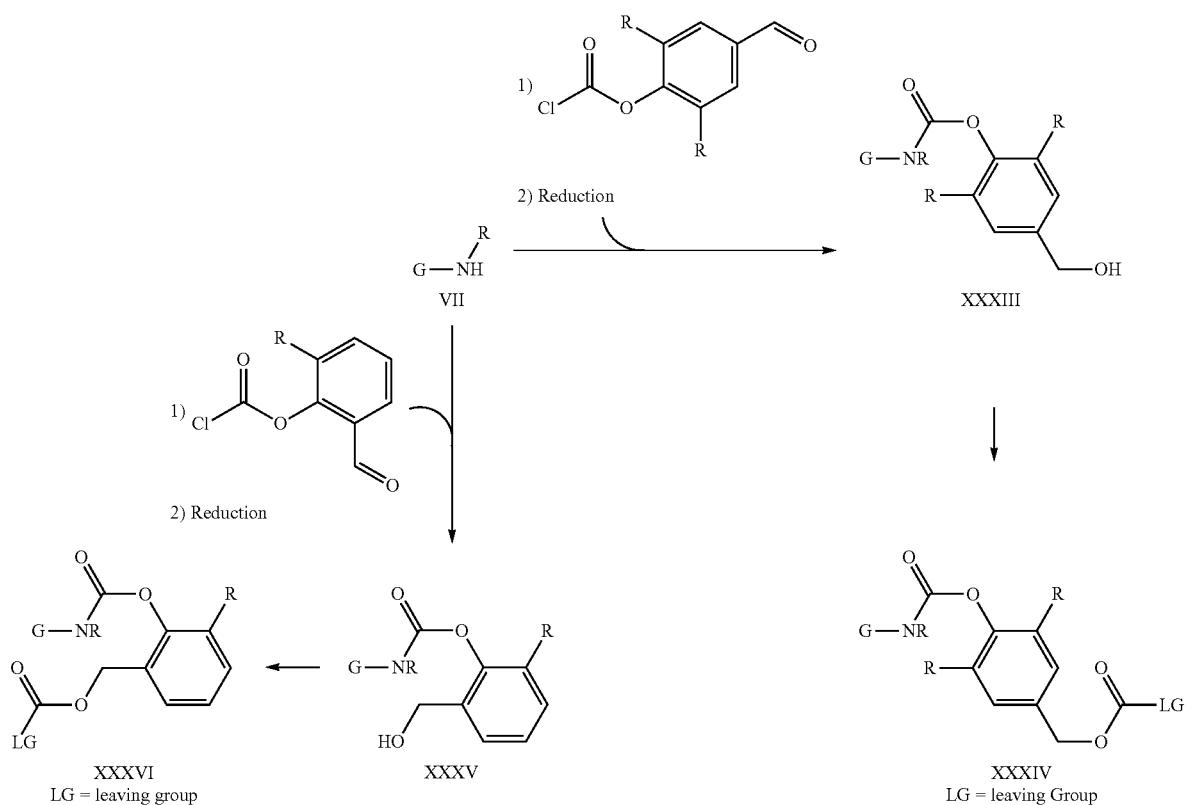

Amines VII can be treated with an o- or p-formylphenyl chloroformate in the presence of a suitable tertiary amine base to furnish the parent carbamates, which upon reduction with a hydride delivering agent, can be converted to O-(hydroxymethylphenyl)carbamates of general formulae XXXIII and XXXV. The resulting free hydroxymethyl group can then be further derivatized as activated carbonates such as XXXIV and XXXVI, by the previously mentioned treatment with a deactivated carbonate or a chloroformate in the presence of a suitable tertiary amine base.

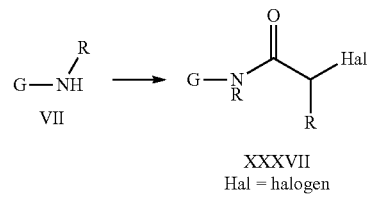

Amines VII can also be converted to α-haloalkanamides of general formula XXXVII by treatment with α-haloalkanoic acids under standard peptide coupling conditions or an α-haloalkanoyl halide in the presence of a tertiary amine base.

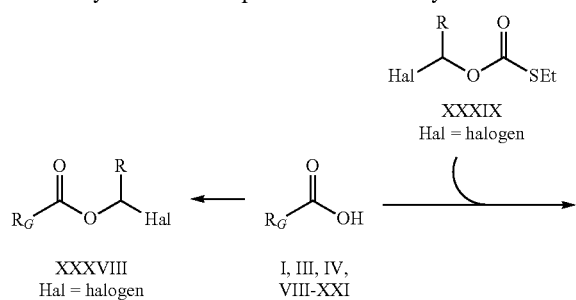

Carboxylic acids I, III, IV and VIII-XXI can be converted to their 1-haloalkyl esters XXXVIII by treatment with 1,1-dihaloalkanes or 1-haloalkyl chlorosulfonates in the presence of a base, generally an alkali metal salt. Carboxylic acids I, III, IV and VIII-XXI can also be converted to 1-(2-thiabutyryloxy)alkyl esters of general formula XL after reaction with the parent S-ethyl O-1-haloalkyl carbonothioate (XXXIX) in the presence of a base, generally an alkali metal salt. Activated acyloxylalkyl carbonates of the general formula XLI can be obtained by transformation of the S-ethyl group into a halide, by treatment with sulfuryl halides, or the subsequent conversion of this halide into an N-oxysuccinimide, a p-nitrophenoxy or an o,p-dinitrophenoxy group by treatment with the corresponding hydroxylamine or alcohol in the presence of a base.

A-2) Synthesis of Oritavancin Poly(Ethylene Glycol) Conjugates

For the purposes of this discussion, oritavancin will be schematically represented, with only the relevant functional groups shown, as:

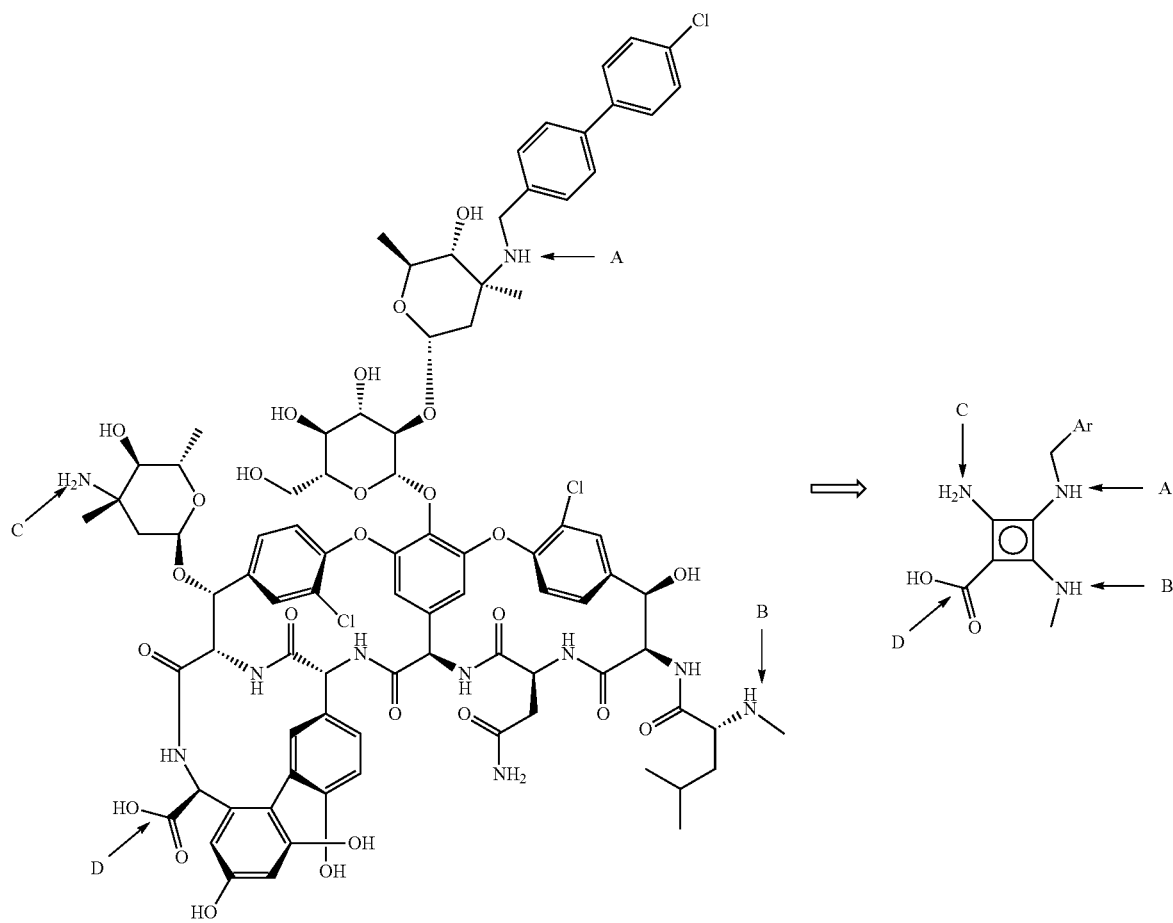
Whereby the letters correlate the functional groups on oritavancin and its schematic representation.
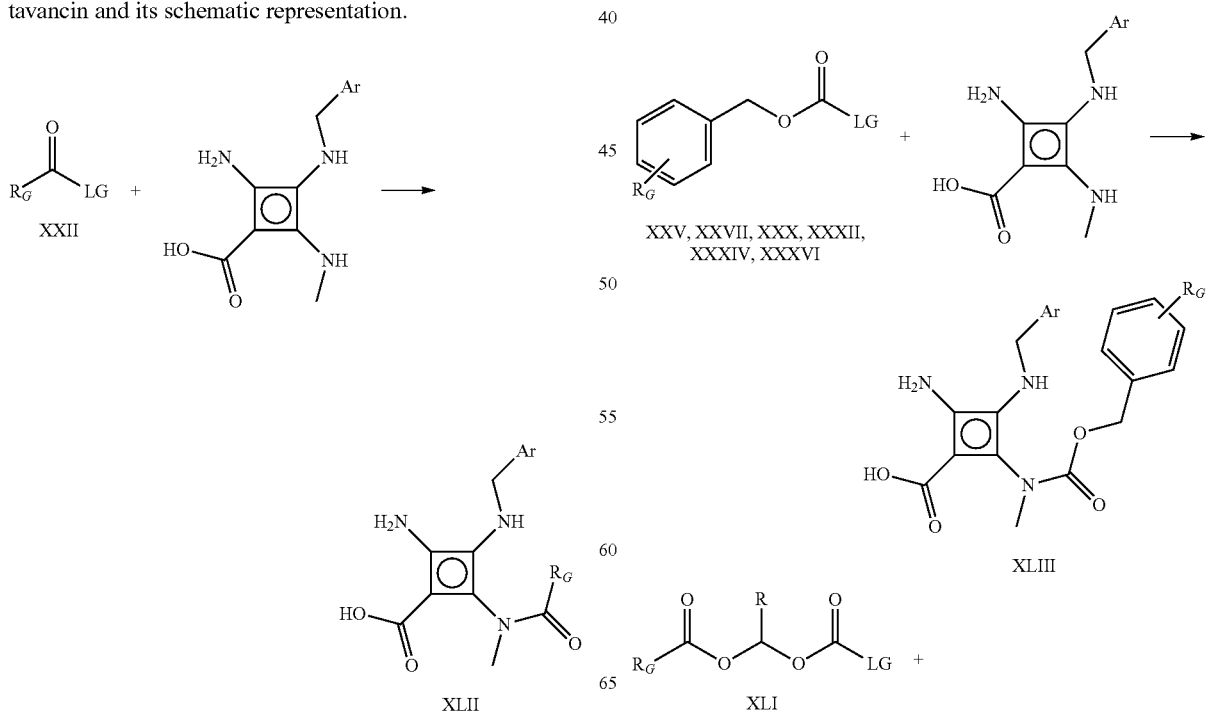

113
-continued

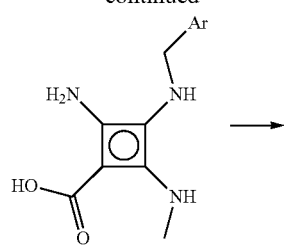

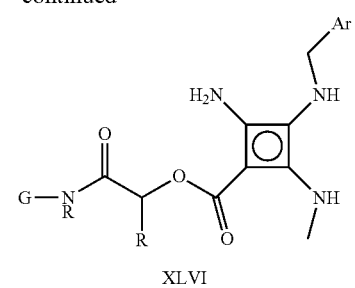
XLVI

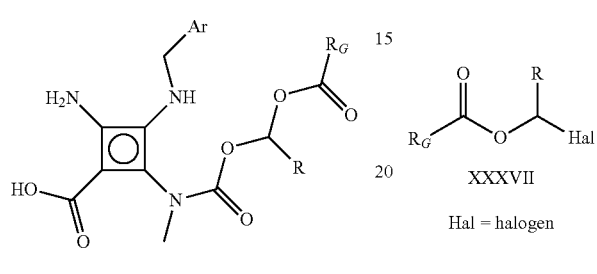
XLIV

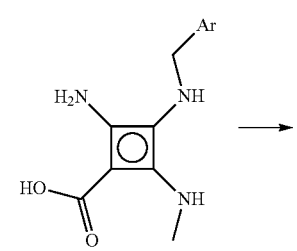
XXXVII

Hal = halogen

Treatment of Oritavancin with activated esters of general formula XXII, activated benzyl carbonates of general formulae XXV, XXVII, XXX, XXXII, XXXIV and XXXVI and activated acyloxyalkyl carbonates of general formula XLI, in the presence of a base affords oritavancin conjugates respectively of the general formulae XLII, XLIII and XLIV. The site of attachment on oritavancin is expected to be the N-methyl leucyl residue based on model systems.

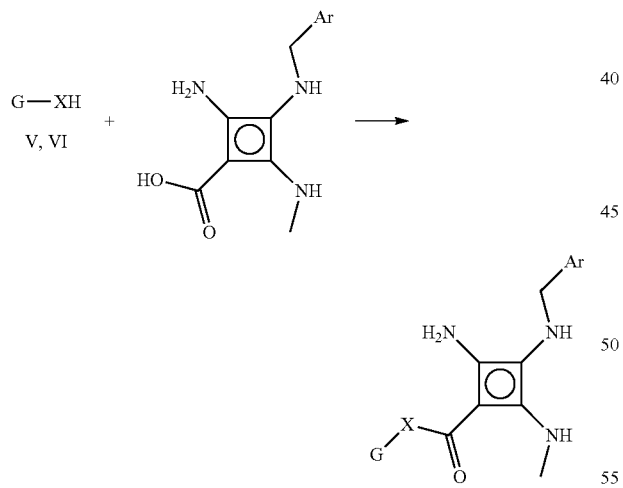
XLV

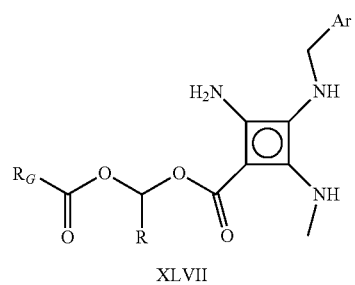
XLVII

Oritavancin conjugates at the C-terminus of oritavancin such as XLV can be made by coupling with compounds V and VI in the presence of a carboxylate activating agent such as a carbodiimide, a phosphoryl chloride or a uranium salt. Alternatively, C-terminus modifications as in XLVI and XLVII can be made by treatment with halides XXXVII and XXXVIII in the presence of a base. In this particular case, protection of some of the amino groups in oritavancin, for example with alkyloxy carbonyl protecting groups, may be necessary if the halide is too reactive.

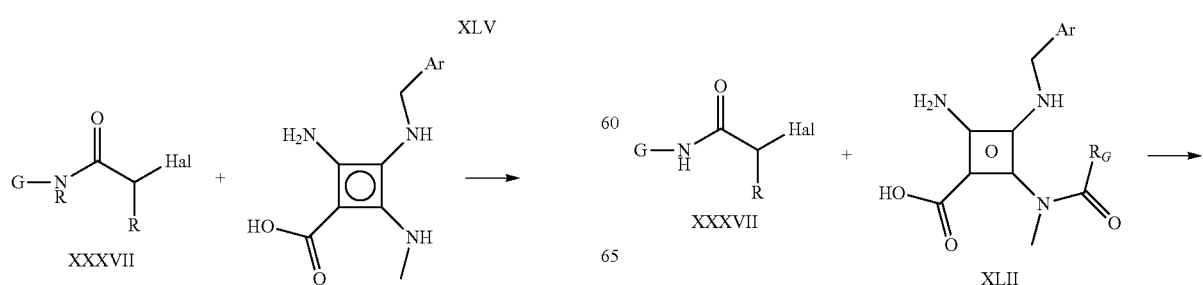
XXXVII    XLII

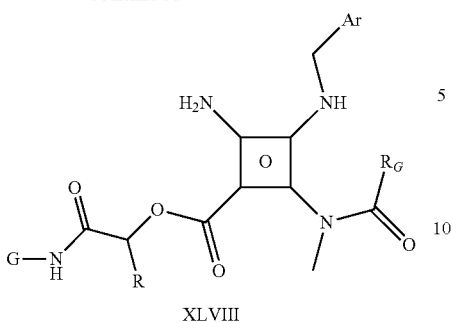

XLVIII

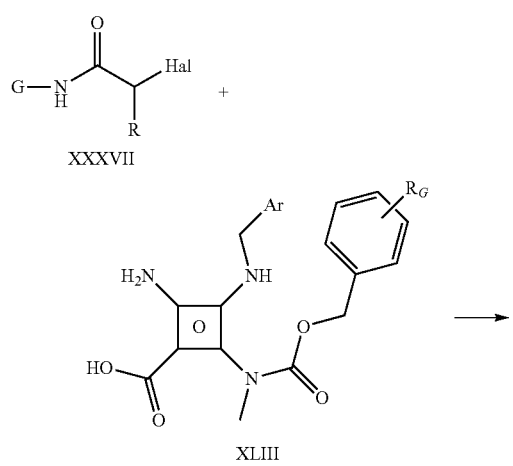

XXXVII

XLIII

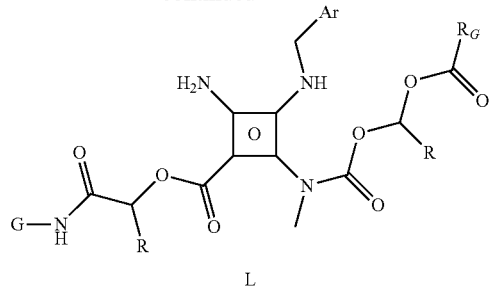

L

Oritavancin respectively of the general formulae XLII, XLIII and XLIV can be further conjugated to an additional solubilizing group at the C-terminus of the glycopeptides as with compounds XLV, XLVI and XLVII. Thus treatment of XLII, XLIII and XLIV with α-haloalkanamide of general formula XXXVII in the presence of a base, generally an alkali metal salt, furnished doubly modified oritavancin conjugates XLVIII, IL and L.

In these procedures, whenever protecting groups are used, they can be selected, put on and removed according to the conventional methods described in the literature, for instance as reviewed in "*Protective Groups in Organic Synthesis*", Greene, T. W. and Wuts, P. M. G., Wiley-Interscience, New York, 1999.

B) Detailed Experimental Procedures

Scheme 1. Preparation of O-(3-(t-Butoxycarbonyl)propanoyloxy)methyl N-succinimidyl carbonate (4).

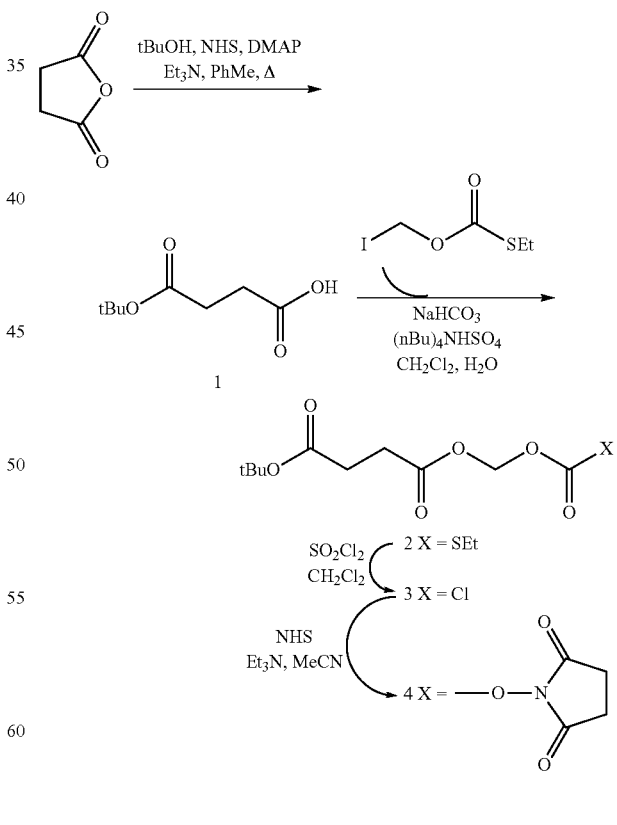

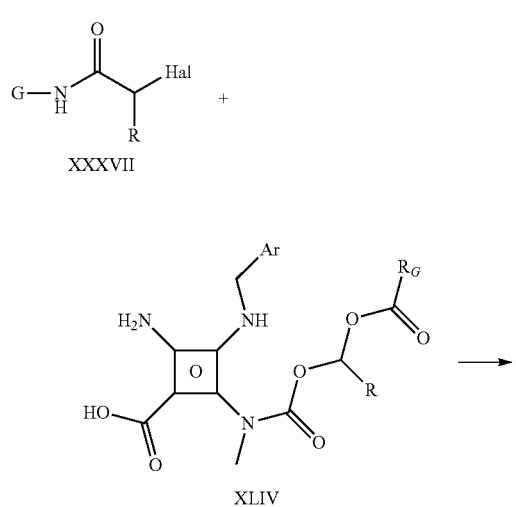

IL

XXXVII

XLIV t-Butyl Succinate (1)

To a solution of succinic anhydride (10 g, 99.9 mmol) in toluene (50 mL) was added N-hydroxysuccinimide (3.45 g, 30.0 mmol), dimethylaminopyridine (1.22 g, 9.99 mmol), t-butanol (12.42 mL, 129.9 mmol) and triethylamine (4.18 mL, 30.0 mmol). After stirring at reflux for 19 h, the mixture was diluted with EtOAc, washed with 5% citric acid solution (2×), saturated NaCl solution, dried over $Na_2SO_4$, filtered and concentrated to dryness. The crude product was dissolved in hot $Et_2O$, treated with activated charcoal and filtered over celite. It was then recrystallized in a mixture of $Et_2O$ and hexanes, yielding 1 as a white crystalline solid (10.33 g, 59%). A second crop of crystals was obtained from the mother liquors (3.26 g, 19%). $^1$H NMR (400 MHz, $CDCl_3$) δ 1.45 (s, 9H), 2.53-2.56 (m, 2H), 2.61-2.65 (m, 2H).

O-(3-(t-Butoxycarbonyl)propanoyloxy)methyl S-ethyl carbonothioate (2)

To a mixture of acid 1 (1.0 g, 5.74 mmol) in $H_2O$ (14.5 mL), and $CH_2Cl_2$ (14.5 mL) was added $NaHCO_3$ (1.00 g, 11.9 mmol) and $TBAHSO_4$ (1.95 g, 5.74 mmol). After stirring for 25 min, S-ethyl O-iodomethyl carbonothioate (1.10 g, 4.42 mmol, prepared according to *Synthesis* 1990, 1159) in $CH_2Cl_2$ (5 mL) was added. The biphasic reaction was stirred vigorously for 2 h 35 min and was diluted with water and $CH_2Cl_2$. The layers were separated, the organic layer was washed with water, 0.5 N HCl solution, saturated $NaHCO_3$ solution, saturated NaCl solution, dried over $Na_2SO_4$, filtered and concentrated to dryness. The crude product was triturated with $Et_2O$ and the solids were removed by filtration and rinsed with small portions of $Et_2O$. After concentration, the combined filtrates were purified by flash chromatography on silica gel, using 20% EtOAc in hexanes as eluent to furnish compound 2 (1.06 g, 82%) as a colorless oil. $^1$H NMR (400 MHz, $CDCl_3$) δ 1.33 (t, J=7.4 Hz, 3H), 1.44 (s, 9H), 2.54-2.58 (m, 2H), 2.63-2.66 (m, 2H), 2.89 (q, J=7.4 Hz, 2H), 5.62 (s, 2H).

t-Butyl (Carbonochloridoyloxy)Methyl Succinate (3)

To a solution of carbonothioate 2 (1.06 g, 3.63 mmol) in ice-cold $CH_2Cl_2$ (18 mL) was added sulfuryl chloride (441 µL, 5.44 mmol) and the mixture was stirred at 0° C. for 2 h 10 min, after which an additional amount of sulfuryl chloride (147 µL, 1.82 mmol) was added. The mixture was concentrated to dryness, providing chloroformate 3 as a colorless oil (1.13 g, >quant.) which was used directly in the next step. $^1$H NMR (400 MHz, $CDCl_3$) δ 1.45 (s, 9H), 2.57-2.60 (m, 2H), 2.66-2.70 (m, 2H), 5.84 (s, 2H).

O-(3-(t-Butoxycarbonyl)propanoyloxy)methyl N-succinimidyl carbonate (4)

To a solution of N-hydroxysuccinimide (418 mg, 3.63 mmol) and triethylamine (506 µL, 3.63 mmol) in dry acetonitrile (9 mL) at 0° C. was added slowly a solution of crude chloroformate 3 (1.13 g, max 3.63 mmol) in dry acetonitrile (9 mL). The mixture was stirred at 0° C. for 5 h 20 min, the solids were removed by filtration and the filtrate was concentrated and redissolved in $CH_2Cl_2$, washed with saturated $NH_4Cl$ solution, saturated NaCl solution, dried over $Na_2SO_4$, filtered and concentrated. The crude product was purified by flash chromatography on silica gel, using a gradient of 0-10% EtOAc in $CH_2Cl_2$ as eluent. Evaporation of pure fractions yielded compound 4 (411 mg, 33% yield over 2 steps) as a colorless oil. $^1$H NMR (400 MHz, $CDCl_3$) δ 1.45 (s, 9H), 2.57-2.60 (m, 2H), 2.67-2.71 (m, 2H), 2.85 (s, 4H), 5.89 (s, 2H).

Scheme 2. Preparation of oritavancin conjugate 7.

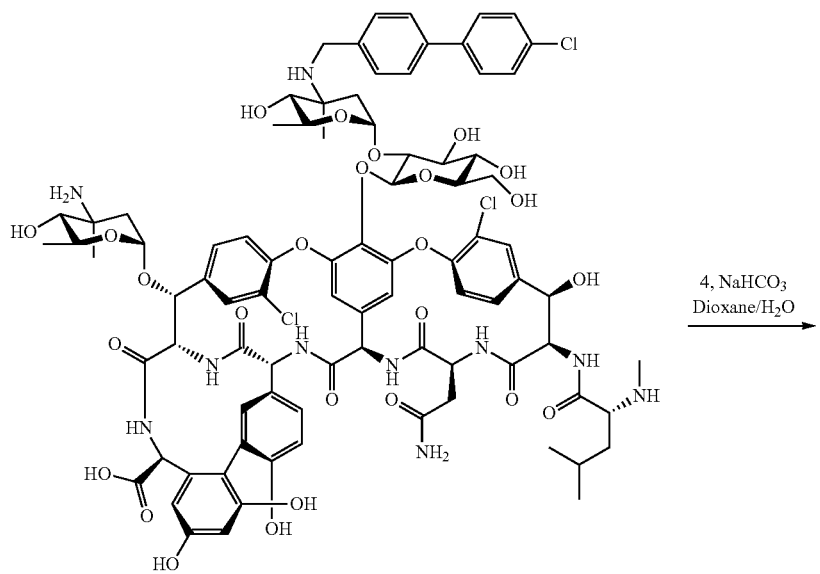

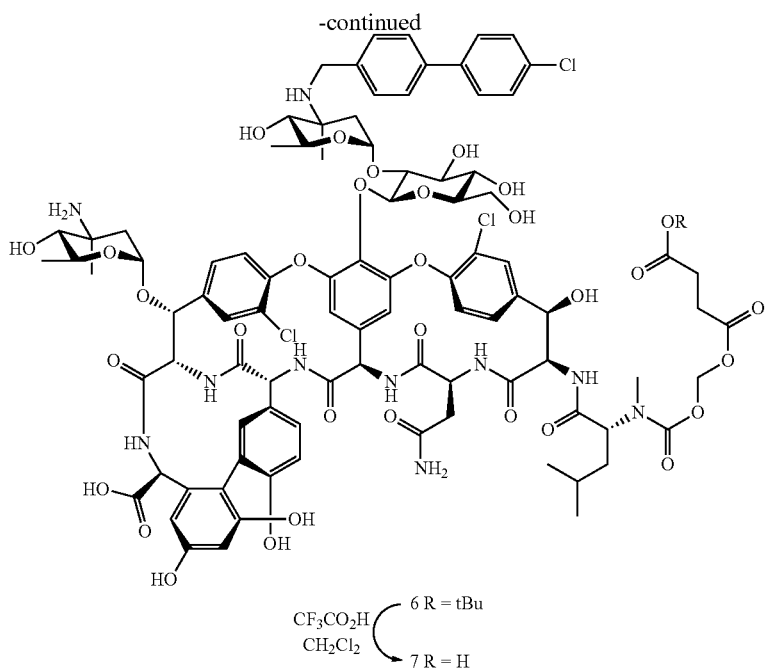

Oritavancin Conjugate 6

To a suspension of oritavancin diphosphate (5, 500 mg, 0.25 mmol) in dioxane/water (1:1, 13 mL) was added $NaHCO_3$ (63 mg, 0.75 mmol). After stirring for 30 minutes, the solids are fully dissolved and succinimide 4 (173 mg, 0.50 mmol) in dioxane (2 mL) was added. After stirring for 5 h 15 min, the reaction mixture was concentrated to remove organics, diluted with water and lyophilized. The crude product was purified by C18 reversed phase chromatography on a Biotage™ flash chromatography system, using a gradient of 15-80% MeCN in $H_2O$, both containing 0.05% TFA. Pure fractions were combined, concentrated and lyophilized to provide oritavancin conjugate 6 di-TFA salt as a white fluffy solid (364 mg, 65%). ESI-MS: m/z calculated for $C_{96}H_{112}Cl_3N_{10}O_{32}^+$ 2024.7. found 2023.6 (M+H)$^+$, 1349.4 (triply-charged dimer), 1012.3 (doubly-charged).

Oritavancin Conjugate 7

To a suspension of t-butyl ester 6 (184 mg, 0.082 mmol) in ice-cold $CH_2Cl_2$ (4.1 mL) was added TFA (4.1 mL) slowly. After stirring for 1.5 h at 0° C., the homogeneous solution was concentrated to dryness without heating and coevaporated twice with $Et_2O$. The crude product was purified twice by C18 reversed phase chromatography on a Biotage™ flash chromatography system, using a gradient of 15-80% MeCN in $H_2O$, both containing 0.05% TFA. Pure fractions were combined, concentrated and lyophilized to provide oritavancin conjugate 7 di-TFA salt as a white fluffy solid (100 mg, 56%). LCMS purity: 99.2% (254 nm), 99.6% (220 nm), 99.4% (290 nm); ESI-MS: m/z calculated for $C_{92}H_{104}Cl_3N_{10}O_{32}^+$ 1967.6. found 1967.4 (M+H)$^+$, 1312.2 (triply-charged dimer), 984.2 (doubly-charged), 656.5 (triply-charged).

Scheme 3. Preparation of N-succinimidyl 3-(bis(((allyloxy)carbonyl)methyl)carbamoyl) propanoate (11).

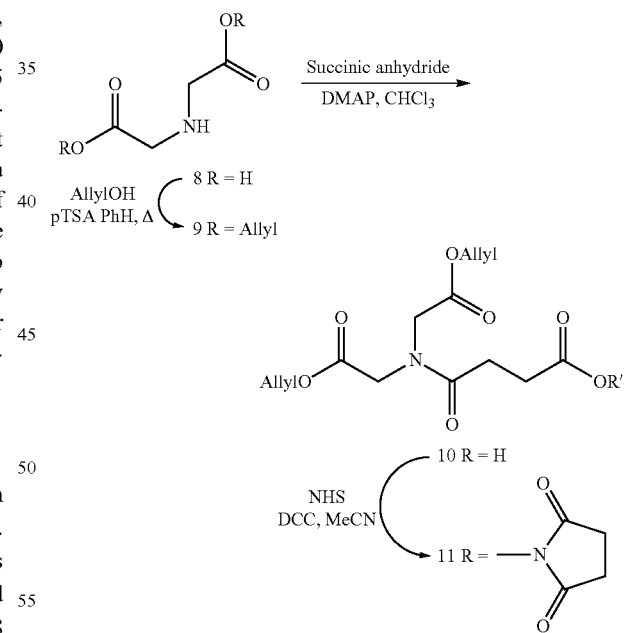

Diallyl 3-Azaglutarate (9)

A solution of iminodiacetic acid 8 (3.0 g, 22.54 mmol), allyl alcohol (18.43 mL, 270 mmol) and p-toluenesulfonic acid (8.57 g, 45.0 mmol) in benzene (60 mL) was heated at reflux with a Dean-Stark distilling trap for 16 h. The mixture was cooled to room temperature and the solvent was evaporated in vacuo. The residue was crystallized from diethyl ether and dried in vacuo to give the compound 9 (8.21 g, 94.6%). $^1$H NMR (400 MHz, CDCl$_3$) δ 2.34 (s, 3H), 4.17 (s, 4H), 4.61 (d, J=6.2, 4H), 5.24 (d, J=11.7, 2H), 5.31 (d, J=17.2, 2H), 5.82 (m, 2H), 7.15 (d, J=7.8, 2H), 7.68 (d, J=8.2, 2H).

3-(Bis(((allyloxy)carbonyl)methyl)carbamoyl)propanoic acid (10)

Compound 9 (4.0 g, 10.39 mmol), succinic anhydride (1.04 g, 10.39 mmol), and 4-di(methylamino)pyridine (1.90 g, 15.59 mmol) were dissolved in CHCl$_3$ (30 mL) and stirred for 24 h. The solvent was evaporated in vacuo and the crude material was purified by silica gel chromatography (40-80% EtOAc in hexanes) to give the compound 10 (1.66 g, 51%). $^1$H NMR (400 MHz, CDCl$_3$) δ 2.64 (t, J=5.8, 2H), 2.70 (t, J=5.8, 2H), 4.21 (d, J=6.2, 4H), 4.61 (d, J=6.2, 2H), 4.65 (d, J=6.2, 2H), 5.22-5.35 (m, 4H), 5.89 (m, 2H).

N-Succinimidyl 3-(bis(((allyloxy)carbonyl)methyl)carbamoyl)propanoate (11)

To a mixture of acid 10 (575 mg, 1.83 mmol) and N-hydroxysuccinimide (568 mg, 2.75 mmol) in acetonitrile (10 mL) at 0° C. was added DCC (317 mg, 2.75 mmol). The mixture was stirred for 4 h at 0° C. and refrigerated overnight. The precipitate was removed by filtration and the filtrate was concentrated then purified by silica gel chromatography (50-100% EtOAc in hexanes) to give the compound 11 (630 mg, 55%). $^1$H NMR (400 MHz, CDCl$_3$) δ 2.75 (t, J=7.0, 2H), 2.82 (s, 4H), 3.0 (t, J=7.0, 2H), 4.21 (d, J=6.2, 4H), 4.61 (d, J=6.2, 2H), 4.65 (d, J=6.2, 2H), 5.22-5.35 (m, 4H), 5.89 (m, 2H): ESI-MS calculated for C$_{18}$H$_{22}$N$_2$O$_9$, 410. found 411 (M+H).

Oritavancin Conjugate 12

To oritavancin bisphosphoric acid salt (5, 400 mg, 0.20 mmol) in 1,4-dioxane (10 mL) and H$_2$O (10 mL) was added NaHCO$_3$ (37.16 mg, 0.44 mmol) and the mixture was stirred until all of 5 had dissolved. A solution of 11 (98.94 mg, 0.24 mmol) in 1,4-dioxane (3 mL) was added and the resulting solution was stirred at room temperature for 2 days. The solvents were evaporated to dryness. The crude product was purified by C18 reversed phase chromatography on a Biotage™ flash chromatography system (10% to 60% MeCN in 0.05% aqueous TFA) to give 12 (102 mg, 24%) as a white solid: ESI-MS calculated for C$_{100}$H$_{114}$Cl$_3$N$_{11}$O$_{32}$, 2088.4. found 2089.3 (M+H).

Oritavancin Conjugate 13

Pd(PPh$_3$)$_4$ (16.6 mg, 0.0144 mmol) was added to a degassed solution of 12 (100 mg, 0.0478 mmol) and morpholine (41.71 µL, 0.478 mmol) in DMF (4 mL). The resulting solution was stirred for 4 h at room temperature. After the removal of the solvent under reduced pressure the crude product was purified by C18 reversed phase chromatography on a Biotage™ flash chromatography system (10% to 60% MeCN in 0.05% aqueous TFA over 15 column volumes) to give the TFA salt of 13 (77 mg, 80%) as a white solid: ESI-MS calculated for C$_{94}$H$_{106}$Cl$_3$N$_{11}$O$_{32}$, 2008. found 2006.6 (M−H).

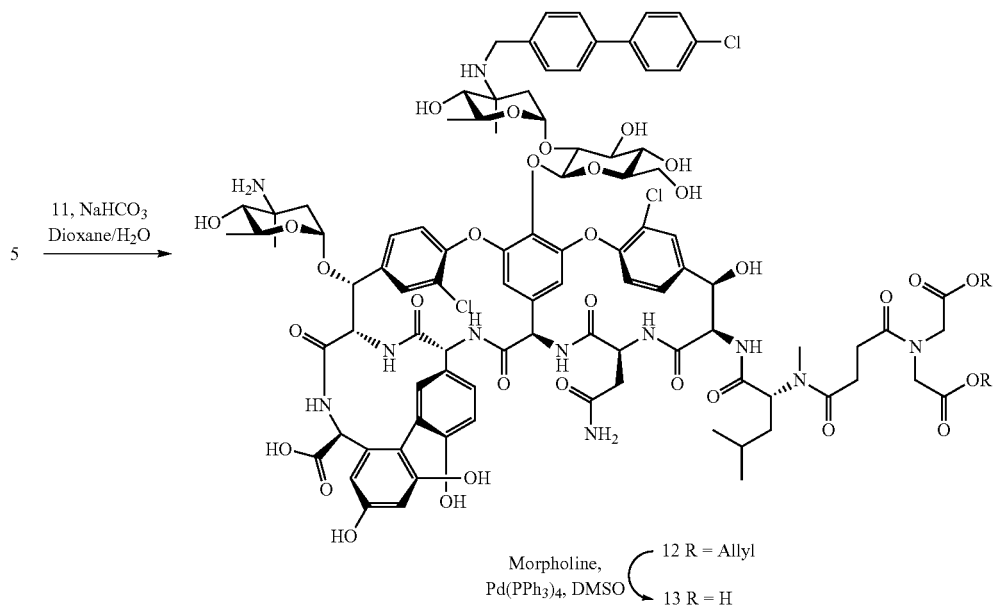

Scheme 4. Preparation of oritavancin conjugate 13.

Scheme 5.
Preparation of O-(3-(bis((t-butyloxycarbonyl)methyl)carbamoyl)propanoyloxy)methyl N-succinimidyl carbonate (18).

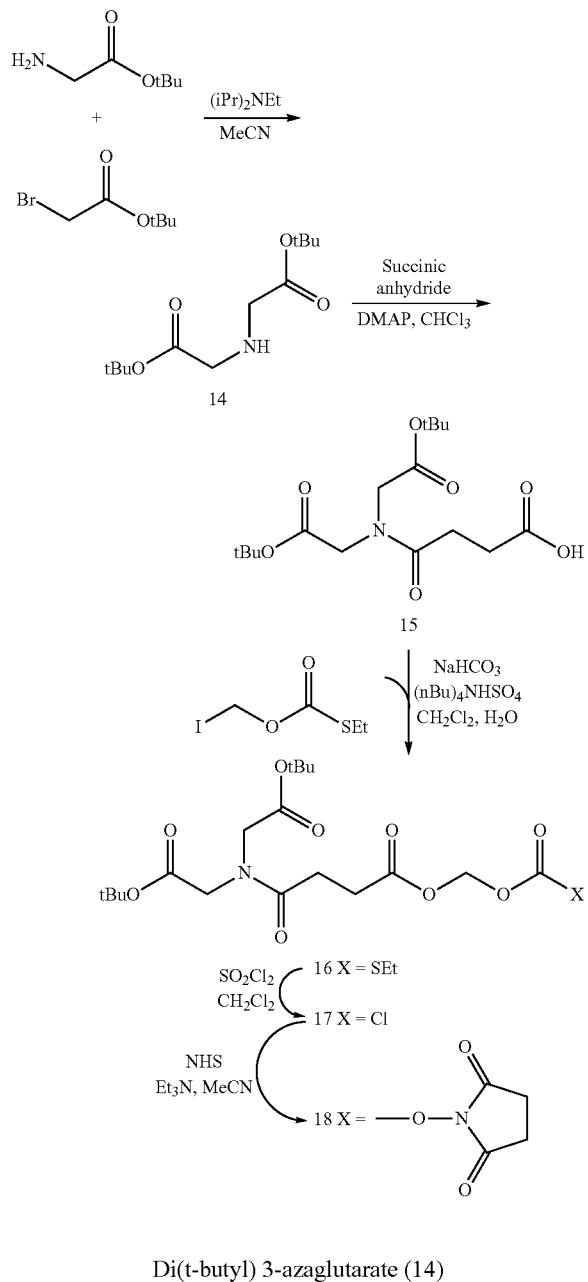

Di(t-butyl) 3-azaglutarate (14)

To a solution of t-butylglycine (1.40 g, 10.67 mmol) in acetonitrile (20 mL) cooled to 0° C. was added ethyldisopropylamine (1.86 mL, 10.67 mmol) and t-butyl bromoacetate (1.57 mL, 10.67 mmol). The resulting solution was stirred for 24 h at room temperature. The mixture was concentrated to dryness in vacuo, water was added and the solution was extracted with dichloromethane (3×70 mL). The combined organic phases were washed with brine (70 mL), dried over $Na_2SO_4$ and concentrated to dryness in vacuo. The crude material was purified by silica gel chromatography (20-80% EtOAc in hexanes) to give the compound 14 (0.88 g, 33.6%). $^1$H NMR (400 MHz, CDCl$_3$) δ 1.43 (s, 18H), 3.30 (s, 4H).

3-(Bis(((t-butyloxy)carbonyl)methyl)carbamoyl) propanoic acid (15)

Compound 14 (0.88 g, 3.59 mmol), succinic anhydride (0.377 g, 3.77 mmol), ethyldiisopropylamine (625 µL, 3.59 mmol) and 4-di(methylamino)pyridine (44 mg, 0.359 mmol) were dissolved in CHCl$_3$ (15 mL) and stirred for 48 h. The mixture was diluted with dichloromethane (140 mL) and the organic layer was washed with H$_2$O (2×75 mL) and saturated aqueous NaCl, dried over Na$_2$SO$_4$ and concentrated under reduced pressure. The crude material was purified by silica gel chromatography (80% EtOAc in hexanes) to give the compound 15 (0.9 g, 72.6%). $^1$H NMR (400 MHz, CDCl$_3$) δ 1.44 (s, 9H), 1.47 (s, 9H), 2.62 (t, J=5.8, 2H), 2.69 (t, J=5.8, 2H), 4.02 (s, 2H), 4.06 (s, 2H). ESI-MS calculated for $C_{16}H_{27}NO_7$, 345.59 found 368.1 (M+Na).

O-(3-(bis((tbutyloxycarbonyl)methyl)carbamoyl) propanoyloxy)methyl S-ethyl carbonothioate (16)

A mixture of 15 (0.90 g, 2.60 mmol), NaHCO$_3$ (438 mg, 5.2 mmol) and tetrabutylammonium hydrogensulfate (885 mg, 2.60 mmol) in CH$_2$Cl$_2$/H$_2$O (1:1, 20 mL) was stirred for 1 h at room temperature, before the addition of a solution of S-ethyl O-iodomethyl carbonothioate (706 mg, 2.87 mmol) in CH$_2$Cl$_2$ (5 mL). The resulting mixture was stirred at room temperature for 2 h. It was diluted with CH$_2$Cl$_2$ (150 mL) and the organic layer was washed with H$_2$O (2×100 mL) and saturated aqueous NaCl, dried over Na$_2$SO$_4$ and concentrated under reduced pressure. The crude material was purified by silica gel chromatography (10%-40% EtOAc in hexanes) to give the compound 16 (1.12 g, 92%): $^1$H NMR (400 MHz, CDCl$_3$) δ 1.32 (t, J=7.4, 3H), 1.45 (s, 9H), 1.48 (s, 9H), 2.64 (t, J=5.8, 2H), 2.75 (t, J=5.8, 2H), 2.88 (q, J=7.4, 2H), 4.03 (s, 2H), 4.06 (s, 2H), 5.81 (s, 2H). ESI-MS calculated for $C_{20}H_{33}NO_9$, 463.54 found 486.1 (M+Na).

(Carbonochloridoyloxy)methyl 3-(bis((methoxycarbonyl)methyl)carbamoyl)propanoate (17)

A solution of 16 (1.12 g, 2.42 mmol) in CH$_2$Cl$_2$ (10 mL) was cooled in an ice-bath. Sulfuryl chloride (392 µL, 4.84 mmol) was added drop-wise and the resulting solution was stirred at room temperature for 1.5 h. The mixture was concentrated to dryness under reduced pressure to give the crude chloroformate 17, which was used without further purification.

O-(3-(Bis((t-butyloxycarbonyl)methyl)carbamoyl) propanoyloxy)methyl N-succinimidyl carbonate (18)

Crude 17 was dissolved in CH$_3$CN (5 mL) then added drop-wise to a stirring solution of N-hydroxysuccinimide (278 mg, 2.42 mmol) and Et$_3$N (370 µL, 2.66 mmol) in CH$_3$CN (5 mL) cooled in an ice-bath. The resulting solution was stirred for 18 h at room temperature. The reaction mixture was filtered, the filtered solids washed with ethyl acetate and the combined filtrate was concentrated to dryness in vacuo. The crude material was purified by silica gel chromatography (30%-80% EtOAc in hexanes) to give the succinimidyl carbonate 18 (255 mg, 20%): $^1$H NMR (400 MHz, CDCl$_3$) δ 1.44 (s, 9H), 1.48 (s, 9H), 2.67 (t, J=5.8, 2H), 2.78 (t, J=5.8, 2H), 2.84 (s, 4H), 4.03 (s, 2H), 4.06 (s, 2H), 5.87 (s, 2H). ESI-MS calculated for $C_{22}H_{32}N_2O_{12}$, 516.5 found 534.2 (M+NH4).

Scheme 6. Preparation of oritavancin conjugate 20.

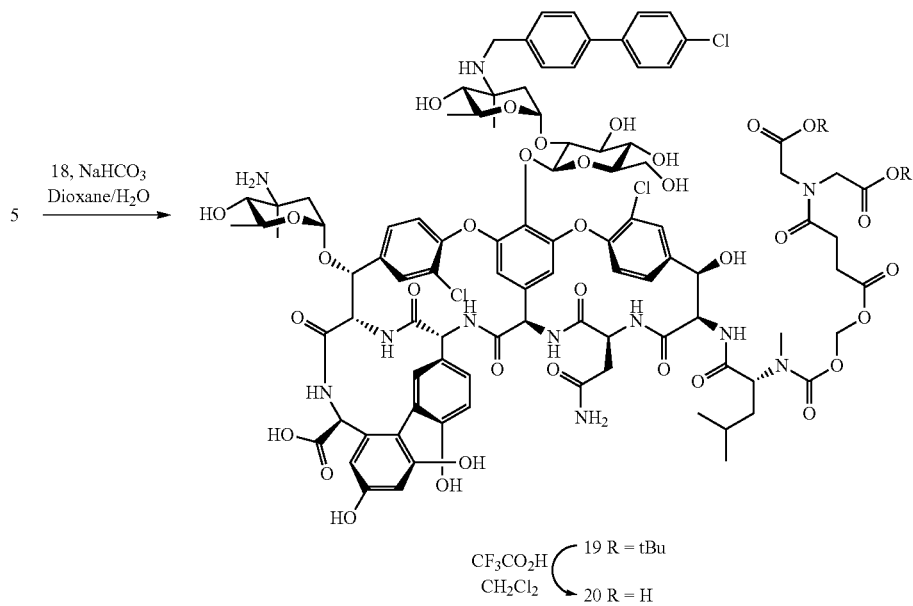

Oritavancin Conjugate 19

To oritavancin bisphosphoric acid salt (5, 1.0 g, 0.50 mmol) in 1,4-dioxane (15 mL) and H$_2$O (15 mL) was added NaHCO$_3$ (92.91 mg, 1.10 mmol) and the mixture was stirred until all of 5 had dissolved. A solution of 18 (311 mg, 0.60 mmol) in 1,4-dioxane (4 mL) was added and the resulting solution was stirred at room temperature for 20 h. The dioxane was evaporated and the product was precipitated by addition of acetone:diethyl ether (1:3, 100 mL), filtered and dried. The crude product was purified by C18 reversed phase chromatography on a Biotage™ flash chromatography system (10% to 70% MeCN in 0.05% aqueous TFA) to give 19 (720 mg, 65%) as a white solid: ESI-MS calculated for C$_{104}$H$_{124}$Cl$_3$N$_{11}$O$_{35}$, 2194.5. found 2195.6 (M+H).

Oritavancin Conjugate 20

A solution of 19 (720 mg, 0.336 mmol) in CH$_2$Cl$_2$/TFA (22.5 mL, 2:1) in an ice bath was stirred for 3 h. The mixture was concentrated to dryness under vacuum and the crude product was purified by C18 reversed phase chromatography on a Biotage™ flash chromatography system (10% to 60% MeCN in 0.05% aqueous TFA) to give the TFA salt of 20 (426 mg, 57%) as a white solid: ESI-MS calculated for C$_{36}$H$_{108}$Cl$_3$N$_{11}$O$_{35}$, 2082.34. found 2082.9 (M+H).

Scheme 7. Preparation of oritavancin conjugate 24.

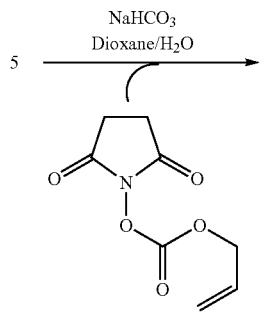

-continued
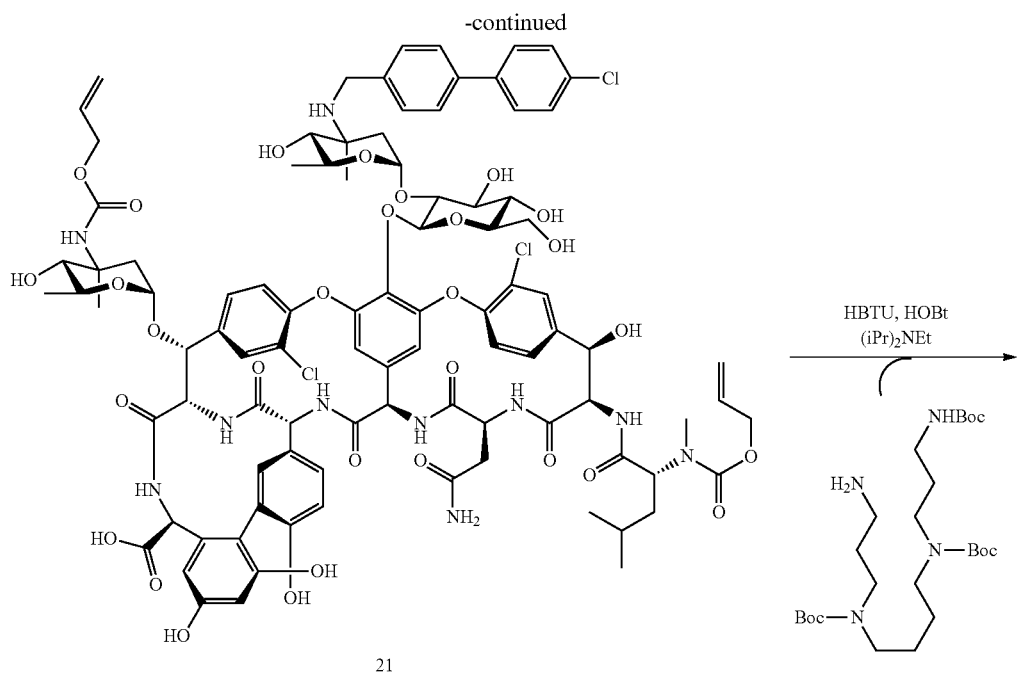
21
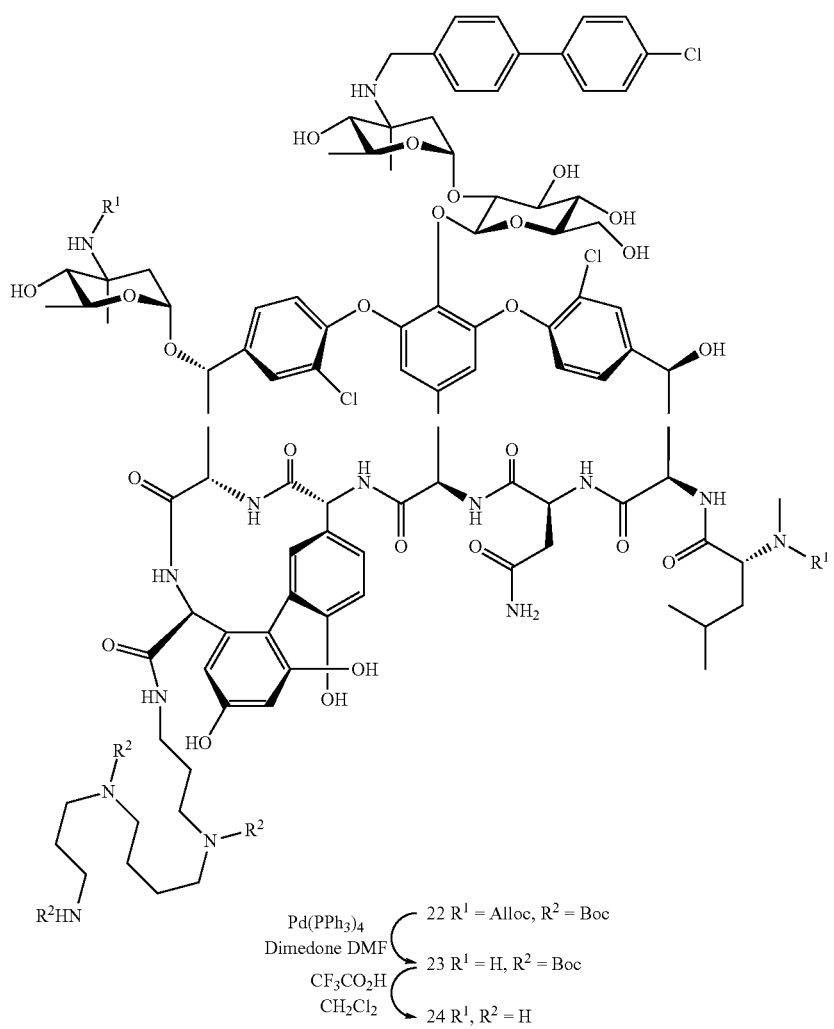
22 R¹ = Alloc, R² = Boc
Pd(PPh₃)₄
Dimedone DMF
23 R¹ = H, R² = Boc
CF₃CO₂H
CH₂Cl₂
24 R¹, R² = H

Di-N-Alloc Oritavancin (21)

To oritavancin bisphosphoric acid salt (5, 2.00 g, 1.01 mmol) in DMF (80 mL) and $H_2O$ (30 mL) was added sodium bicarbonate (676 mg, 8.04 mmol) and the mixture was stirred for 30 min. Allyl N-succinimidyl carbonate (641 mg, 3.22 mmol) was added and the mixture was stirred at room temperature for 48 h. A portion of nBuOH (ca. 10-15 mL) was added and the mixture was concentrated under vacuum to one quarter of its initial volume. $H_2O$ was added and the pH was adjusted to 4.5 by adding aqueous 1N HCl. The precipitate was filtered and washed with $H_2O$ and dried under vacuum to provide di-N-Alloc oritavancin 29 as a white solid (1.85 g, 93%) which was used without further purification. ESI-MS: (M+H) calculated for $C_{94}H_{105}Cl_3N_{10}O_{30}$ 1961. found 1961.4.

Oritavancin Conjugate 22

A solution of $N^1,N^2,N^3$-tri-Boc-spermine (61 mg, 0.120 mmol, synthesized according to Blagbrough I. S, and Geall A. J. *Tetrahedron Letters*, 1998, 439-442) in DMF (2 mL) was added to a stirring solution of 21 (254 mg, 0.130 mmol), HBTU, (102 mg, 0.269 mmol), HOBT (39 µL, 0.29 mmol) and DIEA (68 µL, 0.39 mmol) in DMF (3 mL) cooled to in an ice-bath. The resulting mixture was stirred overnight at room temperature. The solvent was removed under reduced pressure and the crude product was purified by two C18 reversed phase chromatographies (40% to 80% MeCN in 0.2% TEA/phosphate pH 3 over 10 column volumes then 40% to 80% MeCN in 0.05% aqueous TFA over 10 column volumes) to give 22 (110 mg, 37%) as a white solid: ESI-MS (M+H) calculated for $C_{119}H_{153}Cl_3N_{14}O_{35}$, 2446.9. found 2446.4.

Oritavancin Conjugate 23

$Pd(PPh_3)_4$ (5.1 mg, 0.0044 mmol) was added to a degassed solution of 22 (110 mg, 0.045 mmol) and dimedone (19 mg, 0.14 mmol) in DMF (2.5 mL). The resulting solution was stirred at room temperature overnight. After removal of the solvent under reduced pressure, the crude product was purified by C18 reversed phase chromatography on a Biotage™ flash chromatography system (35% to 80% MeCN in 0.05% aqueous TFA) to give 23 (85 mg, 83%) as a white solid: ESI-MS (M+H) calculated for $O_{111}H_{145}Cl_3N_{14}O_{31}$, 2278.8. found 2278.3.

Oritavancin Conjugate 24

A solution of 23 (85 mg, 0.037 mmol) in $CH_2Cl_2$/TFA (10 mL, 1:1) in an ice bath was stirred for 90 min. The solvent was evaporated under vacuum and the crude product was purified by C18 reversed phase chromatography on a Biotage™ flash chromatography system (15% to 70% MeCN in 0.05% aqueous TFA) to give the TFA salt of 24 (33 mg, 33%) as a white solid: ESI-MS (M+H) calculated for $C_{96}H_{121}Cl_3N_{14}O_{25}$, 1977.4. found 1977.5.

Scheme 8. Preparation of oritavancin conjugate 28.

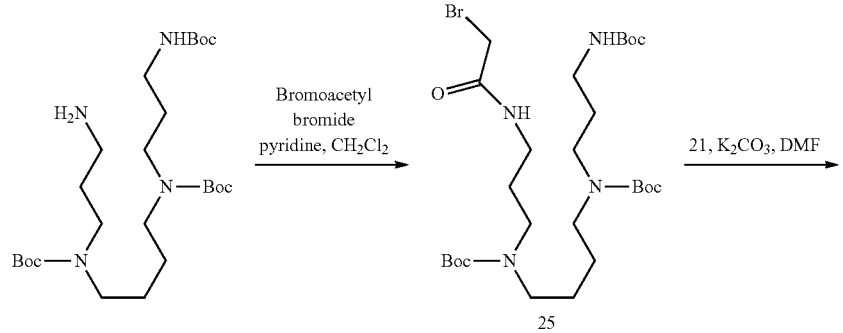

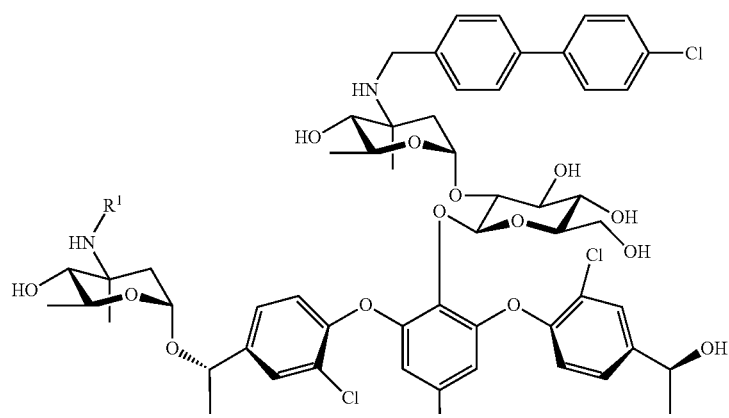

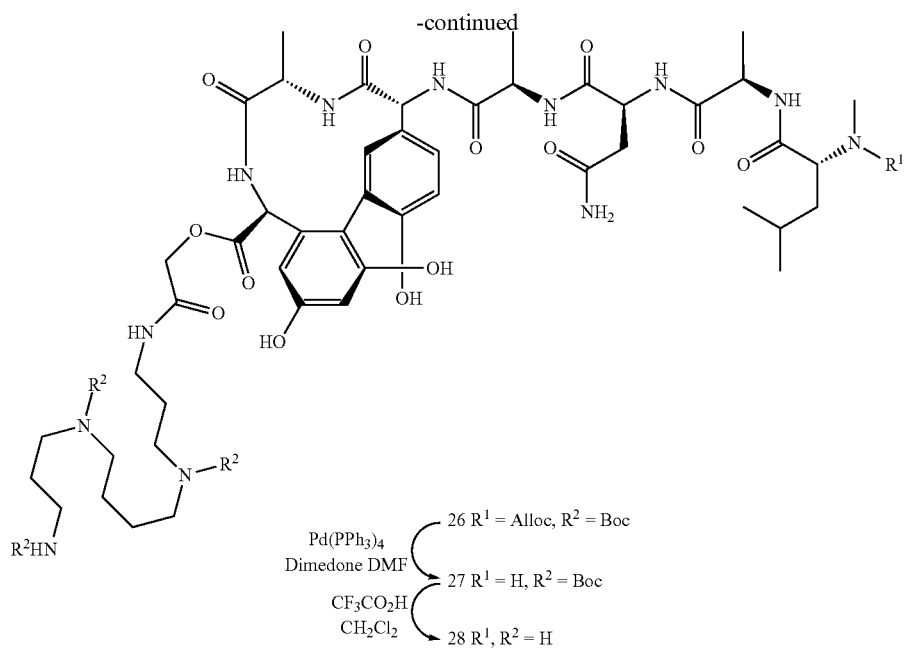

2-Bromo-N—(N⁴,N⁹,N¹³-tri(t-butoxycarbonyl)-4,9,13-triazamidecyl)acetamide (25)

Bromoacetyl bromide (27 µL, 0.31 mmol) was added dropwise to a stirring solution of $N^1,N^2,N^3$-tri-Boc-spermine (141 mg, 0.281 mmol) and pyridine (34 µL, 0.42 mmol) in $CH_2Cl_2$ (3 mL) cooled in an ice bath. The resulting solution was stirred at the same temperature for 20 min then at room temperature for 1 h. The reaction mixture was diluted with $CH_2Cl_2$ and it was washed with 1 N HCl, water and saturated aqueous NaCl, dried over $Na_2SO_4$ and concentrated under reduced pressure. The crude product was purified by silica gel chromatography (0% to 13% MeOH in $CH_2Cl_2$) resulting in 25 (149 mg, 85%) as a pale yellow coloured liquid: $^1$H NMR (400 MHz, $CDCl_3$): δ 1.44-1.48 (m, 31H), 1.66 (bs, 4H), 3.13-3.26 (m, 12H), 3.86 (s, 2H).

Oritavancin Conjugate 26

A mixture of 21 (1.26 g, 0.642 mmol) and $K_2CO_3$ (218 mg, 1.57 mmol) in DMF (10 mL) was stirred at room temperature for 15 min after which 21 was fully dissolved. A solution of 25 (564 mg, 0.903 mmol) in DMF (5 mL) was added and the resulting mixture was stirred at room temperature overnight. Ether was added to the mixture and unreacted 21 was removed by filtration. The filtrate was concentrated under reduced pressure to yield crude 26 (1.55 g, 97%) which was used subsequently without further purification: ESI-MS (M+H) calculated for $C_{121}H_{155}Cl_3N_{14}O_{37}$, 2505.0. found 2504.4.

Oritavancin Conjugate 27

$Pd(PPh_3)_4$ (104 mg, 0.0899 mmol) was added to a degassed solution of 26 (1.55 g, 0.619 mmol) and dimedone (261 mg, 1.86 mmol) in DMF (30 mL). The resulting solution was stirred at room temperature for 16 h. After removal of the solvent under reduced pressure, the crude product was purified by C18 reversed phase chromatography on a Biotage™ flash chromatography system (25% to 75% MeCN in 0.2% TEA/phosphate, pH 3) to give 27 (825 mg, 50%, based on the tri-phosphoric acid salt) as a white solid: ESI-MS (M+2H) calculated for $C_{113}H_{147}Cl_3N_{14}O_{33}$, 1168.9. found 1168.5.

Oritavancin Conjugate 28

A solution of 27 (825 mg, 0.314 mmol) in $CH_2Cl_2$/TFA (30 mL, 1:1) in an ice bath was stirred for 2 h. The solvent was evaporated under vacuum and the crude product was purified by C18 reversed phase chromatographies on a Biotage™ flash chromatography system (8% to 70% MeCN in 0.2% TEA/phosphate pH 3 over 11 column volumes then 0% to 60% MeCN in 0.05% aqueous TFA over 12 column volumes) to give the TFA salt of 28 (100 mg, 10%) as a white solid: ESI-MS (M+2H) calculated for $C_{98}H_{123}Cl_3N_{14}O_{27}$, 1018.7. found 1018.2.

Scheme 9. Preparation of $N^3,N^7,N^{12},N^{16}$-tetra(t-butoxycarbonyl)-3,7,12,16-tetraazahexadecanoic acid (31) and ($N^3,N^7,N^{12},N^{16}$-tetra(t-butoxycarbonyl)-3,7,12,16-tetraazahexadecanoyloxy)-methyl N-succinimidyl carbonate (34).

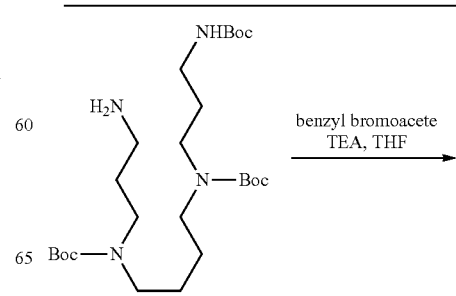

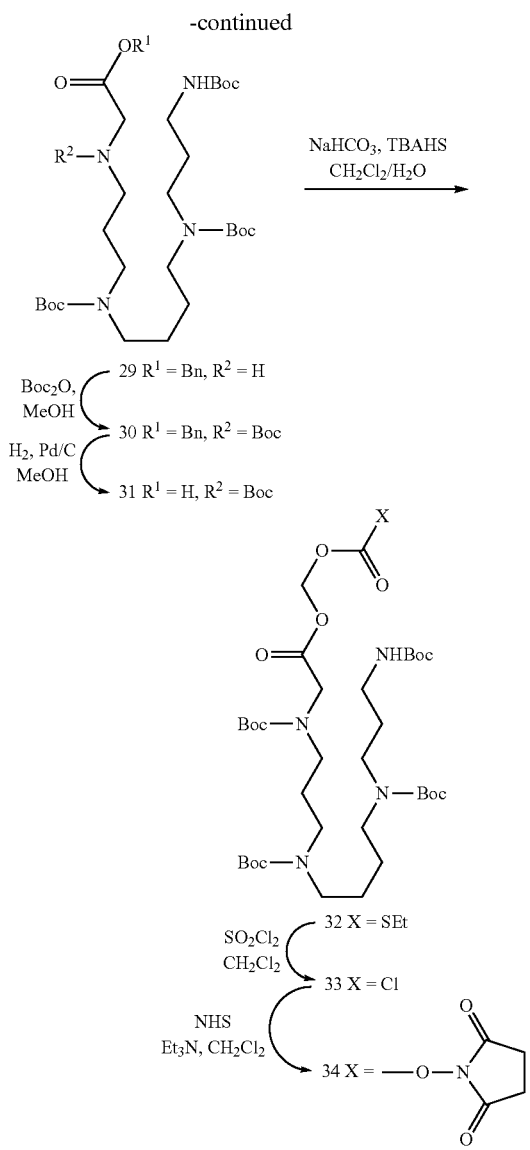

Benzyl $N^7,N^{12},N^{16}$-tri(t-butoxycarbonyl)-3,7,12,16-tetraazahexadecanoate (29)

A solution of $N^1,N^2,N^3$-tri-Boc-spermine (2.96 g, 5.89 mmol), benzyl bromoacetate (925 μL, 5.90 mmol) and TEA (1.23 mL, 8.82 mmol) in THF (60 mL) was stirred at room temperature overnight. The precipitate was filtered off and the filtrate was concentrated under reduced pressure. The crude product was purified by silica gel chromatography (25% to 100% EtOAc in hexane) to give 29 (2.55 g, 67%) as a pale yellow coloured viscous liquid: $^1$H NMR (400 MHz, CDCl$_3$): δ 1.44-1.48 (m, 31H), 1.64-1.73 (m, 4H), 2.72 (t, J=7.0, 2H), 3.10-3.26 (m, 10H), 3.44 (s, 2H), 5.16 (s, 2H), 7.32-7.37 (m, 5H).

Benzyl $N^3,N^7,N^{12},N^{16}$-tetra(t-butoxycarbonyl)-3,7,12,16-tetraazahexadecanoate (30)

A solution of 29 (2.55 g, 3.92 mmol) and Boc$_2$O (941 mg, 4.31 mmol) in MeOH (40 mL) was stirred at room temperature overnight. The solvent was removed under reduced pressure resulting in 30 (2.90 g, 99%) as a pale yellow coloured viscous liquid: $^1$H NMR (400 MHz, CDCl$_3$): δ 1.43-1.53 (m, 40H), 1.64-1.74 (m, 4H), 3.10-3.31 (m, 12H), 3.90 (bs, 4/7 of 2H, rotamer A), 4.00 (s, 3/7 of 2H, rotamer B), 5.16 (s, 2H), 7.32-7.37 (m, 5H).

$N^3,N^7,N^{12},N^{16}$-Tetra(t-butoxycarbonyl)-3,7,12,16-tetraazahexadecanoic acid (31)

A solution of 30 (1.56 g, 2.08 mmol) in MeOH (21 mL) was degassed with argon for 10 min followed by the addition of 10% Pd/C (400 mg). The mixture was then stirred under an atmosphere of hydrogen for 3 h. The mixture was filtered through glassfiber filter paper and the filtrate was concentrated under reduced pressure to give crude 31 (1.37 g, 100%) as a colourless liquid that was used without purification: $^1$H NMR (400 MHz, acetone-d$_6$): δ 1.40 (bs, 9H), 1.44-1.46 (m, 27H), 1.52 (bs, 4H), 1.66-1.83 (m, 4H), 3.06 (bt, J=5.6, 2H), 3.22-3.32 (m, 10H), 3.94 (s, ½ of 2H, rotamer A), 3.97 (s, ½ of 2H, rotamer B), 5.98 (bs, 1H).

S-Ethyl O—($N^3,N^7,N^{12},N^{16}$-tetra(t-butoxycarbonyl)-3,7,12,16-tetraazahexadecanoyl oxy)methyl carbonothioate (32)

S-Ethyl O-iodomethyl carbonothioate (423 mg, 1.72 mmol) was added to a stirring mixture of 31 (1.13 g, 1.71 mmol), NaHCO$_3$ (298 mg, 3.55 mmol) and tetrabutylammonium hydrogensulfate (588 mg, 1.73 mmol) in CH$_2$Cl$_2$/H$_2$O (1:1, 17 mL) and the resulting mixture was stirred at room temperature overnight. The reaction mixture was diluted with CH$_2$Cl$_2$ (80 mL) and the aqueous layer was discarded. The organic layer was washed with saturated aqueous NH$_4$Cl, saturated aqueous NaCl, dried over Na$_2$SO$_4$ then concentrated under reduced pressure. The residue was resuspended in Et$_2$O, filtered and again concentrated under reduced pressure. The crude material was purified by silica gel chromatography (25%-60% EtOAc in hexanes over 10 column volumes) to give the colourless liquid 32 (1.23 g, 92%): $^1$H NMR (400 MHz, CDCl$_3$): δ 1.32 (t, J=7.3, 3H), 1.41-1.47 (m, 40H), 1.61-1.75 (m, 4H), 2.89 (q, J=7.3, 2H), 3.10-3.31 (m, 12H), 3.92 (s, 4/7 of 2H, rotamer A), 4.01 (s, 3/7 of 2H, rotamer B), 5.84 (s, 2H).

($N^3,N^7,N^{12},N^{16}$-Tetra(t-butoxycarbonyl)-3,7,12,16-tetraazahexadecanoyloxy)methyl N-succinimidyl carbonate (34)

A solution of 32 (1.05 g, 1.35 mmol) in CH$_2$Cl$_2$ (5 mL) was cooled in an ice-bath. Sulfuryl chloride (164 μL, 2.02 mmol) was added drop-wise and the resulting solution was stirred at 0° C. for 2 h. The solvent was evaporated under reduced pressure to give the crude chloroformate 33, which was used without purification, after drying under high vacuum for 1 h. Crude 33 was dissolved in CH$_2$Cl$_2$ (5 mL) then added drop-wise to a stirring solution of N-hydroxysuccinimide (155 mg, 1.35 mmol) and proton sponge (289 mg, 1.35 mmol) in CH$_2$Cl$_2$ (5 mL) cooled in an ice-bath. The resulting solution was stirred at 0° C. for 4 h then placed in a fridge overnight. The solution was diluted with CH$_2$Cl$_2$ (20 mL) and washed with saturated aqueous NH$_4$Cl, H$_2$O and saturated aqueous NaCl, then dried over Na$_2$SO$_4$. Filtration and removal of solvent under reduced pressure resulted in the crude succinimidyl carbonate 34 (627 mg, 84%) as a pale yellow solid that was used without purification: $^1$H NMR (400 MHz, CDCl$_3$): δ 1.42-1.47 (m, 40H), 1.63-1.77 (m, 4H), 2.85 (s, 4H), 3.10-3.31 (m, 12H), 3.98 (bs, 4/7 of 2H, rotamer A), 4.05 (s, 3/7 of 2H, rotamer B), 5.91 (s, 1H), 5.92 (s, 1H).

Scheme 10. Preparation of oritavancin conjugate 36.

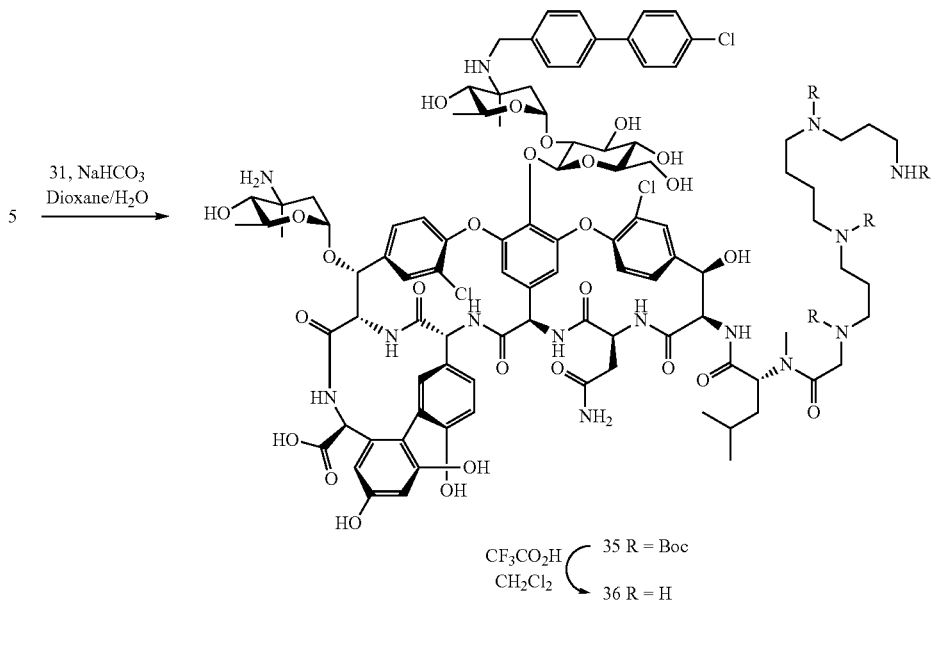

Oritavancin Conjugate 35

Oritavancin Conjugate 36

To oritavancin bisphosphoric acid salt (5, 223 mg, 0.112 mmol) in 1,4-dioxane (5 mL) and H$_2$O (6 mL) was added NaHCO$_3$ (29 mg, 0.35 mmol) and the mixture was stirred until all of 5 had dissolved. A solution of 31 (125 mg, 0.165 mmol) in 1,4-dioxane (2 mL) was added and the resulting solution was stirred at room temperature overnight. The product was precipitated by the addition of H$_2$O and collected by filtration. The crude product was purified by C18 reversed phase chromatography on a Biotage™ flash chromatography system (30% to 80% MeCN in 0.2% TEA/phosphate pH 3) to give 35 (110 mg, 37%, based on the di-phosphoric acid salt) as a white solid: ESI-MS (M+2H) calculated for C$_{118}$H$_{155}$Cl$_3$N$_{14}$O$_{35}$, 1218.9. found 1218.4.

An ice-cold aliquot of TFA (8 mL) was added to an ice-cooled solution of 35 (215 mg, 0.0880 mmol) in CH$_2$Cl$_2$ (8 mL). The resulting solution was stirred at 0° C. for 1 hr then concentrated under reduced pressure. The crude product was purified by two consecutive C18 reversed phase chromatography conditions on a Biotage™ flash chromatography system (7% to 70% MeCN in 0.2% TEA/phosphate, pH 3 then 10% to 50% MeCN in 0.05% aqueous TFA) to give the TFA salt of 36 (19 mg, 19%) as a white solid: ESI-MS (M+2H) calculated for C$_{98}$H$_{123}$Cl$_3$N$_{14}$O$_{27}$, 1018.8. found 1013.3.

Scheme 11. Preparation of oritavancin conjugate 38.

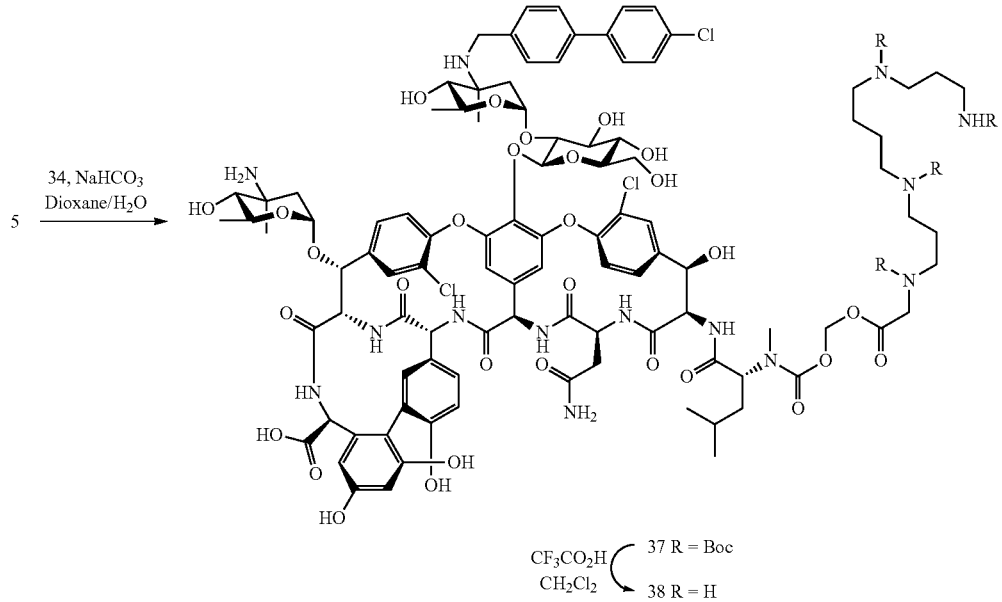

Oritavancin Conjugate 37

To oritavancin bisphosphoric acid salt (5, 180 mg, 0.0905 mmol) in 1,4-dioxane (2 mL) and H$_2$O (2 mL) was added NaHCO$_3$ (25 mg, 0.29 mmol) and the mixture was stirred until all of 5 had dissolved. A solution of 34 (135 mg, 0.164 mmol) in 1,4-dioxane (3 mL) was added and the resulting solution was stirred at room temperature overnight. The product was precipitated by the addition of H$_2$O and collected by filtration. The crude product was purified by C18 reversed phase chromatography on a Biotage™ flash chromatography system (30% to 80% MeCN in 0.2% TEA/phosphate pH 3) to give 37 (135 mg, 55%, based on the di-phosphoric acid salt) as a white solid: ESI-MS (M+2H) calculated for C$_{120}$H$_{157}$Cl$_3$N$_{14}$O$_{38}$ 1256.0. found 1255.4

Oritavancin Conjugate 38

An ice-cold aliquot of TFA (8 mL) was added to an ice-cooled solution of 37 (150 mg, 0.0597 mmol) in CH$_2$Cl$_2$ (8 mL). The resulting solution was stirred at 0° C. for 1 hr then concentrated under reduced pressure. The crude product was purified by C18 reversed phase chromatography on a Biotage™ flash chromatography system (0% to 50% MeCN in 0.05% aqueous TFA) to give the TFA salt of 38 (55 mg, 33%) as a white solid: ESI-MS (M+2H) calculated for C$_{100}$H$_{125}$Cl$_3$N$_{14}$O$_{30}$, 1055.7. found 1055.3.

Scheme 12. Preparation of oritavancin conjugate 44.

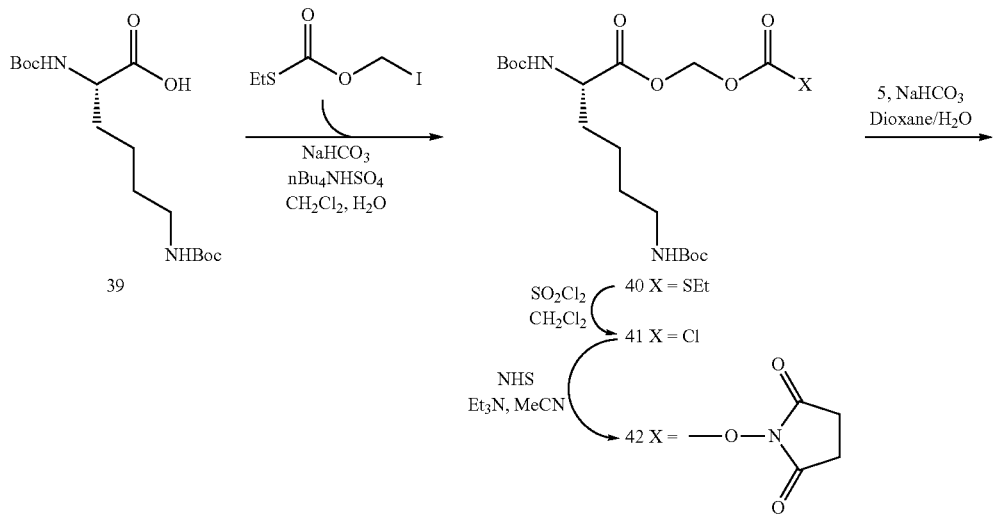

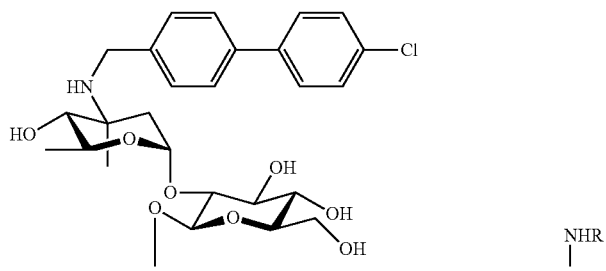

-continued

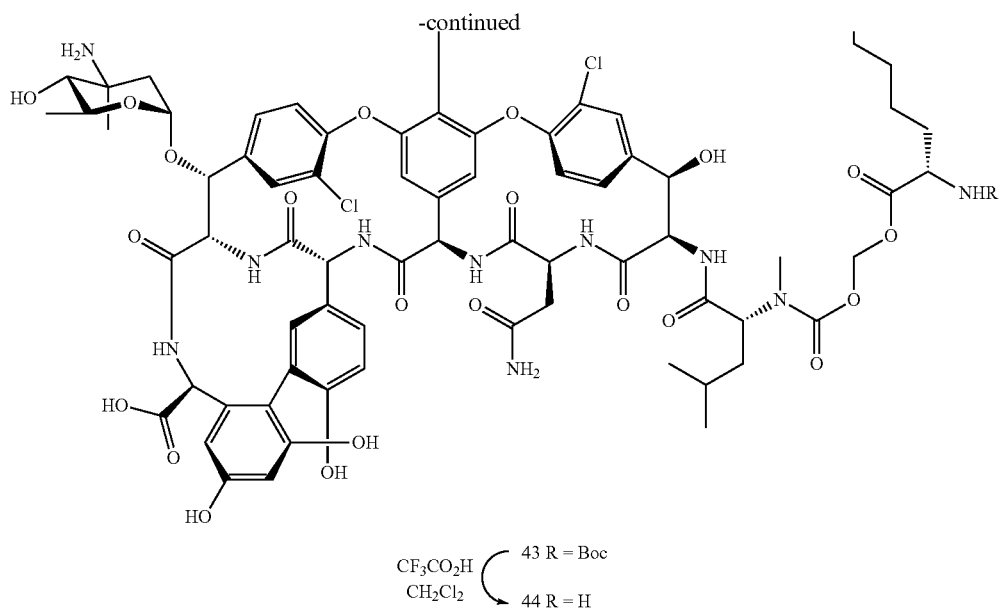

O—(N,N'-Bis(t-butyloxycarbonyl)-L-lysinoyloxy) methyl S-ethyl carbonothioate (40)

To a mixture of Boc-Lys(Boc)-OH dicyclohexylamine salt (39, 8.6 g, 16.3 mmol) in H$_2$O (31 mL), and CH$_2$Cl$_2$ (31 mL) was added NaHCO$_3$ (2.84 g, 33.8 mmol) and TBAHSO$_4$ (5.53 g, 16.3 mmol). After stirring for 20 min, S-ethyl O-iodomethyl carbonothioate (3.10 g, 12.5 mmol) in CH$_2$Cl$_2$ (6.5 mL) was added. The biphasic reaction was stirred vigorously for 5 h and was diluted with water and CH$_2$Cl$_2$. The layers were separated, the organic layer was washed with water, 0.5 N HCl solution, saturated NaHCO$_3$ solution, saturated NaCl solution, dried over MgSO$_4$, filtered and concentrated to dryness. The crude product was triturated with Et$_2$O and the solids were removed by filtration and rinsed with small portions of Et$_2$O. After concentration, the combined filtrates were purified by flash chromatography on silica gel, using a gradient of 20-40% EtOAc in hexanes as eluent, to yield compound 40 (5.03 g, 87%) as a light yellow gum. $^1$H NMR (400 MHz, CDCl$_3$) δ 1.31-1.40 (m, 2H), 1.33 (t, J=7.4 Hz, 3H), 1.41-1.53 (m, 2H), 1.44 (s, 18H), 1.63-1.72 (m, 1H), 1.77-1.86 (m, 1H), 2.90 (q, J=7.4 Hz, 2H), 3.08-3.13 (m, 2H), 4.29-4.35 (m, 1H), 4.58 (bs, 1H), 5.09 (bs, 1H), 5.78 (d, J=5.6 Hz, 1H), 5.90 (d, J=5.6 Hz, 1H).

(Carbonochloridoyloxy)methyl N,N'-bis(t-butyloxycarbonyl)-L-lysine (41)

To a solution of carbonothioate 40 (5.03 g, 10.8 mmol) in ice-cold CH$_2$Cl$_2$ (54 mL) was added sulfuryl chloride (1.32 mL, 16.2 mmol) and the mixture was stirred at 0° C. for 3 h, after which the mixture was concentrated to dryness, providing chloroformate 41 as a bright yellow gum (5.01 g, >quant.) which was used directly in the next step. $^1$H NMR (400 MHz, CDCl$_3$) δ 1.34-1.55 (m, 4H), 1.44 (s, 18H), 1.66-1.75 (m, 1H), 1.79-1.87 (m, 1H), 3.11 (t, J=6.4 Hz, 2H), 4.29-4.35 (m, 1H), 4.56 (bs, 1H), 5.11 (bs, 1H), 5.78 (d, J=5.3 Hz, 1H), 5.93 (d, J=5.3 Hz, 1H).

O—(N,N'-Bis(t-butyloxycarbonyl)-L-lysinoyloxy) methyl N-succinimidyl carbonate (42)

To a solution of N-hydroxysuccinimide (1.24 g, 10.8 mmol) and triethylamine (1.51 mL, 10.8 mmol) in dry acetonitrile (27 mL) at 0° C. was added slowly a solution of crude chloroformate 41 (5.01 g, max 10.8 mmol) in dry acetonitrile (27 mL). The mixture was stirred at 0° C. for 4 h 15 min, solids were removed by filtration and the filtrate was concentrated and redissolved in CH$_2$Cl$_2$, washed with saturated NH$_4$Cl solution, saturated NaCl solution, dried over Na$_2$SO$_4$, filtered and concentrated. The crude product was purified by flash chromatography on silica gel, using a gradient of 0-40% EtOAc in CH$_2$Cl$_2$ as eluent, to yield compound 42 (2.58 g, 46% yield over 2 steps) as a white foam. $^1$H NMR (400 MHz, CDCl$_3$) δ 1.33-1.53 (m, 4H), 1.44 (2s, 18H), 1.67-1.77 (m, 1H), 1.79-1.89 (m, 1H), 1.29 (s, 4H), 3.09-3.14 (m, 2H), 4.32-4.36 (m, 1H), 4.68 (bs, 1H), 5.13 (bs, 1H), 5.78 (d, J=5.4 Hz, 1H), 6.04 (d, J=5.4 Hz, 1H).

Oritavancin Conjugate 43

To a suspension of oritavancin diphosphate salt (5, 389 mg, 0.20 mmol) in dioxane/water (1:1, 8 mL) was added NaHCO$_3$ (49 mg, 0.59 mmol). After stirring for 15 minutes, complete dissolution of 5 is observed and succinimide 42 (190 mg, 0.39 mmol) in dioxane (2 mL) was added. After stirring for 5.5 h, the reaction mixture was concentrated to remove volatile organics and lyophilized. The crude product was purified by C18 reversed phase chromatography on a Biotage™ flash chromatography system, using a gradient of 15-80% MeCN in H$_2$O, both containing 0.05% TFA, to yield the TFA salt of oritavancin conjugate 43 as a white fluffy solid (405 mg, 84%). ESI-MS: m/z calculated for C$_{104}$H$_{128}$Cl$_3$N$_{12}$O$_{34}^+$ 2195.8. found 2196.5 (M+H)$^+$, 1464.3 (triply-charged dimer), 1098.3 (doubly-charged).

Oritavancin Conjugate 44

To a suspension of bis-carbamate 43 (188 mg, 0.081 mmol) in ice-cold CH$_2$Cl$_2$ (4 mL) was added TFA (4 mL) slowly. After stirring for 95 min at 0° C., the homogeneous solution was concentrated to dryness. The crude product was purified twice by C18 reversed phase chromatography on a Biotage™ flash chromatography system, using a gradient of 15-80% MeCN in H$_2$O, both containing 0.05% TFA, to yield the TFA salt of oritavancin conjugate 44 as a white fluffy solid (141 mg, 71%). ESI-MS: m/z calculated for C$_{94}$H$_{112}$Cl$_3$N$_{12}$O$_{30}^+$ 1995.7. found 1996.1 (M+H)$^+$, 1330.4 (triply-charged dimer), 998.2 (doubly-charged), 655.8 (triply-charged), 499.7 (quadruple-charged).

Scheme 13. Preparation of oritavancin conjugates 46.

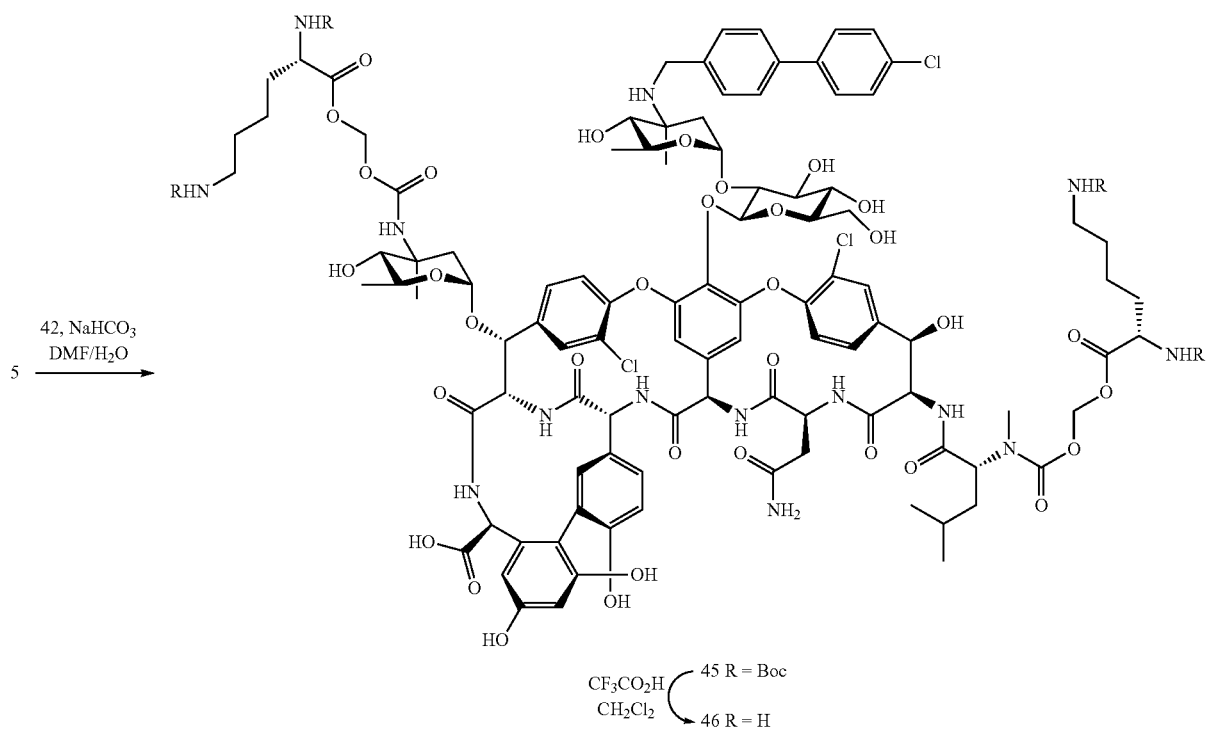

Oritavancin Conjugate 45

To oritavancin diphosphate salt (5, 1.0 g, 0.50 mmol) in a mixture of DMF (40 mL) and water (15 mL) was added NaHCO$_3$ (338 mg, 4.02 mmol). After stirring for 20 minutes, succinimide 42 (732 mg, 1.51 mmol) was added. After stirring for 24 h, another portion of succinimide 42 (732 mg, 1.51 mmol) was added and the reaction mixture was stirred for 3 d, and then concentrated to dryness. The crude product was purified twice by C18 reversed phase chromatography on a Biotage™ flash chromatography system, using a gradient of 30-100% MeCN in aqueous Et$_3$N/H$_3$PO$_4$ buffer (0.2% Et$_3$N+ H$_3$PO$_4$, pH=3), then desalted by reversed phase C18 chromatography, using a gradient of 15-80% MeCN in H$_2$O, both containing 0.05% TFA, to yield the TFA salt of oritavancin conjugate 45 as a white fluffy solid (386 mg, 28%). ESI-MS: m/z calculated for $C_{122}H_{158}Cl_3N_{14}O_{42}^+$ 2598.0. found 2598.9 (M+H)$^+$.

Oritavancin Conjugate 46

To a suspension of 45 (207 mg, 0.076 mmol) in ice-cold CH$_2$Cl$_2$ (3.8 mL) was added TFA (3.8 mL) slowly. After stirring for 1 h at 0° C., the homogeneous solution was concentrated to dryness and coevaporated with Et$_2$O (2×). The crude product was purified by C18 reversed phase chromatography on a Biotage™ flash chromatography system, using a gradient of 0-40% MeCN in H$_2$O, both containing 0.05% TFA, to provide the TFA salt of oritavancin conjugate 46 as a white fluffy solid (134 mg, 64%). LCMS purity: 94.6% (254 nm), 94.9% (220 nm), 94.5% (290 nm); ESI-MS: m/z calculated for $C_{102}H_{126}Cl_3N_{14}O_{34}^+$ 2197.8. found 1465.7 (triply-charged dimer), 1099.2 (doubly-charged), 733.2 (triply-charged), 550.2 (quadruple-charged).

Scheme 14. Preparation of O-(N$^\alpha$-(N$^\alpha$,N$^\varepsilon$-Bis(t-butoxycarbonyl)-L-lysinoyl)-N$^\varepsilon$-(t-butoxycarbonyl)-L-lysinoyloxy)methyl N-succinimidyl carbonate (54).

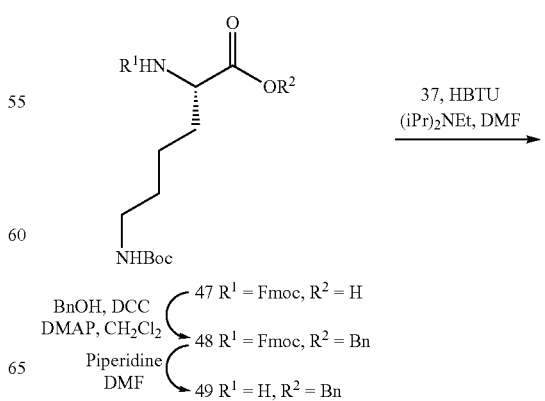

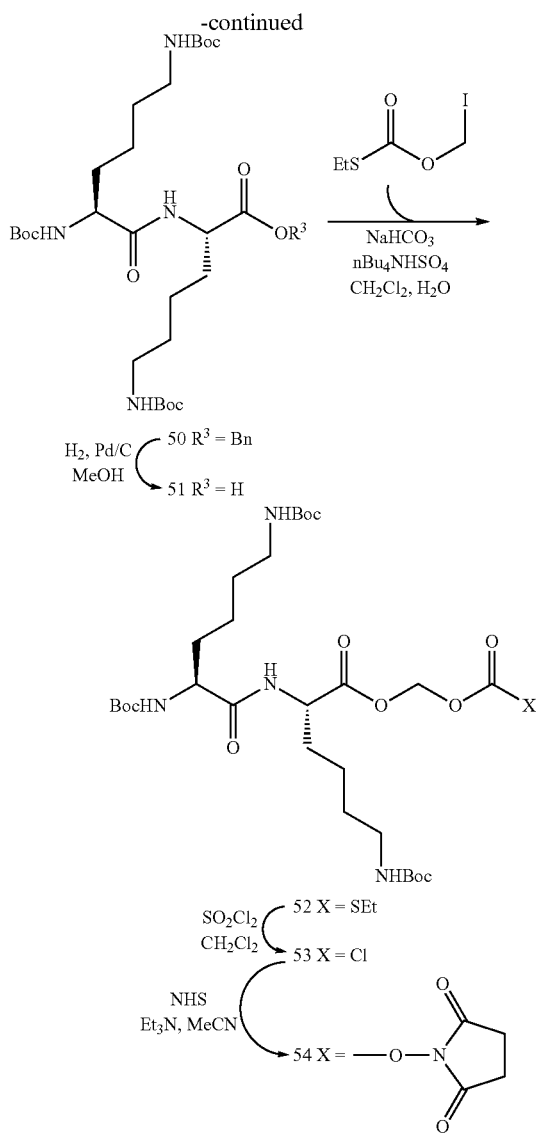

Benzyl N$^\epsilon$-(9-fluorenylmethoxycarbonyl)-N$^\epsilon$-(t-butoxycarbonyl)-L-lysine (48)

To a mixture of Fmoc-Lys(Boc)-OH (47, 2.0 g, 4.27 mmol) and benzyl alcohol (531 µL, 5.12 mmol) in CH$_2$Cl$_2$ (8.5 mL) at 0° C. was added DMAP (52 mg, 0.43 mmol) and DCC (1.06 g, 5.12 mmol). The mixture was stirred for 2 h at 0° C. and 3 h at room temperature, then filtered. Solids were washed with small portions of CH$_2$Cl$_2$ and the combined filtrates were concentrated, redissolved in EtOAc, washed with H$_2$O, 0.5 N aqueous HCl solution, saturated NaHCO$_3$ solution, saturated NaCl solution, dried over Na$_2$SO$_4$, filtered and concentrated. The crude product was purified by flash chromatography on a Biotage™ flash chromatography system, using a gradient of 0-10% EtOAc in CH$_2$Cl$_2$ to furnish compound 48 (2.3 g, 96%) as a white solid. $^1$H NMR (400 MHz, CDCl$_3$) δ 1.25-1.39 (m, 2H), 1.40-1.52 (m, 2H), 1.43 (s, 9H), 1.66-1.75 (m, 1H), 1.82-1.90 (m, 1H), 3.02-3.11 (m, 2H), 4.20-4.24 (m, 1H), 4.35-4.52 (m, 4H), 5.16 (d, J=12.0 Hz, 1H), 5.22 (d, J=12.0 Hz, 1H), 5.39 (bd, J=8.0 Hz, 1H), 7.29-7.42 (m, 9H), 7.60 (d, J=7.5 Hz, 2H), 7.77 (d, J=7.5 Hz, 2H).

Benzyl N$^\epsilon$-(t-butoxycarbonyl)-L-lysine (49)

Fmoc protected amino acid 48 (1.0 g, 1.79 mmol) was treated with a solution of piperidine/DMF (9 mL, 5% v/v) and stirred for 20 min then concentrated to dryness and used directly in the next step.

Benzyl N$^\alpha$—(N$^\alpha$,N$^\epsilon$-bis(t-butoxycarbonyl)-L-lysinoyl)-N$^\epsilon$-(t-butoxycarbonyl)-L-lysine (50)

To a solution of Boc-Lys(Boc)-OH dicyclohexylamine salt (39, 945 mg, 1.79 mmol) in DMF (9 mL) at 0° C. was added DIEA (624 µL, 3.58 mmol) and HBTU (679 mg, 1.79 mmol). After stirring for 15 minutes, the crude amine 49 (1.79 mmol) in DMF (2 mL) was added and the mixture was stirred for 4 h in an ice bath, diluted with EtOAc, washed with H$_2$O, 0.5 N aqueous HCl solution, saturated NaHCO$_3$ solution, saturated NaCl solution, dried over MgSO$_4$, filtered and concentrated. The crude product was purified by flash chromatography on a Biotage™ flash chromatography system, using 50% EtOAc in hexanes as eluent, to yield compound 50 (1.17 g, 97% yield over 2 steps) as a white foam. $^1$H NMR (400 MHz, CDCl$_3$) δ 1.21-1.51 (m, 35H), 1.57-1.74 (m, 2H), 1.77-1.91 (m, 2H), 3.00-3.13 (m, 4H), 4.03-4.09 (m, 1H), 4.58-4.67 (m, 3H), 5.13 (d, J=12.0 Hz, 1H), 5.17-5.21 (m, 2H), 6.65 (bd, J=7.3 Hz, 1H), 7.33-7.37 (m, 5H).

N$^\alpha$—(N$^\alpha$,N$^\epsilon$-Bis(t-butoxycarbonyl)-L-lysinoyl)-N$^\epsilon$-(t-butoxycarbonyl)-L-lysine (51)

A slurry of Pd—C (10% wt, 117 mg) in dry MeOH (2 mL) was added to a solution of benzyl ester 50 (1.17 g, 1.76 mmol) in dry MeOH (8.8 mL). The reaction vessel was flushed with hydrogen gas and stirred with a hydrogen balloon for 2 h 25 min. The reaction mixture was then filtered over celite to remove the catalyst. After rinsing the catalyst with small portions of MeOH, the combined filtrates were concentrated to dryness, providing acid 51 as a white solid (969 mg, 96%). $^1$H NMR (400 MHz, DMSO-d$_6$) δ 1.20-1.48 (m, 36H), 1.52-1.60 (m, 2H), 1.63-1.72 (m, 1H), 2.84-2.89 (m, 4H), 3.85-3.91 (m, 1H), 4.09-4.15 (m, 1H), 6.75 (bs, 2H), 6.80 (d, J=8.1 Hz, 1H), 7.88 (d, J=7.8 Hz, 1H).

O—(N$^\alpha$—(N$^\alpha$,N$^\epsilon$-Bis(t-butoxycarbonyl)-L-lysinoyl)-N$^\epsilon$-(t-butoxycarbonyl)-L-lysinoyloxy)methyl S-ethyl carbonothioate (52)

To a mixture of dipeptide 51 (969 mg, 1.69 mmol) in H$_2$O (3.25 mL) and CH$_2$Cl$_2$ (3.25 mL) was added NaHCO$_3$ (294 mg, 3.50 mmol) and TBAHSO$_4$ (572 mg, 1.69 mmol). After stirring for 15 min, S-ethyl O-iodomethyl carbonothioate (322 mg, 1.30 mmol) in CH$_2$Cl$_2$ (1 mL) was added. The biphasic reaction was stirred vigorously for 2.5 h and was diluted with water and CH$_2$Cl$_2$. The layers were separated, the organic layer was washed with H$_2$O, 0.5 N HCl solution, saturated NaHCO$_3$ solution, saturated NaCl solution, dried over MgSO$_4$, filtered and concentrated to dryness. The crude product was triturated with Et$_2$O and the solids were removed by filtration and rinsed with small portions of Et$_2$O. After concentration, the combined filtrates were purified by flash chromatography on silica gel, using a gradient of 0-50% EtOAc in CH$_2$Cl$_2$ as eluent to provide compound 52 (818 mg, 91%) as a white foam. $^1$H NMR (400 MHz, CDCl$_3$) δ 1.30-1.53 (m, 8H), 1.33 (t, J=7.4 Hz, 3H), 1.44 (s, 27H), 1.60-1.75 (m, 2H), 1.82-1.90 (m, 2H), 2.90 (q, J=7.4 Hz, 2H), 3.06-3.14 (m, 4H), 4.04-4.10 (m, 1H), 4.58-4.64 (m, 1H), 4.70 (bs, 2H), 5.18-5.21 (m, 1H), 5.78 (d, J=5.6 Hz, 1H), 5.90 (d, J=5.6 Hz, 1H) 6.67 (bd, J=6.8 Hz, 1H).

(Carbonochloridoyloxy)methyl $N^\alpha$—($N^\alpha,N^\epsilon$-bis(t-butoxycarbonyl)-L-lysinoyl)-$N^\epsilon$-(t-butoxycarbonyl)-L-lysine (53)

To a solution of carbonothioate 52 (787 mg, 1.14 mmol) in ice-cold $CH_2Cl_2$ (5.7 mL) was added sulfuryl chloride (138 µL, 1.70 mmol) and the mixture was stirred at 0° C. for 3.5 h, after which the mixture was concentrated to dryness, providing chloroformate 53 as a off-white foam (806 mg, >quant.) which was used directly in the next step. $^1$H NMR (400 MHz, $CDCl_3$) δ 1.34-1.55 (m, 34H), 1.72-1.93 (m, 5H), 3.08-3.13 (m, 4H), 4.06-4.12 (m, 1H), 4.58-4.64 (m, 1H), 4.65-4.74 (m, 1H), 5.18-5.25 (m, 1H), 5.79 (d, J=5.6 Hz, 1H), 5.91 (d, J=5.3 Hz, 1H), 6.79-6.84 (m, 1H), 8.15-8.31 (m, 1H).

O—($N^\alpha$—($N^\alpha,N^\epsilon$-Bis(t-butoxycarbonyl)-L-lysinoyl)-$N^\epsilon$-(t-butoxycarbonyl)-L-lysinoyloxy)methyl N-succinimidyl carbonate (54)

To a solution of N-hydroxysuccinimide (131 mg, 1.14 mmol) and triethylamine (159 µL, 1.14 mmol) in dry acetonitrile (2.9 mL) at 0° C. was added slowly a solution of crude chloroformate 53 (806 mg, max 1.14 mmol) in dry acetonitrile (2.9 mL), cooled in an ice bath. The mixture was stirred at 0° C. for 1.5 h then at 4° C. for 20 h. The reaction mixture was concentrated and redissolved in $CH_2Cl_2$, washed with saturated $NH_4Cl$ solution, saturated NaCl solution, dried over $Na_2SO_4$, filtered and concentrated. The crude product was purified by flash chromatography on a Biotage™ flash chromatography system, using a gradient of 0-50% EtOAc in $CH_2Cl_2$ as eluent, to yield compound 54 (133 mg, 16% yield over 2 steps) as a white foam. $^1$H NMR (400 MHz, $CDCl_3$) δ 1.33-1.54 (m, 36H), 1.60-1.91 (m, 3H), 2.86 (s, 4H), 3.06-3.14 (m, 4H), 4.06-4.11 (m, 1H), 4.59-4.64 (m, 1H), 4.65-4.72 (m, 1H), 4.76-4.80 (m, 1H), 5.20-5.24 (m, 1H), 5.80 (d, J=5.6 Hz, 1H), 6.02 (d, J=5.6 Hz, 1H), 6.72-6.76 (m, 1H).

Oritavancin Conjugate 55

To oritavancin diphosphate salt (5, 177 mg, 0.089 mmol) in a mixture of dioxane (4 mL) and water (4 mL) was added $NaHCO_3$ (23 mg, 0.27 mmol). After stirring for 20 minutes, reaction mixture was cooled down to 0° C. and succinimide 54 (133 mg, 0.18 mmol) in dioxane (1 mL) was added. After stirring for 3 h 35 min at that temperature, the mixture was concentrated to remove dioxane and remaining aqueous solution was freeze-dried. The crude product was purified by $C_{18}$ reversed phase chromatography on a Biotage™ flash chromatography system, using a gradient of 15-80% MeCN in water, both containing 0.05% TFA, to furnish the TFA salt of oritavancin conjugate 55 as a white fluffy solid (212 mg, 90%). ESI-MS: m/z calculated for $C_{115}H_{148}Cl_3N_{14}O_{37}^+$ 2423.9. found 2424.6 (M+H)$^+$, 1616.4 (triply-charged dimer), 1212.4 (doubly-charged).

Oritavancin Conjugate 56

To a suspension of 55 (212 mg, 0.084 mmol) in ice-cold $CH_2Cl_2$ (4 mL) was added TFA (4 mL) slowly. After stirring for 1 h 40 min at 0° C., the homogeneous solution was concentrated to dryness and coevaporated with $Et_2O$ (2×). The crude product was purified by two consecutive C18 reversed phase chromatographies on a Biotage™ flash chromatography system, using a gradient of 10-60% MeCN in $H_2O$, both containing 0.05% TFA, for the first one and a gradient of 0-40% MeCN in $H_2O$, both containing 0.05% TFA, for the second one, to yield the TFA salt of oritavancin conjugate 56 as a white fluffy solid (74 mg, 33%). LCMS purity: 95.7% (254 nm), 95.7% (220 nm), 95.7% (290 nm); ESI-MS: m/z calculated for $C_{100}H_{124}Cl_3N_{14}O_{31}^+$ 2123.8. found 1416.3 (triply-charged dimer), 1062.3 (doubly-charged), 708.5 (triply-charged), 531.7 (quadruple-charged), 425.5 (5-times-charged).

Scheme 15. Preparation of oritavancin conjugate 56.

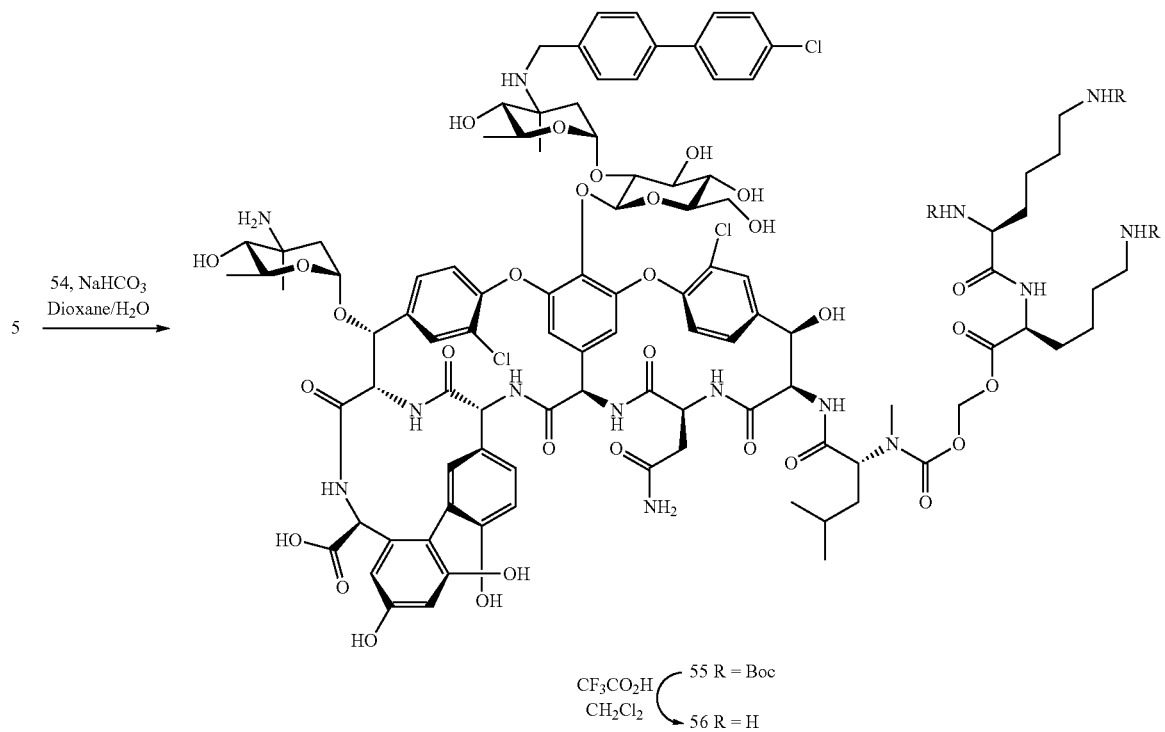

Scheme 16. Preparation of oritavancin conjugate 61.

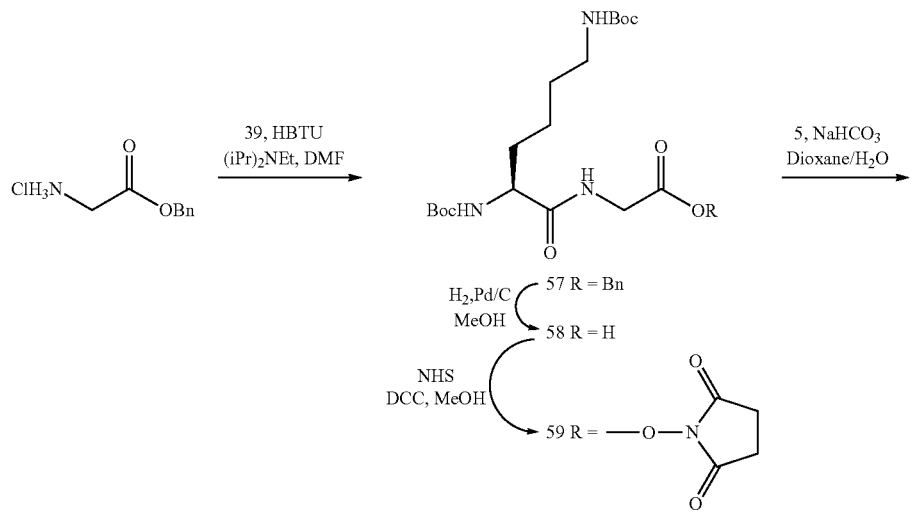

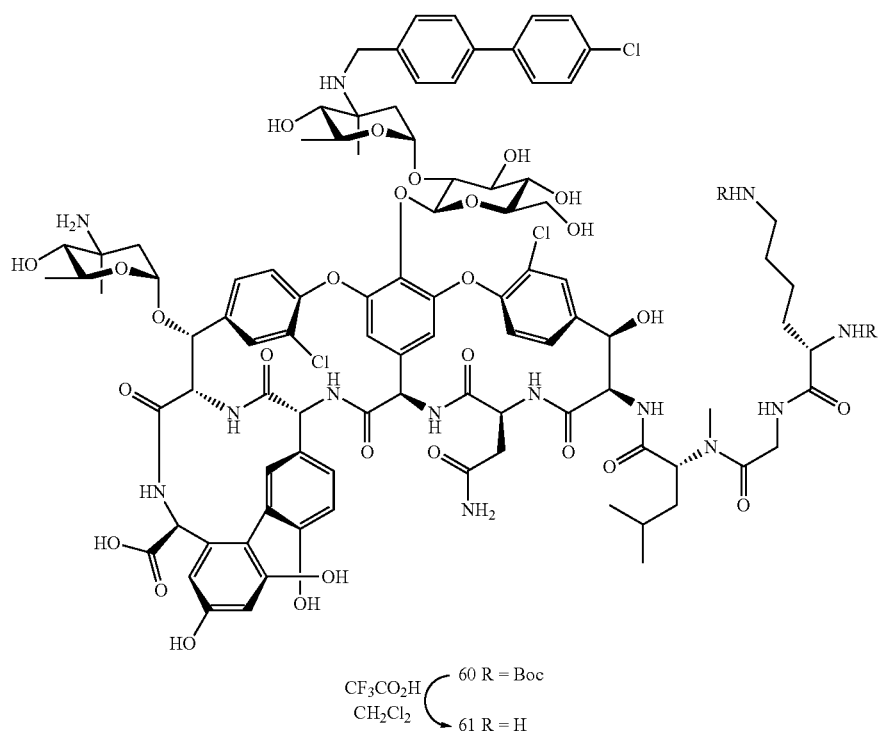

Benzyl N—(N$^\alpha$,N$^\epsilon$-bis(t-butoxycarbonyl)-L-lysinoyl)-glycine (57)

To a solution of Boc-Lys(Boc)-OH dicyclohexylamine salt (39, 1.20 g, 2.27 mmol) in DMF (11.4 mL) at 0° C. was added DIEA (792 µL, 4.55 mmol) and HBTU (862 mg, 2.27 mmol). After stirring for 15 minutes, glycine benzyl ester hydrochloride (459 mg, 2.27 mmol) was added and the mixture was stirred for 3 h at 0° C., diluted with EtOAc, washed with H$_2$O, 0.5 N aqueous HCl solution, saturated NaHCO$_3$ solution, saturated NaCl solution, dried over MgSO$_4$, filtered and concentrated. The crude product was purified by flash chromatography on a Biotage™ flash chromatography system, using a gradient of 40-60% EtOAc in hexanes as eluent to yield compound 57 (1.09 g, 97%) as a white foam. $^1$H NMR (400

MHz, CDCl$_3$) δ 1.34-1.53 (m, 4H), 1.44 (s, 18H), 1.59-1.67 (m, 1H), 1.81-1.90 (m, 1H), 3.08-3.12 (m, 2H), 4.07 (d, J=5.4 Hz, 1H), 4.08 (d, J=5.4 Hz, 1H), 4.10-4.15 (m, 1H), 4.62 (bs, 1H), 5.11 (bs, 1H), 5.18 (s, 2H), 6.64 (bs, 1H), 7.31-7.39 (m, 5H).

N—(N$^\alpha$,N$^\epsilon$-Bis(t-butoxycarbonyl)-L-lysinoyl)-glycine (58)

To a solution of benzyl ester 57 (1.09 g, 2.21 mmol) in MeOH (11 mL) was added palladium on carbon (10% wt, 100 mg) slurried in MeOH (1 mL). Hydrogen gas was bubbled through the solution to saturate, and the mixture was stirred under hydrogen atmosphere (balloon) for 1.5 h. The reaction mixture was filtered through celite, solids were rinsed with several small portions of MeOH. The combined filtrates were concentrated to dryness to provide acid 58 (887 mg, 99%) as a white foam. $^1$H NMR (400 MHz, DMSO-d$_6$) δ 1.21-1.43 (m, 4H), 1.37 (2s, 18H), 1.43-1.53 (m, 1H), 1.55-1.63 (m, 1H), 2.84-2.90 (m, 2H), 3.68 (dd, J=17.6, 5.8 Hz, 1H), 3.78 (dd, J=17.6, 5.8 Hz, 1H), 3.87-3.92 (m, 1H), 6.74-6.77 (m, 1H), 6.82 (d, J=8.0 Hz, 1H), 8.03 (t, J=5.8 Hz, 1H).

N-Succinimidyl N—(N$^\alpha$,N$^\epsilon$-bis(t-butoxycarbonyl)-L-lysinoyl)-glycine (59)

To a solution of acid 58 (887 mg, 2.20 mmol) in dry MeCN (11 mL) at 0° C. was added N-hydroxysuccinimide (278 mg, 2.42 mmol) and DCC (499 mg, 2.42 mmol). After stirring for 4.5 h at 0° C., the reaction mixture was filtered, solids were washed with several small portions of MeCN and the combined filtrates were concentrated to dryness. The crude product was purified by flash chromatography on a Biotage™ flash chromatography system, using a gradient of 60-75% EtOAc in CH$_2$Cl$_2$ as eluent. Evaporation of pure fractions yielded compound 59 (744 mg, 68%) as a white foam. $^1$H NMR (400 MHz, CDCl$_3$) δ 1.35-1.53 (m, 3H), 1.44 (s, 18H), 1.61-1.71 (m, 2H), 1.83-1.92 (m, 1H), 2.85 (s, 4H), 3.07-3.13 (m, 2H), 4.10-4.15 (m, 1H), 4.40 (d, J=5.7 Hz, 2H), 4.62 (bs, 1H), 5.16 (bs, 1H), 6.86 (bs, 1H).

Oritavancin Conjugate 60

To oritavancin diphosphate salt (5, 739 mg, 0.37 mmol) in a mixture of dioxane (9 mL) and water (9 mL) was added NaHCO$_3$ (93 mg, 1.11 mmol). After stirring for 30 minutes, succinimide 59 (372 mg, 0.74 mmol) was added. After stirring for 24 h at room temperature, additional NaHCO$_3$ (93 mg, 1.11 mmol) and succinimide 59 (372 mg, 0.74 mmol) were added and the mixture was stirred for 3 days, then the mixture was concentrated to remove dioxane and the remaining aqueous solution was lyophilized. The crude product was purified by C$_{18}$ reversed phase chromatography on a Biotage™ flash chromatography system, using a gradient of 10-70% MeCN in aqueous Et$_3$N/H$_3$PO$_4$ buffer (0.2% Et$_3$N+H$_3$PO$_4$, pH=3), then desalted by reversed phase C$_{18}$ chromatography, using a gradient of 15-80% MeCN in H$_2$O, both containing 0.05% TFA, to yield the TFA salt of oritavancin conjugate 60 as a white fluffy solid (203 mg, 23%). ESI-MS: m/z calculated for C$_{104}$H$_{129}$Cl$_3$N$_{13}$O$_{32}{}^+$ 2178.8. found 2179.3 (M+H)$^+$, 1452.7 (triply-charged dimer), 1089.8 (doubly-charged).

Oritavancin Conjugate 61

To a suspension of 60 (200 mg, 0.083 mmol) in ice-cold CH$_2$Cl$_2$ (4.2 mL) was added TFA (4.2 mL) slowly. After stirring for 1.5 h at 0° C., the homogeneous solution was concentrated to dryness and coevaporated with Et$_2$O (3×). The crude product was purified by C$_{18}$ reversed phase chromatography on a Biotage™ flash chromatography system, using a gradient of 10-60% MeCN in H$_2$O, both containing 0.05% TFA to provide the TFA salt of oritavancin conjugate 61 as a white fluffy solid (122 mg, 60%). LCMS purity: 98.7% (254 nm), 98.3% (220 nm), 99.0% (290 nm); ESI-MS: m/z calculated for C$_{34}$H$_{113}$Cl$_{13}$N$_{13}$O$_{28}{}^+$ 1978.7. found 1979.2 (M+H)$^+$, 1319.5 (triply-charged dimer), 989.7 (doubly-charged), 660.3 (triply-charged), 495.5 (quadruple-charged).

Scheme 17. Preparation of oritavancin conjugate 66.

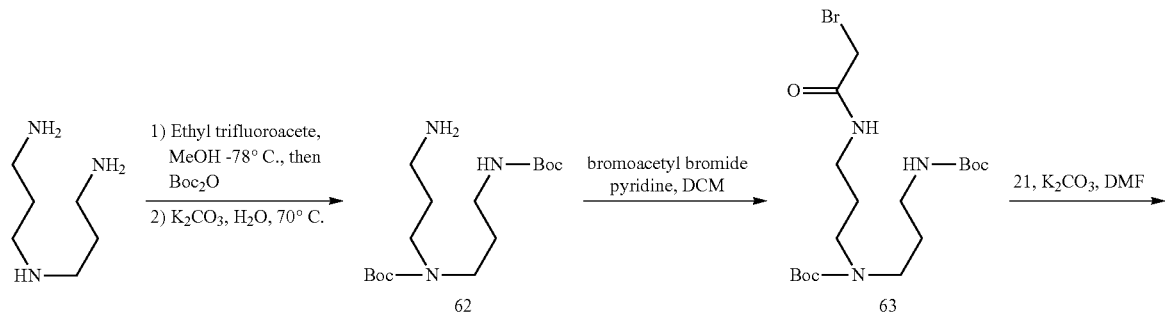

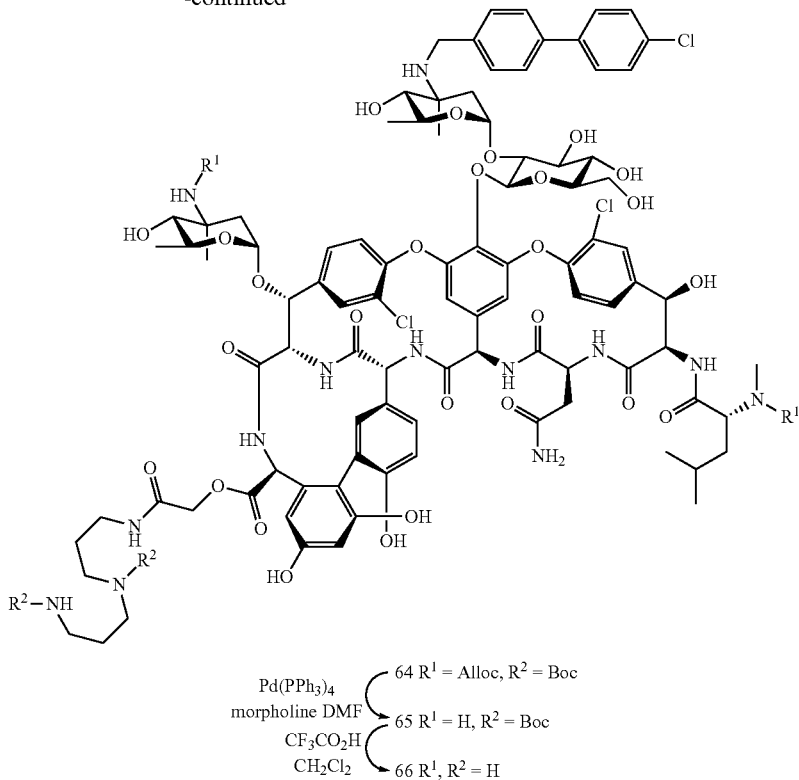

$N^1$,4-Di-tert-butoxycarbonyl-1,7-diamino-4-azaheptane (62)

A solution of $N^1$-(3-aminopropyl)propane-1,3-diamine (10 g, 76 mmol) in MeOH (200 mL) was cooled in a dry ice/acetone bath followed by the slow addition of ethyl trifluoroacetate (9.1 mL, 76 mmol) over 1 h. The resulting solution was stirred while warming to 0° C. over 1 hr. Di-tert-butyl dicarbonate (50 g, 230 mmol) was added and the resulting solution was stirred for 2 h while warming to room temperature. $K_2CO_3$ (31.6 g, 228 mmol) and $H_2O$ (50 mL) were added and the resulting mixture was stirred at 70° C. overnight. The methanol was removed under reduced pressure and the residue was resuspended in 200 mL $H_2O$ and the product was extracted with $CH_2Cl_2$/isopropanol (3:1, 150 mL×3). The organic phase was dried over $Na_2SO_4$, filtered and concentrated under reduced pressure. The crude material was purified by silical gel chromatography (0% to 10% MeOH in $CH_2Cl_2$) resulting in 62 as a pale yellow coloured liquid (11 g, 61%): $^1$H NMR (400 MHz, CDCl$_3$): δ 1.43 (s, 9H), 1.46 (s, 9H), 1.61-1.68 (m, 4H), 2.69 (t, J=6.9, 2H), 3.09-3.26 (m, 6H).

1-(α-Bromoacetamido)-4,$N^7$-di-tert-butoxycarbonyl-7-amino-4-azaheptane (63)

Bromoacetyl bromide (1.55 mL, 17.8 mmol) was added drop-wise over 5 min to a stirring solution of 62 (3.43 g, 14.8 mmol) and pyridine (2.40 mL, 29.7 mmol) in $CH_2Cl_2$ (30 mL) cooled in an ice-bath. The resulting solution was stirred at 0° C. for 3.5 h. The reaction was diluted with $CH_2Cl_2$ and washed with cold 1 N HCl, water, saturated aqueous NaCl, dried over $Na_2SO_4$, filtered and concentrated under reduced pressure. The crude product was purified by silica gel chromatography (0% to 75% EtOAc in hexanes) resulting in 63 (3.81 g, 57%) as a pale yellow coloured liquid: $^1$H NMR (400 MHz, CDCl$_3$): δ 1.44 (s, 9H) 1.48 (s, 9H), 1.63-1.70 (m, 4H), 3.08-3.28 (m, 8H), 3.86 (s, 2H).

Oritavancin Conjugate 64

A mixture of 21 (2.13 g, 1.09 mmol) and $K_2CO_3$ (225 mg, 1.63 mmol) in DMF (20 mL) was stirred at room temperature for 15 min after which 21 was mostly dissolved. A solution of 63 (737 mg, 1.63 mmol) in DMF (5 mL) was added and the resulting mixture was stirred at room temperature overnight. Water was added to the mixture and the crude product was collected by filtration. The crude material was purified by C18 reversed phase chromatography on a Biotage™ flash chromatography system (35% to 85% MeCN with 0.05% TFA in water with 0.05% TFA) to give 64 as a white solid (1.22 g, 44%): ESI-MS (M+H) calculated for $C_{112}H_{138}Cl_3N_{13}O_{35}$, 2332.7. found 2332.9.

Oritavancin Conjugate 65

Pd(PPh$_3$)$_4$ (27 mg, 0.024 mmol) was added to a degassed solution of 64 (550 mg, 0.236 mmol) and morpholine (1.03 mL, 11.8 mmol) in THF (15 mL). The resulting solution was stirred at room temperature for 19 h. After the removal of the solvent under reduced pressure the crude product was purified by C18 reversed phase chromatography on a Biotage™ flash chromatography system (15% to 70% MeCN with 0.05% formic acid in water with 0.05% formic acid) to give the formic acid salt of 65 (410 mg, 80%) as a beige coloured solid: ESI-MS (M+2H) calculated for $C_{104}H_{130}Cl_3N_{13}O_{31}$, 1083.3. found 1082.9.

Oritavancin Conjugate 66

A solution of 65 (140 mg, 0.065 mmol) in $CH_2Cl_2$/TFA (15 mL, 1:2) at 0° C. was stirred for 4 h. The solvent was evaporated under reduced pressure and the crude product was purified by C18 reversed phase chromatography on a Biotage™ flash chromatography system (5% to 40% MeCN with 0.05% formic acid in water with 0.05% formic acid) to give the TFA salt of 66 (500 mg, 32%) as a white solid: ESI-MS (M+H) calculated for $C_{93}H_{114}Cl_3N_{13}O_{27}$, 1964.3. found 1964.6.

ture. The reaction was diluted with $CH_2Cl_2$ (20 mL) and washed with saturated aqueous $NH_4Cl$ and saturated aqueous NaCl then dried over $Na_2SO_4$. After filtration the solvent was removed under reduced pressure to give 68 as a pale yellow coloured liquid (297 mg, 94%) which was used without purification. $^1$H NMR (400 MHz, $CDCl_3$): δ 0.03 (s, 18H), 1.10-

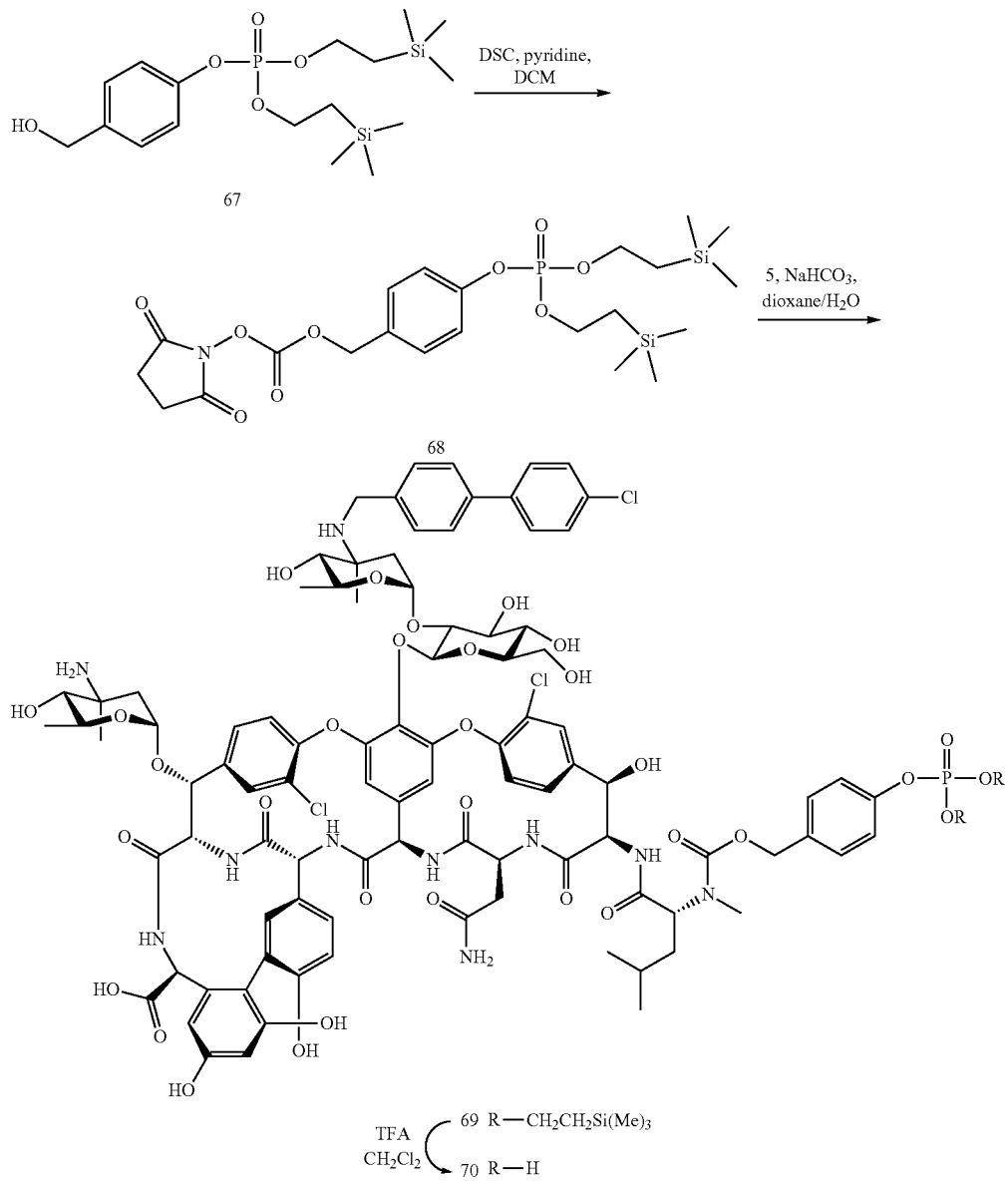

Scheme 18. Preparation of oritavancin conjugate 70.

4-((N-succinimidylcarbonoyl)oxymethyl)phenyl bis(2-(trimethylsilyl)ethyl)phosphate (68)

A solution of 4-(Hydroxymethyl)phenyl bis(2-(trimethylsilyl)ethyl)phosphate (67, 234 mg, 0.578 mmol), synthesized according to Li, et al. *Bioorganic Med. Chem. Lett.* 1998, 8, 3159-64) in $CH_2Cl_2$ was cooled in an ice-bath followed by the addition of pyridine (47 µL, 0.58 mmol) and N,N-disuccinimidyl carbonate (148 mg, 0.578 mmol). The resulting solution was stirred overnight while warming to room tempera- 1.14 (m, 4H), 2.84 (s, 4H), 4.21-4.29 (m, 4H), 5.28 (s, 2H), 7.25 (d, J=8.5, 2H), 7.38 (d, J=8.5, 2H): $^{31}$P (162 MHz, $CDCl_3$): δ −5.58 (s, 1P).

Oritavancin Conjugate 69

A suspension of 5 (538 mg, 0.270 mmol) and $NaHCO_3$ (68 mg, 0.81 mmol) in dioxane/water (1:1, 12 mL) was stirred at room temperature for approximately 15 min, after which all 5 had dissolved. A solution of 68 (295 mg, 0.541 mmol) in 2 mL dioxane was then added and the resulting solution was stirred at room temperature for 18 h. Cold water was added and the resulting mixture was stirred for 1 h then the precipitate was collected by filtration to give 69 (620 mg, 103%). The crude material which likely contained NaHCO$_3$ was found to be a mixture of the desired product and the monodeprotected material that was used without purification: ESI-MS (M+2H) calculated for C$_{104}$H$_{130}$Cl$_3$N$_{10}$O$_{32}$PSi$_2$, 1112.4. found 1112.5.

Oritavancin Conjugate 70

A solution of 69 (247 mg, 0.111 mmol) in CH$_2$Cl$_2$ (5 mL) was cooled in an ice-bath followed by the drop-wise addition of TFA (2.5 mL). The resulting solution was stirred at 0° C. for 2 h then concentrated to dryness. The crude material was purified by C18 reversed phase chromatography on a Biotage™ flash chromatography system (15 to 75% MeCN in water both containing 0.05% NH$_4$OH) to give the ammonium salt of 70 (85 mg, 37%) as a white solid: ESI-MS (M+H) calculated for C$_{94}$H$_{105}$Cl$_3$N$_{10}$O$_{32}$P, 2024.2. found 2023.9.

Scheme 19. Preparation of 3-(1,5-di(t-butoxycarbonyl-3(2-t-butoxycarbonyl)ethyl)pentan-3-ylcarbamoyl)propanoyloxymethyl N-succinimidyl carbonate (76).

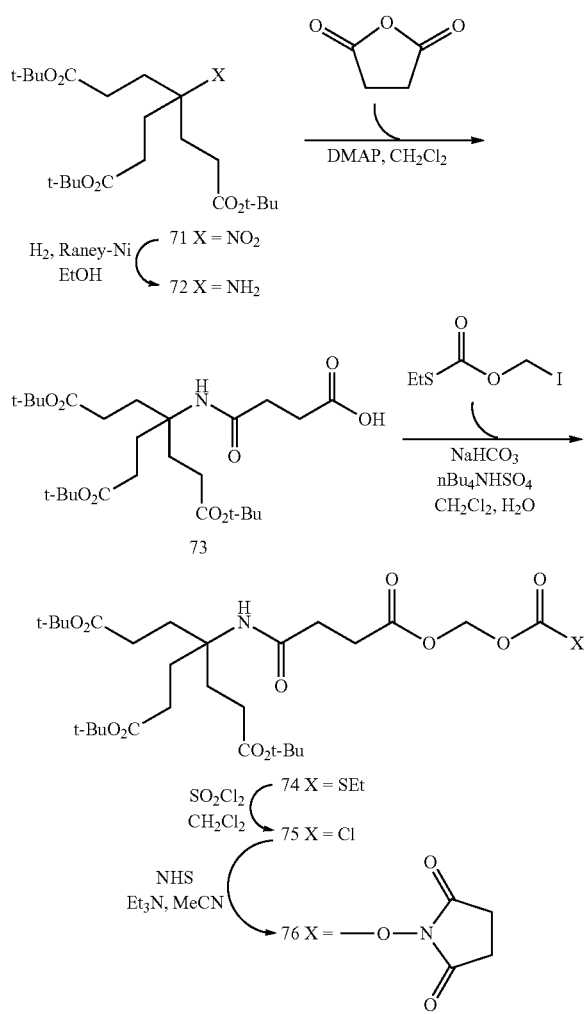

Di-t-butyl 4-(2-(t-butoxycarbonyl)ethyl)-4-aminoheptanedioate (72)

Raney-Nickel slurry in H$_2$O (2.48 g) was rinsed 3 times with absolute ethanol (decanted without drying), and transferred as a slurry in absolute ethanol to a hydrogenation vessel containing absolute ethanol (100 mL). Di-t-butyl 4-(2-(t-butoxycarbonyl)ethyl)-4-nitroheptanedioate (71, 4.0 g, 8.98 mmol) was added and the reaction mixture was hydrogenated at 60 psi in a Parr shaker over 19 h. The catalyst was removed by careful filtration of the reaction mixture over celite. The solids were rinsed with several portions of absolute ethanol and the combined filtrates were concentrated to provide amine 72 as a white solid (3.79 g, quant.): $^1$H NMR (400 MHz, CDCl$_3$) δ 1.43 (s, 27H), 1.57-1.61 (m, 6H), 2.21-2.25 (m, 6H).

3-(1,5-Di(t-butoxycarbonyl)-3-(2-(t-butoxycarbonyl)ethyl)pentan-3-ylcarbamoyl)propanoic acid (73)

To a solution of amine 72 (513 mg, 1.23 mmol) in CH$_2$Cl$_2$ (6.2 mL) was added succinic anhydride (135 mg, 1.35 mmol) and DMAP (8 mg, 0.062 mmol). The mixture was stirred for 6 h 15 min and concentrated to dryness. The crude product was purified by flash chromatography on a Biotage™ flash chromatography system, using a gradient of 50-100% EtOAc in CH$_2$Cl$_2$ as eluent to yield acid 73 (407 mg, 64%) as a white foam: $^1$H NMR (400 MHz, CDCl$_3$) δ 1.44 (s, 27H), 1.97-2.01 (m, 6H), 2.23-2.26 (m, 6H), 2.47-2.51 (m, 2H), 2.65-2.68 (m, 2H), 6.83 (s, 1H).

O-(3-(1,5-di(t-butoxycarbonyl)-3-(2-(t-butoxycarbonyl)ethyl)pentan-3-ylcarbamoyl)propanoyloxy)methyl S-ethyl carbonothioate (74)

To a mixture of acid 73 (519 mg, 1.01 mmol) in H$_2$O (3 mL) and CH$_2$Cl$_2$ (3 mL) was added NaHCO$_3$ (176 mg, 2.09 mmol) and TBAHSO$_4$ (342 mg, 1.01 mmol). After stirring for 20 min, S-ethyl O-iodomethyl carbonothioate (192 mg, 0.77 mmol) in CH$_2$Cl$_2$ (1 mL) was added. The biphasic reaction was stirred vigorously for 3 h and was diluted with water and CH$_2$Cl$_2$. The layers were separated and the organic layer was washed with H$_2$O, 0.5 N HCl solution, saturated NaHCO$_3$ solution, saturated NaCl solution, dried over MgSO$_4$, filtered and concentrated to dryness. The crude product was triturated with Et$_2$O and the solids were removed by filtration and rinsed with small portions of Et$_2$O. After concentration, the combined filtrates were purified by flash chromatography on a Biotage™ flash chromatography system, using a gradient of 20-60% EtOAc in CH$_2$Cl$_2$ as eluent, to furnish compound 74 (351 mg, 72%) as a white solid. $^1$H NMR (400 MHz, CDCl$_3$) δ 1.33 (t, J=7.4 Hz, 3H), 1.44 (s, 27H), 1.94-1.98 (m, 6H), 2.20-2.24 (m, 6H), 2.43 (t, J=6.9 Hz, 2H), 2.70 (t, J=6.9 Hz, 2H), 2.89 (q, J=7.4 Hz, 2H), 5.81 (s, 2H), 5.98 (s, 1H).

3-(1,5-Di(t-butoxycarbonyl)-3-(2-(t-butoxycarbonyl)ethyl)pentan-3-ylcarbamoyl)propanoyloxymethyl chloroformate (75)

To a solution of carbonothioate 74 (351 mg, 0.55 mmol) in ice-cold CH$_2$Cl$_2$ (3 mL) was added sulfuryl chloride (67 μL, 0.83 mmol) and the mixture was stirred at 0° C. for 3 h, after which the mixture was concentrated to dryness, providing chloroformate 75 as a colorless gum (334 mg, quant.) which was used directly in the next step: $^1$H NMR (400 MHz, CDCl$_3$) δ 1.44 (s, 27H), 1.94-1.98 (m, 6H), 2.21-2.24 (m, 6H), 2.46 (t, J=6.6 Hz, 2H), 2.74 (t, J=6.6 Hz, 2H), 5.83 (s, 2H), 6.15 (s, 1H).

3-(1,5-Di(t-butoxycarbonyl)-3-(2-(t-butoxycarbonyl)ethyl)pentan-3-ylcarbamoyl)propanoyloxymethyl N-succinimidyl carbonate (76)

To a solution of N-hydroxysuccinimide (63 mg, 0.55 mmol) and triethylamine (77 µL, 0.55 mmol) in dry acetonitrile (1.5 mL) at 0° C. was added slowly a solution of crude chloroformate 75 (334 mg, 0.55 mmol) in dry acetonitrile (1.5 mL). The mixture was stirred at 0° C. for 5 h, then the reaction mixture was concentrated, diluted with CH$_2$Cl$_2$, washed with saturated NH$_4$Cl solution, saturated NaCl solution, dried over MgSO$_4$, filtered and concentrated. The crude product was purified by flash chromatography on a Biotage™ flash chromatography system, using a gradient of 0-30% EtOAc in CH$_2$Cl$_2$ as eluent, to yield compound 76 (219 mg, 58%) as a white foam: $^1$H NMR (400 MHz, CDCl$_3$) δ 1.43 (s, 27H), 1.92-1.96 (m, 6H), 2.19-2.23 (m, 6H), 2.45 (t, J=6.7 Hz, 2H), 2.75 (t, J=6.7 Hz, 2H), 2.87 (s, 4H), 5.89 (s, 2H), 5.97 (s, 1H).

Oritavancin Conjugate 77

To oritavancin diphosphate salt (5, 317 mg, 0.16 mmol) in a mixture of dioxane (4 mL) and water (4 mL) was added NaHCO$_3$ (40 mg, 0.48 mmol). After stirring for 20 minutes, succinimide 76 (219 mg, 0.32 mmol) in dioxane (1 mL) was added. After stirring for 5 h at room temperature the mixture was concentrated to remove dioxane and remaining aqueous solution was freeze-dried. The crude product was purified by C$_{18}$ reversed phase chromatography on a Biotage™ flash chromatography system, using a gradient of 15-80% MeCN in H$_2$O, both containing 0.05% TFA to provide the TFA salt of oritavancin conjugate 77 as a white fluffy solid (219 mg, 53%): ESI-MS: m/z calculated for C$_{114}$H$_{143}$Cl$_3$N$_{11}$O$_{37}^+$ 2365.9. found 2365.6 (M+H)$^+$, 1577.2 (triply-charged dimer), 1182.9 (doubly-charged).

Oritavancin Conjugate 78

To a suspension of di-carbamate 77 (100 mg, 0.039 mmol) in ice-cold CH$_2$Cl$_2$ (1.9 mL) was added TFA (1.9 mL) slowly. After stirring for 2.5 h at 0° C., the homogeneous solution was concentrated to dryness and coevaporated with Et$_2$O (2×).

Scheme 20. Preparation of oritavancin conjugaate 78.

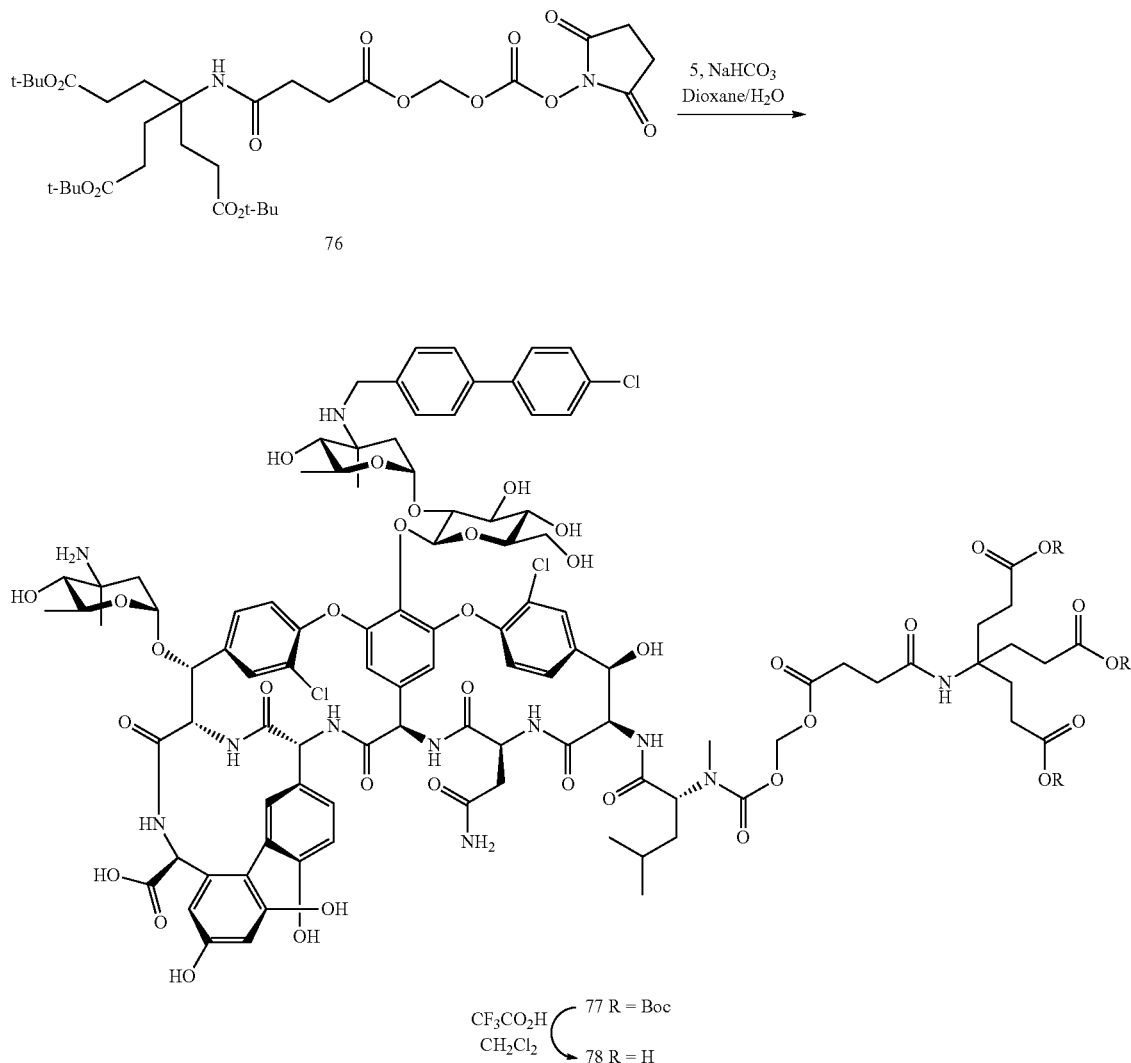

The crude product was purified by $C_{18}$ reversed phase chromatography on a Biotage™ flash chromatography system, using a gradient of 15-80% MeCN in $H_2O$, both containing 0.05% TFA to provide the TFA salt of oritavancin conjugate 78 as a white fluffy solid (36 mg, 38%): LCMS purity: 96.3% (254 nm), 98.7% (220 nm), 97.4% (290 nm); ESI-MS: m/z calculated for $C_{102}H_{119}Cl_3N_{11}O_{37}{}^+$ 2195.7. found 2197.0 $(M+H)^+$, 1465.1 (triply-charged dimer), 1098.8 (doubly-charged), 732.8 (triply-charged).

min and was diluted with water and $CH_2Cl_2$. The layers were separated, the organic layer was washed with $H_2O$, 0.5 N HCl solution, saturated $NaHCO_3$ solution, saturated NaCl solution, dried over $MgSO_4$, filtered and concentrated to dryness. The crude product was triturated with $Et_2O$ and the solids were removed by filtration and rinsed with small portions of $Et_2O$. After concentration, the combined filtrates were purified by flash chromatography on a Biotage™ flash chromatography system, using EtOAc as the eluent, to yield com-

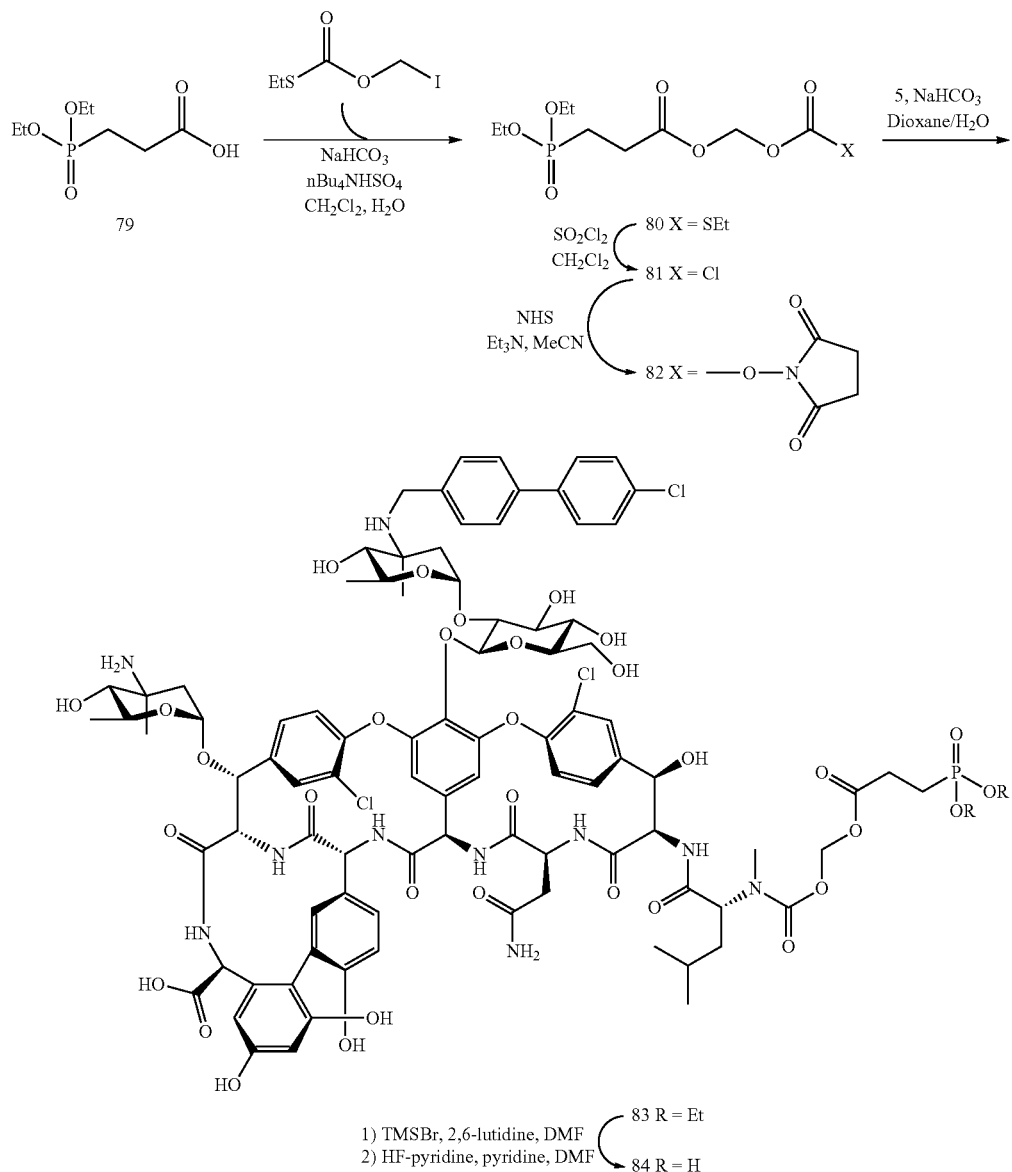

Scheme 21. Preparation of oritavancin conjugate 84.

S-Ethyl 3-(diethylphosphono)propionyloxymethyl carbonothioate (80)

To a mixture of 3-(diethylphosphono)propanoic acid (79, 1.0 g, 4.76 mmol) in $H_2O$ (12 mL) and $CH_2Cl_2$ (12 mL) was added $NaHCO_3$ (1.0 g, 11.9 mmol) and TBAHSO$_4$ (1.62 g, 4.76 mmol). After stirring for 20 min, S-ethyl O-iodomethyl carbonothioate (1.17 g, 4.76 mmol) in $CH_2Cl_2$ (2 mL) was added. The biphasic reaction was stirred vigorously for 4 h 20 pound 80 (1.29 g, 83%) as a colorless oil: $^1$H NMR (400 MHz, $CDCl_3$) δ 1.30-1.65 (m, 9H), 2.03-2.12 (m, 2H), 2.64-2.71 (m, 2H), 2.90 (q, J=7.4 Hz, 2H), 4.06-4.14 (m, 4H), 5.82 (s, 2H). $^{31}$P NMR (162 MHz, $CDCl_3$) δ 30.45 (s).

(Carbonochloridoyloxy)methyl 3-(diethylphosphono)propanoate (81)

To a solution of carbonothioate 80 (1.29 g, 3.93 mmol) in ice-cold $CH_2Cl_2$ (20 mL) was added sulfuryl chloride (478

μL, 5.89 mmol) and the mixture was stirred at 0° C. for 2 h 35 min, after which the mixture was concentrated to dryness, providing chloroformate 81 as a colorless gum (1.44 g, >quant.) which was used directly in the next step: $^1$H NMR (400 MHz, CDCl$_3$) δ 1.33 (t, J=7.1 Hz, 6H), 2.05-2.14 (m, 2H), 2.68-2.75 (m, 2H), 4.07-4.15 (m, 4H), 5.84 (s, 2H): $^{31}$P NMR (162 MHz, CDCl$_3$) δ 30.08 (s).

O-3-(Diethylphosphono)propanoyloxymethyl N-succinimidyl carbonate (82)

To a solution of N-hydroxysuccinimide (452 mg, 3.93 mmol) and triethylamine (548 μL, 3.93 mmol) in dry acetonitrile (10 mL) at 0° C. was added slowly a solution of crude chloroformate 81 (1.44 g, max 3.93 mmol) in dry acetonitrile (10 mL). The mixture was stirred at 0° C. for 1 h, and stirred at −20° C. 18 h, then the reaction mixture was concentrated, diluted with CH$_2$Cl$_2$, washed with saturated NH$_4$Cl solution, saturated NaCl solution, dried over MgSO$_4$, filtered and concentrated. The crude product was purified by flash chromatography on a Biotage™ flash chromatography system, using a gradient of 0-5% MeOH in EtOAc as eluent, to yield compound 82 (1.14 g, 76% yield over 2 steps) as a thick light yellow oil: $^1$H NMR (400 MHz, CDCl$_3$) δ 1.33 (t, J=7.1 Hz, 6H), 2.04-2.14 (m, 2H), 2.69-2.76 (m, 2H), 2.85 (s, 4H), 4.07-4.15 (m, 4H), 5.88 (s, 2H): $^{31}$P NMR (162 MHz, CDCl$_3$) δ 30.09 (s).

Oritavancin Conjugate 83

To oritavancin diphosphate salt (5, 1.0 g, 0.50 mmol) in a mixture of dioxane (12.5 mL) and water (12.5 mL) was added NaHCO$_3$ (127 mg, 1.51 mmol). After stirring for 20 minutes, succinimide 82 (383 mg, 1.01 mmol) in dioxane (1 mL) was added. After stirring for 4 h 45 min at room temperature the mixture was concentrated to remove dioxane and remaining aqueous solution was freeze-dried. Crude product was purified by C$_{18}$ reversed phase chromatography on a Biotage™ flash chromatography system, using a gradient of 15-80% MeCN in H$_2$O, both containing 0.05% TFA to provide the TFA salt of oritavancin conjugate 83 as a white fluffy solid (647 mg, 57%): ESI-MS: m/z calculated for C$_{85}$H$_{113}$Cl$_3$N$_{10}$O$_{33}$P$^+$ 2058.6. found 2060.3 (M+H)$^+$, 1373.3 (triply-charged dimer), 1030.2 (doubly-charged), 687.0 (triply-charged).

Oritavancin Conjugate 84

To a solution of diethyl phosphonate 83 (181 mg, 0.079 mmol) in DMF (4 mL) at −78° C. was added 2,6-lutidine (643 μL, 3.17 mmol), followed by a dropwise addition of trimethylsilyl bromide (418 μL, 3.17 mmol). The reaction mixture was stirred for 1 h at −78° C. and 24 h at room temperature, after which it was concentrated to dryness and dried under vacuum. The crude material was redissolved in DMF (4 mL), pyridine (514 μL, 6.32 mmol) and HF-pyridine solution (70%, 79 μL, 3.17 mmol). After stirring for 1 h at room temperature, the reaction mixture was concentrated to dryness and dried under vacuum. The crude product was purified by C$_{18}$ reversed phase chromatography on a Biotage™ flash chromatography system, using a gradient of 15-80% MeCN in aqueous Et$_3$N/H$_3$PO$_4$ buffer (0.2% Et$_3$N+H$_3$PO$_4$, pH=3) and desalted by reversed phase C18 chromatography on a Biotage™ flash chromatography system, using a gradient of 15-80% MeCN in H$_2$O, both containing 0.05% TFA, to provide the TFA salt of oritavancin conjugate 84 as a white fluffy solid (50 mg, 28%): ESI-MS: m/z calculated for C$_{91}$H$_{105}$Cl$_3$N$_{10}$O$_{33}$P$^+$ 2004.6. found 2003.6 (M+H)$^+$, 1336.1 (triply-charged dimer), 1002.2 (doubly-charged), 668.0 (triply-charged).

Scheme 22. Synthesis of O-allyl N-(-(2-bromoacetylamino)alkyl)carbamates 88a-c.

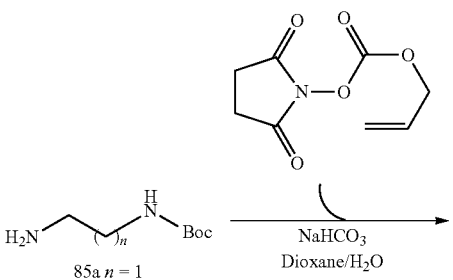

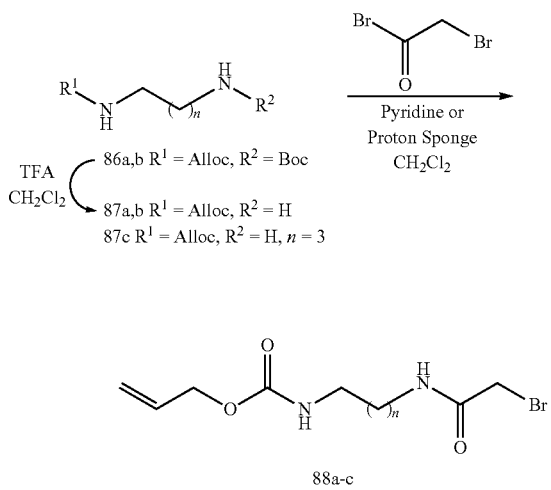

O-Allyl-O-(tert-butyl) N,N-ethane-1,2-diylbiscarbamate (86a)

To a solution of tert-butyl (2-aminoethyl)carbamate (85a, 473 mg, 2.95 mmoles) in 15 mL of a mixture of dioxane and water (1:1) was added sodium bicarbonate (496 mg, 5.90 mmoles) and a solution of allyl N-succinimidyl carbonate (706 mg, 3.54 mmoles) in 1.5 mL of dioxane. The mixture was stirred for 2.5 h at room temperature. Ethyl acetate was added and the separated organic layer was collected. The aqueous layer was extracted twice more with ethyl acetate and the combined organic phases were washed with saturated brine, dried over $MgSO_4$ and concentrated to dryness in vacuo. The residue was purified by two consecutive $SiO_2$ chromatographies on a Biotage™ flash chromatography system using 0-50% ethyl acetate in hexanes and 0-30% ethyl acetate in $CH_2Cl_2$ as the respective eluents to furnish 86a (578 mg, 2.37 mmoles, 80% yield) as a solid. $^1$H NMR (400 MHz, $CDCl_3$) δ 1.44 (s, 9H), 3.28 (m, 4H), 4.56 (d, J=5.5 Hz, 2H), 4.82 (broad s, 1H), 5.11 (broad s, 1H), 5.21 (broad dq, J=1.3, 10.4 Hz, 1H), 5.30 (dq, J=1.5, 17.2 Hz, 1H), 5.92 (octet, J=5.5 Hz, 1H).

O-Allyl-O-(tert-butyl) N,N-propane-1,3-diylbiscarbamate (86b)

The conversion was performed as for 86a starting with tert-butyl (3-aminopropyl)carbamate (85b, 1 g, 5.74 mmoles) but with a single chromatographic separation using 0-30% ethyl acetate in $CH_2Cl_2$ as the eluent to furnish 86b (1.35 g, 5.23 mmoles, 91% yield). $^1$H NMR (400 MHz, $CDCl_3$) δ 1.44 (s, 9H), 1.63 (quintet, J=6.4 Hz, 2H), 3.21 (m, 4H), 4.56 (d, J=5.6 Hz, 2H), 4.82 (broad s, 1H), 5.23 (broad s, 1H), 5.21 (broad dq, J=1.3, 10.4 Hz, 1H), 5.30 (dq, J=1.6, 17.2 Hz, 1H), 5.91 (octet, J=5.6 Hz, 1H).

2-((Allyloxycarbonyl)amino)ethan-1-ammonium trifluoroacetate (87a)

To a solution of 86a (578 mg, 2.36 mmoles) in 2.4 mL of $CH_2Cl_2$ was added 2.4 mL of TFA. After 30 min at room temperature, the mixture was concentrated to dryness in vacuo, taken up in 1:1 ether/hexanes and concentrated again. This material was used in the next stage without further purification. $^1$H NMR (400 MHz, DMSO) δ 2.85 (sextet, J=6.0 Hz, 2H), 3.22 (q, J=6.1 Hz, 2H), 4.48 (d, J=5.3 Hz, 2H), 5.19 (broad doublet of quintets, J=1.4, 10.4 Hz, 1H), 5.29 (doublet of quintets, J=1.6, 17.2 Hz, 1H), 5.91 (octet, J=5.5 Hz, 1H), 7.35 (bt, J=5.4 Hz, 1H).

3-((Allyloxycarbonyl)amino)propan-1-ammonium trifluoroacetate (87b)

The conversion was performed as for 87a but starting with 86b (1.35 g, 5.23 mmoles). $^1$H NMR (400 MHz, DMSO) δ 1.67 (quintet, J=7.0 Hz, 2H), 2.79 (broad sextet, J=6.8 Hz, 2H), 3.05 (q, J=6.4 Hz, 2H), 4.47 (d, J=5.2 Hz, 2H), 5.18 (broad doublet of quintets, J=1.3, 10.5 Hz, 1H), 5.27 (broad doublet of quintets, J=1.6, 17.2 Hz, 1H), 5.89 (octet, J=5.5 Hz, 1H), 7.34 (bt, J=5.3 Hz, 1H).

4-((Allyloxycarbonyl)amino)butan-1-amine (3c)

The material was obtained from 1,4-diaminobutane according to literature (*Synthesis*, 2002, 15, 2195).

O-Allyl N-(2-(2-bromoacetylamino)ethyl)carbamate (88a)

To a solution of the crude 87a obtained previously (max. 2.36 mmoles) in 12 mL $CH_2Cl_2$ in an ice bath was added pyridine (554 μL, 6.84 mmoles), followed by the dropwise addition of bromoacetyl bromide (246 μL, 2.83 mmoles). The mixture was stirred in the ice bath for 30 min. It was diluted with $CH_2Cl_2$ and washed with saturated aqueous ammonium chloride. The organic layer was collected and the aqueous layer was extracted twice more with $CH_2Cl_2$. The combined organic layers were dried over $MgSO_4$ and concentrated to dryness in vacuo. The residue was purified by $SiO_2$ chromatography on a Biotage™ flash chromatography system, using 40-60% EtOAc in $CH_2Cl_2$ as the eluent, to furnish 88a (452 mg, 1.61 mmoles, 68% yield over two steps) as a solid. $^1$H NMR (400 MHz, $CDCl_3$) δ 3.37 (q, J=5.6 Hz, 2H), 3.44 (q, J=5.4 Hz, 2H), 3.87 (s, 2H), 4.58 (d, J=5.5 Hz, 2H), 5.10 (broad s, 1H), 5.23 (broad dq, J=0.9, 10.4 Hz, 1H), 5.31 (dq, J=1.4, 17.2 Hz, 1H), 5.92 (octet, J=5.5 Hz, 1H), 6.97 (broad s, 1H).

O-Allyl N-(3-(2-bromoacetylamino)propyl)carbamate (88b)

The conversion was performed as for 88a but using the crude 87b (max. 5.23 mmoles) to give 88b (1.05 g, 3.56 mmoles, 68% yield) as a solid. $^1$H NMR (400 MHz, $CDCl_3$) δ 1.69 (quintet, J=6.2 Hz, 2H), 3.25 (q, J=6.3, 2H), 3.36 (q, J=6.3, 2H), 3.88 (s, 2H), 4.57 (d, J=5.5 Hz, 2H), 5.12 (broad s, 1H), 5.22 (broad dq, J=1.2, 10.4 Hz, 1H), 5.31 (dq, J=1.4, 17.2 Hz, 1H), 5.92 (octet, J=5.5 Hz, 1H), 7.00 (broad s, 1H).

O-Allyl N-(4-(2-bromoacetylamino)butyl)carbamate (88c)

4-((Allyloxycarbonyl)amino)butan-1-amine (87c, 1.18 g, 6.852 mmol, prepared according to *Synthesis*, 2002, 15, 2195) and proton sponge (1.468 g, 6.850 mmol) were dissolved in 14 mL of dichloromethane followed by the dropwise addition of 0.6 mL (6.908 mmol) of bromoacetyl bromide. After overnight stirring at room temperature, the mixture was diluted with dichloromethane, washed with water (2×) and brine (1×) and dried over sodium sulfate. The concentrated crude material was subjected to a Biotage™ flash chromatography system on a silica gel column with 40:1 (v/v) dichloromethane/methanol as the eluent. Product 88c (1.52 g, 76% yield) was obtained as an off-white solid. $^1$H NMR (400 MHz, $CDCl_3$) δ 1.69 (m, 4H), 3.22 (q, J=6.2, 2H), 3.32 (q, J=6.2, 2H), 3.88 (s, 2H), 4.56 (d, J=5.1, 2H), 4.80 (broad s, 1H), 5.21 (dd, J=1.1, 10.6, 1H), 5.30 (dd, J=1.8, 17.2, 1H), 5.92 (octet, J=5.6 Hz, 1H), 6.58 (broad s, 1H).

Scheme 23. Preparation of oritavancin derivatives 90a-c.

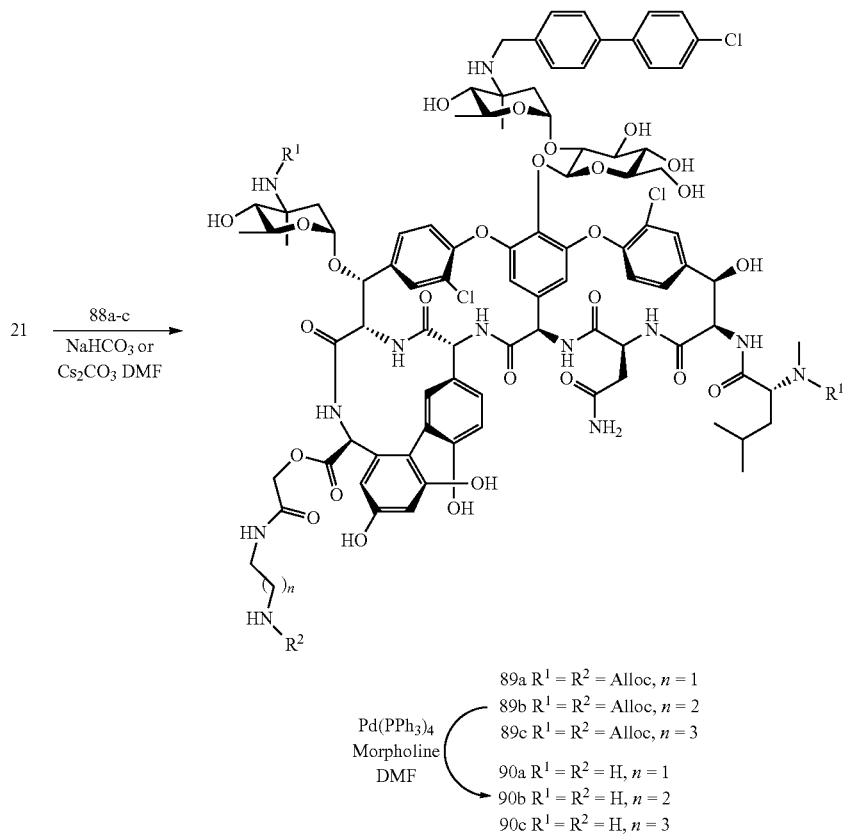

89a $R^1 = R^2$ = Alloc, $n = 1$
89b $R^1 = R^2$ = Alloc, $n = 2$
89c $R^1 = R^2$ = Alloc, $n = 3$
90a $R^1 = R^2$ = H, $n = 1$
90b $R^1 = R^2$ = H, $n = 2$
90c $R^1 = R^2$ = H, $n = 3$ Pd(PPh$_3$)$_4$
Morpholine
DMF Oritavancin Derivative 89a To 21 (1.0 g, 0.51 mmoles) in 10 mL of DMF was added sodium bicarbonate (86 mg, 1.02 mmoles). After stirring at room temperature for 20 min, 88a (135 mg, 0.51 mmoles) was added. The mixture was stirred overnight at room temperature, at which point another portion of sodium bicarbonate (43 mg, 0.51 mmoles) and 88a (135 mg, 0.51 mmoles) were added. After another 24 h at room temperature, the mixture was concentrated to dryness in vacuo, and the residue was purified by two successive $C_{18}$—$SiO_2$ chromatographies on a Biotage™ flash chromatography system, using 40-100% acetonitrile in 0.2% triethylamine in water brought to pH 3 with phosphoric acid and 30-70% of acetonitrile (0.05% TFA) in water (0.05% TFA) as the respective eluents to furnish 89a (440 mg, 0.20 mmoles, 39% yield) as a solid. ESI-MS: Calculated for $C_{102}H_{117}Cl_3N_{12}O_{33}+H^+$ 2146. found 2145.6.

Oritavancin Derivative 89b

The conversion was performed as for 89a but using 88b (142 mg, 0.51 mmoles) twice with 21 (1.0 g, 0.51 mmoles) and a single $C_{18}$—$SiO_2$ chromatography, using 30-70% of acetonitrile (0.05% TFA) in water (0.05% TFA) to give 88b (405 mg, 0.18 mmoles, 35% yield) as a solid. ESI-MS: m/z calculated for $C_{103}H_{119}Cl_3N_{12}O_{33}+H^+$ 2160. found 2160.3.

Oritavancin Derivative 90a

Argon was bubbled through a solution of 89a (108.8 mg, $4.95 \times 10^{-5}$ moles) and morpholine (45 μL, $5.14 \times 10^{-4}$ moles) in 4 mL of DMF for 15 min. Tetrakis(triphenylphosphine) palladium (20 mg, $1.73 \times 10^{-5}$ moles) were added and the mixture was stirred at room temperature for 24 h. Diethyl ether (40 mL) was added and the precipitate was collected, washed copiously with diethyl ether and dried in vacuo. It was subjected to a Biotage™ flash chromatography system on a $C_{18}$—$SiO_2$ column with gradient elution of 5-60% of methanol in water (0.1% formic acid, pH 2) to give 90a (69.5 mg, 67% yield, mixed salt of bis-formate and trifluoroacetate) as a solid. ESI-MS: m/z calculated for $C_{90}H_{105}Cl_3N_{12}O_{27}+H^+$ 1893. found 1893.4.

Oritavancin Derivative 90b

The conversion and the purification were performed as for 90a but using 89b (117.2 mg, $5.24 \times 10^{-5}$ moles) to furnish 90b as a solid (10.4 mg, 10% yield, mono-formate). ESI-MS: m/z calculated for $C_{91}H_{107}Cl_3N_{12}O_{27}+H^+$ 1907. found 1907.2.

Oritavancin Derivative 90c

To 21 (205 mg, 0.1045 mmole) in 3 mL of DMF was added cesium carbonate (34.2 mg, 0.1050 mmole). After stirring at room temperature for 15 min, 88c (51.7 mg, 0.1764 mmole) in 1 mL DMF was added plus 1 mL DMF rinse. The reaction was stirred overnight at room temperature, at which point $L^c$-MS analysis revealed a mixture of mainly product 89c and some unreacted 21. The system was purged and protected under argon atmosphere, and morpholine (0.27 mL, 3.099 mmol) and tetrakis(triphenylphosphine)palladium (18.6 mg, 0.01610 mmol) were added. After 2 h, the reaction was complete as indicated by $L^c$-MS and diethyl ether (20 mL) was added. Filtration through glass-fiber filter paper and drying in vacuo afforded a solid that was subjected to C18 reverse phase chromatography on a Biotage™ flash chromatography system using a gradient of 5-100% methanol in an aqueous buffer containing 30 mM of phosphoric acid and 20 mM of triethylamine (pH 3) as the eluent. The white solid obtained after lyophilization was desalted on a Biotage™ flash chromatography system (C18 column) using a gradient elution of 0-100% methanol in water (0.1% (v/v) formic acid, pH 2) to furnish the formate salt of 90c (17.2 mg, 7.5% yield over 2 steps). ESI-MS: m/z calculated for $C_{92}H_{109}Cl_3N_{12}O_{27}+H^+$ 1921. found 1921.9.

mmoles) in 4 mL of DMSO and 8 mL of DMF was stirred vigorously to near complete dissolution, before the addition of 250 µL of DIPEA (1.4 mmoles). After stirring for 15 min at room temperature, a solution of 92 (250 mg, 1 mmole) in 2×1 mL of DMF was added to the clear mixture. The resulting solution was stirred at room temperature for 44 h, and 80 mL of diethyl ether were added. The precipitate was collected, copiously washed with diethyl ether and dried in vacuo. It was subjected to $C_{18}$—$SiO_2$ chromatography on a Biotage™ flash chromatography system, using 20-100% of 0.1% formic acid in methanol in 0.1% formic acid in water as the eluent to Scheme 24. Preparation of oritavancin derivative 93

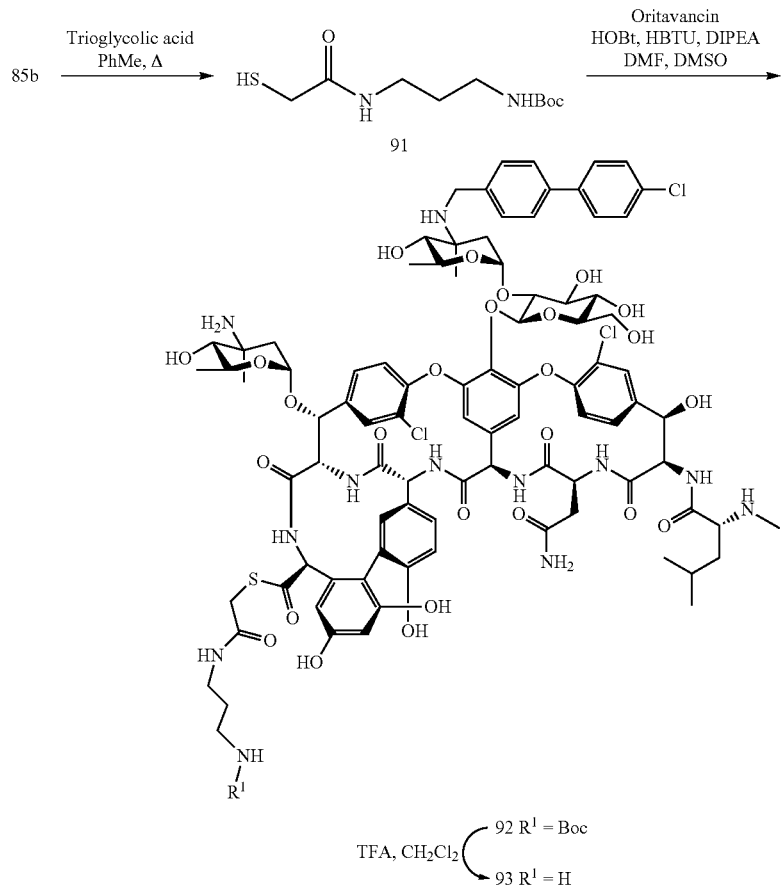

O-Allyl N-(3(2-sulfanylacetylamino)propyl)carbamate (91)

To a solution of tert-butyl 3-aminopropylcarbamate (85b, 2 g, 11.48 mmoles) in toluene (8 mL), in a pressure tube, was added 900 µL of thioglycolic acid (12.95 mmoles). Argon was bubbled through the solution for 15 min, and the mixture was capped and heated to 115° C. (bath temperature) for 24 h. The solution was then concentrated to dryness in vacuo and the residue was subjected to $SiO_2$ chromatography on a Biotage™ flash chromatography system using 25-0% hexanes in EtOAc as the eluent to furnish 91 (1.19 g, 4.77 mmoles, 42% yield) as a colourless oil. $^1$H NMR (400 MHz, $CDCl_3$) δ 1.65 (quintet, J=6.3 Hz, 2H), 1.94 (t, J=9.0 Hz, 1H), 3.17 (t, J=6.2, 2H), 3.24 (d, J=8.9 Hz, 2H), 3.33 (q, J=6.3 Hz, 2H), 4.11 (q, J=7.1 Hz, 1H), 4.87 (broad s, 1H), 7.12 (broad s, 1H).

Oritavancin Derivative 92

A mixture of oritavancin phosphate (5, 500 mg, $2.51\times10^{-4}$ moles), HOBt (135 mg, 1 mmole) and HBTU (475 mg, 1.25 furnish 92 (137.2 mg, $6.35\times10^{-4}$ moles, 25% yield) as a white solid. ESI-MS: m/z calculated for $(C_{96}H_{115}Cl_3N_{12}O_{28}S+2H^+)$ 1012.5. found 1012.0; Calculated for $(C_{96}H_{115}Cl_3N_{12}O_{28}S+3H^+)$ 675.3. found 675.1.

Oritavancin Derivative 93

To 92 (137.2 mg, $6.35\times10^{-4}$ moles) in an ice bath was added 2 mL of an ice cold 1:1 mixture of $CH_2Cl_2$ and TFA. The mixture was stirred in an ice bath for 2 h and 40 mL of diethyl ether was added. The precipitate was collected by filtration through a glass fiber filter paper, washed copiously with diethyl ether and dried in vacuo. It was subjected to $C_{18}$—$SiO_2$ chromatography on a Biotage™ flash chromatography system, using 20-100% of 0.1% formic acid in methanol in 0.1% formic acid in water as the eluent to furnish 93 (38.4 mg, $1.82\times10^{-5}$ moles, 29% yield) as a white solid. ESI-MS: m/z calculated for $(C_{91}H_{107}Cl_3N_{12}O_{26}S+2H^+)$ 962.5. found 962.2; Calculated for $(C_{91}H_{107}Cl_3N_{12}O_{26}S+3H^+)$ 642. found 641.8.

Scheme 25. Preparation of oritavancin derivative 95.

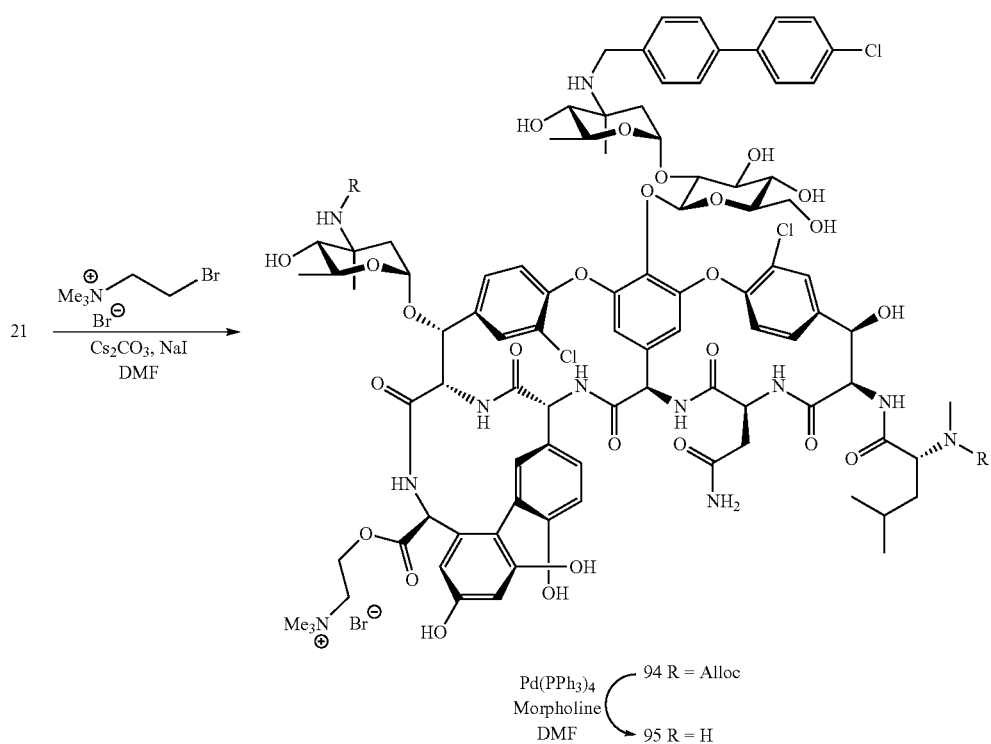

Oritavancin Derivative 95

A mixture of 21 (197.7 mg, 0.1008 mmol) and caesium carbonate (33.5 mg, 0.1028 mmol) in 4 mL DMF was stirred at room temperature for 30 min, upon which time a colorless clear solution was obtained. Sodium iodide (30.8 mg, 0.2055 mmol) and (2-bromoethyl)trimethylammonium bromide (49.6 mg, 0.2008 mmol) were then added and stirred at room temperature overnight to yield mainly the product 94 and some unreacted 21 as indicated by L$^c$/MS analysis (ESI-MS for product 94: Calculated for cation ($C_{99}H_{117}Cl_3N_{11}O_{30}^+$) 2047.4. found 2047.3). The reaction mixture was purged and protected under an atmosphere of argon, and morpholine (0.18 mL, 2.066 mmol) and tetrakis(triphenylphosphine)palladium (12.0 mg, 0.01038 mmol) were added. The reaction progress was monitored by L$^c$/MS and after 2 h two additional batches of tetrakis(triphenylphospine)palladium were added to bring the total catalyst loading to 63.1 mg (0.0546 mmol). When the reaction was complete, the solvent was removed in vacuo. The crude material was subjected to C18 reverse phase chromatography on a Biotage™ flash chromatography system using a gradient of 0-100% methanol in water (0.1% (v/v) formic acid, pH 2) as the eluent to furnish the formate salt of 95 (70.5 mg, 32% yield over 2 steps) as a white solid. ESI-MS: m/z calculated for cation ($C_{91}H_{109}Cl_3N_{11}O_{26}^+$+H$^+$) 939. found 939.7; Calculated for cation ($C_{91}H_{109}Cl_3N_{11}O_{26}^+$+2H$^+$) 626.7. found 626.8; Calculated for cation ($C_{91}H_{109}Cl_3N_{11}O_{26}^+$+3H$^+$) 470.2. found 470.5.

Scheme 26. Preparation of oritavancin derivative 98

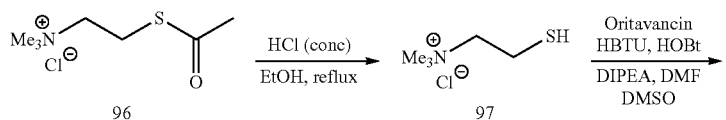

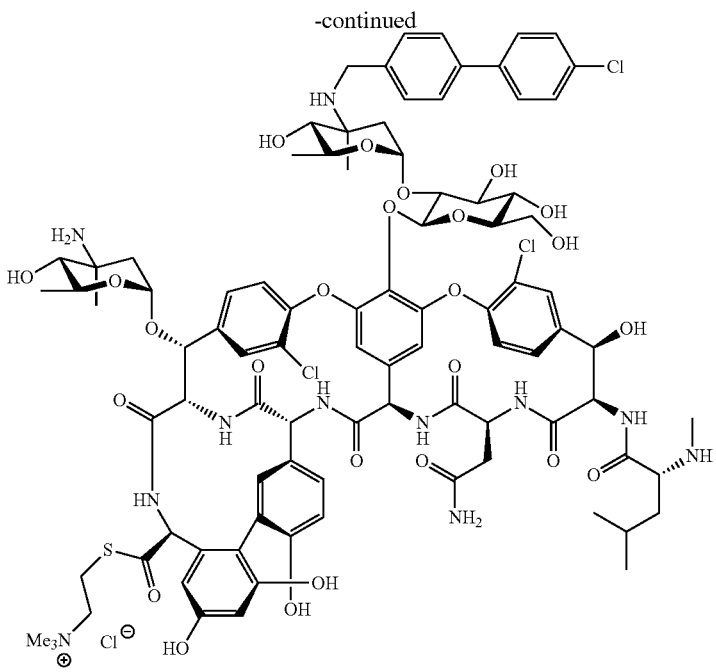

98

Thiocholine Chloride 97

Commerically available acetylthiocholine chloride 96 (496.9 mg, 2.513 mmol) was dissolved in 16 mL of absolute ethanol and 4 mL of concentrated hydrochloric acid was added. The mixture was brought to reflux over night under argon atmosphere. After concentration, more ethanol was added and removed. The sequence was repeated twice and the residue was dried in vacuo. Crystallization in diethyl ether/ethanol failed to give crystals and the solvents were removed. The residual material was triturated in diethyl ether for 4 days, upon which time an off-white solid was easily scratched off the flask, filtered and dried in vacuo to afford thiocholine chloride 97 (371.2 mg, 95% yield) that was used directly in the following step without further purification. $^1$H NMR (400 MHz, CD$_3$OD) δ 2.91-2.95 (m, 2H), 3.16 (s, 9H), 3.52-3.56 (m, 2H).

Oritavancin Derivative 98

DIPEA (0.24 mL, 1.378 mmol) was added to a solution of oritavancin diphosphate (5, 500.9 mg, 0.2518 mmol), HBTU (478.7 mg, 1.262 mmol) and HOBt (137.4 mg, 1.017 mmol) in a mixture of DMSO (4 mL) and DMF (8 mL). After 20 minutes, 97 (157.5 mg, 1.012 mmol) was added and the mixture was stirred at room temperature overnight, upon which time the reaction was completed as indicated by L$^c$/MS. The solution was poured into 60 mL of diethyl ether and the precipitate was collected after filtration and was dried in vacuo. The crude product was subjected to repetitive C18 reverse phase chromatography on a Biotage™ flash chromatography system using a gradient of 0-100% methanol in an aqueous buffer (pH 3, 30 mM phosphoric acid and 20 mM triethylamine). The resulting purified white solid was desalted by C18 reverse phase chromatography on a Biotage™ flash chromatography system using a gradient of 0-100% methanol in an aqueous buffer containing either 0.1% (v/v) formic acid (pH 2) or 10 mM ammonium acetate with 0.1% (v/v) acetic acid (pH 4.5) to afford the formate salt of 98 (48.2 mg, 9% yield) or the acetate salt of 98 (70 mg, 12% yield), respectively. ESI-MS: m/z calculated for cation (C$_{91}$H$_{109}$Cl$_3$N$_{11}$O$_{29}$S$^+$) 1894.6. found 1894.3; calculated for (C$_{91}$H$_{199}$Cl$_3$N$_{11}$O$_{29}$S$^+$+H$^+$) 947.3. found 947.5; calculated for cation (C$_{91}$H$_{199}$Cl$_3$N$_{11}$O$_{29}$S$^+$+2H$^+$) 632.5. found 632.2; calculated for cation (C$_{91}$H$_{109}$Cl$_3$N$_{11}$O$_{29}$S$^+$+3H$^+$) 474.6. found 474.4.

Scheme 27. Preparation of oritavancin derivative 103

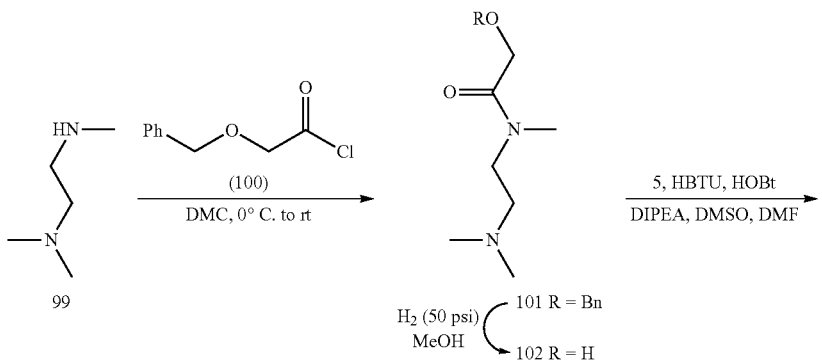

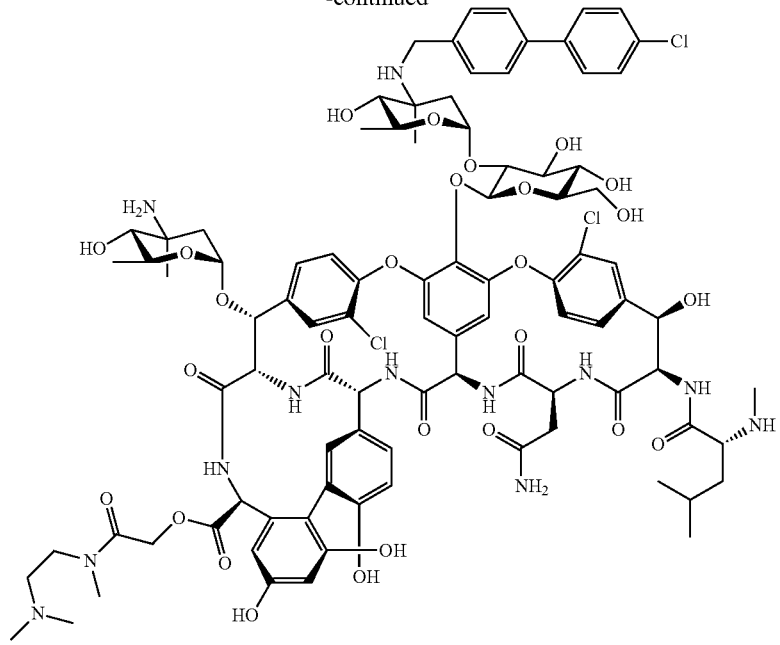

103

2-Benzyloxy-N-(2-(dimethylamino)ethyl)-N-methylacetamide (101)

N,N,N'-Trimethylethylenediamine (99, 0.17 mL, 1.308 mmol) was dissolved in 5 mL of dichloromethane and cooled to 0° C. in an ice-water bath. 2-Benzyloxyacetyl chloride (100, 0.2 mL, 1.267 mmol) was added to the above solution dropwise and the mixture was allowed to warm to room temperature. After overnight, the reaction was complete and the mixture was concentrated and used in the next step without purification as HCl salt: $^1$H NMR (400 MHz, CDCl$_3$): δ 2.86 (s, 3H), 2.87 (s, 3H), 3.09 (s, 3H), 3.16 (q, J=5.5, 2H), 3.85 (t, J=6.6, 2H), 4.24 (s, 2H), 4.63 (s, 2H), 7.30-7.39 (m, 5H).

N-(2-(Dimethylamino)ethyl)-2-Hydroxy-N-methylacetamide (102)

Crude HCl salt of 101 was mixed with 201.8 mg (0.1896 mmol) of palladium on charcoal (10%) in 15 mL of methanol. The mixture was subjected to hydrogen atmosphere at 50 psi on a Parr apparatus at room temperature. After overnight, another 200.9 mg of catalyst was needed. After overnight, reaction was completed and the insolubles was filtered off through glass fiber filter paper. The filtrate was concentrated to yield 254.6 mg (quant.) of product 102 as HCl salt: $^1$H NMR (400 MHz, CDCl$_3$): δ 2.89 (s, 6H), 3.06 (s, 3H), 3.21 (t, J=6.6, 2H), 3.93 (t, J=6.6, 2H), 4.25 (s, 2H).

Oritavancin Conjugate 103

Oritavancin diphosphate 5 (630.7 mg, 0.3171 mmol), HBTU (601.1 mg, 1.585 mmol) and HOBt (173.4 mg, 1.283 mmol) was dissolved in the mixture of DMSO (4 mL) and DMF (8 mL) and 0.4 mL (2.296 mmol) of DIPEA was added. After stirring at room temperature for 30 min, the solution of 102 in 1 mL DMF was added plus 1 mL rinse. A yellow clear solution was obtained. After 2 days, 250 mL of diethyl ether was added to the reaction while stirring. After stand for a few min, the clear solution was decanted. The process was repeated with another 150 mL of diethyl ether. The residual mixture was dried in vacuo. The product was purified on repetitive C18 flash columns on a Biotage automatic chromatography system with gradient elution of H$_3$PO$_4$ (30 mM)-triethylamine (20 mM) buffer (aq, pH3)/methanol and then C18 column on Biotage system with gradient elution of 0.1% formic acid buffer (aq, pH2)/methanol. The purified product is a white solid as penta-formate salt (43.2 mg, 6%): ESI-MS calculated for $C_{93}H_{111}Cl_3N_{12}O_{27}$: calculated 484.8 (M/4+H), 646.1 (M/3+H), 967.6 (M/2+H). found: 484.6, 646.0, 967.6.

Example 2

Solubility of Oritavancin Conjugates in Phosphate Buffer Saline

The ability of the molecules from Example 1 to dissolve in 10 mM phosphate buffered saline (0.138 M NaCl, 2.7 mM KCl), pH 7.4. To a sample of the material of known mass were added known volumes of phosphate buffered saline until complete dissolution is observed. Suspensions were centrifuged for 5 min at 10000 rpm. Under these conditions, complete dissolution of the diphosphate salt of oritavancin is not observed at concentrations of 0.1 mg/mL, the lowest concentration tested. Data for the in vitro solubility are summarized in Table 1. Upon complete dissolution, the solution is diluted until the final concentration is 0.5 mg/mL to ensure that the material remains soluble over the entire range of concentrations.

This experiment demonstrates that clear improvements in solubility are obtained by the substitution at the N-methylleucyl residue of oritavancin with a negatively charged functional group (which results in the loss of a positive charge and the gain of at least one negative charge), but especially by blocking the carboxy terminus with a positively charged functional group (that is replacement of a negative charge with a positive charge).

TABLE 1

Solubility of compounds in phosphate buffer saline

| Compound | Solubility (mg/mL) PBS |
|---|---|
| Oritavancin (5) | <0.1 |
| 7 | <0.5 |
| 13 | 5.5 |
| 20 | 5.5 |
| 24 | ≥100 |
| 28 | ≥100 |
| 36 | — |
| 38 | <0.5 |
| 44 | <0.5 |
| 46 | <0.5 |
| 56 | >5 |
| 61 | <0.5 |
| 66 | >100 |
| 70 | 8 |
| 78 | 4 |
| 84 | 0.5-1 |
| 90a | ≥100 |
| 90b | ≥100 |
| 90c | <1.6 |
| 93 | ≥100 |
| 95 | ≥100 |
| 98 (formate salt) | ≥100 |
| 98 (acetate salt) | 20 |
| 103 | ≥100 |

Example 3

Determination of In Vitro Antibacterial Activity

Susceptibility of S. aureus strain ATCC13709 to oritavancin (5) and synthesized compounds was determined following the guidelines set by the Clinical and Laboratory Standards Institute (formerly the National Committee for Clinical Laboratory Standards) (M26-A). Compounds were serially diluted two-fold in either DMSO (Oritavancin 5) or in PBS and transferred to cation-adjusted Mueller Hinton broth (CAMHB; Becton Dickinson). 50 µL of compounds diluted in CAMHB was mixed with 100 µL of bacteria diluted in CAMHB in 96-well microtiter plates. The final number of micro-organisms in the assay was $5 \times 10^5$ c.f.u. per mL and the final concentration of DMSO in the assay, if present, was 1.25%. All solutions may contain 0.002% Tween as indicated. Assays were set up in duplicate and incubated at 37° C. for 18 h. The concentration of compound that inhibited visible growth was reported as the minimum inhibitory concentration (MIC). The data are summarized in Table 2.

TABLE 2

Antibacterial susceptibility of bacteria to selected compounds
(Minimum inhibitory concentrations)
MIC against S. aureus ATCC 13709 (µg/mL)

| Compound | CAMHB[a] | CAMHB + 0.002% tween | CAMHB + 50% human serum | CAMHB + 50% mouse serum | CAMHB + 50% rat serum |
|---|---|---|---|---|---|
| Oritavancin (5) | 1 | 0.125 | 0.125 | 0.25 | 0.25 |
| 7 | 2 | 0.125 | 0.5 | 0.5 | 0.25 |
| 13 | 4 | 2 | 64 | 64 | 32 |
| 20 | 4 | 4 | 16 | 16 | 2 |
| 24 | 1 | 0.5 | 1 | 0.06 | 0.06 |
| 28 | 2 | 0.125 | 0.25 | 0.25 | 0.063 |
| 36 | 1 | 0.06 | 0.125 | 0.25 | 0.125 |
| 38 | 2 | 0.25 | 1 | 1 | 0.5 |
| 44 | 4 | 0.5 | 4 | 0.25 | 0.5 |
| 46 | 1 | 0.25 | 0.5 | 1 | 0.25 |
| 56 | 2 | 0.5 | 4 | 0.5 | 0.25 |
| 61 | 2 | 0.25 | 0.25 | 1 | 0.5 |
| 66 | 2 | 0.25 | 0.125 | 1 | 0.125 |
| 70 | 2 | 1 | 32 | 32 | >32 |
| 78 | 8 | 1 | 16 | 32 | — |
| 84 | 1 | 0.125 | 0.5 | 2 | — |
| 90a | 1 | 0.5 | 0.25 | 0.5 | — |
| 90b | 1 | 0.5 | 0.25 | 0.5 | — |
| 90c | 1 | 0.25 | 0.125 | 0.5 | — |
| 93 | 0.5 | 0.125 | 0.25 | 1 | — |
| 95 | 1 | 0.25 | 0.5 | 2 | 0.125 |
| 98 | 1 | 0.25 | 0.25 | 2 | 0.125 |
| 103 | 2 | 0.25 | 0.25 | 0.5 | 0.125 |

[a]Cation-adjusted Mueller-Hinton broth.

It can be broadly deduced that oritavancin derivatives 7, 24, 28, 38, 44, 46, 56, 61, 66, 84, 90a, 90b, 90c, 93, 95, 98, and 103 possess antibacterial activities which are within an order of magnitude of that of oritavancin 5. On the other hand, compounds 13, 20, 70 and 78 show weaker activities. Compounds showing weaker activity are not expected to be transformed into oritavancin under the assay conditions.

Example 4

Determination of In Vivo Antibacterial Activity

The susceptibility of *S. aureus* strain ATCC13709 to oritavancin (5) and selected synthesized compounds in vivo was evaluated with the well accepted neutropenic mouse thigh infection model (Craig, W. A. et al. Journal of Antimicrobial Chemotherapy (1991), 27 (Suppl. C):29-40). Mice were made neutropenic by treatment with cyclophosphamide (150 and 100 mg/kg of body weight administered intraperitoneally 4 days and 1 day prior to infection). Mice were anesthetized briefly with approximately 4% isoflurane just prior to inoculation. The bacterial suspension (0.1 mL) was injected intramuscularly into each thigh (approximately $10^5$ colony forming units (CFU)/thigh). The selected agents were administered in 10% (w/w) β-hydroxypropylcyclodextrin in water at a concentration of 10 mg/mL one hour following bacterial inoculation. The animals were humanely sacrificed by $CO_2$ asphyxiation 24 h postinfection. The entire thigh muscle mass including the bone was homogenized and diluted in 0.9% saline and aliquots were plated on Brain-Heart Infusion agar. Following overnight incubation at 37° C., bacteria were enumerated for each thigh and expressed as $\log_{10}$ CFU per thigh. This was performed over three independent experiments and oritavancin (5) was used as a comparator in each. The results are summarized in Table 3.

TABLE 3

Recovered bacterial titers per thigh in mice infected with approximately $10^5$ CFU and treated with selected compounds (Three independent experiments)

| | | $\log_{10}$ CFU/thigh | | | |
|---|---|---|---|---|---|
| | Compound | Starting | 1 mg/kg | 10 mg/kg | 40 mg/kg |
| Experiment 1 | Oritavancin (5) | 5.38 ± 0.15 | 7.96 ± 0.93 | 3.81 ± 1.16 | 2.62 ± 0.51 |
| | 66 | 5.38 ± 0.15 | 8.16 ± 0.49 | 3.96 ± 1.74 | 4.04 ± 0.51 |
| Experiment 2 | Oritavancin (5) | 6.07 ± 0.07 | 7.98 ± 0.11 | 3.03 ± 0.53 | 2.29 ± 0.70 |
| | 90a | 6.07 ± 0.07 | 8.38 ± 0.23 | 6.13 ± 2.53 | 5.27 ± 2.66 |
| | 90b | 6.07 ± 0.07 | 8.61 ± 0.16 | 6.44 ± 1.82 | 2.97 ± 2.35 |
| Experiment 3 | Oritavancin (5) | 6.02 ± 0.07 | 8.16 ± 0.38 | 5.19 ± 1.86 | 2.62 ± 0.18 |
| | 93 | 6.02 ± 0.07 | 8.53 ± 0.49 | 4.45 ± 1.68 | 4.18 ± 1.70 |
| | 95 | 6.02 ± 0.07 | 8.32 ± 0.17 | 3.95 ± 1.57 | 2.96 ± 0.96 |

From these data in a well accepted animal model, it can be broadly deduced that oritavancin derivatives 66, 93 and 95 possess in vivo antibacterial efficacy that is within the same order of magnitude than oritavancin itself.

It is understood that the examples and embodiments described herein are for illustrative purposes only and that various modifications or changes in light thereof will be suggested to persons skilled in the art and are to be included within the spirit and purview of this application and scope of the appended claims.

All documents, including but not limited to publications, patents, patent applications, books, manuals, articles, papers, abstracts, and posters, and other materials referenced herein are expressly incorporated herein by reference in their entireties.

What is claimed is:
1. A compound represented by Formula (I):

$$[[[L^a{}_\beta\text{-M}]_\alpha\text{-}L^b{}_\delta]_\gamma\text{-}L^c{}_\epsilon]_y\text{-}A \qquad (I)$$

or a pharmaceutically acceptable salt, ester, or stereoisomer thereof,
wherein:
each M is independently selected from the group consisting of

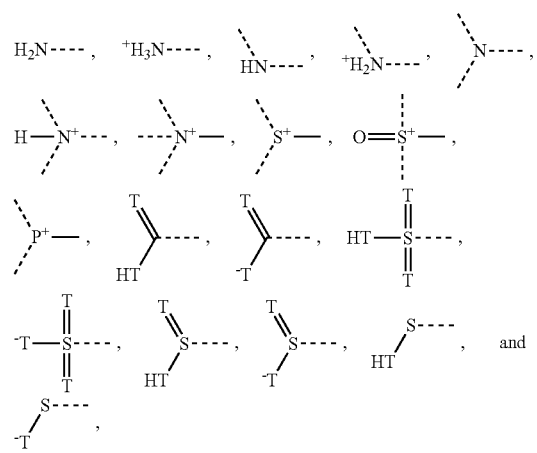

wherein each T is O or S, and the dashed bonds - - - indicate the points of attachment to another M, $L^a$, $L^b$, $L^c$ or A;
each $L^a$ is independently a chemical group structurally or electronically assisting M in maintaining a charge;
each $L^b$ is independently a bond or a multivalent linking group, wherein each $L^b$ links between 1 and 6 $[L^a{}_\beta\text{-M}]$ groups to each other, to $L^c$, or to each other and to $L^c$, wherein when $L^b$ is present, at least one $L^b$ links at least one $[L^a{}_\beta\text{-M}]$ group to at least one $L^c$;
each $L^c$ is independently a bond or a multivalent linking group which is cleavable under physiological conditions, wherein each $L^c$ links between 1 and 10 $[[L^a{}_\beta\text{-M}]_\alpha\text{-}L^b{}_\delta]$ groups to A, or links each $[L^a{}_\beta\text{-M}]$ group to A when δ is 0;
α is an integer between 1 and 6;
γ is an integer between 1 and 10;
β is an integer ≤3;
δ is an integer ≤2α;
ε is an integer ≤αγ;
y is an integer between 1 and 7; and A is a glycopeptide or lipoglycopeptide antimicrobial molecule having a structure represented by the following Formula (A₁):

(A₁)

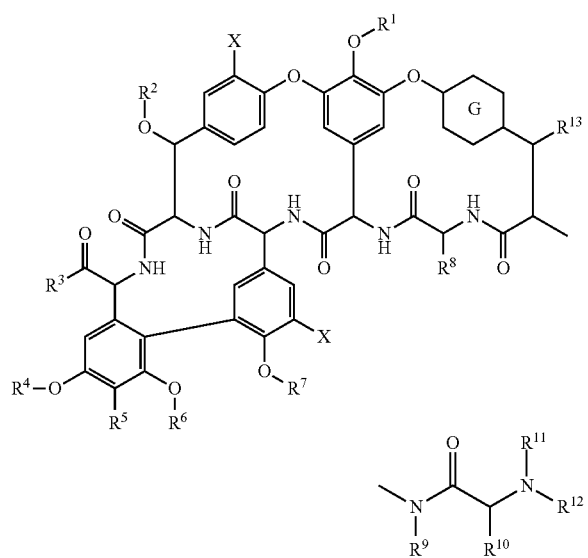

wherein:
R¹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —Rᵃ—Y—Rᵇ—(Z)ₓ; or R¹ is a saccharide group optionally substituted with —Rᵃ—Y—Rᵇ—(Z)ₓ, Rᶠ, —C(O)Rᶠ, or —Rᵃ—(Rᵇ)_z—(Z)ₓ, —C(O)—Rᵃ—Y—Rᵇ—(Z)ₓ;

R² is hydrogen or a saccharide group optionally substituted with —Rᵃ—Y—Rᵇ—(Z)ₓ, Rᶠ, —C(O)Rᶠ, —Rᵃ—(Rᵇ)_z—(Z)ₓ or —C(O)—Rᵃ—Y—Rᵇ—(Z)ₓ;

R³ is selected from the group consisting of —ORᶜ, —NRᶜRᶜ, —O—Rᵃ—Y—Rᵇ—(Z)ₓ, —NRᶜ—Rᵃ—Y—Rᵇ—(Z)ₓ, —NRᶜRᵉ, and —O—Rᵉ;

R⁴ is selected from the group consisting of hydrogen, alkyl, substituted alkyl, alkenyl, substituted alkenyl, alkynyl, substituted alkynyl, —Rᵃ—Y—Rᵇ—(Z)ₓ, —C(O)Rᵈ and a saccharide group optionally substituted with —Rᵃ—Y—Rᵇ—(Z)ₓ, Rᶠ, or —C(O)—Rᵃ—Y—Rᵇ—(Z)ₓ, or R⁴ and R⁵ can be joined, together with the atoms to which they are attached, to form a heterocyclic ring optionally substituted with —NRᶜ—Rᵃ—Y—Rᵇ—(Z)ₓ;

R⁵ is selected from the group consisting of hydrogen, halo, —CH(Rᶜ)—NRᶜRᶜ, —CH(Rᶜ)—NRᶜRᵉ, —CH(Rᶜ)—NRᶜ—Rᵃ—Y—Rᵇ—(Z)ₓ, —CH(Rᶜ)—Rˣ, and —CH(Rᶜ)—NRᶜ—Rᵃ—C(O)—Rˣ;

R⁶ is selected from the group consisting of hydrogen, alkyl, substituted alkyl, alkenyl, substituted alkenyl, alkynyl, substituted alkynyl, —Rᵃ—Y—Rᵇ—(Z)ₓ, —C(O)Rᵈ and a saccharide group optionally substituted with —Rᵃ—Y—Rᵇ—(Z)ₓ, —Rᵃ—(Rᵇ)_z—(Z)ₓ, Rᶠ, —C(O)Rᶠ, or —C(O)—Rᵃ—Y—Rᵇ—(Z)ₓ, or R⁵ and R⁶ can be joined, together with the atoms to which they are attached, to form a heterocyclic ring optionally substituted with —NRᶜ—Rᵃ—Y—Rᵇ—(Z)ₓ;

R⁷ is selected from the group consisting of hydrogen, alkyl, substituted alkyl, alkenyl, substituted alkenyl, alkynyl, substituted alkynyl, —Rᵃ—Y—Rᵇ—(Z)ₓ, and —C(O)Rᵈ;

R⁸ is selected from the group consisting of hydrogen, alkyl, substituted alkyl, alkenyl, substituted alkenyl, alkynyl, substituted alkynyl, cycloalkyl, substituted cycloalkyl; cycloalkenyl, substituted cycloalkenyl, aryl, heteroaryl, heterocyclic and —Rᵃ—Y—Rᵇ—(Z)ₓ;

R⁹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R¹⁰ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or R⁸ and R¹⁰ are joined to form —Ar¹—O—Ar²—, where Ar¹ and Ar² are independently arylene or heteroarylene;

R¹¹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or R¹⁰ and R¹¹ are joined, together with the carbon and nitrogen atoms to which they are attached, to form a heterocyclic ring;

R¹² is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)Rᵈ, —C(NH)Rᵈ, —C(O)NRᶜRᶜ, —C(O)ORᵈ, —C(NH)NRᶜRᶜ, —Rᵃ—Y—Rᵇ—(Z)ₓ, and —C(O)—Rᵇ—Y—Rᵇ—(Z)ₓ, or R¹¹ and R¹² are joined, together with the nitrogen atom to which they are attached, to form a heterocyclic ring;

R¹³ is selected from the group consisting of hydrogen and —OR¹⁴;

R¹⁴ is selected from the group consisting of hydrogen, —C(O)Rᵈ and a saccharide group;

each Rᵃ is independently selected from the group consisting of alkylene, substituted alkylene, alkenylene, substituted alkenylene, alkynylene and substituted alkynylene;

each Rᵇ is independently selected from the group consisting of a covalent bond, arylene, alkylene, substituted alkylene, alkenylene, substituted alkenylene, alkynylene and substituted alkynylene;

each Rᶜ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)Rᵈ;

each Rᵈ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

each Rᵉ is a saccharide group;

each Rᶠ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, and heterocyclic;

R$^x$ is an N-linked amino saccharide or an N-linked heterocycle;

each X is independently selected from the group consisting of hydrogen, fluoro, chloro, bromo and iodo;

each Y is independently selected from the group consisting of, —CH$_2$—, oxygen, sulfur, —S—S—, —NR$^c$—, —S(O)—, —SO$_2$—, —NR$^c$C(O)—, —OSO$_2$—, —OC(O)—, —N(R$^c$)SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, OC(O)NR$^c$—, —C(O)—, and —N(R$^c$)SO$_2$NR$^c$—;

each Z is independently selected from the group consisting of hydrogen, aryl, cycloalkyl, cycloalkenyl, heteroaryl, heterocyclic, and a saccharide;

x is 1 or 2;

z is 1, 2, 3 or 4; and

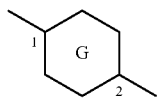

is selected from

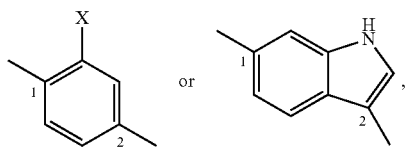

wherein each $[[[L^a{}_\beta\text{-}M]_\alpha\text{-}L^b{}_\delta]_\gamma\text{-}L^c{}_\epsilon]_y$ is independently coupled to one or more of a hydroxyl, amino or carboxyl functionality on said glycopeptide or lipoglycopeptide antimicrobial molecule A.

2. The compound of claim 1, wherein α is 1, 2 or 3 and y is 1 or 2.

3. The compound of claim 1, wherein each L$^a$ is individually selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and

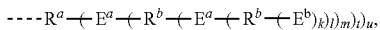

wherein:

each R$^a$ is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, —(CO)-(substituted alkenylene)-, —(CO)-alkynylene-, —(CO)-(substituted alkynylene)-, —(CO)-arylene- and —(CO)-(substituted arylene)-;

each R$^b$ is independently selected from the group consisting of a covalent bond, alkylene, substituted alkylene, alkenylene, substituted alkenylene, alkynylene, substituted alkynylene, arylene and substituted arylene;

each E$^a$ is independently selected from the group consisting of a covalent bond, methylene, oxygen, sulfur,

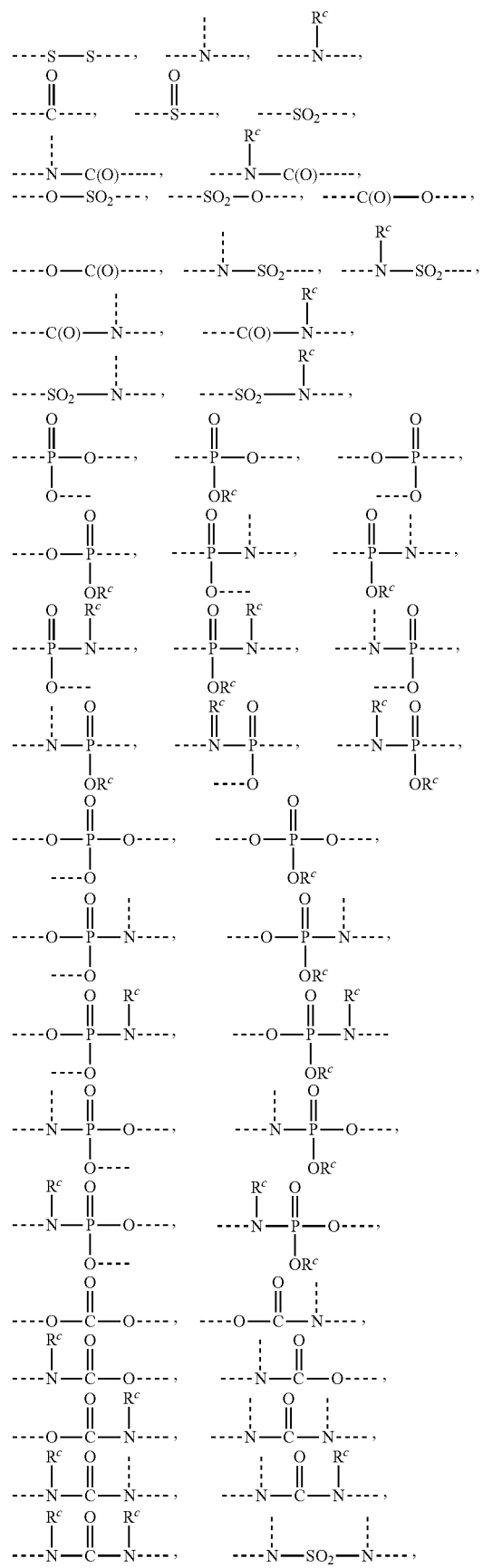

----N—SO₂—N----, ----N—SO₂—N---- and
 |          |              |
 R^c        R^c            R^c ----N—SO₂—N----;
 |          |
 R^c        R^c

- each R^c is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R^d;
- each R^d is independently selected from the group consisting of alkyl, substituted alkyl, alkenyl, substituted alkenyl, alkynyl, substituted alkynyl, cycloalkyl, substituted cycloalkenyl, substituted cycloalkenyl, aryl, heteroaryl and heterocyclic;
- each E^b is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, and substituted aryloxy; and
- each k, l, m, t, u is independently a nonnull integer ≤ 5.

4. The compound of claim 1, wherein each $L^b$ is individually selected from the group consisting of a covalent bond, alkylene, substituted alkylene, alkenylene, substituted alkenylene, alkynylene, substituted alkynylene, cycloalkylene, substituted cycloalkylene, cycloalkenylene, substituted cycloalkenylene, arylene, heteroarylene and $$----R^a{-}(\!\!-E^a{-}\!\!-R^b{-}\!\!)\!\!-(\!\!-E^a{-}\!\!-R^b{-}\!)_l\!-\!)_m\!-\!)_t\!-\!)_u\!-\!-\!,$$

wherein:
- each R^a is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, —(CO)-(substituted alkenylene)-, —(CO)-alkynylene-, —(CO)-(substituted alkynylene)-, —(CO)-arylene- and —(CO)-(substituted arylene)-;
- each R^b is independently selected from the group consisting of a covalent bond, alkylene, substituted alkylene, alkenylene, substituted alkenylene, alkynylene, substituted alkynylene, arylene and substituted arylene;
- each E^a is independently selected from the group consisting of a covalent bond, methylene, oxygen, sulfur ----S—S----, ----N----, ----N----,
                 ||         |
                 O          R^c

----C----, ----S----, ----SO₂---,
 ||         ||
 O          O

----N—C(O)-----, ----N—C(O)-----,
                        |
                        R^c

----O—SO₂---, ----SO₂—O----, ----C(O)—O----,

----O—C(O)-----, ----N—SO₂----, ----N—SO₂----,
                                       |
                                       R^c

----C(O)—N----, ----C(O)—N----,
                        |
                        R^c

----SO₂—N----, ----SO₂—N----,
                       |
                       R^c

----P—O----,   ----P—O----,   ----O—P----,
  ||             ||              ||
  O              O               O
  |              |               |
  O----          OR^c            O----

----O—P----,   ----P—N----,   ----P—N----,
  ||             ||              ||
  O              O----           O
  |                              |
  OR^c                           OR^c

----P—N----,   ----P—N----,   ----N—P----,
  ||   |         ||  |           |   ||
  O    R^c       O   R^c         R^c O
  |              |                   |
  O----          OR^i                O

----N—P----,   ----N—P----,   ----N—P----,
  |   ||         |   ||          |   ||
  R^i O          R^c O           R^c O
      |              |               |
      OR^i           O               OR^c

----O—P—O----,   ----O—P—O----,
     ||               ||
     O                O
     |                |
     O----            OR^c

----O—P—N----,   ----O—P—N----,
     ||               ||
     O                O
     |                |
     O----            OR^c

----O—P—N----,   ----O—P—N----,
     ||  |            ||  |
     O   R^c          O   R^c
     |                |
     O----            OR^i

----N—P—O----,   ----N—P—O----,
     ||               ||
     O                O
     |                |
     O----            OR^c

----N—P—O----,   ----N—P—O----,
  |  ||           |   ||
  R^c O           R^i O
     |                |
     O----            OR^c

----O—C—O----,   ----O—C—N----,
     ||               ||
     O                O

----N—C—N----,   ----N—C—O----,
  |  ||  |        |   ||
  R^c O  R^c      R^c O

----O—C—N----,   ----N—C—N----,
     ||  |            ||  |
     O   R^c          O   R^c
     |                |
     N----            N----
     |                |
     R^c              R^c

----N—C—N----,   ----N—SO₂—N----,
  |  ||  |        |         |
  R^c O  R^c      R^c       R^c
     |
     N----
     |
     R^c

----N—SO₂—N----, ----N—SO₂—N---- and
  |         |       |
  R^c       R^c     R^c ----N—SO₂—N----;
  |         |
  R^c       R^c each R^c is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R^d;

each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; and each l, m, t, u is independently a nonnull integer ≤5.

5. The compound of claim 1, wherein each $L^c$ is independently selected from the group consisting of a covalent bond, alkylene, substituted alkylene, alkenylene, substituted alkenylene, alkynylene, substituted alkynylene, cycloalkylene, substituted cycloalkylene, cycloalkenylene, substituted cycloalkenylene, arylene, and heteroarylene, or $L^c$ is individually represented by the following formula ($L_1$):

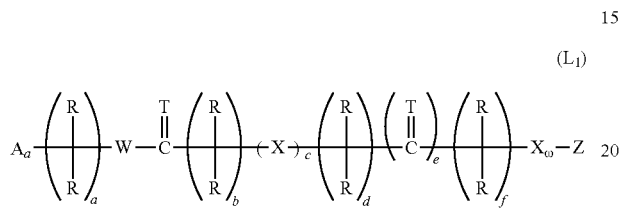

wherein:
$A_a$ indicates the point of attachment to the glycopeptide or lipoglycopeptide antimicrobial molecule A;
W is a covalent bond or is selected from the group of consisting of

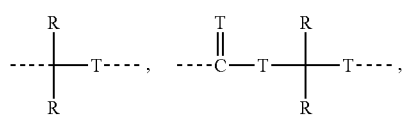

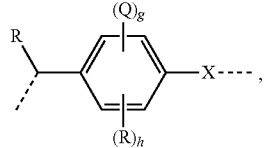

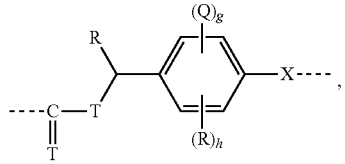

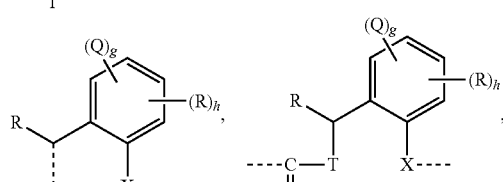

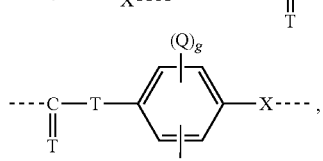

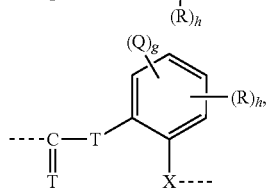

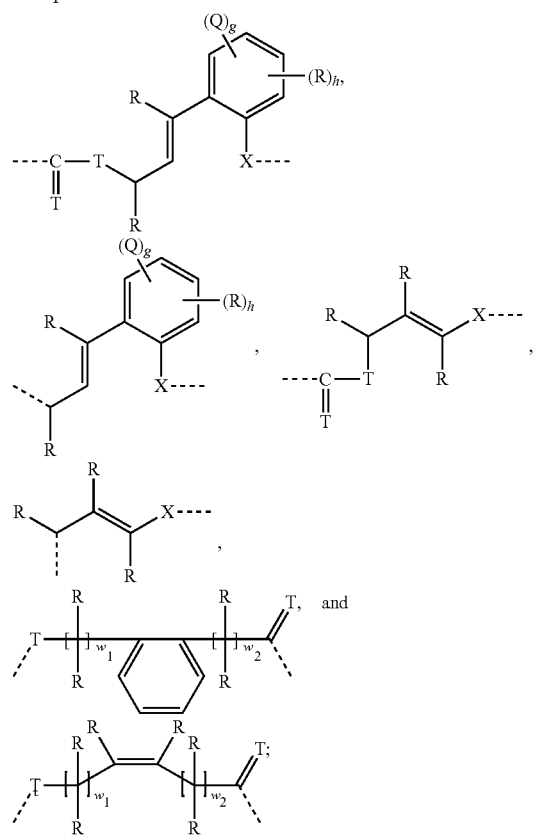

each T is independently oxygen or sulfur;
each R is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, substituted aryloxy, $M_a$ and —$R^a$—Y—$R^b$—Y—$R^b$-$M_a$;
each $R^a$ is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, (CO)-(substituted alkenylene)-, —(CO)-alkynylene-, —(CO)-(substituted alkynylene)-, —(CO)-arylene- and —(CO)-(substituted arylene)-;
each $R^b$ is independently selected from the group consisting of a covalent bond, alkylene, substituted alkylene, alkenylene, substituted alkenylene, alkynylene, substituted alkynylene, arylene and substituted arylene;

$M_a$ indicates the point of attachment to $[[L^a{}_\beta\text{-M}]_\alpha\text{-}L^b{}_\delta]$;

each Q is independently nitro, chloro, bromo, iodo or fluoro;

each X is independently —O—, —S— or —N(R)—;

each Y is independently selected from the group consisting of a covalent bond, methylene, oxygen, sulfur,

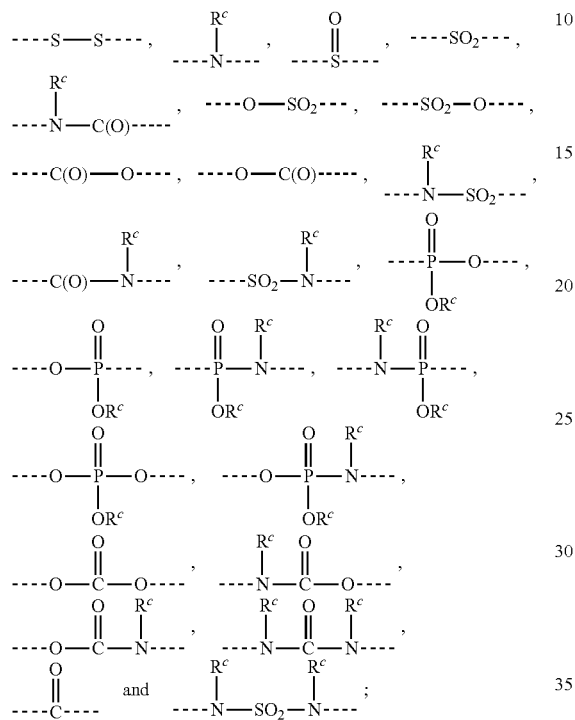

each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

Z is selected from the group consisting of hydrogen, acyl, substituted acyl, aroyl, substituted aroyl, alkoxycarbonyl, substituted alkoxycarbonyl, aryloxycarbonyl, substituted aryloxycarbonyl, R—,

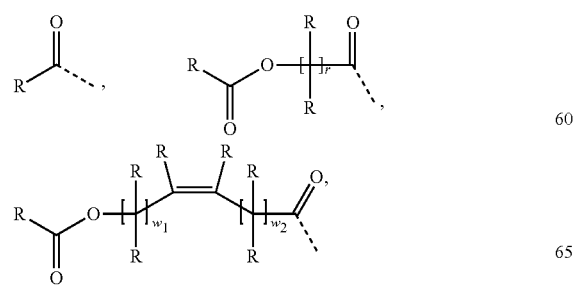

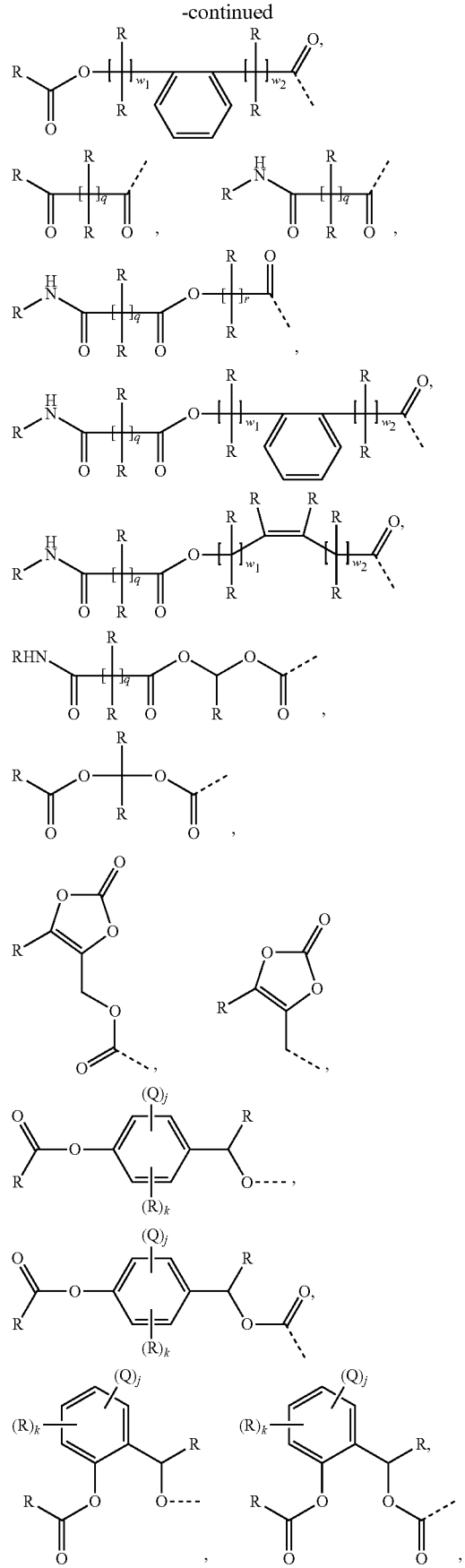

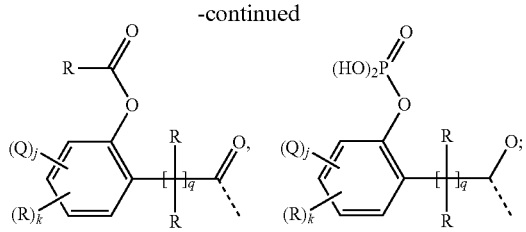

q is 2 or 3;
r is 1, 2, 3, 4 or 5;
j and k are each independently 0, 1, 2, 3 or 4;
$w_1$ and $w_2$ are each integers $\geq 0$ such that their sum ($w_1+w_2$) is 1, 2 or 3;
a is an integer $\leq 10$;
b, c, d, e and f are integers such that b+c+d+e+f$\leq$7 or null;
g and h are integers $\geq 0$ such that g+h=4;
ω is 0 or 1;
with the proviso that at least one R is -$M_a$ or —R—Y—$R^b$—Y—$R^b$-$M_a$; and
with the further proviso that either W is a group of atoms or a+b+d+f$\geq$1.

6. The compound of claim 1, wherein at least one of said linker $L^c$ couples at least one of said [[$L^a{}_\beta$-M]$_\alpha$-$L^b{}_\delta$] to a hydroxyl functionality on said glycopeptide or lipoglycopeptide antimicrobial molecule A, and wherein each of said linker $L^c$ coupling [[$L^a{}_\beta$-M]$_\alpha$-$L^b{}_\delta$] to the hydroxyl functionality is independently selected from the group consisting of:

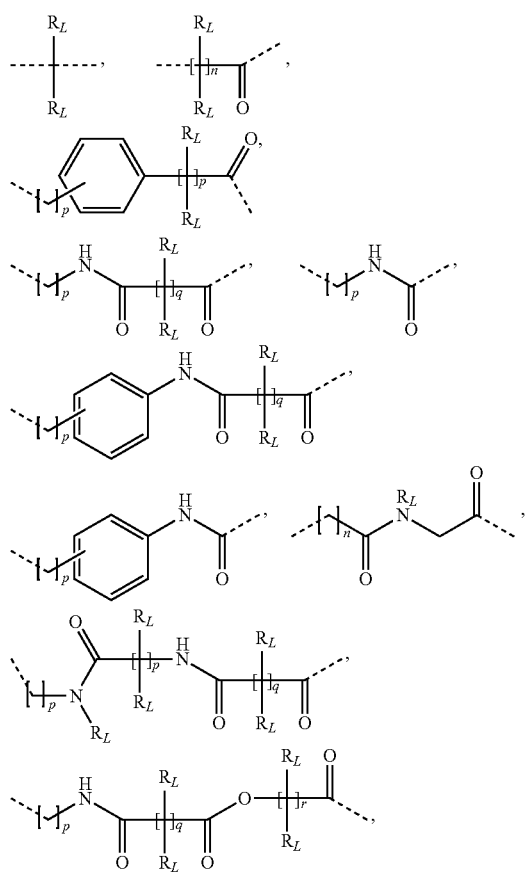

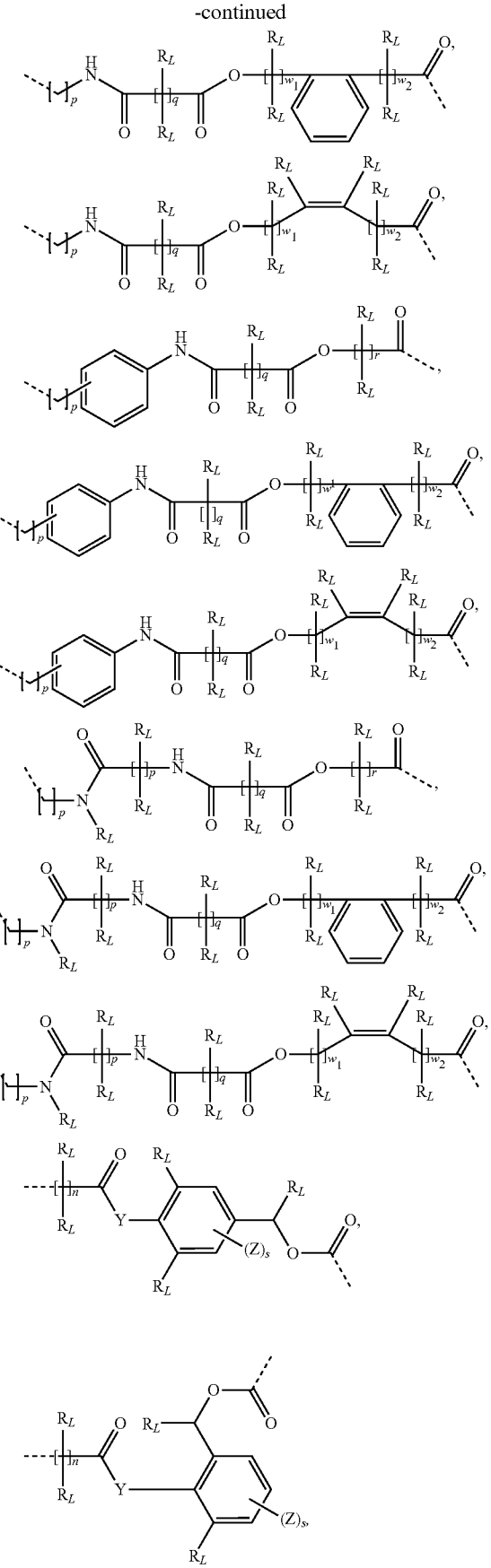

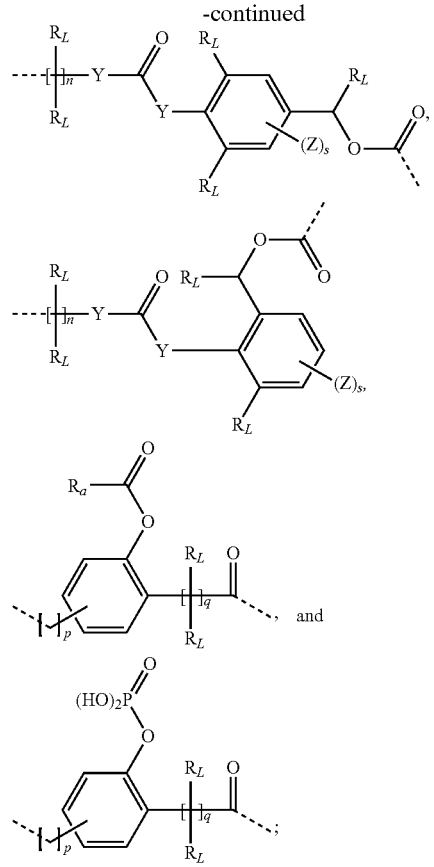

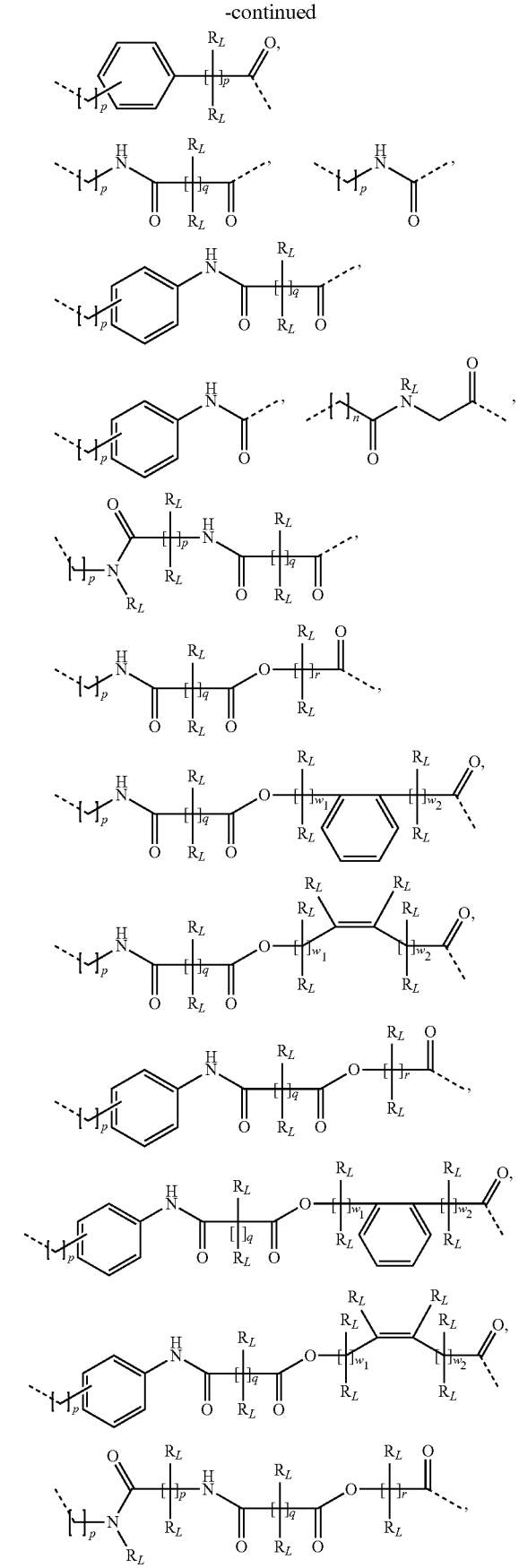

wherein:
  each p is independently 0 or an integer ≤10;
  each $R_L$ is independently selected from the group consisting of H, ethyl and methyl;
  q is 2 or 3;
  n is an integer ≤10;
  r is 1, 2, 3, 4 or 5;
  $w_1$ and $w_2$ are each integers ≤0 such that their sum ($w_1+w_2$) is 1, 2 or 3;
  each Y is independently selected from the group consisting of —O—, —S—, and —$NR_L$—;
  each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro;
  s is 1, 2, 3 or 4; and
  $R_a$ is $C_xH_y$, where x is an integer of 0 to 20 and y is an integer of 1 to 2x+1.

7. The compound of claim 1, wherein at least one of said linker $L^c$ couples at least one of said $[[L^a_\beta-M]_\alpha-L^b_\delta]$ to a nitrogen atom on said glycopeptide or lipoglycopeptide antimicrobial molecule A, and wherein each of said linker $L^c$ coupling $[[L^a_\beta-M]_\alpha-L^b_\delta]$ to a nitrogen atom is independently selected from the group consisting of:

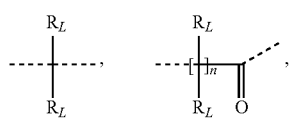

-continued
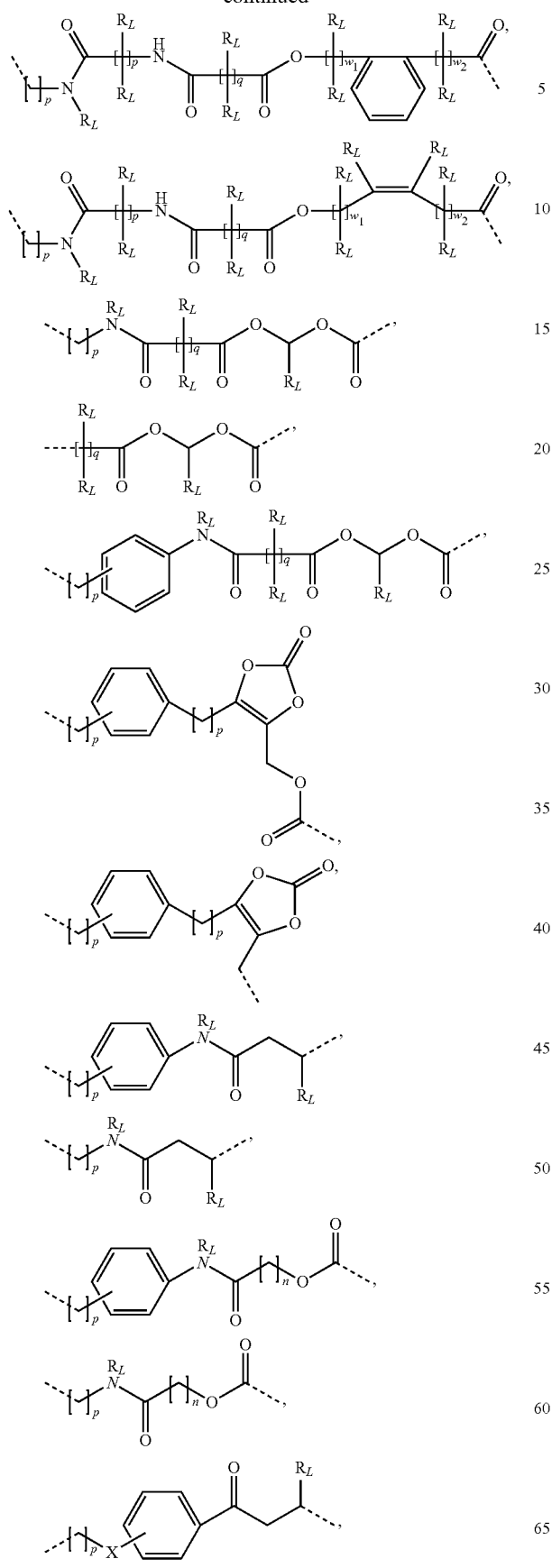
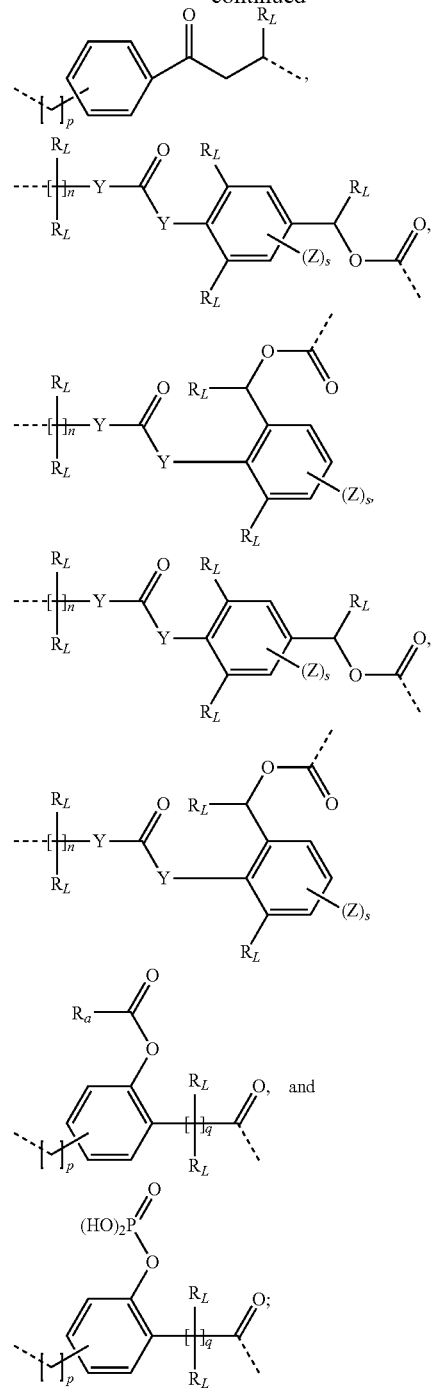
wherein:
n is an integer ≤10;
each p is independently 0 or an integer ≤10;
each $R_L$ is independently selected from the group consisting of H, ethyl and methyl;
q is 2 or 3;
r is 1, 2, 3, 4 or 5;
$w_1$ and $w_2$ are each integers ≥0 such that their sum ($w_1+w_2$) is 1, 2 or 3;
X is $CH_2$, —$CONR_L$—, —CO—O—$CH_2$—, or —CO—O—;

each Y is independently selected from —O—, —S—, and —NR$_L$—;

each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro;

s is 1, 2, 3 or 4; and

R$_a$ is C$_x$H$_y$, where x is an integer of 0 to 20 and y is an integer of 1 to 2x+1.

8. The compound of claim 1, wherein at least one of said linker L$^c$ couples at least one of said [[L$^a_\beta$-M]$_\alpha$-L$^b_\delta$] to the carbonyl of a carboxylate group on said glycopeptide or lipoglycopeptide antimicrobial molecule A, and wherein each of said linker L$^c$ coupling [[L$^a_\beta$-M]$_\alpha$-L$^b_\delta$] to the carbonyl of a carboxylate group is independently selected from the group consisting of: a covalent bond,

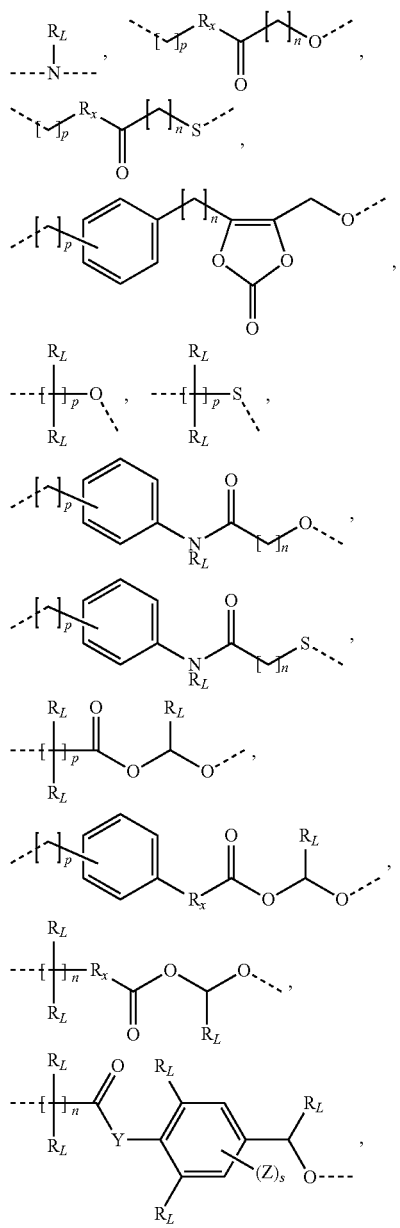

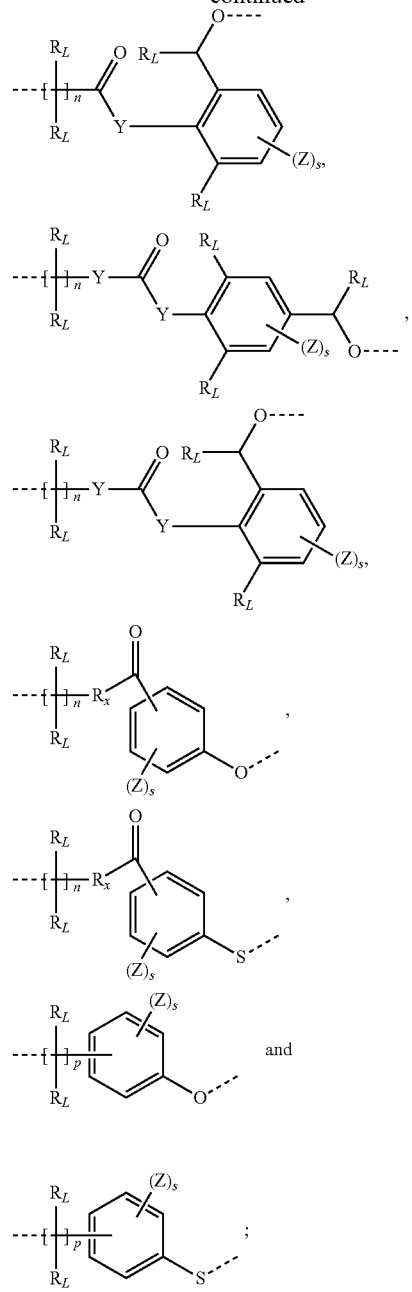

wherein:

n is an integer ≤10;

p is 0 or an integer ≤10;

each R$_L$ is independently selected from the group consisting of H, ethyl and methyl;

R$_x$ is S, C(R$_L$)$_2$, NR$_L$ or O;

each Y is independently selected from —O—, —S—, and —NR$_L$—;

each Z is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro; and s is 1, 2, 3 or 4.

9. The compound of claim 1, wherein A is vancomycin.
10. The compound of claim 1, wherein A is teicoplanin.
11. The compound of claim 1, wherein A is oritavancin.
12. The compound of claim 1, wherein A is dalbavancin.
13. The compound of claim 1, wherein A is telavancin.
14. The compound of claim 1, wherein A is selected from the group consisting of compound A35512 A, compound A35512 C, compound A35512 E, compound A35512 F, compound A35512 G, compound A35512 H, compound A40926 A, compound A40926 B, compound A40926 PB, parvodicin B2, parvodicin C1, parvodicin C3, compound A41030, compound A42867, compound A477, compound A47934, compound A51568A, N-demethylvancomycin, compound A80407, compound A83850, compound A84575, compound AB65, compound AM374, actaplanin, compound A4696, actinoidin, ardacin, aricidin, compound AAD216, avoparcin, compound LL-AV290, azureomycin, balhimycin, balhimycin V, chloroorienticin, compound A82846B, compound LY264826, chloroeremomycin, chloropeptin, chloropolysporin, complestatin, decaplanin, dechlorobalhimycin, dechlorobalhimycin V, chlorobalhimycin, chlorobromobalhimycin, fluorobalhimycin, deglucobalhimycin, N-demethylbalhimycin, N-demethylvancomycin, devancosamine-vancomycin, eremomycin, galacardin, helvecardin, izupeptin, kibdelin, kistamicin, mannopeptin, methylbalhimycin, compound MM47761, compound MM47766, compound MM47767, compound MM49721, compound MM49727, compound MM55256, compound MM55260, compound MM55266, compound MM55268, compound MM55270, compound MM55272, compound MM56597, compound MM56598, nogabecin F, compound OA7653, orienticin, dechloroeremomycin, compound PA42867, compound PA45052, chloroorienticin, parvodicin, rhamnosyl-balhimycin, ristomycin, ristocetin, spontin, symnonicin, teichomycin, Targocid, ureido-balhimycin and [Ψ[CH$_2$NH]Tpg$^4$]Vancomycin.

15. A compound selected from the group consisting of:

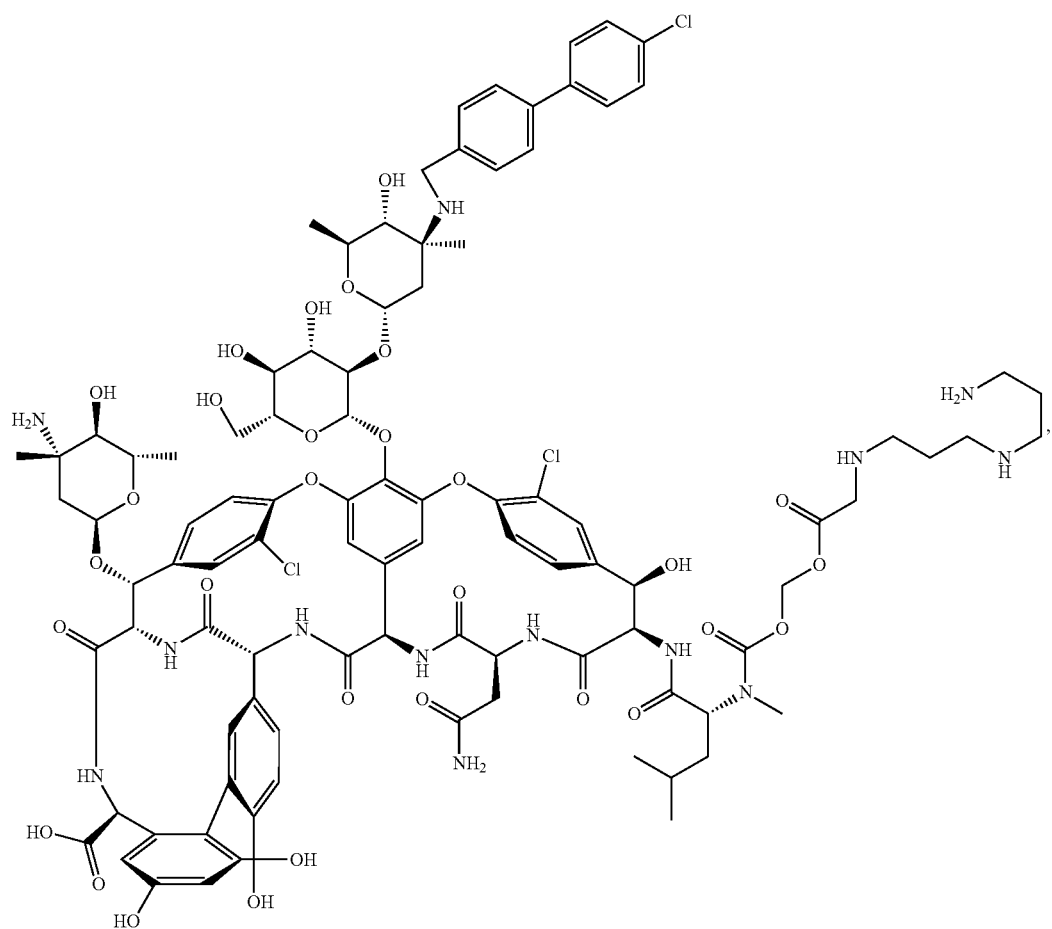

-continued
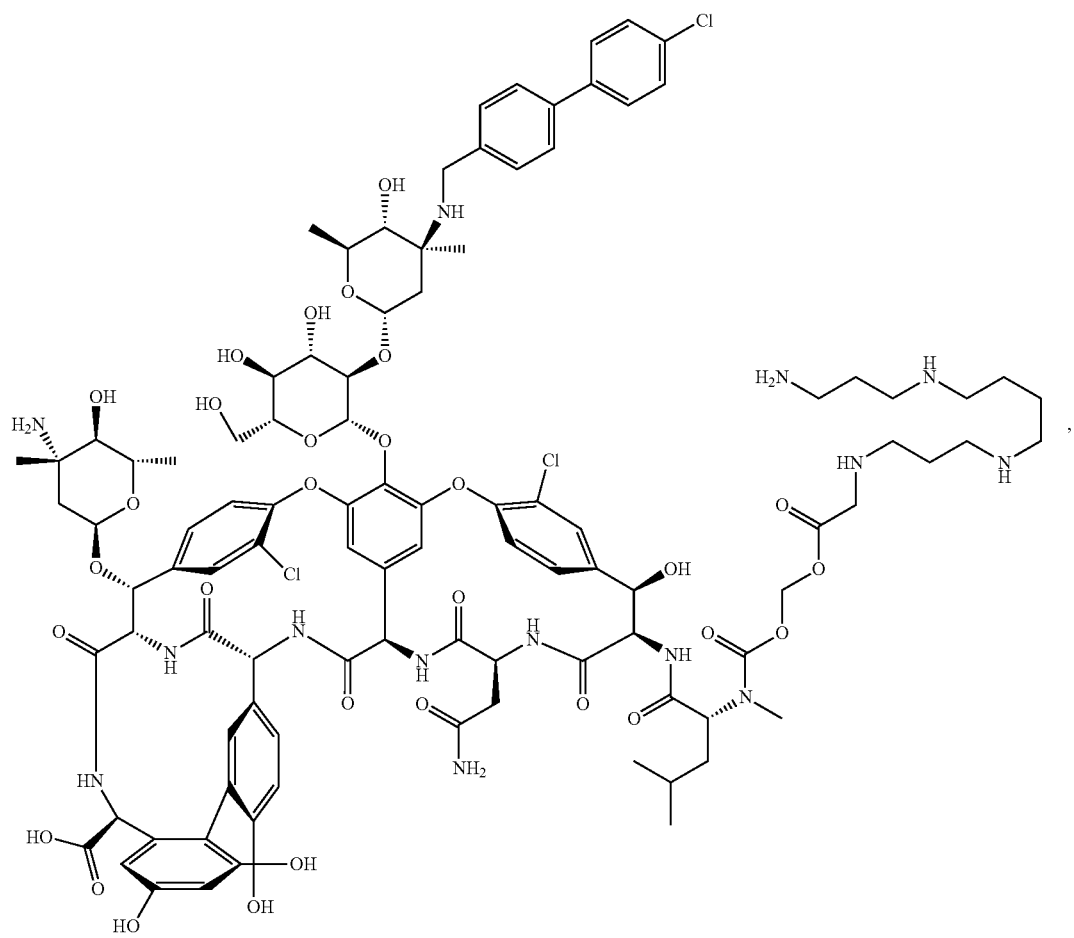

-continued
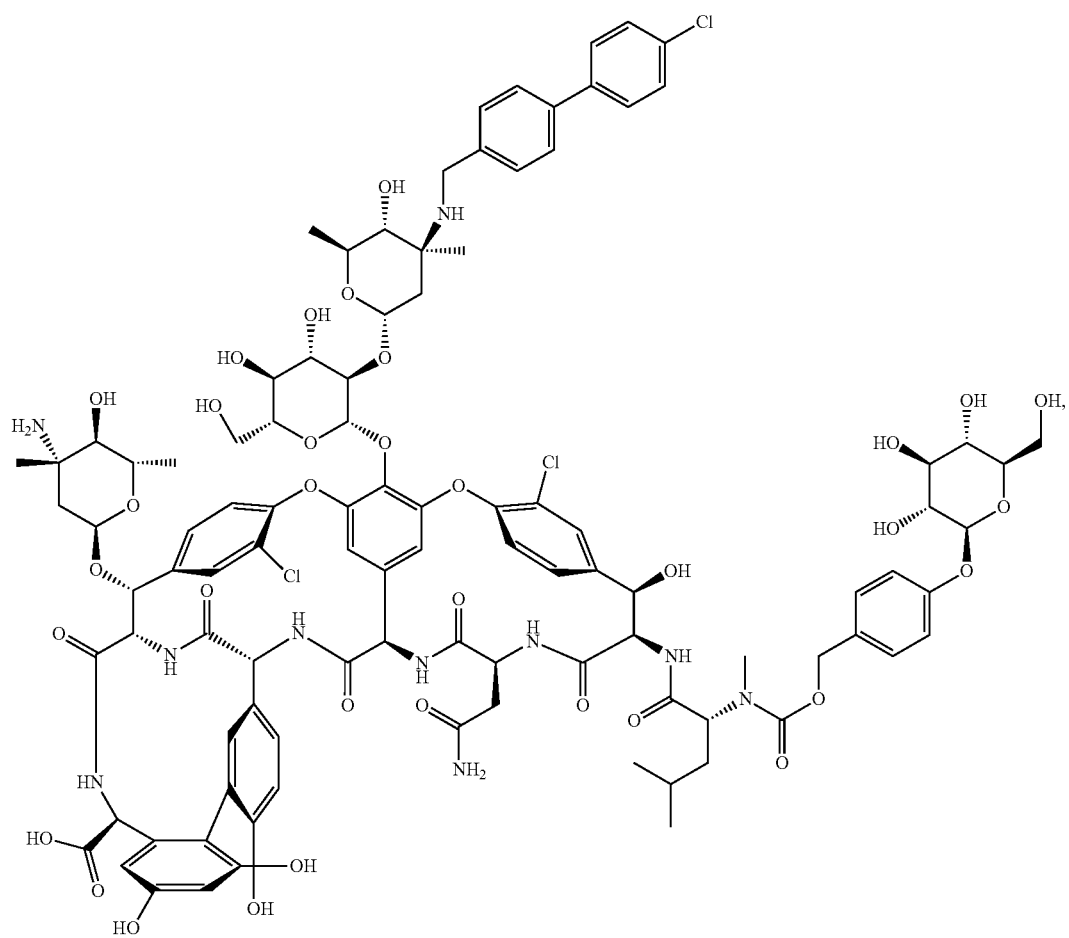

-continued
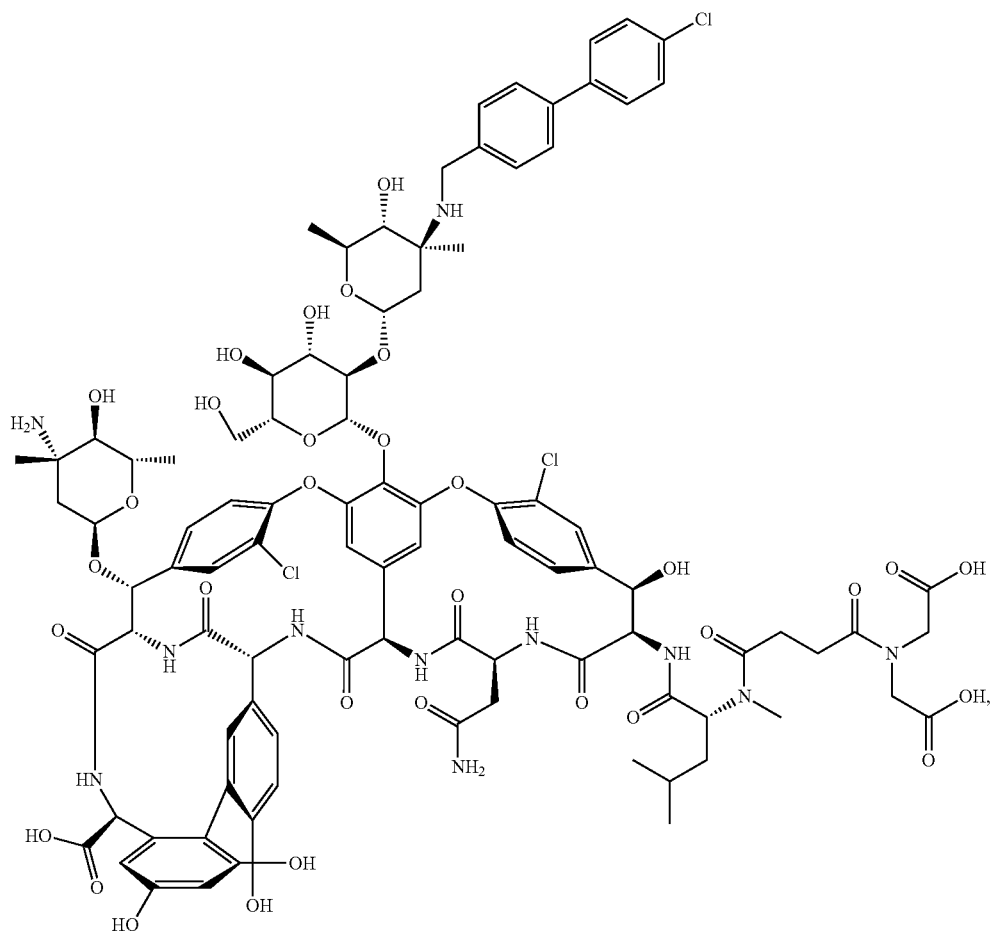

-continued
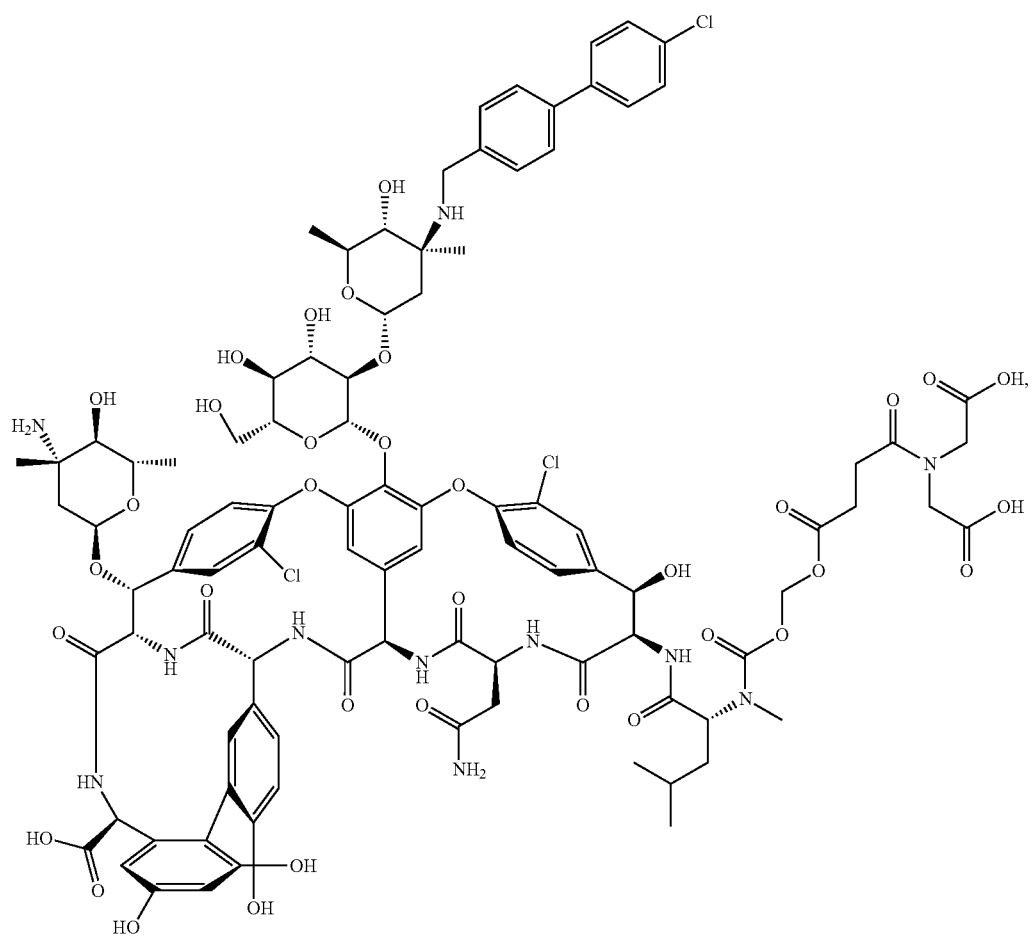

-continued
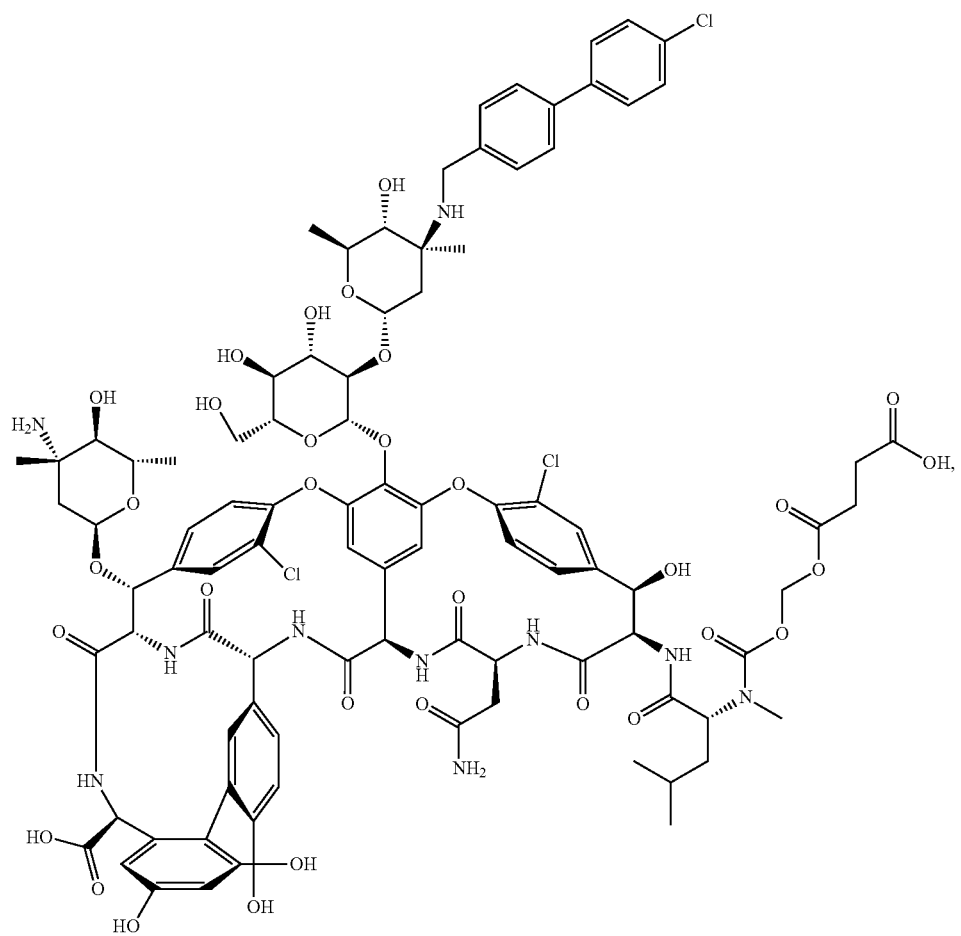

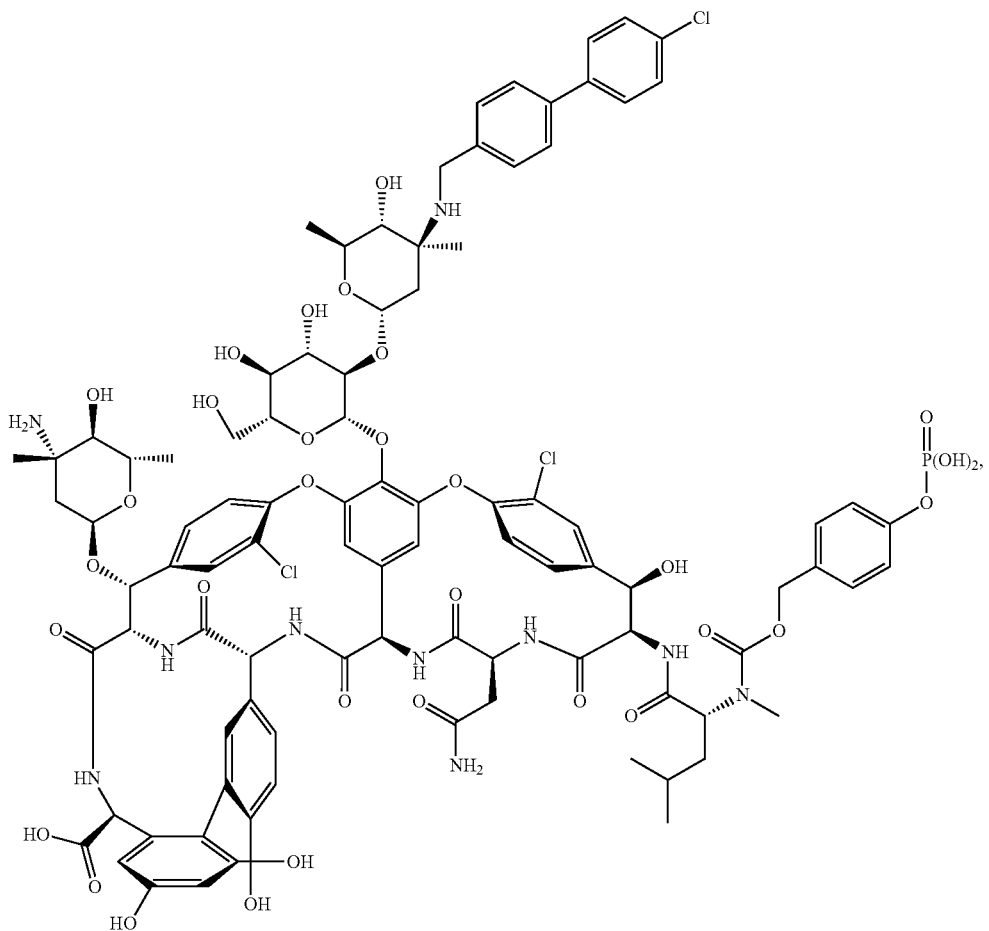

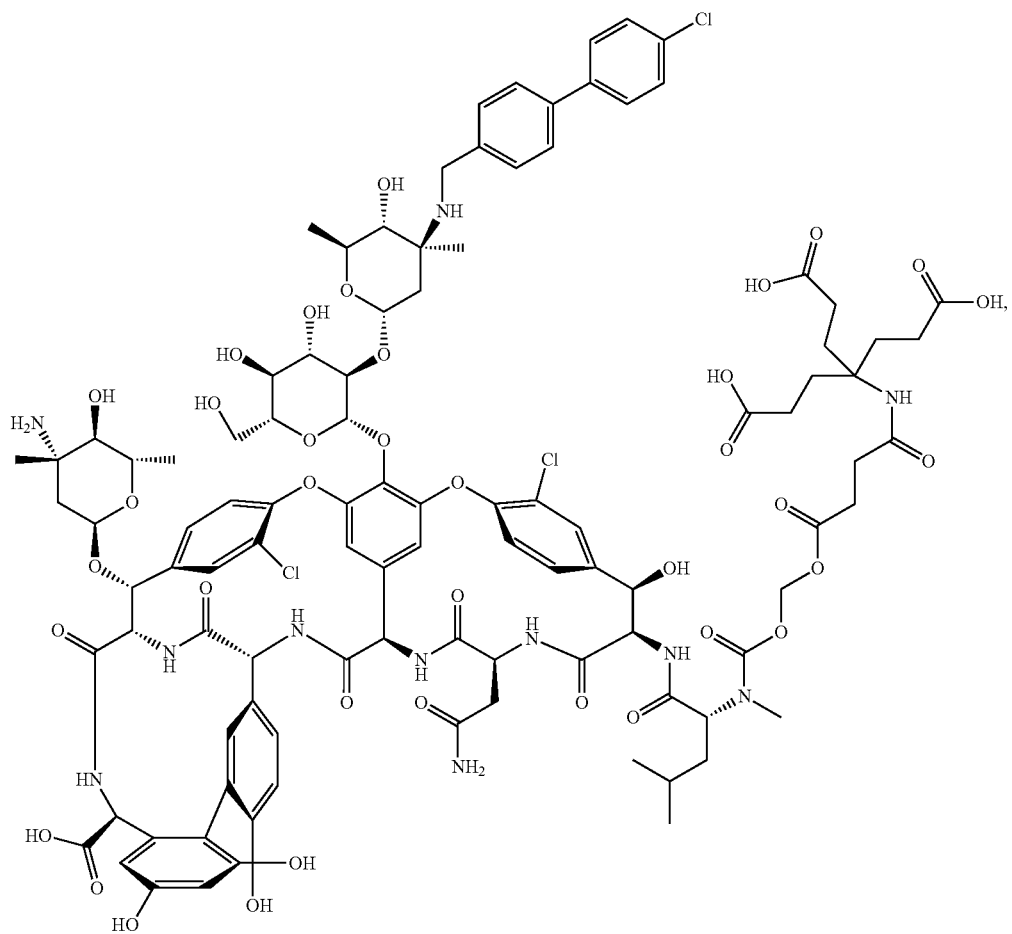

-continued
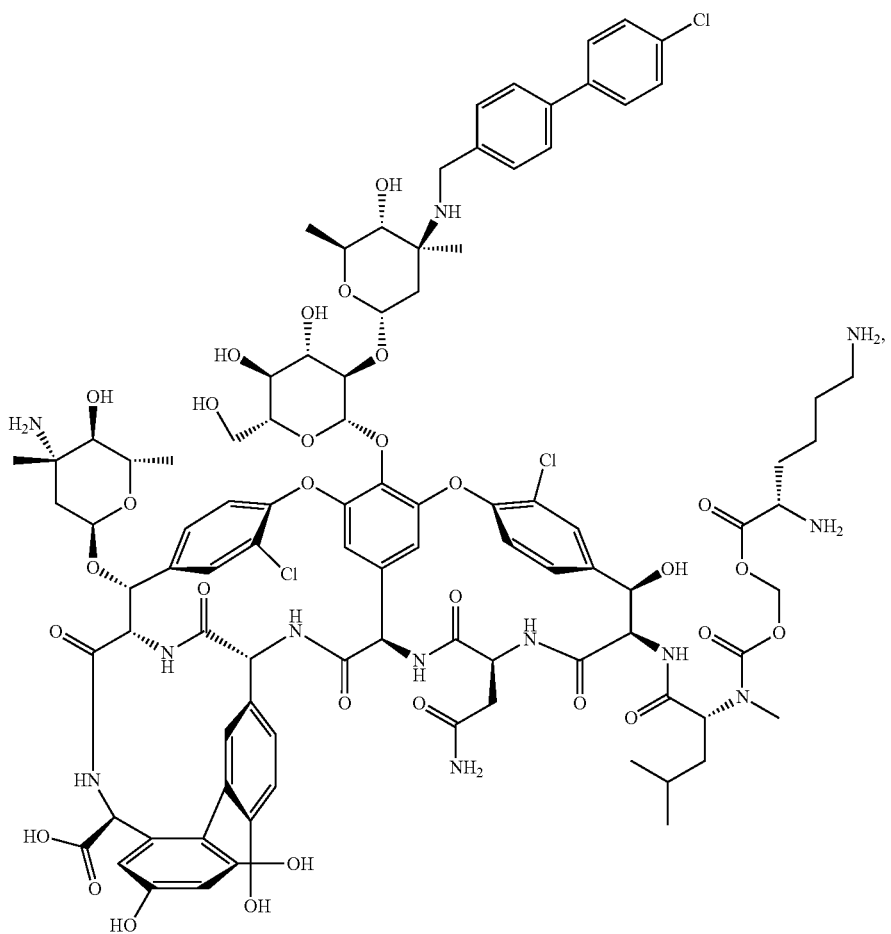

-continued
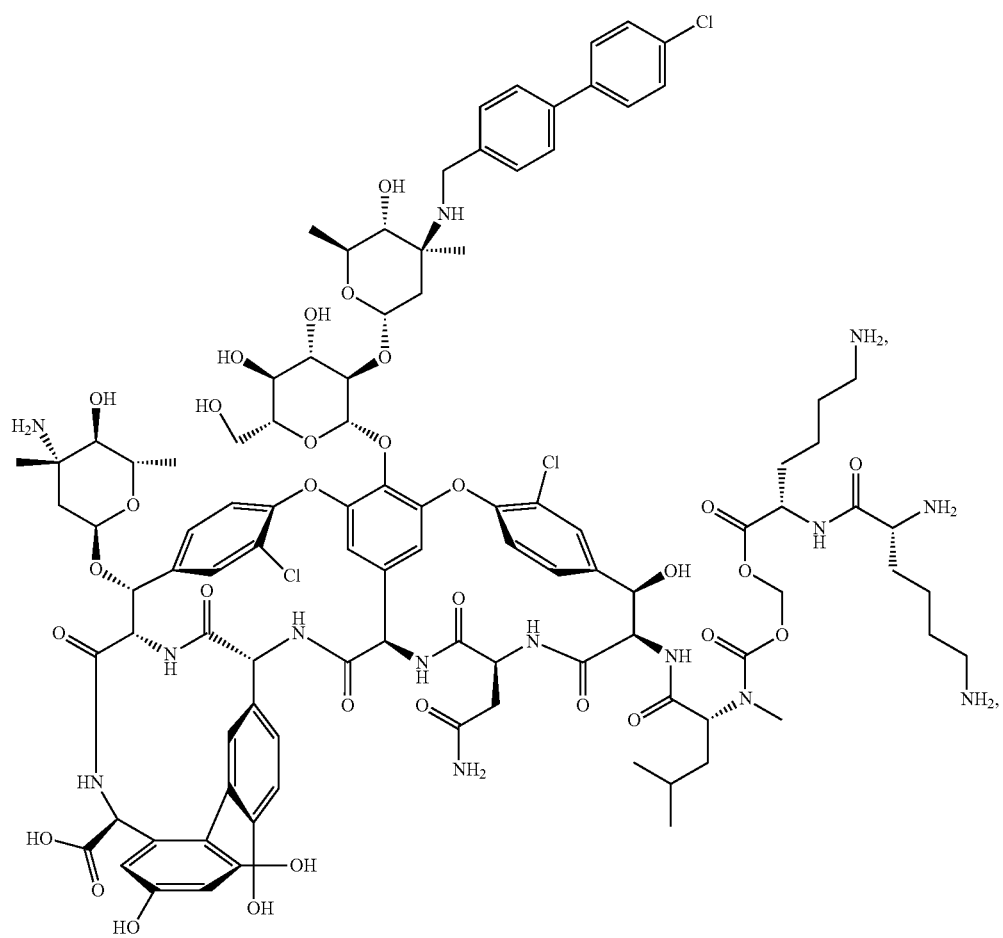

-continued
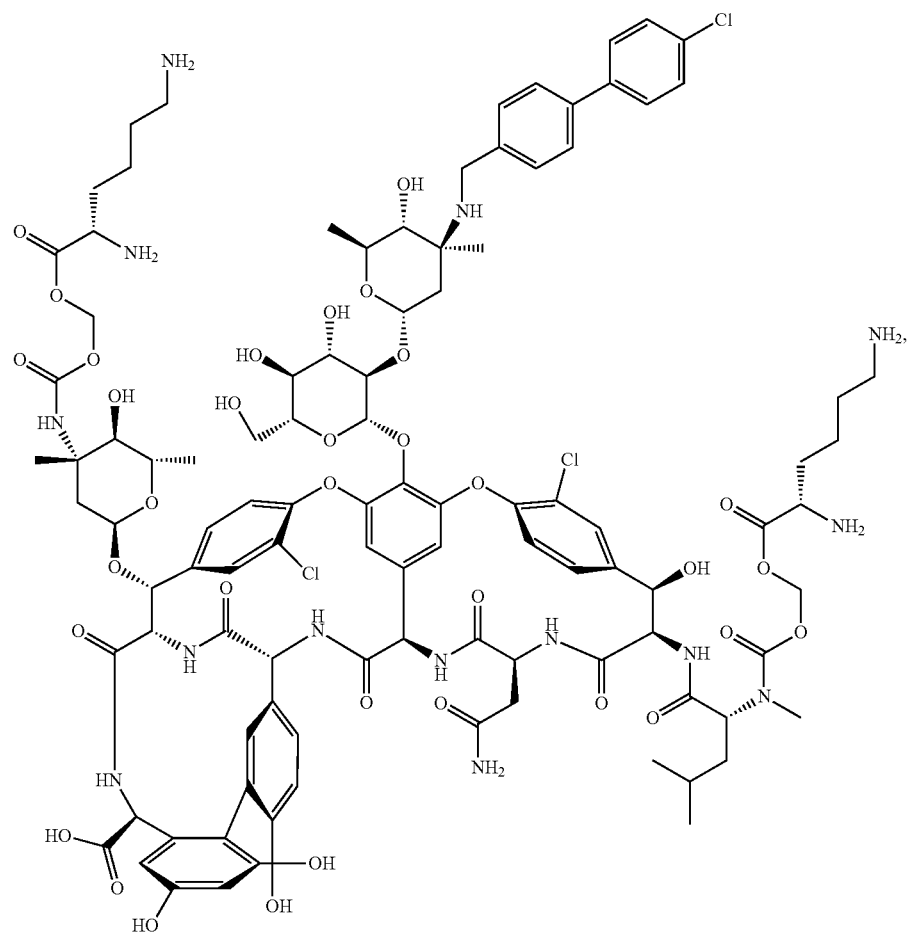

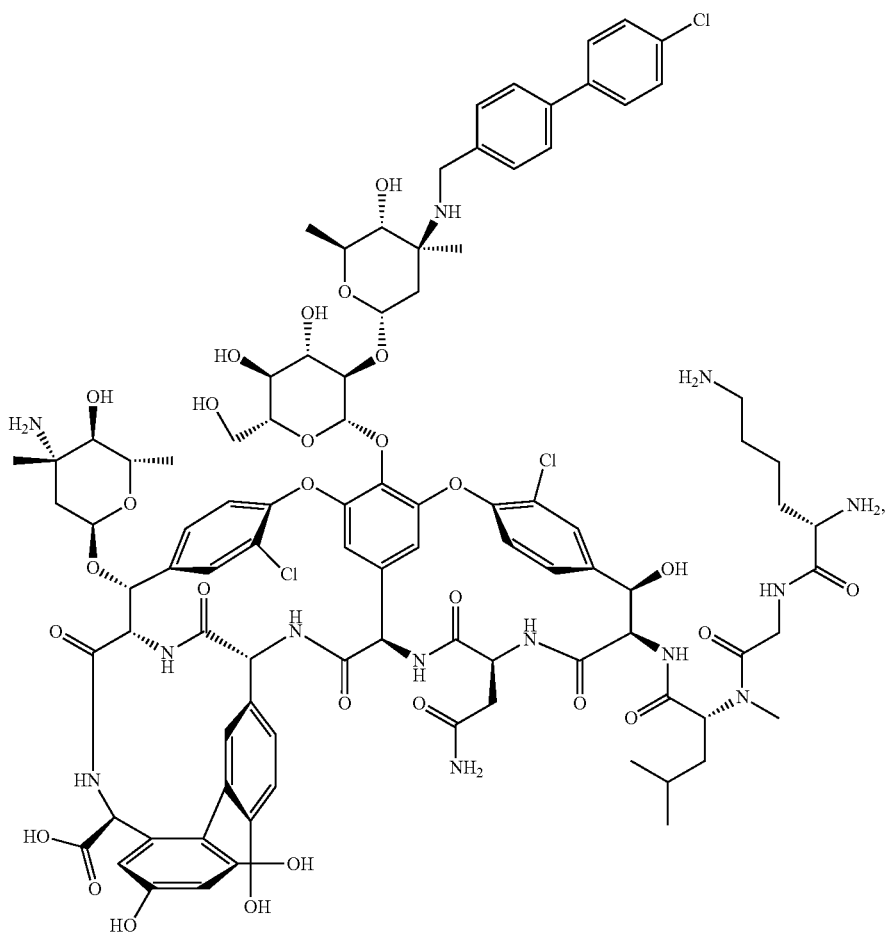

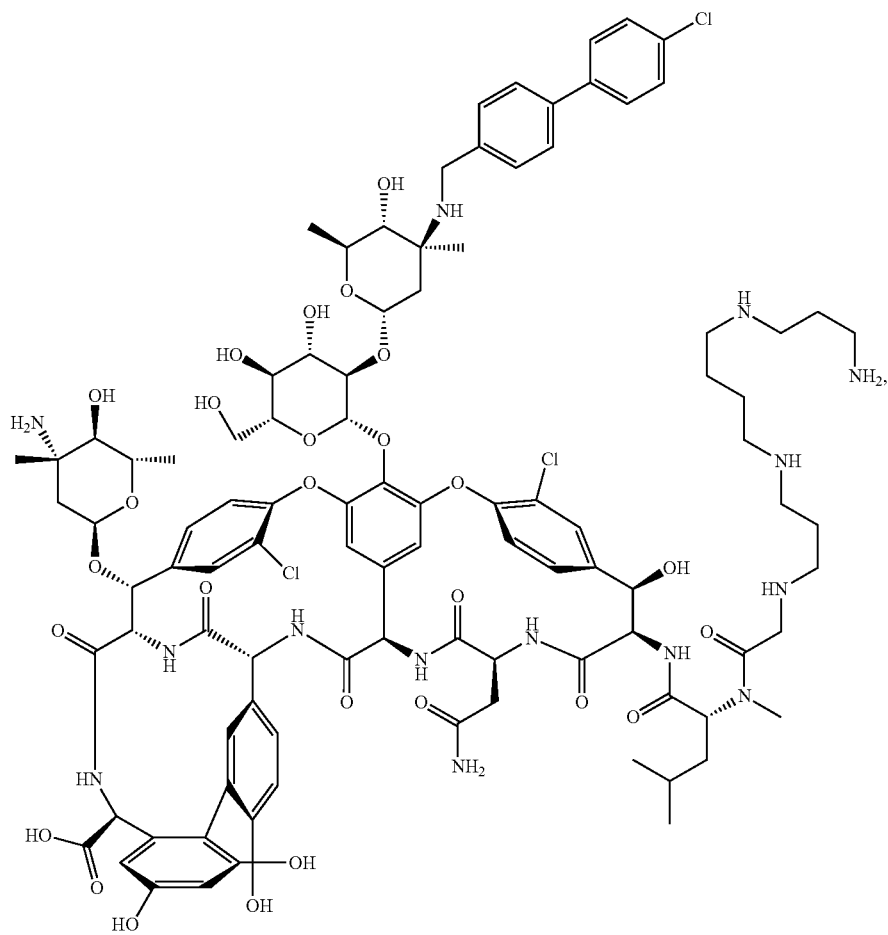

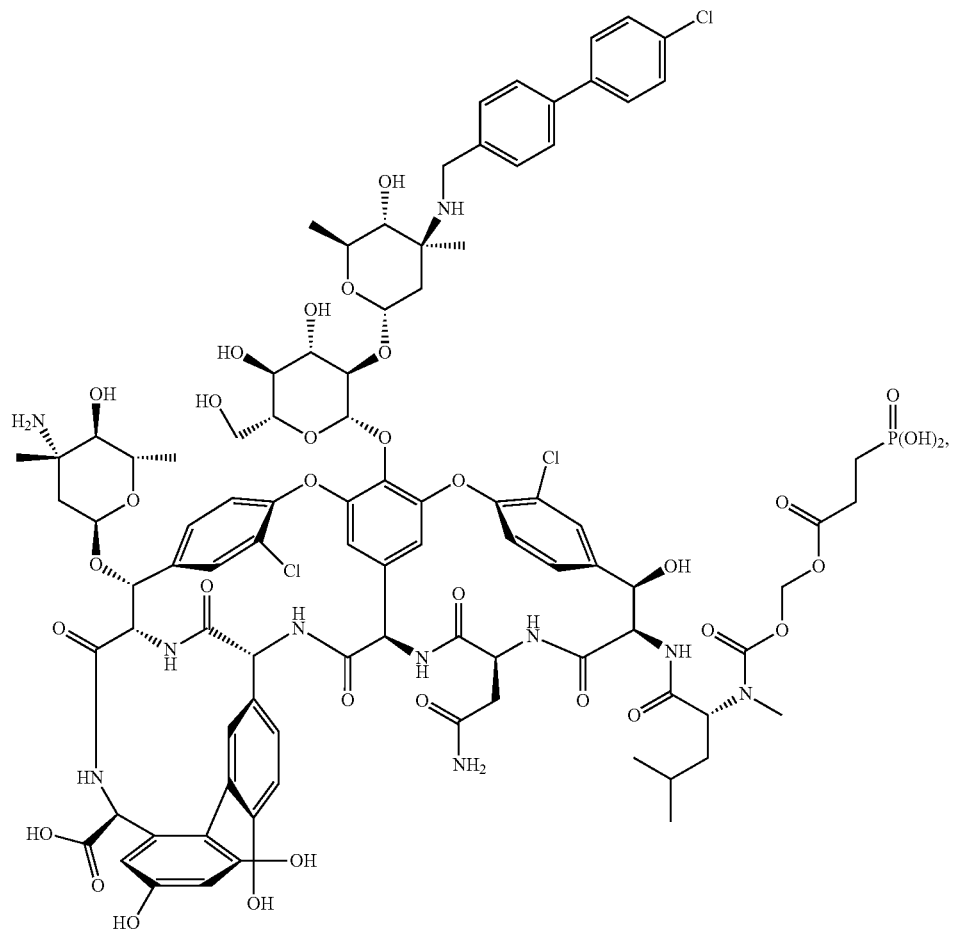

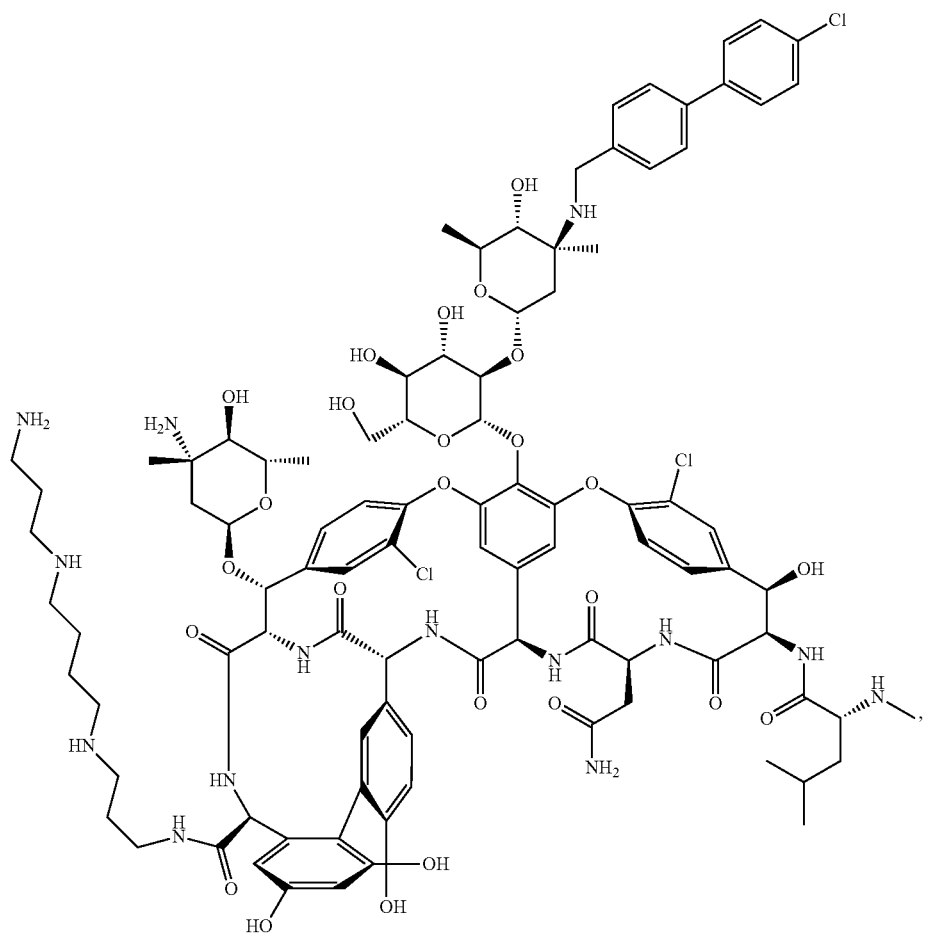

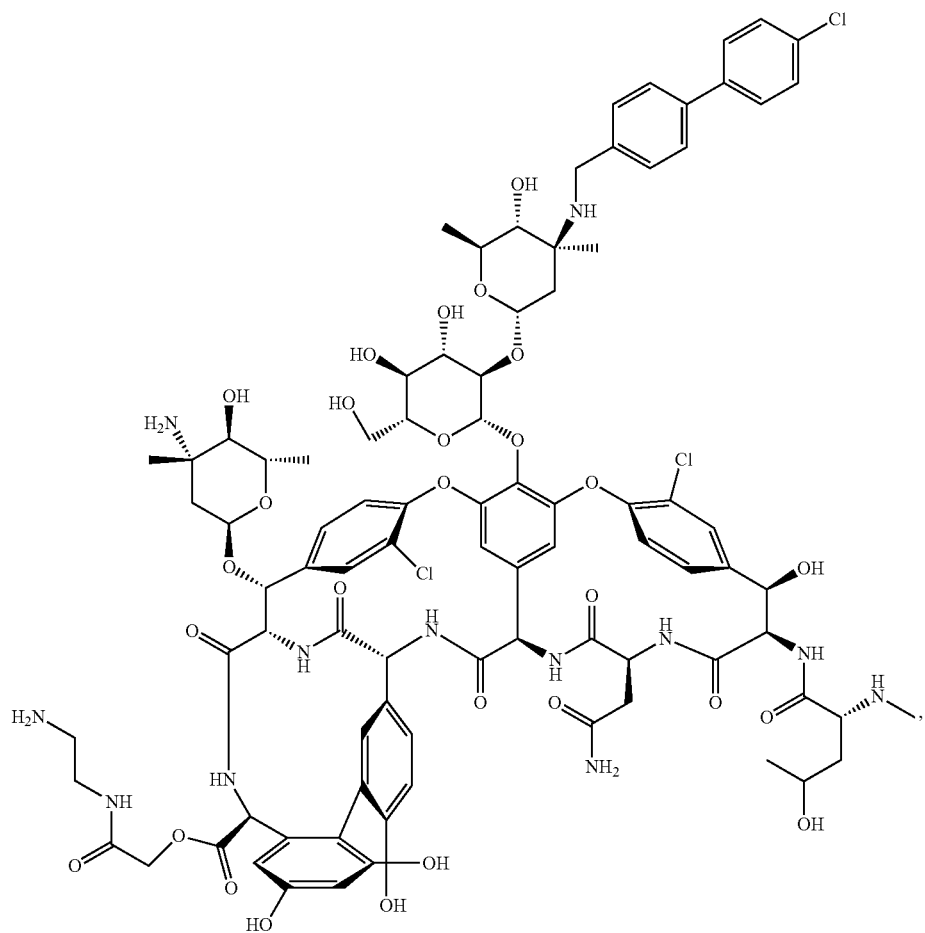

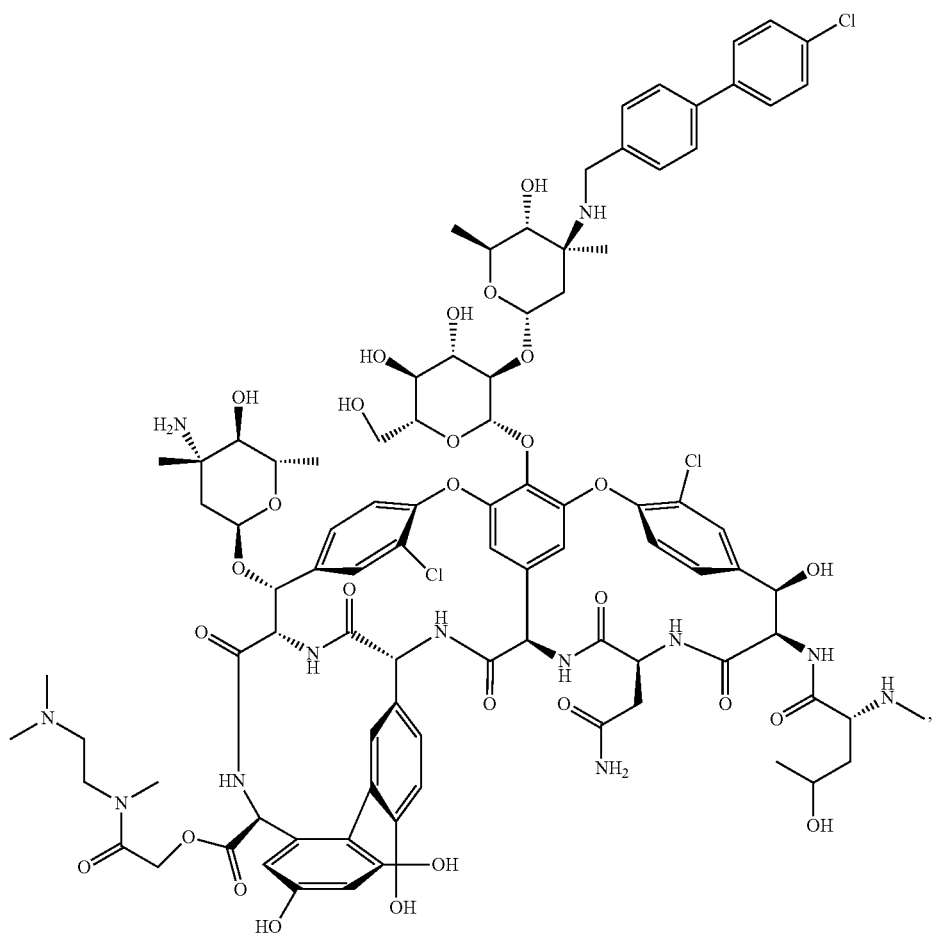

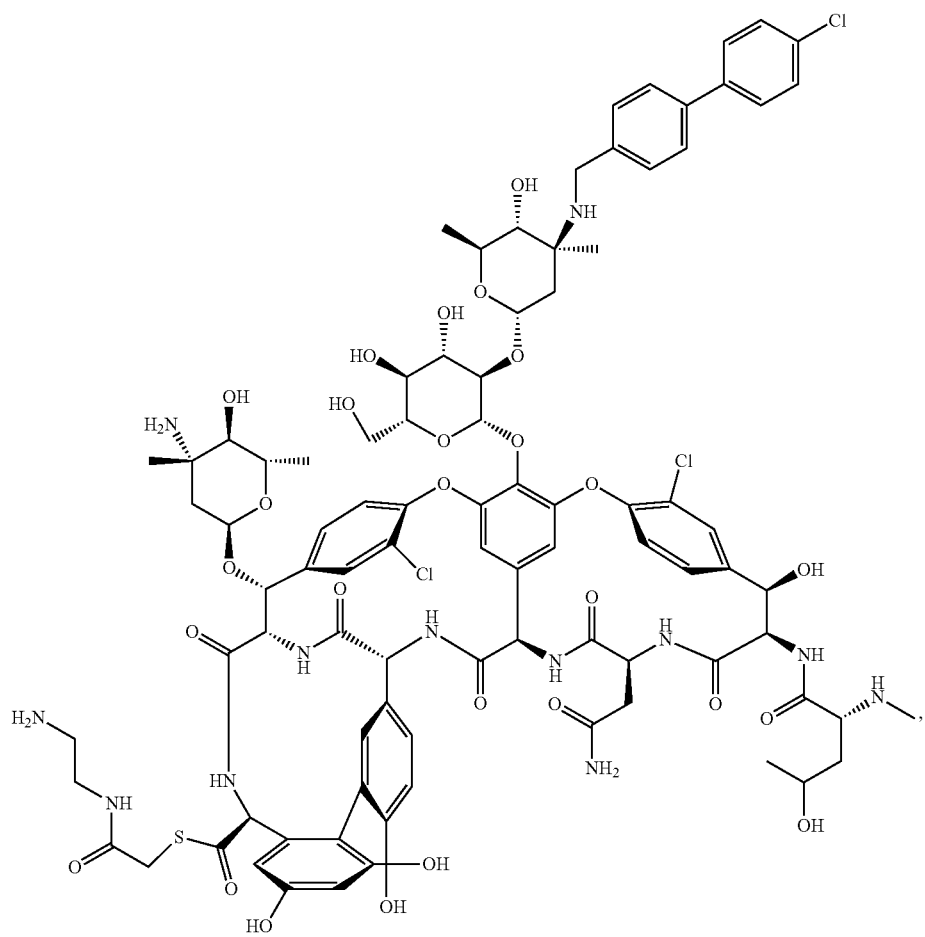

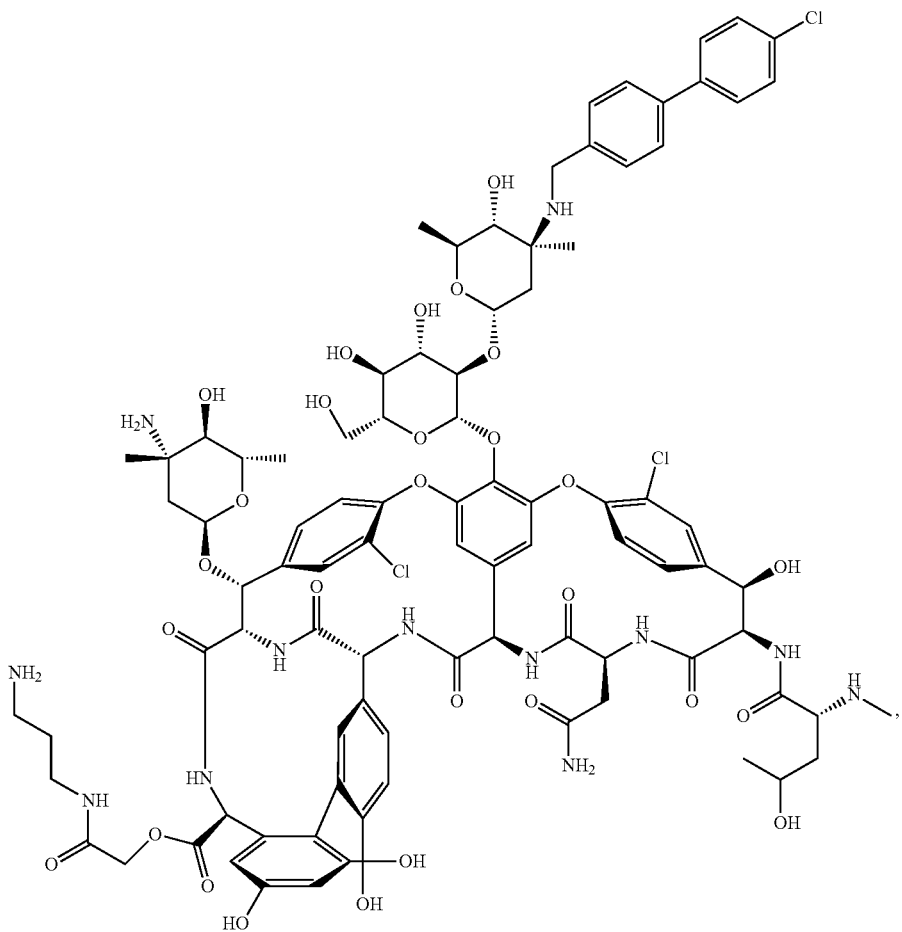

-continued
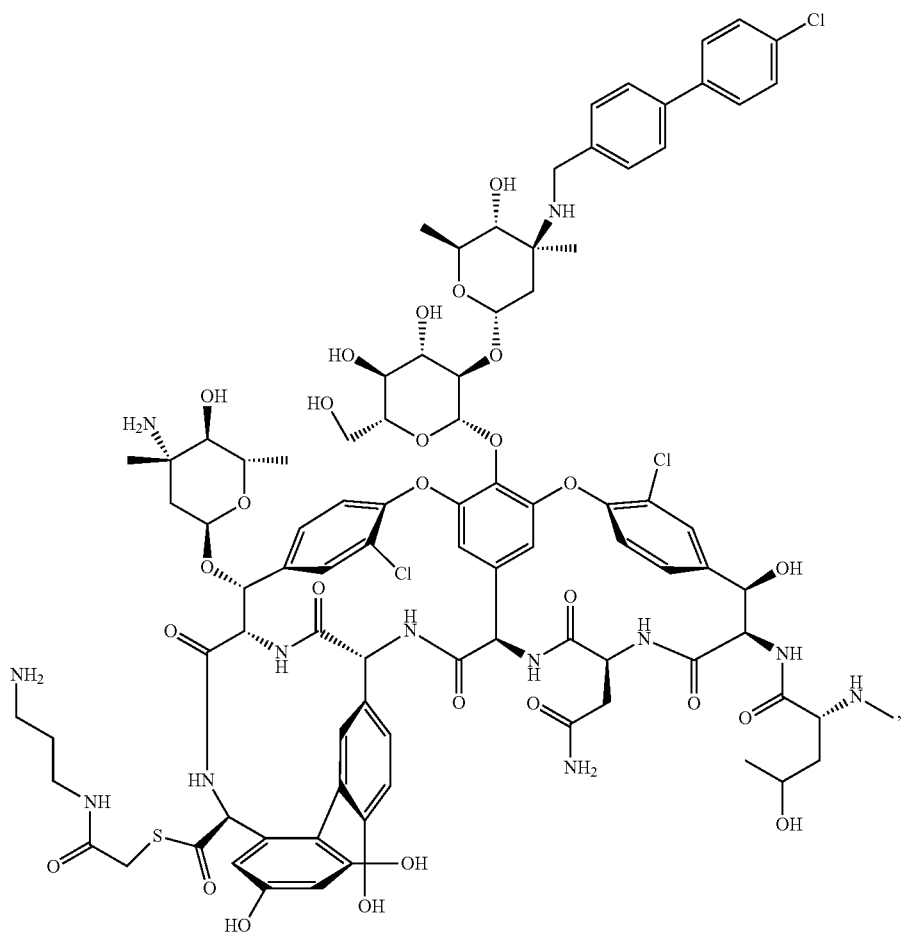

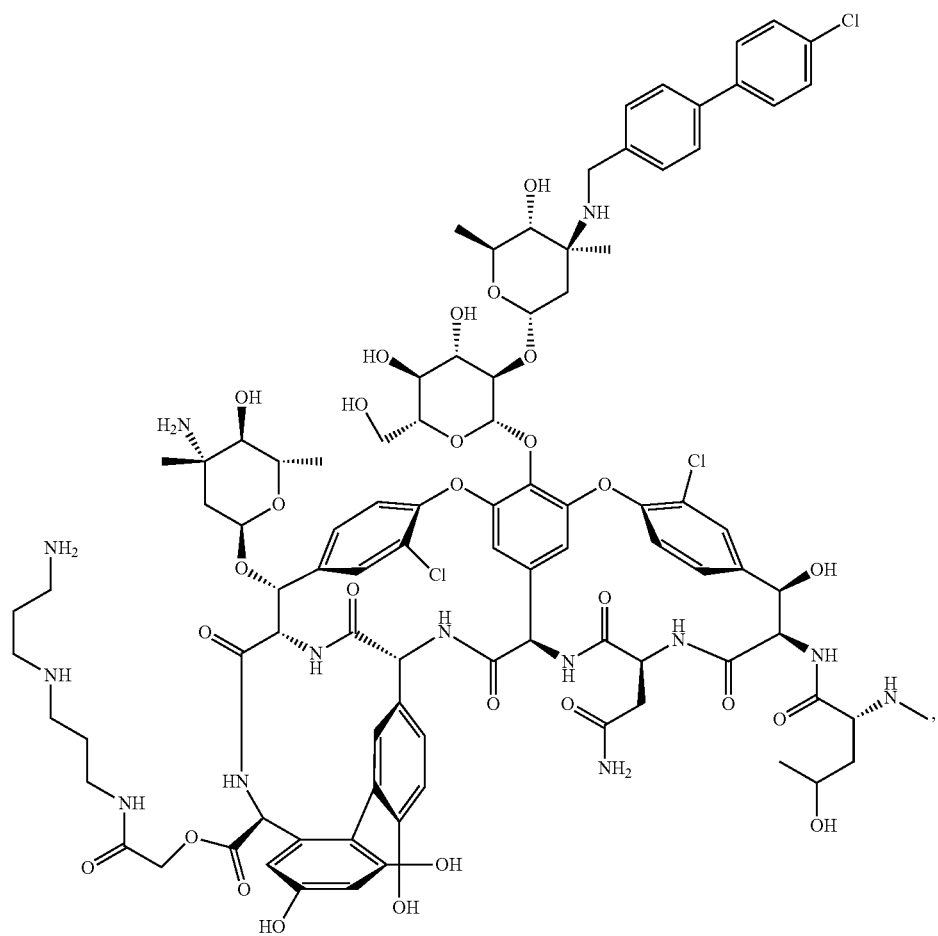

-continued
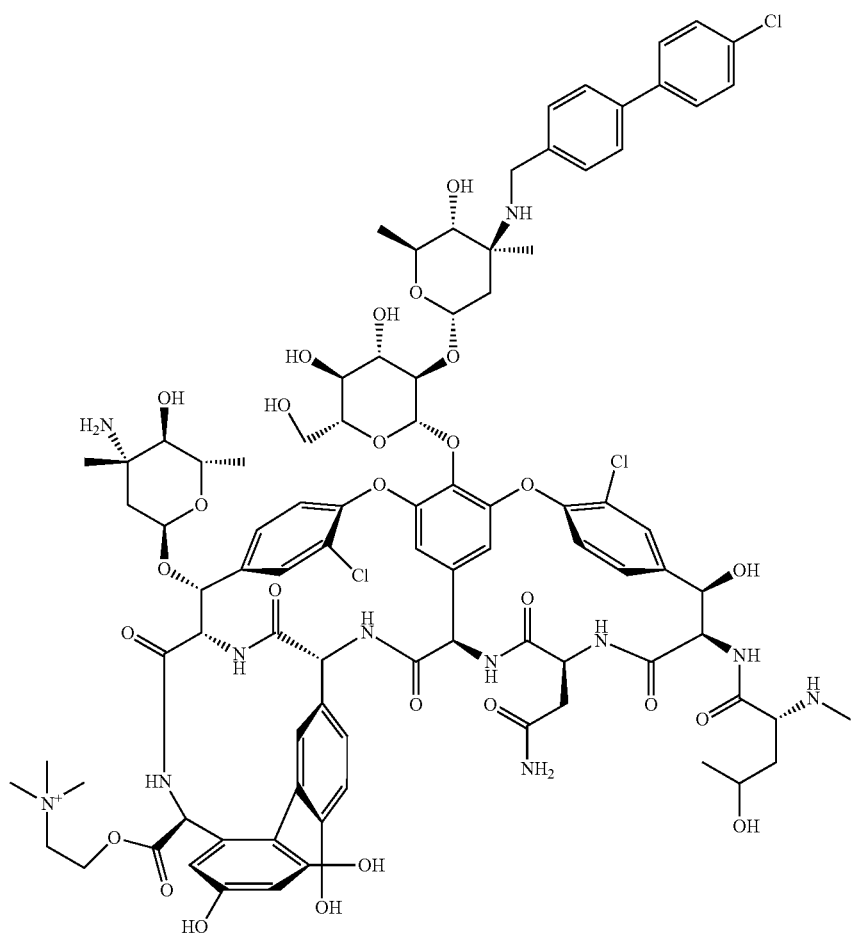

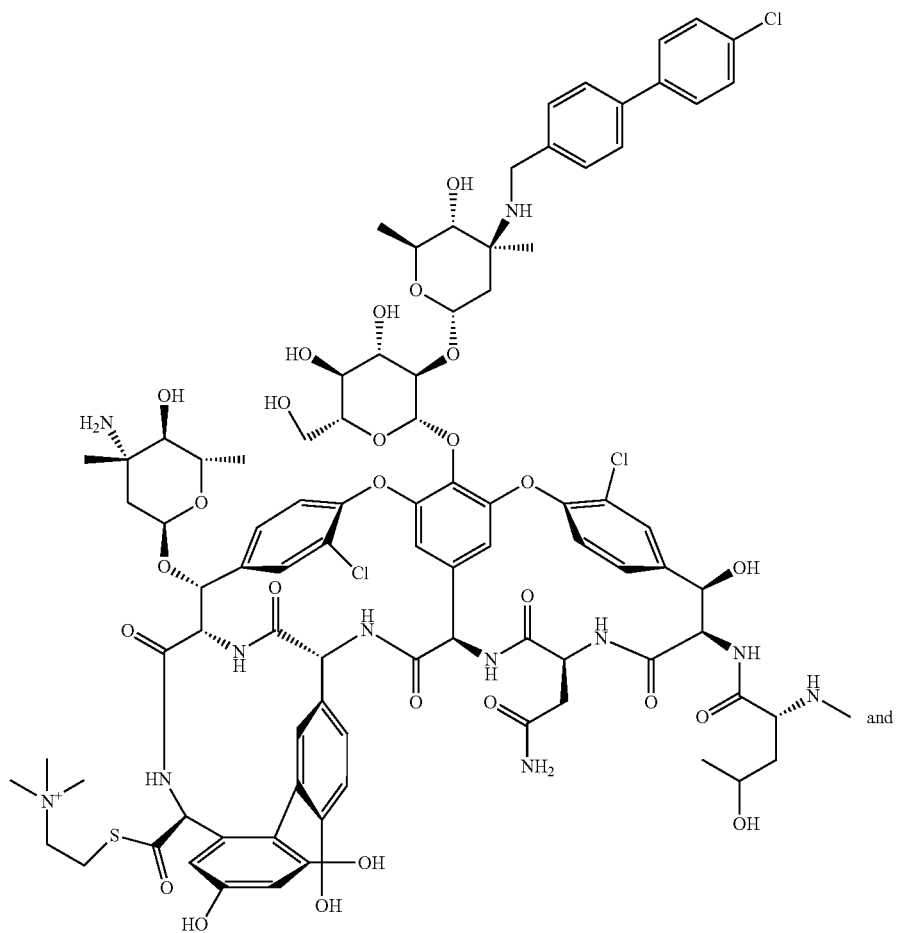 and

-continued
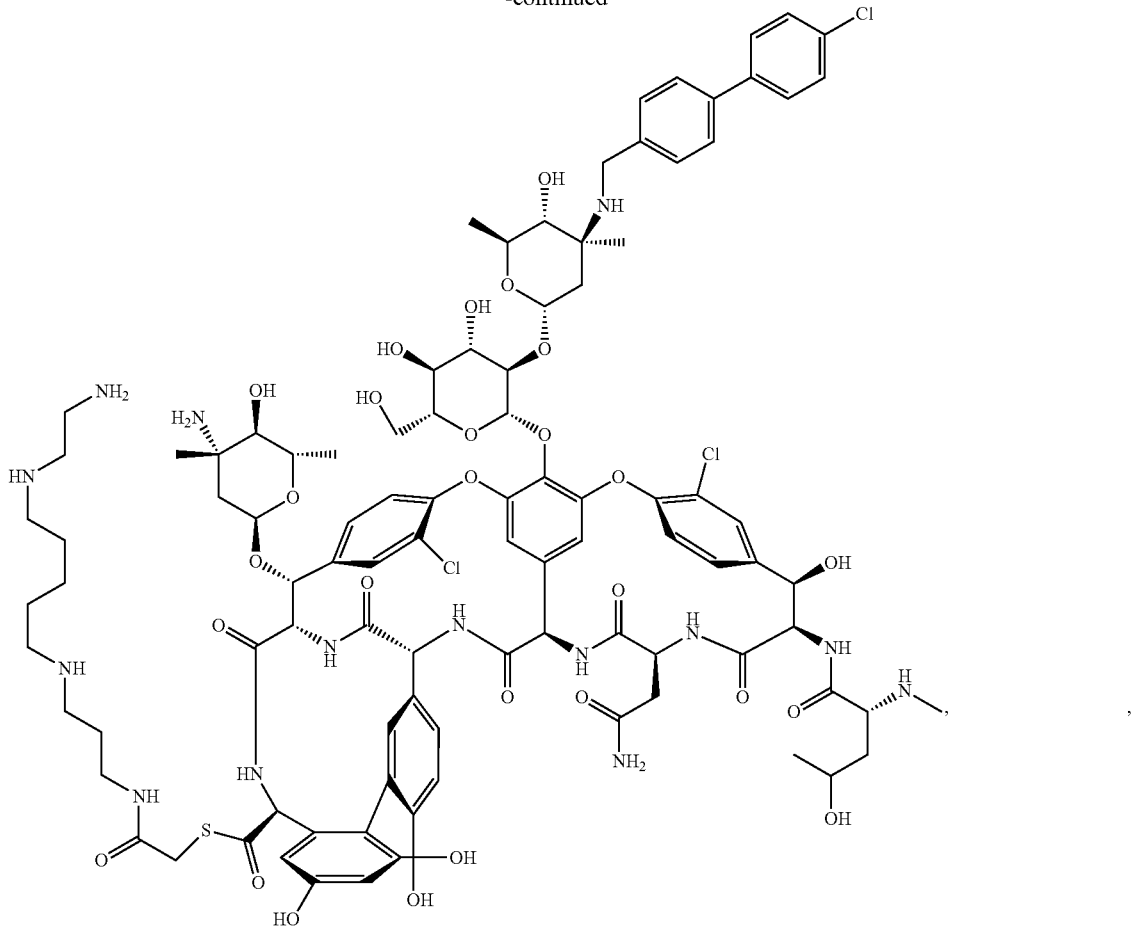
a pharmaceutically acceptable salt, ester, or stereoisomer thereof.
16. A compound represented by Formula (II):
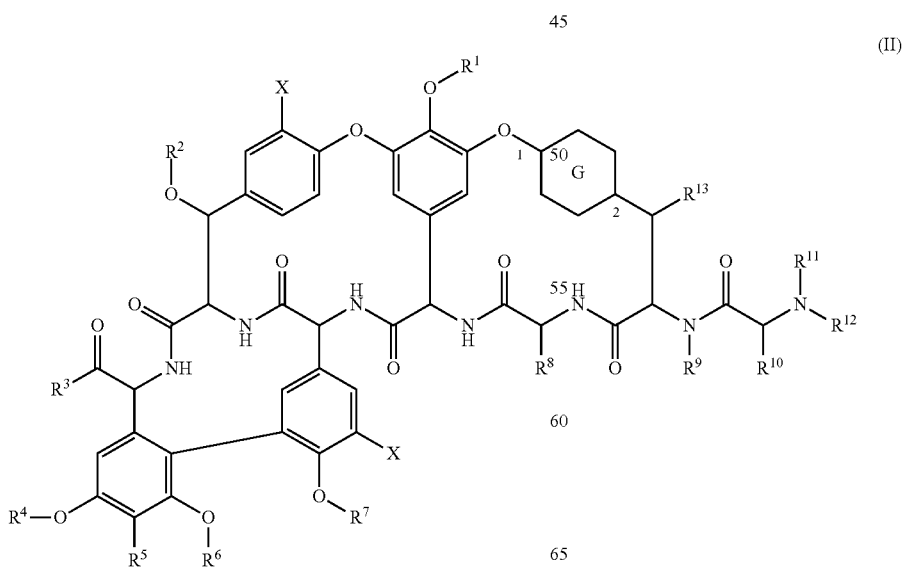

or a pharmaceutically acceptable salt, ester, or stereoisomer thereof, wherein:

$R^1$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —R—Y—$R^b$—$(Z)_x$ and -$L^{c1}$; or $R^1$ is a saccharide group optionally substituted with —$R^a$—Y—$R^b$—$(Z)_x$, $R^f$, —C(O)$R^f$, —C(O)—$R^a$Y—$R^b$—$(Z)_x$, C(N$L^{c2}$)$R^f$, —$R^a$—$(R^b)_z$—$(Z)_x$ or —C(N$L^{c3}$)-$R^a$—Y—$R^b$—$(Z)_x$;

$R^2$ is hydrogen, -$L^{c4}$ or a saccharide group optionally substituted with —$R^a$—Y—$R^b$—$(Z)_x$, $R^f$, —C(O)$R^f$, —C(O)—$R^a$Y—$R^b$—$(Z)_x$, —C(N$L^{c5}$)$R^f$, —$R^a$—$(R^b)_z$—$(Z)_x$ or —C(N$L^{c6}$)-$R^a$—Y—$R^b$—$(Z)_x$;

$R^3$ is selected from the group consisting of —O$R^c$, —N$R^cR^c$, —S$R^c$, —O—$R^a$—Y—$R^b$—$(Z)_x$, N$R^c$—$R^a$Y—$R^b$—$(Z)_x$, —N$R^cR^e$, —O—$R^e$, -$L^{c7}$, —N$L^{c8}R^c$, and —N$L^{c9}R^e$;

$R^4$ is selected from the group consisting of hydrogen, alkyl, substituted alkyl, alkenyl, substituted alkenyl, alkynyl, substituted alkynyl, -$L^{c10}$, —$R^a$—Y—$R^b$—$(Z)_x$, —C(O)$R^d$, —C(N$L^{c11}$)$R^d$ and a saccharide group optionally substituted with —$R^a$ Y—$R^b$—$(Z)_x$, $R^f$, —C(O)—$R^a$—Y—$R^b$—$(Z)_x$, or —C(N$L^{c2}$)-$R^a$—Y—$R^b$—$(Z)_x$, or $R^4$ and $R^5$ can be joined, together with the atoms to which they are attached, to form a heterocyclic ring optionally substituted with —N$R^c$—$R^a$—Y—$R^b$—$(Z)_x$ or —N$L^{c13}$-$R^a$Y—$R^b$—$(Z)_x$;

$R^5$ is selected from the group consisting of hydrogen, halo, —CH($R^c$)—N$R^cR^c$, —CH($R^c$)—N$R^cR^e$, —CH($R^c$)—N$R^c$—$R^a$—Y—$R^b$—$(Z)_x$, —CH($R^c$)—$R^x$, —CH($R^c$)—N$R^c$—$R^a$—C(O)—$R^x$; —CH($R^c$)—N$L^{c14}R^c$, —CH($R^c$)—N$L^{c15}R^e$, —CH($R^c$)—N$L^{c16}$-$R^a$—Y—$R^b$—$(Z)_x$, —CH($R^c$)—N$L^{c17}$-$R^a$—C(O)—$R^x$ and —CH($R^c$)—N$R^c$—$R^a$—C(N$L^{c18}$)-$R^x$;

$R^6$ is selected from the group consisting of hydrogen, alkyl, substituted alkyl, alkenyl, substituted alkenyl, alkynyl, substituted alkynyl, -$L^{c19}$, —$R^a$—Y—$R^b$—$(Z)_x$, —C(O)$R^d$, —C(N$L^{c20}$)$R^d$ and a saccharide group optionally substituted with —$R^a$—Y—$R^b$—$(Z)_x$, —$R^a$—$(R^b)_z$—$(Z)_x$, $R^f$, —C(O)$R^f$, —C(O)—$R^a$—Y—$R^b$—$(Z)_x$, —C(N$L^{c21}$)$R^f$, or —C(N$L^{c22}$)-$R^a$—Y—$R^b$—$(Z)_x$, or $R^5$ and $R^6$ can be joined, together with the atoms to which they are attached, to form a heterocyclic ring optionally substituted with —N$R^c$—$R^a$—Y—$R^b$—$(Z)_x$ or —N$L^{c23}$-$R^a$—Y—$R^b$—$(Z)_x$;

$R^7$ is selected from the group consisting of hydrogen, alkyl, substituted alkyl, alkenyl, substituted alkenyl, alkynyl, substituted alkynyl, -$L^{c24}$, —$R^a$—Y—$R^b$—$(Z)_x$, —C(O)$R^d$, and —C(N$L^{c25}$)$R^d$;

$R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$R^a$—Y—$R^b$—$(Z)_x$;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, and -$L^{c26}$;

$R^{10}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or $R^8$ and $R^{10}$ are joined to form —$Ar^1$—O—$Ar^2$—, where $Ar^1$ and $Ar^2$ are independently arylene or heteroarylene which may optionally be substituted with —O$L^{c27}$;

$R^{11}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and -$L^{c28}$, or $R^{10}$ and $R^{11}$ are joined, together with the carbon and nitrogen atoms to which they are attached, to form a heterocyclic ring which may optionally be substituted with —O$L^{c29}$, —C(O)-$L^{c30}$ or —N$L^{c31}R^c$;

$R^{12}$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, -$L^{c32}$, —C(O)$R^d$, —C(NH)$R^d$, —C(O)N$R^cR^c$, —C(O)O$R^d$, —C(NH)N$R^cR^c$, —$R^a$—Y—$R^b$—$(Z)_x$, —C(O)—$R^b$—Y—$R^b$—$(Z)_x$, —C(N$L^{c33}$)$R^d$, —C(O)N$L^{c34}R^c$, —C(O)-$L^{c35}$, —C(NH)N$L^{c36}R^c$, —C(N$L^{c37}$)N$R^cR^c$ and —C(N$L^{c3}$)-$R^b$—Y—$R^b$—$(Z)_x$, or $R^{11}$ and $R^{12}$ are joined, together with the nitrogen atom to which they are attached, to form a heterocyclic ring which may optionally be substituted with —O$L^{c39}$, —C(O)-$L^{c40}$ or —N$L^{c41}R^c$;

$R^{13}$ is selected from the group consisting of hydrogen and —O$R^{14}$;

$R^{14}$ is selected from the group consisting of hydrogen, -$L^{c42}$, —C(O)$R^d$, —C(N$L^{c43}$)$R^d$ and a saccharide group optionally substituted with —$R^a$ Y—$R^b$—$(Z)_x$, $R^f$, —C(O)$R^f$, —C(O)—$R^a$Y—$R^b$ $(Z)_x$, —C(N$L^{c44}$)$R^f$, or —C(N$L^{c45}$)-$R^a$—Y—$R^b$—$(Z)_x$;

each $R^a$ is independently selected from the group consisting of alkylene, substituted alkylene, alkenylene, substituted alkenylene, alkynylene and substituted alkynylene;

each $R^b$ is independently selected from the group consisting of a covalent bond, alkylene, substituted alkylene, alkenylene, substituted alkenylene, alkynylene and substituted alkynylene;

each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

each $R^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

each $R^e$ is a saccharide group optionally substituted with —$R^a$—Y—$R^b$—$(Z)_x$, $R^f$, —C(O)$R^f$, —C(O)—$R^a$Y—$R^b$—$(Z)_x$, —C(N$L^{c46}$)$R^f$, or —C(N$L^{c47}$)-$R^a$—Y—$R^b$—$(Z)_x$;

each $R^f$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, and heterocyclic;

$R^x$ is an N-linked amino saccharide or an N-linked heterocycle both of which may be optionally substituted with —$R^a$—Y—$R^b$—$(Z)_x$, $R^f$, —C(O)$R^f$, —C(O)—$R^a$—Y—$R^b$—$(Z)_x$, —C(N$L^{c48}$)$R^f$, or —C(N$L^{c49}$)-$R^a$—Y—$R^b$—$(Z)_x$;

each X is independently selected from the group consisting of hydrogen, fluoro, chloro, bromo and iodo;

each Y is independently selected from the group consisting of —CH$_2$—, oxygen, sulfur, —S—S—, —NR$^c$—, —S(O)—, —SO$_2$—, —NR$^c$C(O)—, —OSO$_2$—, —OC(O)—, —N(R$^c$)SO$_2$—, —C(O)NR$^c$—, —C(O)O—, —SO$_2$NR$^c$—, —SO$_2$O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$—, —C(O)—, —N(R$^c$)SO$_2$NR$^c$—, —NL$^{c50}$-, —NL$^{c51}$C(O)-, —OSO$_2$—, —OC(O)—, —N(L$^{c52}$)SO$_2$—, —C(O)NL$^{c53}$-, —SO$_2$NL$^{c54}$-, —P(O)(L$^{c55}$)O—, —P(O)(L$^{c56}$)NR$^c$—, —P(O)(OR$^c$)NL$^{c57}$-, —OP(O)(L$^{c58}$)O—, —OP(O)(L$^{c59}$)NR$^c$—, —OP(O)(OR$^c$)NL$^{c60}$-, —NL$^{c61}$C(O)O—, —NL$^{c62}$C(O)NR$^c$—, —NR$^c$C(O)NL$^{c63}$-, —OC(O)NL$^{c64}$-, —N(L$^{c6}$S)SO$_2$NR$^c$— and —N(R$^c$)SO$_2$NL$^{c66}$-;

each Z is independently selected from the group consisting of hydrogen, aryl, cycloalkyl, cycloalkenyl, heteroaryl, heterocyclic, a saccharide, -L$^{c67}$, -L$^{c68}$ and -L$^{c69}$;

x is 1 or 2;

z is 1, 2, 3 or 4; and

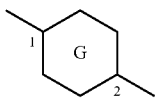

is selected from or

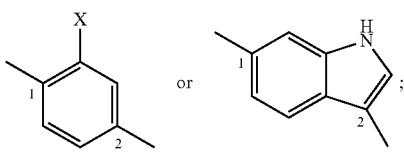

each L$^{c1}$, L$^{c4}$, L$^{c10}$, L$^{c19}$, L$^{c24}$, L$^{27}$, L$^{c29}$, L$^{c39}$, L$^{c42}$, and L$^{c67}$ is a linker independently selected from the group of consisting of the following linkers:

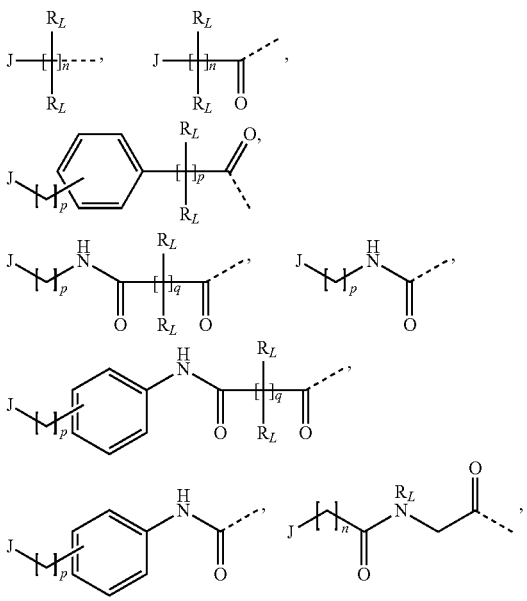

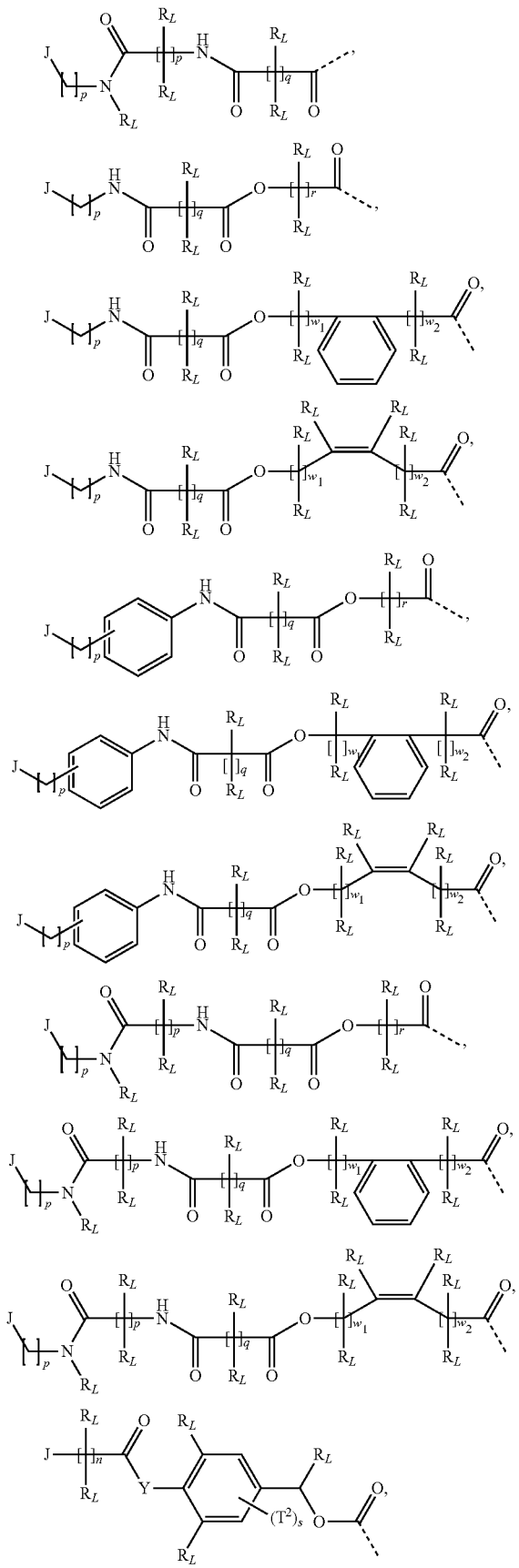

249
-continued
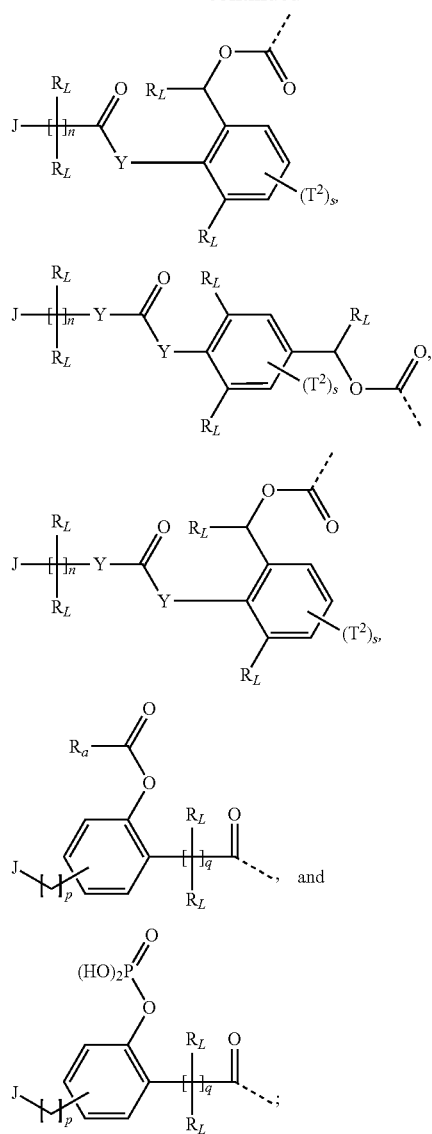
and
each $L^{c8}$, $L^{c9}$, $L^{c13}$, $L^{c14}$, $L^{c15}$, $L^{c16}$, $L^{c17}$, $L^{c23}$, $L^{c26}$, $L^{c28}$, $L^{c31}$, $L^{c32}$, $L^{c34}$, $L^{c36}$, $L^{c37}$, $L^{c41}$, $L^{c50}$, $L^{c51}$, $L^{c52}$, $L^{c53}$, $L^{c54}$, $L^{c57}$, $L^{c60}$, $L^{c61}$, $L^{c62}$, $L^{c63}$, $L^{c64}$, $L^{c65}$, $L^{c66}$ and $L^{c68}$ is a linker independently selected from the group of consisting of the following linkers:
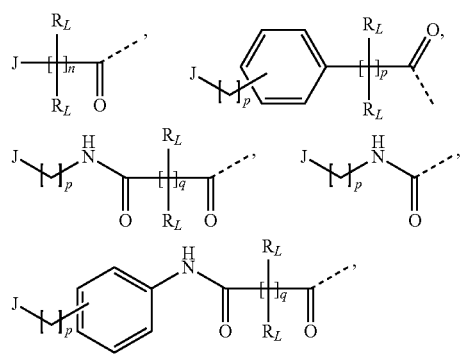
250
-continued
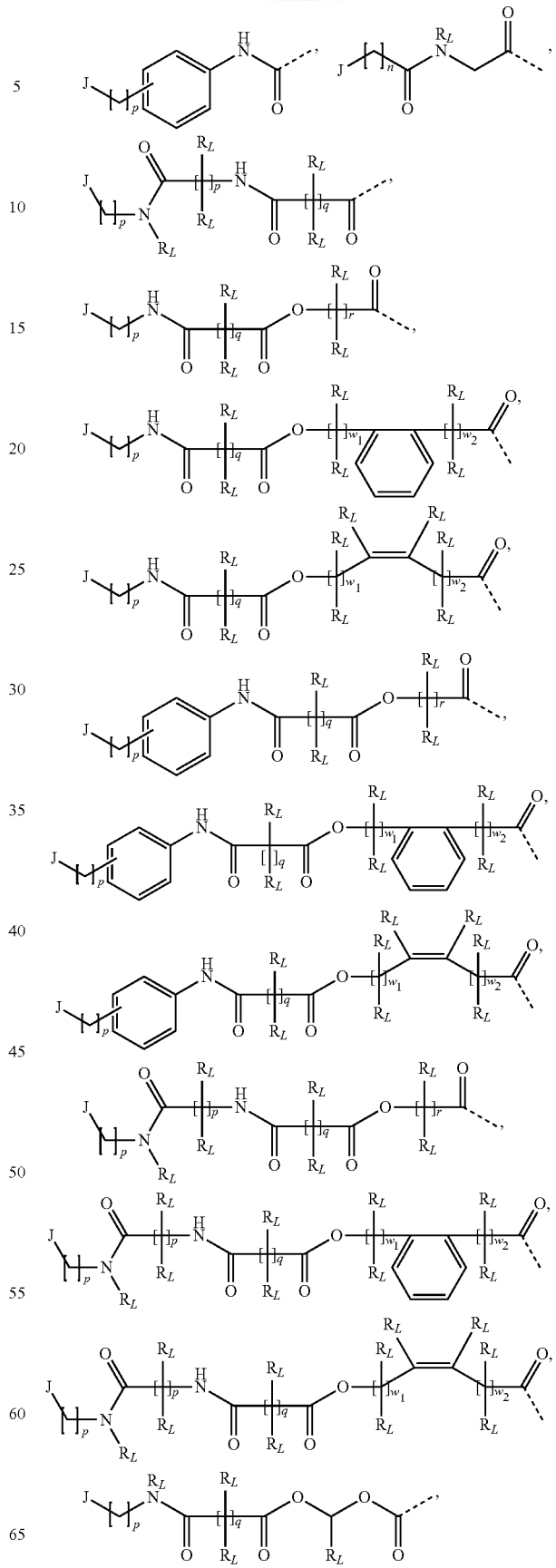

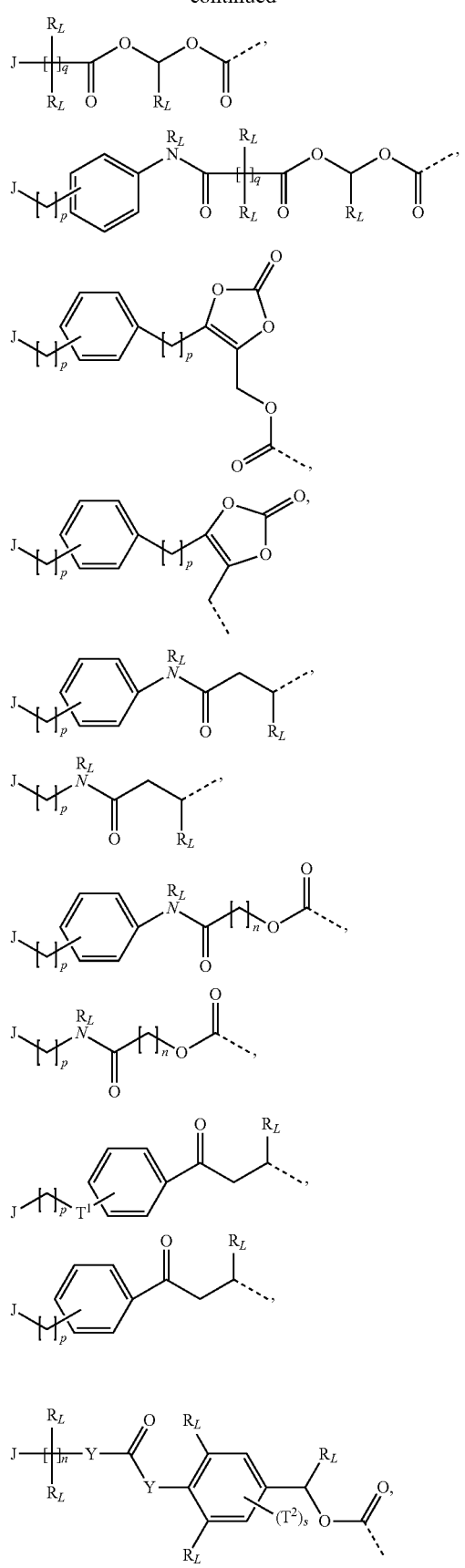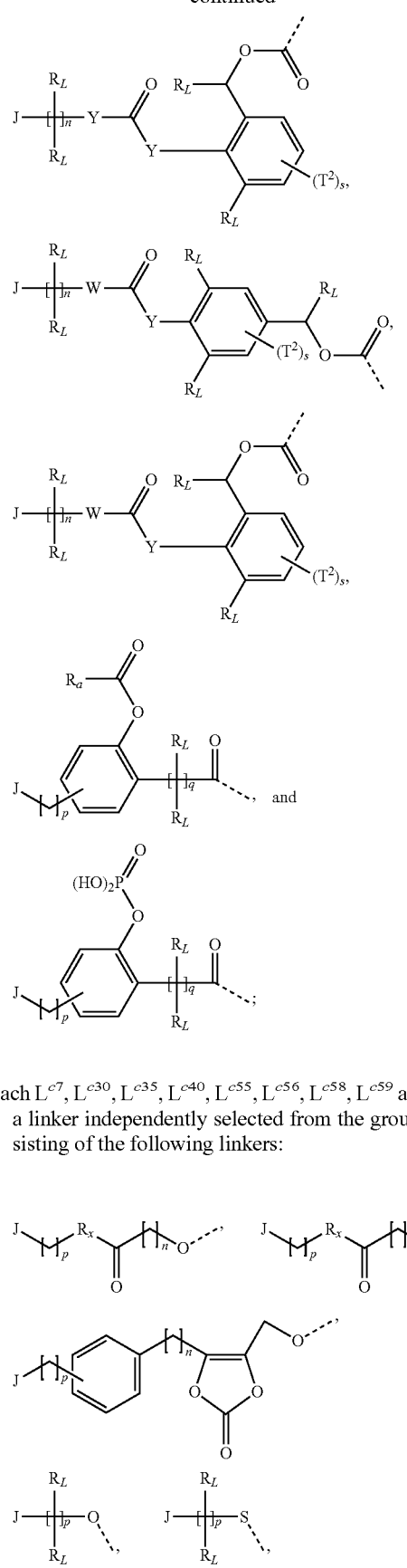
each $L^{c7}$, $L^{c30}$, $L^{c35}$, $L^{c40}$, $L^{c55}$, $L^{c56}$, $L^{c58}$, $L^{c59}$ and $L^{c69}$ is a linker independently selected from the group of consisting of the following linkers:

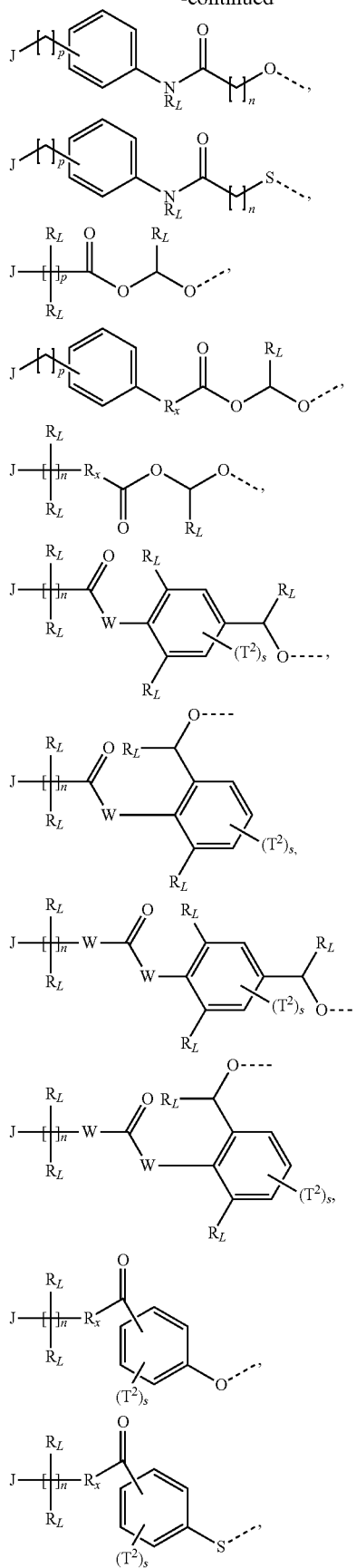

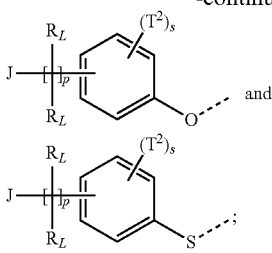

and

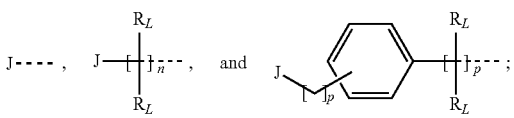

each $L^{c2}$, $L^{c3}$, $L^{c5}$, $L^{c6}$, $L^{c11}$, $L^{c12}$, $L^{c18}$, $L^{c20}$, $L^{c21}$, $L^{c25}$, $L^{c25}$, $L^{c33}$, $L^{c38}$, $L^{c43}$, $L^{c44}$, $L^{c45}$, $L^{c46}$, $L^{c47}$ $L^{c48}$, and $L^{c49}$ is a linker independently selected from the group of consisting of

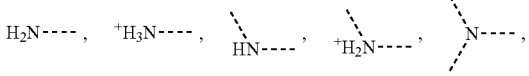

wherein:

n is an integer $\leq 10$;

each p is independently 0 or an integer $\leq 10$;

each $R_L$ is independently selected from the group consisting of H, ethyl and methyl;

q is 2 or 3;

r is 1, 2, 3, 4 or 5;

$w_1$ and $w_2$ are each integers $\geq 0$ such that their sum ($w_1+w_2$) is 1, 2 or 3;

each W is independently selected from —O—, —S—, and —$NR_L$—;

$T^1$ is $CH_2$, —$CONR_L$—, —CO—O—$CH_2$—, or —CO—O—;

each $T^2$ is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro;

s is 1, 2, 3 or 4;

$R_a$ is $C_xH_y$ where x is an integer of 0 to 20 and y is an integer of 1 to 2x+1;

$R_x$ is selected from the group consisting of a covalent bond, S, $NR_L$ and O; and J is $[[L^a{}_\beta\text{-}M]_\alpha\text{-}L^b{}_\delta]$;

wherein:

each M is individually selected from the group of:

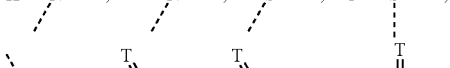

-continued

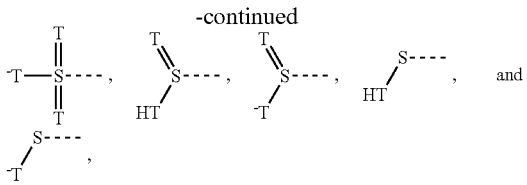

wherein:
  each T is O or S; and
  the dashed bonds - - - indicate the points of attachment to $L^a$, $L^b$, or the linker;
  each $L^a$ is individually selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and

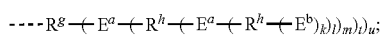

each $L^b$ is individually selected from the group consisting of a covalent bond, alkylene, substituted alkylene, alkenylene, substituted alkenylene, alkynylene, substituted alkynylene, cycloalkylene, substituted cycloalkylene, cycloalkenylene, substituted cycloalkenylene, arylene, heteroarylene and

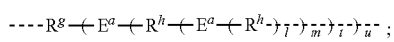

wherein:
  each $R^g$ is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, —(CO)-(substituted alkenylene)-, —(CO)-alkynylene-, —(CO)-(substituted alkynylene)-, —(CO)-arylene- and —(CO)-(substituted arylene)-;
  each $R^h$ is independently selected from the group consisting of a covalent bond, alkylene, substituted alkylene, alkenylene, substituted alkenylene, alkynylene, substituted alkynylene, arylene and substituted arylene;
  each $E^a$ is independently selected from the group consisting of a covalent bond, methylene, oxygen, sulfur,

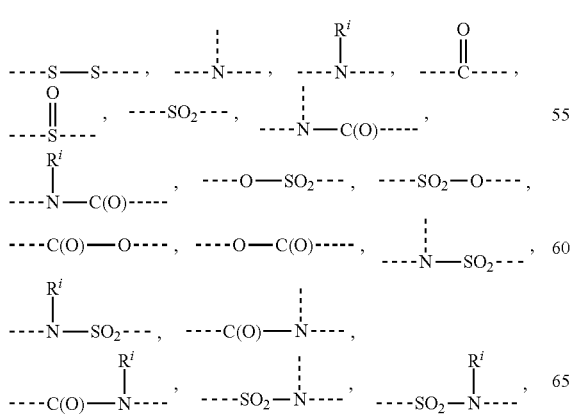

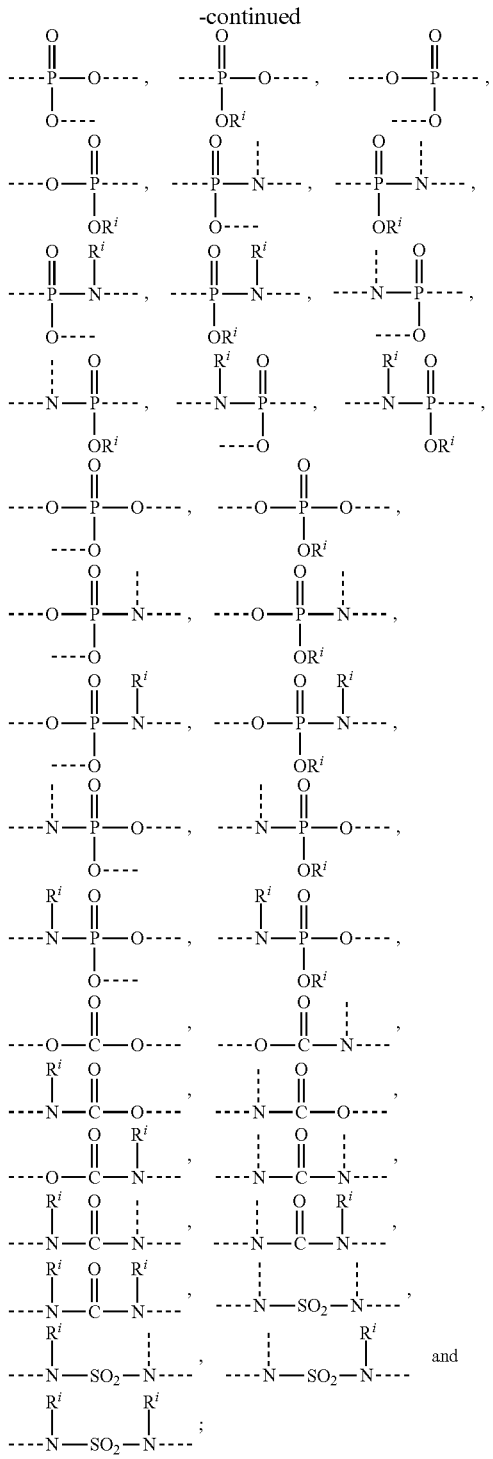

each $R^i$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^j$;
  each $R^j$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

each $E^b$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, and substituted aryloxy;

each k, l, m, t, u is independently a nonnull integer ≤5;

α is an integer between 1 and 6;

β is an integer ≤3; and

δ is an integer ≤2α;

and with the further proviso that at least one of $L^{c1}$, $L^{c2}$, $L^{c3}$, $L^{c4}$, $L^{c5}$, $L^{c6}$, $L^{c7}$, $L^{c8}$, $L^{c9}$, $L^{c10}$, $L^{c11}$, $L^{c12}$, $L^{c13}$, $L^{c14}$, $L^{c15}$, $L^{c16}$, $L^{c17}$, $L^{c18}$, $L^{c19}$, $L^{c20}$, $L^{c21}$, $L^{c22}$, $L^{c23}$, $L^{c24}$, $L^{c25}$, $L^{c26}$, $L^{c27}$, $L^{c28}$, $L^{c29}$, $L^{c30}$, $L^{c31}$, $L^{c32}$, $L^{c33}$, $L^{c34}$, $L^{c35}$, $L^{c36}$, $L^{c37}$, $L^{c38}$, $L^{c39}$, $L^{c40}$, $L^{c41}$, $L^{c42}$, $L^{c43}$, $L^{c44}$, $L^{c45}$, $L^{c46}$, $L^{c47}$, $L^{c48}$, $L^{c49}$, $L^{c50}$, $L^{c51}$, $L^{c52}$, $L^{c53}$, $L^{c54}$, $L^{c55}$, $L^{c56}$, $L^{c57}$, $L^{c58}$, $L^{c59}$, $L^{c60}$, $L^{c61}$, $L^{c62}$, $L^{c63}$, $L^{c64}$, $L^{c65}$, $L^{c66}$, $L^{c67}$, $L^{c68}$ and $L^{c69}$ is present.

17. A compound represented by Formula (III):

$R^5$ is selected from the group consisting of hydrogen, alkyl, substituted alkyl, alkenyl, substituted alkenyl, alkynyl, substituted alkynyl, —$R^a$—$R^b$—$(Z)_x$, —$C(O)R^d$, and a saccharide group optionally substituted with —$R^a$—Y—$R^b$—$(Z)_x$, —$R^a$—$(R^b)_z$—$(Z)_x$, $R^f$, —$C(O)R^f$, and —$C(O)$—$R^a$—Y—$R^b$—$(Z)_x$;

$R^6$ is selected from the group consisting of —$CH_2(CO)NH_2$, benzyl, 4-hydroxyphenyl, and 3-chloro-4-hydroxyphenyl;

$R^7$ is selected from the group consisting of —$CH_2CH(CH_3)_2$, 3-chloro-4-hydroxyphenyl, 4-rhamnosylphenyl, 4-(rhamnosyl-galactosyl)phenyl, 4-(galactosyl-galactosyl)phenyl, and 4(methoxyrhamnosyl)phenyl; or $R^6$ and $R^7$ are joined to form

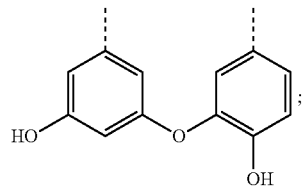

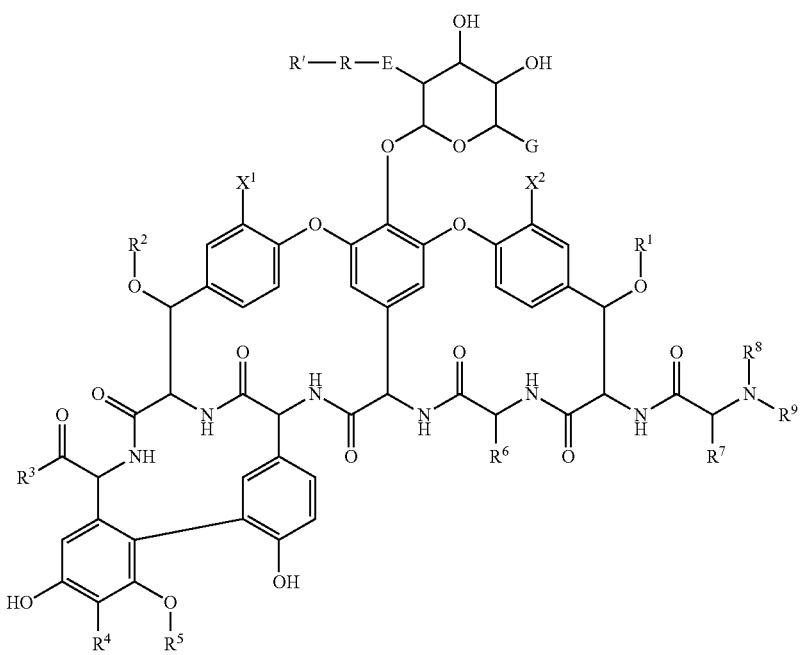

(III)

or a pharmaceutically acceptable salt, ester, or stereoisomer thereof, wherein:

R is selected from the group consisting of —$C(O)R^f$, vancosaminyl, 4-epi-vancosaminyl, L-acosaminyl, L-ristosaminyl, and L-actinosaminyl;

R' is attached to the amino group of R and is selected from the group of —$R^a$—Y—$R^b$—$(Z)_x$, —$R^f$, —$C(O)R^f$, —$C(O)$—R—Y—$R^b$—$(Z)_x$, and —R—$(R^b)_z$—$(Z)_x$ or R' is absent if R is —$C(O)R^f$;

$R^1$ is hydrogen or mannopyranosyl;

$R^2$ is hydrogen or a saccharide group optionally N-substituted with —$R^a$—Y—$R^b$—$(Z)_x$, —$R^f$, —$C(O)R^f$, —$C(O)$—$R^a$—Y—$R^b$—$(Z)_x$, or —$R^a$—$(R^b)_z$—$(Z)_x$;

$R^3$ is hydroxyl or -$L^c$;

$R^4$ is selected from the group consisting of hydrogen, halo, —$CH(R^c)$—$NR^cR^c$ and —$CH(R^c)$—$NR^c$—$R^a$—Y—$R^b$—$(Z)_x$;

$R^8$ is hydrogen or methyl;

$R^9$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, acyl and substituted acyl;

G is —$CH_2OH$, —$CO_2H$ or —$C(O)$-$L^c$;

E is —O— or —NH—;

$R^a$ is each independently selected from the group consisting of alkylene, substituted alkylene, alkenylene, substituted alkenylene, alkynylene and substituted alkynylene;

$R^b$ is each independently selected from the group consisting of a covalent bond, alkylene, substituted alkylene, alkenylene, substituted alkenylene, alkynylene and substituted alkynylene;

$R^c$ is each independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)$R^d$;

$R^d$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

$R^f$ is each independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, and heterocyclic;

each $X^1$ and $X^2$ is independently selected from the group consisting of hydrogen, and chloro;

each Y is independently selected from the group consisting of —$CH_2$—, oxygen, sulfur, —S—S—, —N($R^c$)—, —S(O)—, —$SO_2$—, —N($R^c$)—C(O)—, —$OSO_2$—, —OC(O)—, —N($R^c$)$SO_2$—, —C(O)—N($R^c$)—, —C(O)O—, —$SO_2$—N($R^c$)—, —$SO_2$O—, —P(O)(O$R^c$)O—, —P(O)(O$R^c$)N($R^c$)—, —OP(O)(O$R^c$)O—, —OP(O)(O$R^c$)N($R^c$)—, —OC(O)O—, —N($R^c$)—C(O)—O—, —N($R^c$)—C(O)—N($R^c$)—, —O—C(O)—N($R^c$)—, —C(O)—, and —N($R^c$)—$SO_2$—N($R^c$)—;

each Z is independently selected from the group consisting of hydrogen, aryl, cycloalkyl, cycloalkenyl, heteroaryl, heterocyclic, and a saccharide;

x is 1 or 2;

z is 1, 2, 3 or 4;

each $L^c$ is a linker independently selected from the group of consisting of the following linkers:

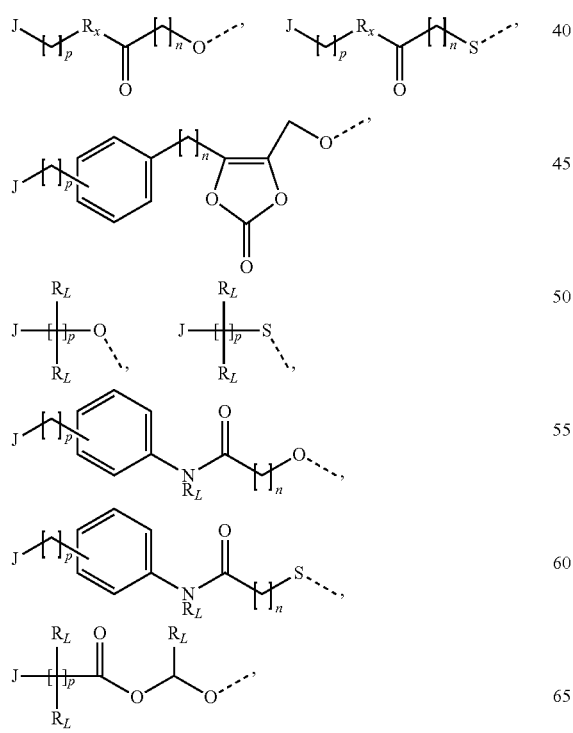

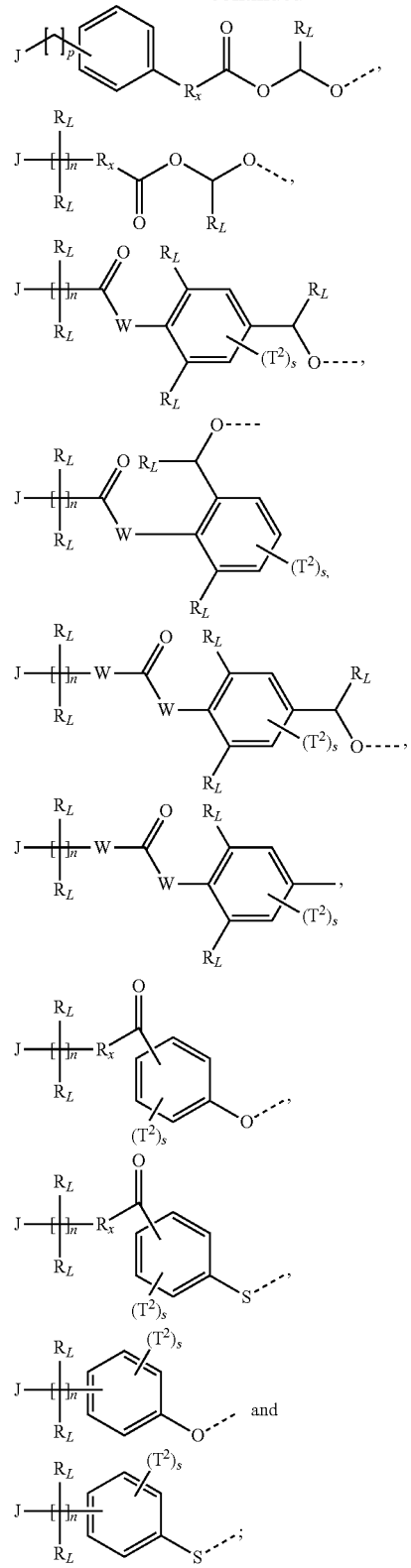

n is an integer ≤10;

each p is independently 0 or an integer ≤10;

each $R_L$ is independently selected from the group consisting of H, ethyl and methyl;

each W is independently selected from —O—, —S—, and —NR$_L$—;

each T$^2$ is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro;

s is 1, 2, 3 or 4;

R$_x$ is selected from the group consisting of a covalent bond, S, NR$_L$ and O; and J is $[[L^a{}_\beta\text{-M}]_\alpha\text{-}L^b{}_\delta]$;

wherein:

each M is individually selected from the group of:

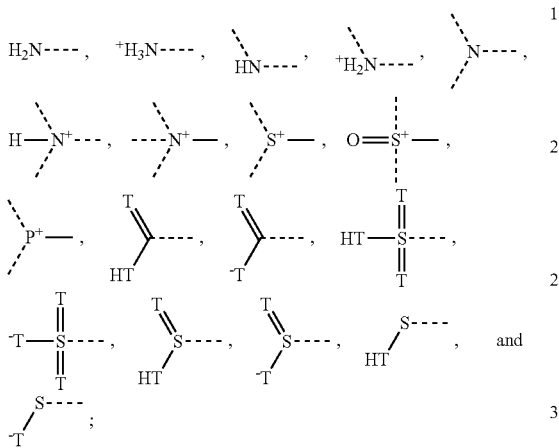

wherein:
each T is O or S; and
the dashed bonds - - - indicate the points of attachment to L$^a$, L$^b$, or the linker;

each L$^a$ is individually selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and

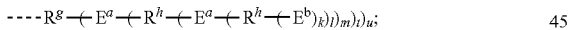

each L$^b$ is individually selected from the group consisting of a covalent bond, alkylene, substituted alkylene, alkenylene, substituted alkenylene, alkynylene, substituted alkynylene, cycloalkylene, substituted cycloalkylene, cycloalkenylene, substituted cycloalkenylene, arylene, heteroarylene and

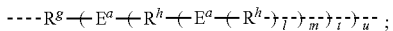

wherein:
each R$^g$ is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, —(CO)-(substituted alkenylene)-, —(CO)-alkynylene-, —(CO)-(substituted alkynylene)-, —(CO)-arylene- and —(CO)-(substituted arylene)-;

each R$^h$ is independently selected from the group consisting of a covalent bond, alkylene, substituted alkylene, alkenylene, substituted alkenylene, alkynylene, substituted alkynylene, arylene and substituted arylene;

each E$^a$ is independently selected from the group consisting of a covalent bond, methylene, oxygen, sulfur,

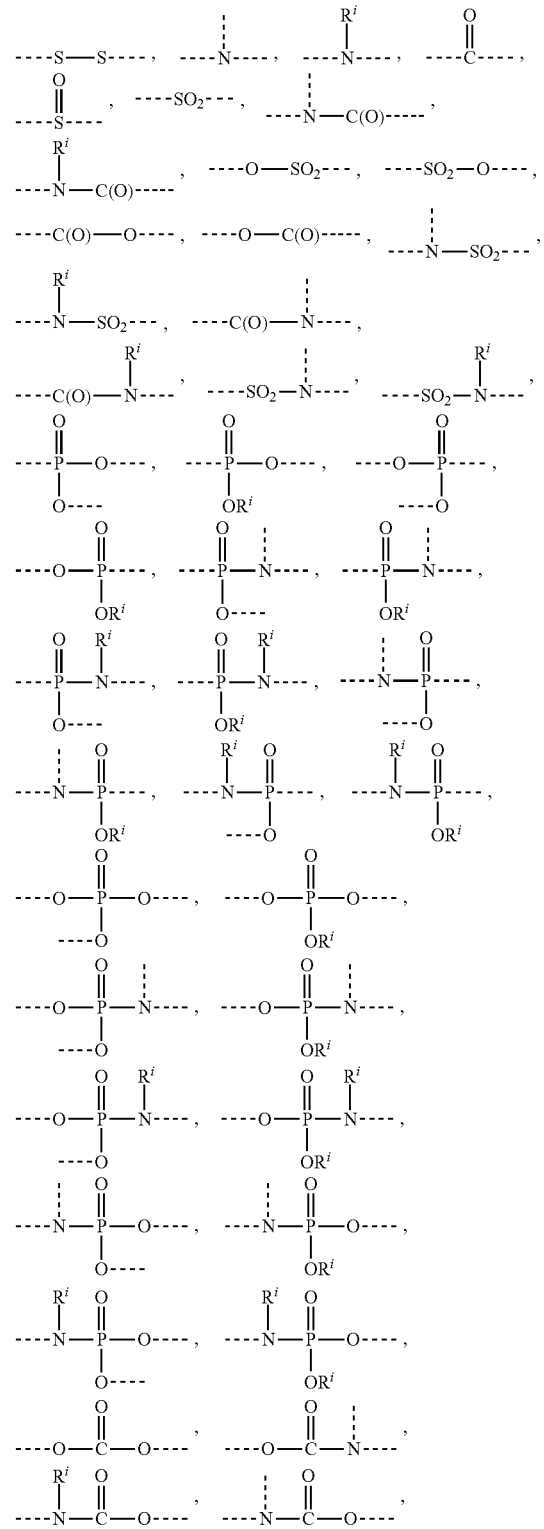

-continued

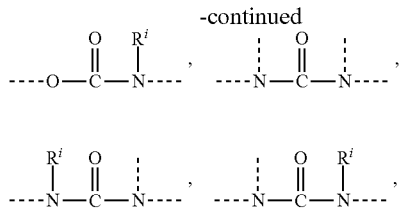

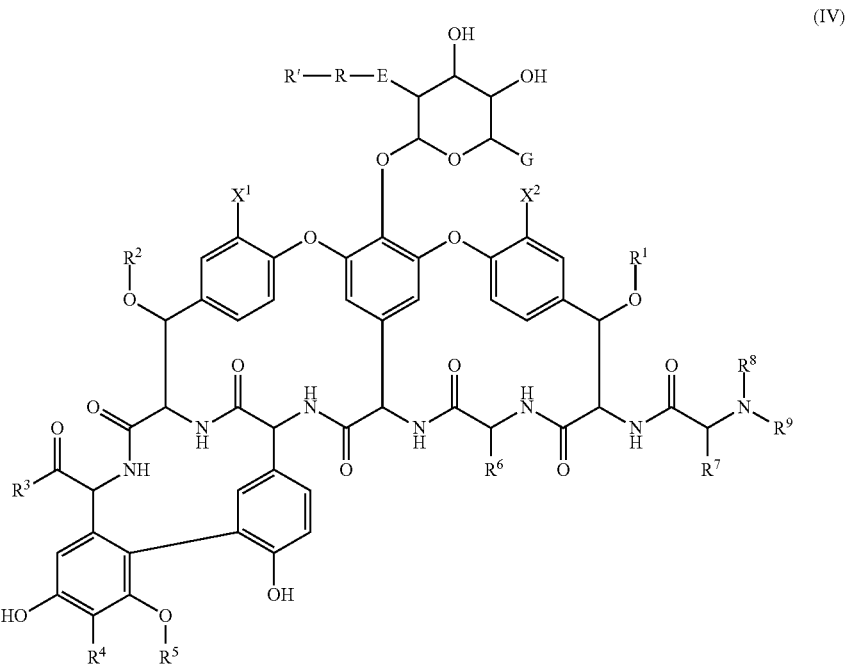

each k, l, m, t, u is independently a nonnull integer ≤5;
α is an integer between 1 and 6;
β is an integer ≤3; and
δ is an integer ≤2α; and
with the proviso that either $R^3$ is $L^c$, or G is —C(O)-$L^c$, or both $R^3$ is $L^c$ and G is —C(O)-$L^c$.

18. A compound represented by Formula (IV):

-continued

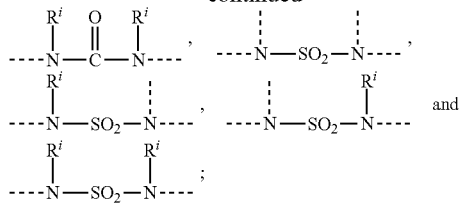

each $R^i$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R;

each $R^j$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

each $E^b$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, and substituted aryloxy;

or a pharmaceutically acceptable salt, ester, or stereoisomer thereof, wherein:

R is selected from the group consisting of —C(O)$R^f$, vancosaminyl, 4-epi-vancosaminyl, L-acosaminyl, L-ristosaminyl, and L-actinosaminyl;

R' is attached to the amino group of R and is selected from the group of —$R^a$—Y—$R^b$—$(Z)_x$, —$R^f$, —C(O)$R^f$, —C(O)—$R^a$—Y—$R^b$—$(Z)_x$, —$R^a$—$(R^b)_z$—(Z) and $L^c$, or R' is absent if R is —C(O)$R^f$;

$R^1$ is hydrogen or mannopyranosyl;

$R^2$ is hydrogen or a saccharide group optionally N-substituted with —$R^a$—Y—$R^b$—$(Z)_x$, —$R^f$, —C(O)$R^f$, —C(O)—$R^a$—Y—$R^b$—$(Z)_x$, —$R^a$—$(R^b)_z$—$(Z)_x$ or $L^c$;

$R^3$ is selected from the group consisting of hydroxyl, —N($R^c$)—R—Y—$R^b$—$(Z)_x$, —O—$R^a$—Y—$R^b$—$(Z)_x$ and —S—R—Y—$R^b$—$(Z)_x$;

$R^4$ is selected from the group consisting of hydrogen, halo, —CH($R^c$)—NR$^c$R$^c$, and —CH($R^c$)—NR$^c$—$R^a$—Y—$R^b$—$(Z)_x$;

$R^5$ is selected from the group consisting of hydrogen, alkyl, substituted alkyl, alkenyl, substituted alkenyl, alkynyl, substituted alkynyl, —$R^a$—Y—$R^b$—$(Z)_x$, —C(O)$R^d$, and a saccharide group optionally substituted with —$R^a$—Y—$R^b$—$(Z)_x$, —$R^a$—$(R^b)_z$—$(Z)_x$, $R^f$, —C(O)$R^f$, or —C(O)—$R^a$—Y—$R^b$—$(Z)_x$;

$R^6$ is selected from the group consisting of —$CH_2$(CO)$NH_2$, benzyl, 4-hydroxyphenyl, and 3-chloro-4-hydroxyphenyl;

R⁷ is selected from the group consisting of —CH₂CH(CH₃)₂, 3-chloro-4-hydroxyphenyl, 4-rhamnosylphenyl, 4-(rhamnosyl-galactosyl)phenyl, 4-(galactosyl-galactosyl)phenyl, and 4(methoxyrhamnosyl)phenyl; or R⁶ and R⁷ are joined to form

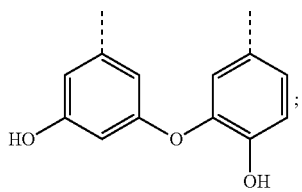

R⁸ is hydrogen, methyl or -L$^c$;
R⁹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, acyl, substituted acyl and -L$^c$;
G is —CH₂OH or —CO₂H;
E is —O— or —NH—;
each R$^a$ is independently selected from the group consisting of alkylene, substituted alkylene, alkenylene, substituted alkenylene, alkynylene and substituted alkynylene;
each R$^b$ is independently selected from the group consisting of a covalent bond, alkylene, substituted alkylene, alkenylene, substituted alkenylene, alkynylene and substituted alkynylene;
each R$^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$;
each R$^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;
each R$^f$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, and heterocyclic;
each X¹ and X² is independently selected from the group consisting of hydrogen, and chloro;
each Y is independently selected from the group consisting of —CH₂—, oxygen, sulfur, —S—S—, —N(R$^c$)—, —N(L$^c$)-, —S(O)—, —SO₂—, —N(R$^c$)—C(O)—, —OSO₂—, —OC(O)—, —N(R$^c$)SO₂—, —C(O)—N(R$^c$)—, —C(O)O—, —SO₂—N(R$^c$)—, —SO₂O—, —P(O)(OR$^c$)O—, —P(O)(OR$^c$)N(R$^c$)—, —OP(O)(OR$^c$)O—, —OP(O)(OR$^c$)N(R$^c$)—, —OC(O)O—, —N(R$^c$)—C(O)—O—, —N(R$^c$)—C(O)—N(R$^c$)—, —O—C(O)—N(R$^c$)—, —C(O)—, and —N(R$^c$)—SO₂—N(R$^c$)—;
each Z is independently selected from the group consisting of hydrogen, aryl, cycloalkyl, cycloalkenyl, heteroaryl, heterocyclic, and a saccharide;
x is 1 or 2;
z is 1, 2, 3 or 4;

each L$^c$ is a linker independently selected from the group of consisting of the following linkers:

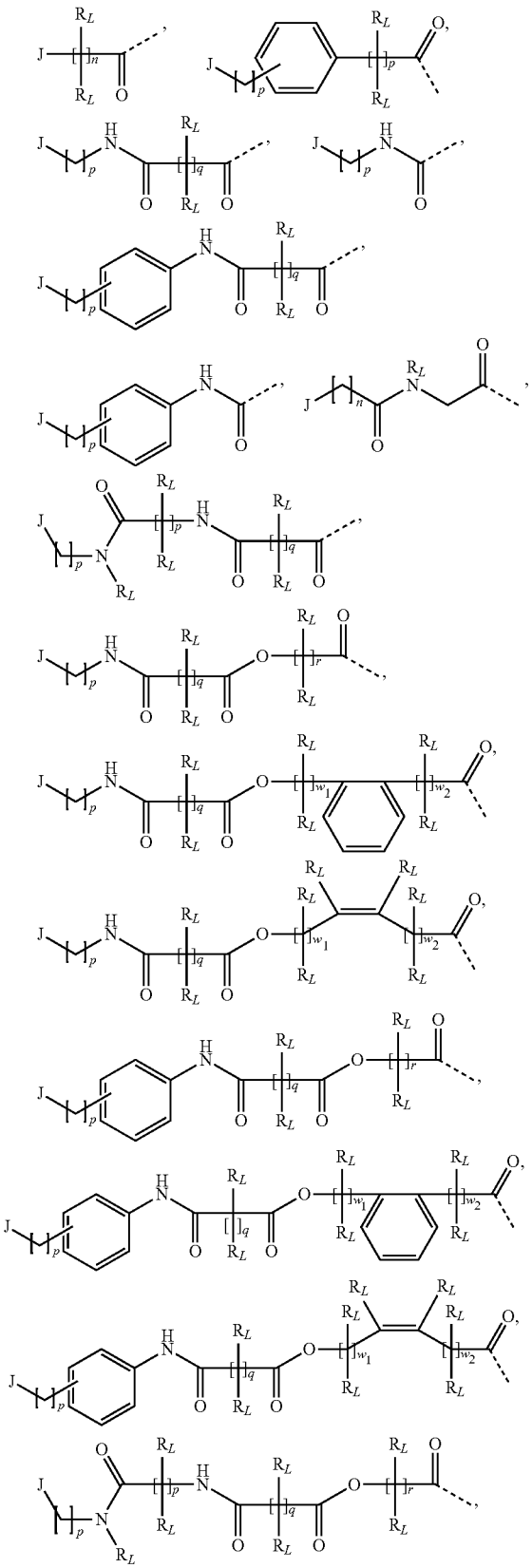

-continued
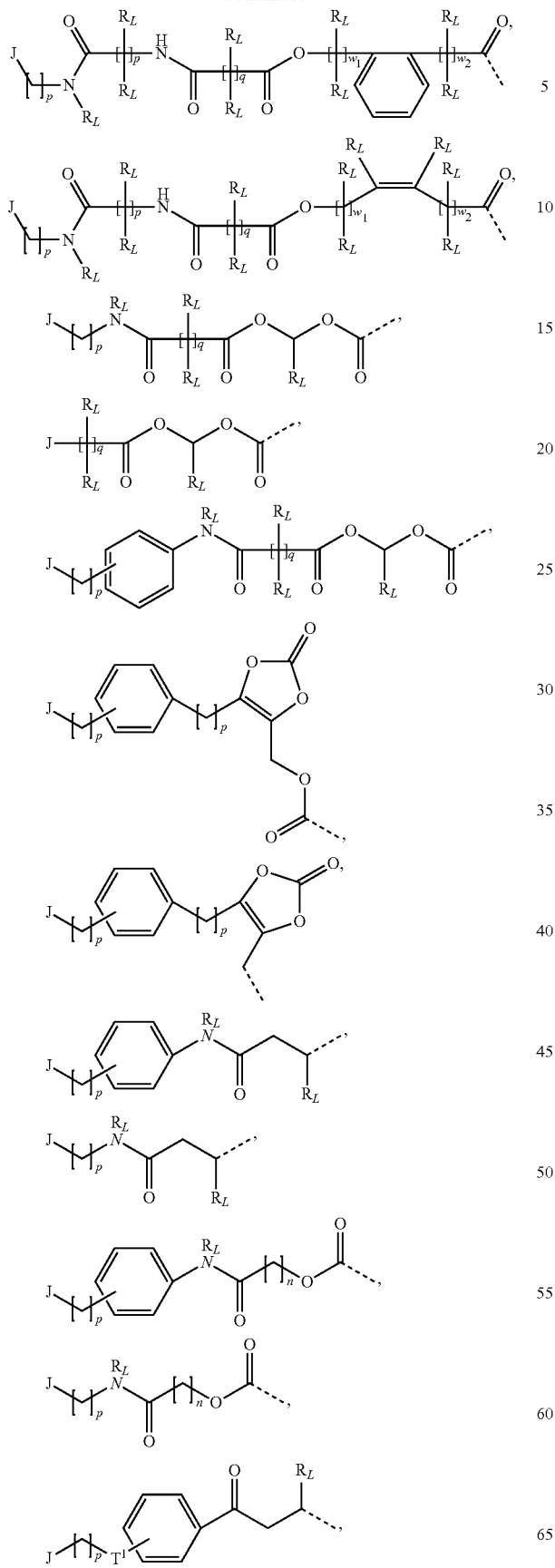
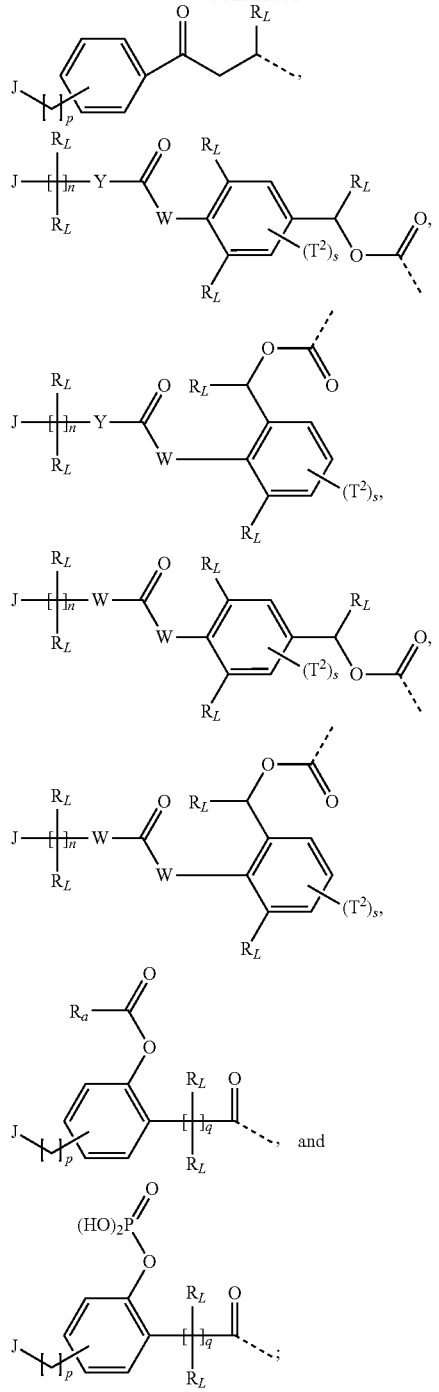
n is an integer ≤10;
each p is independently 0 or an integer ≤10;
each $R_L$ is independently selected from the group consisting of H, ethyl and methyl;
q is 2 or 3;
r is 1, 2, 3, 4 or 5;
$w_1$ and $w_2$ are each integers ≥0 such that their sum ($w_1+w_2$) is 1, 2 or 3;
each W is independently selected from —O—, —S—, and —$NR_L$—;
$T^1$ is $CH_2$, —$CONR_L$—, —CO—O—$CH_2$—, and —CO—O—;

each T² is independently selected from the group consisting of hydrogen, halogen, alkyl, alkoxy, acyl, acyloxy, carboxy, carbamoyl, sulfuryl, sulfinyl, sulfenyl, sulfonyl, mercapto, amino, hydroxyl, cyano and nitro;

s is 1, 2, 3 or 4;

$R_a$ is $C_xH_y$ where x is an integer of 0 to 20 and y is an integer of 1 to 2x+1;

$R_x$, is selected from the group consisting of a covalent bond, S, $NR_L$ and O; and J is $[[L^a{}_\beta-M]_\alpha-L^b{}_\delta]$;

wherein:

each M is individually selected from the group of:

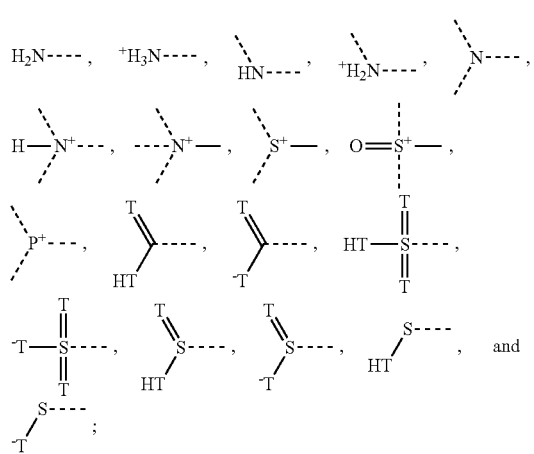

wherein:

each T is O or S; and the dashed bonds - - - indicate the points of attachment to $L^a$, $L^b$, or the linker;

each $L^a$ is individually selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and

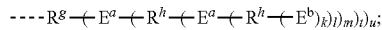

each $L^b$ is individually selected from the group consisting o a covalent bond, alkylene, substituted alkylene, alkenylene, substituted alkenylene, alkynylene, substituted alkynylene, cycloalkylene, substituted cycloalkylene, cycloalkenylene, substituted cycloalkenylene, arylene, heteroarylene and

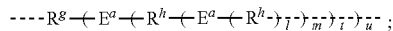

wherein:

each $R^g$ is independently selected from the group consisting of a covalent bond, alkylene, substituted alkylene, alkenylene, substituted alkenylene, alkynylene, substituted alkynylene, arylene, substituted arylene, —(CO)-alkylene-, —(CO)-(substituted alkylene)-, —(CO)-alkenylene-, —(CO)-(substituted alkenylene)-, —(CO)-alkynylene-, —(CO)-(substituted alkynylene)-, —(CO)-arylene- and —(CO)-(substituted arylene)-;

each $R^h$ is independently selected from the group consisting of a covalent bond, alkylene, substituted alkylene, alkenylene, substituted alkenylene, alkynylene, substituted alkynylene, arylene and substituted arylene;

each $E^a$ is independently selected from the group consisting of a covalent bond, methylene, oxygen, sulfur,

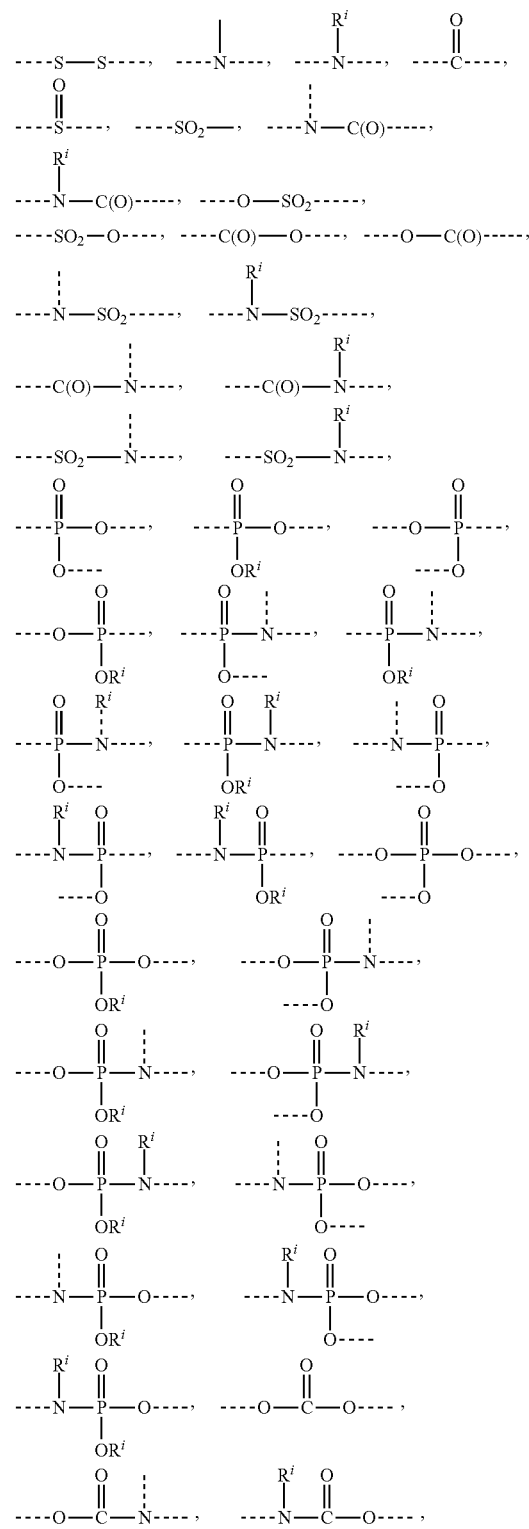

-continued

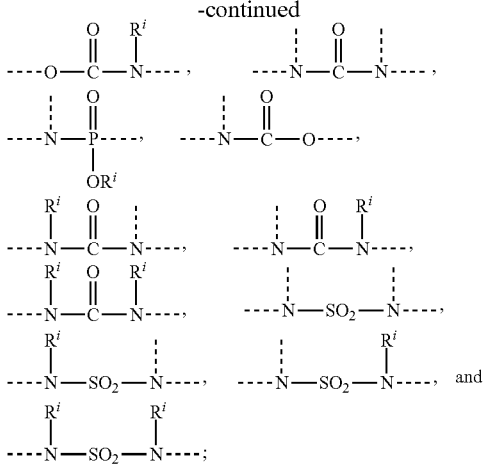

each $R^i$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^j$;

each $R^j$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

each $E^b$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, amino, substituted amino, hydroxyl, alkoxy, substituted alkoxy, aryloxy, and substituted aryloxy;

each k, l, m, t, u is independently a nonnull integer ≤5;

α is an integer between 1 and 6;

β is an integer ≤3;

δ is an integer ≤2α; and with the proviso that one or more of the following is present: R' is $L^c$, $R^8$ is $L^c$, $R^9$ is $L^c$ or Y is —N($L^c$)-.

19. A pharmaceutical composition comprising a compound of claim and a pharmaceutically acceptable carrier or excipient.

20. A method for treating a bacterial infection in a subject, comprising administering to a subject in need of treatment a pharmaceutical composition comprising a pharmaceutically effective amount of a compound of claim 1 and a pharmaceutically acceptable carrier or excipient, thereby treating a bacterial infection in a subject.

21. The method of claim 20, wherein the subject is a human.

* * * * *